United States Patent
Miyawaki et al.

(10) Patent No.: US 8,420,781 B2
(45) Date of Patent: Apr. 16, 2013

(54) FLUORESCENT PROTEIN

(75) Inventors: Atsushi Miyawaki, Saitama (JP); Takako Kogure, Saitama (JP); Hiroshi Hama, Saitama (JP); Masataka Kinjo, Hokkaido (JP); Kenta Saito, Hokkaido (JP); Satoshi Karasawa, Nagano (JP); Toshio Araki, Nagano (JP)

(73) Assignees: Riken, Saitama (JP); Medical & Biological Laboratories Co., Ltd., Aichi (JP)

( * ) Notice: Subject to any disclaimer, the term of this patent is extended or adjusted under 35 U.S.C. 154(b) by 0 days.

(21) Appl. No.: 13/196,499

(22) Filed: Aug. 2, 2011

(65) Prior Publication Data

US 2012/0034643 A1 Feb. 9, 2012

Related U.S. Application Data

(62) Division of application No. 10/581,551, filed as application No. PCT/JP2004/018437 on Dec. 3, 2004, now Pat. No. 8,017,746.

(30) Foreign Application Priority Data

Dec. 3, 2003 (JP) .................................. 2003-404472
Jan. 27, 2004 (JP) .................................. 2004-018344

(51) Int. Cl.
*C07K 1/00* (2006.01)
*C08B 37/08* (2006.01)

(52) U.S. Cl.
USPC ........................................... 530/350; 536/20

(58) Field of Classification Search .................. None
See application file for complete search history.

(56) References Cited

U.S. PATENT DOCUMENTS

| 7,226,993 | B2 | 6/2007 | Miyawaki et al. |
| 7,247,449 | B2 | 7/2007 | Miyawaki et al. |
| 7,345,157 | B2 | 3/2008 | Miyawaki et al. |
| 7,541,451 | B2 | 6/2009 | Miyawaki et al. |
| 7,956,172 | B2 | 6/2011 | Miyawaki et al. |
| 2007/0031912 | A1 | 2/2007 | Miyawaki et al. |
| 2007/0072259 | A1 | 3/2007 | Miyawaki et al. |
| 2007/0292491 | A1 | 12/2007 | Hansen et al. |

FOREIGN PATENT DOCUMENTS

| EP | 1464701 | 10/2004 |
| WO | 02/070703 | 9/2002 |
| WO | 03/033693 | 4/2003 |
| WO | 03/054191 | 7/2003 |

(Continued)

OTHER PUBLICATIONS

Gurskaya et al. (GFP-like chromoproteins as a source of far-red fluorescent proteins., FEBS Lett. (Oct. 19, 2001), vol. 507(1), pp. 16-20.*

(Continued)

*Primary Examiner* — Alexander Kim
(74) *Attorney, Agent, or Firm* — Greenblum & Bernstein, P.L.C.

(57) ABSTRACT

An object of the present invention is to provide a red or orange fluorescent protein, which is characterized in that the difference (stokes shift) between an excitation peak value (wavelength of maximum absorption) and a fluorescence peak value (wavelength of maximum fluorescence) is greatened, so that the maximum fluorescence can be obtained by the maximum excitation. The present invention provides a novel fluorescent protein monomerized by introducing a mutation into a florescent protein derived from *Fungia* sp., and a novel chromoprotein and fluorescent protein derived from *Montipora*. sp.

8 Claims, 29 Drawing Sheets

FOREIGN PATENT DOCUMENTS

| WO | 2004/018671 | 3/2004 |
| WO | 2004/000235 | 12/2004 |
| WO | 2004/000236 | 12/2004 |
| WO | 2004/111235 | 12/2004 |
| WO | 2004/111236 | 12/2004 |

OTHER PUBLICATIONS

Guo et al., Protein tolerance to random amino acid change, 2004, Proc. Natl. Acad. Sci. USA 101: 9205-9210.*

Lazar et al., Transforming Growth Factor α: Mutation of Aspartic Acid 47 and Leucine 48 Results in Different Biological Activity, 1988, Mol. Cell. Biol. 8:1247-1252.*

Hill et al., Functional Analysis of conserved Histidines in ADP-Glucose Pyrophosphorylase from *Escherichia coli*, 1998, Biochem. Biophys. Res. Comm. 244:573-577.*

Wacey et al., Disentangling the perturbational effects of amino acid substitutions in the DNA-binding domain of p53., Hum Genet, 1999, vol. 104, pp. 15-22.*

Database EMBL [Online] Apr. 2, 2003 "Sequence 86 from Patent WO 02/070703." XP002557190 retrieved from EBI accession No. EPOP: AX699818 Database accession No. AX699818.

Database EPO Proteins [Online] Apr. 2, 2003 "Sequence 166 from Patent WO 02/070703." XP002557191 retrieved from EBI accession No. EPOP: AX699898 Database accession No. AX699898.

Extended European Search Report issued with respect to counterpart application EP 09170616.8, May 6, 2010.

Y. Labas et al., "Diversity and Evolution of the Green Fluorescent Protein Family", Proc. Nat. Acad. Sci., vol. 99, No. 7, pp. 4256-4261 (2002).

S. Karasawa et al., "Cyan-Emitting and Orange-Emitting Fluprescent Proteins as a Donor/Aceeptor Pair for Fluorescence Resonance Energy Transfer", Biochemical Journal, vol. 381, No. 1, pp. 307-312 (2004).

Campbell R. E., et al. "A monomeric red fluorescent protein", Proceedings of the National Academy of Sciences of the United States of America, vol. 99 (2002), No. 12, pp. 7877-7882.

Karasawa S., et al. "A Green-emitting Fluorescent Protein from Galaxeida Coral and Its Monomeric Version for Use in Fluorescent Labeling" The Journal of Biological Chemistry, vol. 278 (2003), No. 36, pp. 34167-34171.

Tsien, R.Y., "The Green Fluorescent Protein," Annual Review of Biochemistry, vol. 67, 1998, pp. 509-544.

Timms-Wilson et al., "Reliable use of green fluorescent protein in fluoresenct preudomonads", Journal of Microbiological Methods, 2001, vol. 46 , pp. 77-80.

Database Geneseq [Online] Jan. 22, 2003, "Colour Facilitating molecule (DFM) related sequence #SEQ ID 60", retrieved from EBI accession No. GSP:ABP69944, Database accession No. ABP69944.

Database Geneseq [ Online] Jan. 22, 2003, "Colour Facilitating molecule (DVM) related sequence #SEQ ID 74", retrieved from EBI accession No. GSP:ABP69952, Database accession No. ABP69952.

Extended European Search Report, European Patent Application No. 10181290.7, dated Jul. 28, 2011.

\* cited by examiner

The left figures are magnifications of square portion

440AF21, 455DRLP, 480ALP
T 1%, binning 4, Exposure 187 ms
X40 Uapo/340, Interval 30sec

SEQUENCE LISTING

```
<160> NUMBER OF SEQ ID NOS: 84

<210> SEQ ID NO 1
<211> LENGTH: 218
<212> TYPE: PRT
<213> ORGANISM: Fungia sp.

<400> SEQUENCE: 1

Met Val Ser Val Ile Lys Pro Glu Met Lys Met Arg Tyr Tyr Met Asp
  1               5                  10                  15

Gly Ser Val Asn Gly His Glu Phe Thr Ile Glu Gly Glu Gly Thr Gly
                 20                  25                  30

Arg Pro Tyr Glu Gly His Gln Glu Met Thr Leu Arg Val Thr Met Ala
             35                  40                  45

Lys Gly Gly Pro Met Pro Phe Ala Phe Asp Leu Val Ser His Val Phe
         50                  55                  60

Cys Tyr Gly His Arg Pro Phe Thr Lys Tyr Pro Glu Glu Ile Pro Asp
 65                  70                  75                  80

Tyr Phe Lys Gln Ala Phe Pro Glu Gly Leu Ser Trp Glu Arg Ser Leu
                 85                  90                  95

Glu Phe Glu Asp Gly Gly Ser Ala Ser Val Ser Ala His Ile Ser Leu
            100                 105                 110

Arg Gly Asn Thr Phe Tyr His Lys Ser Lys Phe Thr Gly Val Asn Phe
        115                 120                 125

Pro Ala Asp Gly Pro Ile Met Gln Asn Gln Ser Val Asp Trp Glu Pro
    130                 135                 140

Ser Thr Glu Lys Ile Thr Ala Ser Asp Gly Val Leu Lys Gly Asp Val
145                 150                 155                 160
```

```
Thr Met Tyr Leu Lys Leu Glu Gly Gly Gly Asn His Lys Cys Gln Phe
            165                 170                 175

Lys Thr Thr Tyr Lys Ala Ala Lys Lys Ile Leu Lys Met Pro Gly Ser
                180                 185                 190

His Tyr Ile Ser His Arg Leu Val Arg Lys Thr Glu Gly Asn Ile Thr
            195                 200                 205

Glu Leu Val Glu Asp Ala Val Ala His Ser
        210                 215

<210> SEQ ID NO 2
<211> LENGTH: 657
<212> TYPE: DNA
<213> ORGANISM: Fungia sp.
<220> FEATURE:
<221> NAME/KEY: CDS
<222> LOCATION: (1)..(654)

<400> SEQUENCE: 2 atg gtg agt gtg att aaa cca gag atg aag atg agg tac tac atg gac      48
Met Val Ser Val Ile Lys Pro Glu Met Lys Met Arg Tyr Tyr Met Asp
  1               5                  10                  15 ggc tcc gtc aat ggg cat gag ttc aca att gaa ggt gaa ggc aca ggc      96
Gly Ser Val Asn Gly His Glu Phe Thr Ile Glu Gly Glu Gly Thr Gly
             20                  25                  30 aga cct tac gag gga cat caa gag atg aca cta cgc gtc aca atg gcc     144
Arg Pro Tyr Glu Gly His Gln Glu Met Thr Leu Arg Val Thr Met Ala
         35                  40                  45 aag ggc ggg cca atg cct ttc gcg ttt gac tta gtg tca cac gtg ttc     192
Lys Gly Gly Pro Met Pro Phe Ala Phe Asp Leu Val Ser His Val Phe
     50                  55                  60 tgt tac ggc cac aga cct ttt act aaa tat cca gaa gag ata cca gac     240
Cys Tyr Gly His Arg Pro Phe Thr Lys Tyr Pro Glu Glu Ile Pro Asp
 65                  70                  75                  80 tat ttc aaa caa gca ttt cct gaa ggc ctg tca tgg gaa agg tcg ttg     288
Tyr Phe Lys Gln Ala Phe Pro Glu Gly Leu Ser Trp Glu Arg Ser Leu
                 85                  90                  95 gag ttc gaa gat ggt ggg tcc gct tca gtc agt gcg cat ata agc ctt     336
Glu Phe Glu Asp Gly Gly Ser Ala Ser Val Ser Ala His Ile Ser Leu
            100                 105                 110 aga gga aac acc ttc tac cac aaa tcc aaa ttt act ggg gtt aac ttt     384
Arg Gly Asn Thr Phe Tyr His Lys Ser Lys Phe Thr Gly Val Asn Phe
        115                 120                 125 cct gcc gat ggt cct atc atg caa aac caa agt gtt gat tgg gag cca     432
Pro Ala Asp Gly Pro Ile Met Gln Asn Gln Ser Val Asp Trp Glu Pro
    130                 135                 140 tca acc gag aaa att act gcc agc gac gga gtt ctg aag ggt gat gtt     480
Ser Thr Glu Lys Ile Thr Ala Ser Asp Gly Val Leu Lys Gly Asp Val
145                 150                 155                 160 acg atg tac cta aaa ctt gaa gga ggc aat cac aaa tgc caa ttc         528
Thr Met Tyr Leu Lys Leu Glu Gly Gly Asn His Lys Cys Gln Phe
                165                 170                 175 aag act act tac aag gcg gca aaa aag att ctt aaa atg cca gga agc     576
Lys Thr Thr Tyr Lys Ala Ala Lys Lys Ile Leu Lys Met Pro Gly Ser
                180                 185                 190 cat tac atc agc cat cgc ctc gtc agg aaa acc gaa ggc aac att act     624
His Tyr Ile Ser His Arg Leu Val Arg Lys Thr Glu Gly Asn Ile Thr
            195                 200                 205 gag ctg gta gaa gat gca gta gct cat tcc tga                         657
Glu Leu Val Glu Asp Ala Val Ala His Ser
        210                 215
```

```
<210> SEQ ID NO 3
<211> LENGTH: 218
<212> TYPE: PRT
<213> ORGANISM: Fungia sp.

<400> SEQUENCE: 3

Met Val Ser Val Ile Lys Pro Glu Met Lys Met Arg Tyr Tyr Met Asp
  1               5                  10                  15

Gly Ser Val Asn Gly His Glu Phe Thr Ile Glu Gly Glu Gly Thr Gly
             20                  25                  30

Arg Pro Tyr Glu Gly His Gln Glu Met Thr Leu Arg Val Thr Met Ala
         35                  40                  45

Lys Gly Gly Pro Met Pro Phe Ala Phe Asp Leu Val Ser His Val Phe
     50                  55                  60

Cys Tyr Gly His Arg Cys Phe Thr Lys Tyr Pro Glu Glu Ile Pro Asp
 65                  70                  75                  80

Tyr Phe Lys Gln Ala Phe Pro Glu Gly Leu Ser Trp Glu Arg Ser Leu
                 85                  90                  95

Glu Phe Glu Asp Gly Gly Ser Ala Ser Val Ser Ala His Ile Ser Leu
            100                 105                 110

Arg Gly Asn Thr Phe Tyr His Lys Ser Lys Phe Thr Gly Val Asn Phe
        115                 120                 125

Pro Ala Asp Gly Pro Ile Met Gln Asn Gln Ser Val Asp Trp Glu Pro
    130                 135                 140

Ser Thr Glu Lys Ile Thr Ala Ser Asp Gly Val Leu Lys Gly Asp Asp
145                 150                 155                 160

Thr Leu Tyr Leu Lys Leu Glu Gly Gly Gly Asn His Lys Cys Gln Met
                165                 170                 175

Lys Thr Thr Tyr Lys Ala Ala Lys Lys Ile Leu Lys Met Pro Gly Ser
            180                 185                 190

His Tyr Ile Ser His Arg Leu Val Arg Lys Thr Glu Gly Asn Ile Thr
        195                 200                 205

Glu Leu Val Glu Asp Ala Val Ala His Ser
    210                 215

<210> SEQ ID NO 4
<211> LENGTH: 657
<212> TYPE: DNA
<213> ORGANISM: Fungia sp.
<220> FEATURE:
<221> NAME/KEY: CDS
<222> LOCATION: (1)..(654)

<400> SEQUENCE: 4 atg gtg agt gtg att aaa cca gag atg aag atg agg tac tac atg gac      48
Met Val Ser Val Ile Lys Pro Glu Met Lys Met Arg Tyr Tyr Met Asp
  1               5                  10                  15 ggc tcc gtc aat ggg cat gag ttc aca att gaa ggt gaa ggc aca ggc      96
Gly Ser Val Asn Gly His Glu Phe Thr Ile Glu Gly Glu Gly Thr Gly
             20                  25                  30 aga cct tac gag gga cat caa gag atg aca cta cgc gtc aca atg gcc     144
Arg Pro Tyr Glu Gly His Gln Glu Met Thr Leu Arg Val Thr Met Ala
         35                  40                  45 aag ggc ggg cca atg cct ttc gcg ttt gac tta gtg tca cac gtg ttc     192
Lys Gly Gly Pro Met Pro Phe Ala Phe Asp Leu Val Ser His Val Phe
     50                  55                  60 tgc tac ggc cac aga tgt ttt act aaa tat cca gaa gag ata cca gac     240
Cys Tyr Gly His Arg Cys Phe Thr Lys Tyr Pro Glu Glu Ile Pro Asp
 65                  70                  75                  80
```

```
tat ttc aaa caa gca ttt cct gaa ggc ctg tca tgg gaa agg tcg ttg      288
Tyr Phe Lys Gln Ala Phe Pro Glu Gly Leu Ser Trp Glu Arg Ser Leu
            85                  90                  95 gag ttc gaa gat ggt ggg tcc gct tca gtc agt gcg cat ata agc ctt      336
Glu Phe Glu Asp Gly Gly Ser Ala Ser Val Ser Ala His Ile Ser Leu
        100                 105                 110 aga gga aac acc ttc tac cac aaa tcc aaa ttt act ggg gtt aac ttt      384
Arg Gly Asn Thr Phe Tyr His Lys Ser Lys Phe Thr Gly Val Asn Phe
    115                 120                 125 cct gcc gat ggt cct atc atg caa aac caa agt gtt gat tgg gag cca      432
Pro Ala Asp Gly Pro Ile Met Gln Asn Gln Ser Val Asp Trp Glu Pro
130                 135                 140 tca acc gag aaa att act gcc agc gac gga gtt ctg aag ggt gat gac      480
Ser Thr Glu Lys Ile Thr Ala Ser Asp Gly Val Leu Lys Gly Asp Asp
145                 150                 155                 160 acg ttg tac cta aaa ctt gaa gga ggc ggc aat cac aaa tgc caa atg      528
Thr Leu Tyr Leu Lys Leu Glu Gly Gly Gly Asn His Lys Cys Gln Met
                165                 170                 175 aag act act tac aag gcg gca aaa aag att ctt aaa atg cca gga agc      576
Lys Thr Thr Tyr Lys Ala Ala Lys Lys Ile Leu Lys Met Pro Gly Ser
            180                 185                 190 cat tac atc agc cat cgc ctc gtc agg aaa acc gaa ggc aac att act      624
His Tyr Ile Ser His Arg Leu Val Arg Lys Thr Glu Gly Asn Ile Thr
        195                 200                 205 gag ctg gta gaa gat gca gta gct cat tcc taa                          657
Glu Leu Val Glu Asp Ala Val Ala His Ser
    210                 215

<210> SEQ ID NO 5
<211> LENGTH: 218
<212> TYPE: PRT
<213> ORGANISM: Fungia sp.

<400> SEQUENCE: 5

Met Val Ser Val Ile Lys Pro Glu Met Lys Met Arg Tyr Tyr Met Asp
 1               5                  10                  15

Gly Ser Val Asn Gly His Glu Phe Thr Ile Glu Gly Glu Gly Thr Gly
            20                  25                  30

Arg Pro Tyr Glu Gly His Gln Glu Met Thr Leu Arg Val Thr Met Ala
        35                  40                  45

Lys Gly Gly Pro Met Pro Phe Ala Phe Asp Leu Val Ser His Val Phe
    50                  55                  60

Gly Tyr Gly His Arg Gly Phe Thr Lys Tyr Pro Glu Glu Ile Pro Asp
65                  70                  75                  80

Tyr Phe Lys Gln Ala Phe Pro Glu Gly Leu Ser Trp Glu Arg Ser Leu
                85                  90                  95

Glu Phe Glu Asp Gly Gly Ser Ala Ser Val Ser Ala His Ile Ser Leu
            100                 105                 110

Arg Gly Asn Thr Phe Tyr His Lys Ser Lys Phe Thr Gly Val Asn Phe
        115                 120                 125

Pro Ala Asp Gly Pro Ile Met Gln Asn Gln Ser Val Asp Trp Glu Pro
    130                 135                 140

Ser Thr Glu Lys Ile Thr Ala Ser Asp Gly Val Leu Lys Gly Asp Asp
145                 150                 155                 160

Thr Met Tyr Leu Lys Leu Glu Gly Gly Gly Asn His Lys Cys Gln Met
                165                 170                 175

Lys Thr Thr Tyr Lys Ala Ala Lys Lys Ile Leu Lys Met Pro Gly Ser
            180                 185                 190
```

```
His Tyr Ile Ser His Arg Leu Val Arg Lys Thr Glu Gly Asn Ile Thr
        195                 200                 205

Glu Leu Val Glu Asp Ala Val Ala His Ser
    210                 215

<210> SEQ ID NO 6
<211> LENGTH: 657
<212> TYPE: DNA
<213> ORGANISM: Fungia sp.
<220> FEATURE:
<221> NAME/KEY: CDS
<222> LOCATION: (1)..(654)

<400> SEQUENCE: 6 atg gtg agt gtg att aaa cca gag atg aag atg agg tac tac atg gac      48
Met Val Ser Val Ile Lys Pro Glu Met Lys Met Arg Tyr Tyr Met Asp
 1               5                  10                  15 ggc tcc gtc aat ggg cat gag ttc aca att gaa ggt gaa ggc aca ggc      96
Gly Ser Val Asn Gly His Glu Phe Thr Ile Glu Gly Glu Gly Thr Gly
             20                  25                  30 aga cct tac gag gga cat caa gag atg aca cta cgc gtc aca atg gcc     144
Arg Pro Tyr Glu Gly His Gln Glu Met Thr Leu Arg Val Thr Met Ala
         35                  40                  45 aag ggc ggg cca atg cct ttc gcg ttt gac tta gtg tca cac gtg ttc     192
Lys Gly Gly Pro Met Pro Phe Ala Phe Asp Leu Val Ser His Val Phe
     50                  55                  60 ggg tac ggc cac aga ggt ttt act aaa tat cca gaa gag ata cca gac     240
Gly Tyr Gly His Arg Gly Phe Thr Lys Tyr Pro Glu Glu Ile Pro Asp
 65                  70                  75                  80 tat ttc aaa caa gca ttt cct gaa ggc ctg tca tgg gaa agg tcg ttg     288
Tyr Phe Lys Gln Ala Phe Pro Glu Gly Leu Ser Trp Glu Arg Ser Leu
                 85                  90                  95 gag ttc gaa gat ggt ggg tcc gct tca gtc agt gcg cat ata agc ctt     336
Glu Phe Glu Asp Gly Gly Ser Ala Ser Val Ser Ala His Ile Ser Leu
            100                 105                 110 aga gga aac acc ttc tac cac aaa tcc aaa ttt act ggg gtt aac ttt     384
Arg Gly Asn Thr Phe Tyr His Lys Ser Lys Phe Thr Gly Val Asn Phe
        115                 120                 125 cct gcc gat ggt cct atc atg caa aac caa agt gtt gat tgg gag cca     432
Pro Ala Asp Gly Pro Ile Met Gln Asn Gln Ser Val Asp Trp Glu Pro
    130                 135                 140 tca acc gag aaa att act gcc agc gac gga gtt ctg aag ggt gat gat     480
Ser Thr Glu Lys Ile Thr Ala Ser Asp Gly Val Leu Lys Gly Asp Asp
145                 150                 155                 160 acg atg tac cta aaa ctt gaa gga ggc aat cac aaa tgc caa atg         528
Thr Met Tyr Leu Lys Leu Glu Gly Gly Asn His Lys Cys Gln Met
                165                 170                 175 aag act act tac aag gcg gca aaa aag att ctt aaa atg cca gga agc     576
Lys Thr Thr Tyr Lys Ala Ala Lys Lys Ile Leu Lys Met Pro Gly Ser
            180                 185                 190 cat tac atc agc cat cgc ctc gtc agg aaa acc gaa ggc aac att act     624
His Tyr Ile Ser His Arg Leu Val Arg Lys Thr Glu Gly Asn Ile Thr
        195                 200                 205 gag ctg gta gaa gat gca gta gct cat tcc taa                         657
Glu Leu Val Glu Asp Ala Val Ala His Ser
    210                 215

<210> SEQ ID NO 7
<211> LENGTH: 218
<212> TYPE: PRT
<213> ORGANISM: Fungia sp.

<400> SEQUENCE: 7
```

```
Met Val Ser Val Ile Lys Pro Glu Met Lys Met Arg Tyr Tyr Met Asp
 1               5                  10                  15

Gly Ser Val Asn Gly His Glu Phe Thr Ile Glu Gly Glu Gly Thr Gly
            20                  25                  30

Arg Pro Tyr Glu Gly His Gln Glu Met Thr Leu Arg Val Thr Met Ala
        35                  40                  45

Lys Gly Gly Pro Met Pro Phe Ala Phe Asp Leu Val Ser His Val Phe
 50                  55                  60

Ala Tyr Gly His Arg Gly Phe Thr Lys Tyr Pro Glu Glu Ile Pro Asp
 65                  70                  75                  80

Tyr Phe Lys Gln Ala Phe Pro Glu Gly Leu Ser Trp Glu Arg Ser Leu
                85                  90                  95

Glu Phe Glu Asp Gly Gly Ser Ala Ser Val Ser Ala His Ile Ser Leu
            100                 105                 110

Arg Gly Asn Thr Phe Tyr His Lys Ser Lys Phe Thr Gly Val Asn Phe
        115                 120                 125

Pro Ala Asp Gly Pro Ile Met Gln Asn Gln Ser Val Asp Trp Glu Pro
130                 135                 140

Ser Thr Glu Lys Ile Thr Ala Ser Asp Gly Val Leu Lys Gly Asp Val
145                 150                 155                 160

Thr Met Tyr Leu Lys Leu Glu Gly Gly Asn His Lys Cys Gln Phe
                165                 170                 175

Lys Thr Thr Tyr Lys Ala Ala Lys Lys Ile Leu Lys Met Pro Gly Ser
            180                 185                 190

His Tyr Ile Ser His Arg Leu Val Arg Lys Thr Glu Gly Asn Ile Thr
        195                 200                 205

Glu Leu Val Glu Asp Ala Val Ala His Ser
        210                 215

<210> SEQ ID NO 8
<211> LENGTH: 657
<212> TYPE: DNA
<213> ORGANISM: Fungia sp.
<220> FEATURE:
<221> NAME/KEY: CDS
<222> LOCATION: (1)..(654)

<400> SEQUENCE: 8 atg gtg agt gtg att aaa cca gag atg aag atg agg tac tac atg gac     48
Met Val Ser Val Ile Lys Pro Glu Met Lys Met Arg Tyr Tyr Met Asp
 1               5                  10                  15 ggc tcc gtc aat ggg cat gag ttc aca att gaa ggt gaa ggc aca ggc     96
Gly Ser Val Asn Gly His Glu Phe Thr Ile Glu Gly Glu Gly Thr Gly
            20                  25                  30 aga cct tac gag gga cat caa gag atg aca cta cgc gtc aca atg gcc    144
Arg Pro Tyr Glu Gly His Gln Glu Met Thr Leu Arg Val Thr Met Ala
        35                  40                  45 aag ggc ggg cca atg cct ttc gcg ttt gac tta gtg tca cac gtg ttc    192
Lys Gly Gly Pro Met Pro Phe Ala Phe Asp Leu Val Ser His Val Phe
 50                  55                  60 gct tac ggc cac aga ggt ttt act aaa tat cca gaa gag ata cca gac    240
Ala Tyr Gly His Arg Gly Phe Thr Lys Tyr Pro Glu Glu Ile Pro Asp
 65                  70                  75                  80 tat ttc aaa caa gca ttt cct gaa ggc ctg tca tgg gaa agg tcg ttg    288
Tyr Phe Lys Gln Ala Phe Pro Glu Gly Leu Ser Trp Glu Arg Ser Leu
                85                  90                  95 gag ttc gaa gat ggt ggg tcc gct tca gtc agt gcg cat ata agc ctt    336
Glu Phe Glu Asp Gly Gly Ser Ala Ser Val Ser Ala His Ile Ser Leu
            100                 105                 110
```

```
                                  100                     105                     110
aga gga aac acc ttc tac cac aaa tcc aaa ttt act ggg gtt aac ttt          384
Arg Gly Asn Thr Phe Tyr His Lys Ser Lys Phe Thr Gly Val Asn Phe
            115                     120                     125 cct gcc gat ggt cct atc atg caa aac caa agt gtt gat tgg gag cca          432
Pro Ala Asp Gly Pro Ile Met Gln Asn Gln Ser Val Asp Trp Glu Pro
    130                     135                     140 tca acc gag aaa att act gcc agc gac gga gtt ctg aag ggt gat gtt          480
Ser Thr Glu Lys Ile Thr Ala Ser Asp Gly Val Leu Lys Gly Asp Val
145                     150                     155                     160 acg atg tac cta aaa ctt gaa gga ggc aat cac aaa tgc caa ttc              528
Thr Met Tyr Leu Lys Leu Glu Gly Gly Asn His Lys Cys Gln Phe
                165                     170                     175 aag act act tac aag gcg gca aaa aag att ctt aaa atg cca gga agc          576
Lys Thr Thr Tyr Lys Ala Ala Lys Lys Ile Leu Lys Met Pro Gly Ser
            180                     185                     190 cat tac atc agc cat cgc ctc gtc agg aaa acc gaa ggc aac att act          624
His Tyr Ile Ser His Arg Leu Val Arg Lys Thr Glu Gly Asn Ile Thr
    195                     200                     205 gag ctg gta gaa gat gca gta gct cat tcc taa                              657
Glu Leu Val Glu Asp Ala Val Ala His Ser
210                     215

<210> SEQ ID NO 9
<211> LENGTH: 218
<212> TYPE: PRT
<213> ORGANISM: Fungia sp.

<400> SEQUENCE: 9

Met Val Ser Val Ile Lys Pro Glu Met Lys Met Arg Tyr Tyr Met Asp
 1               5                  10                  15

Gly Ser Val Asn Gly His Glu Phe Thr Ile Glu Gly Glu Gly Thr Gly
                20                  25                  30

Arg Pro Tyr Glu Gly His Gln Glu Leu Thr Leu Arg Val Thr Met Ala
            35                  40                  45

Glu Gly Gly Pro Met Pro Phe Ala Phe Asp Leu Val Ser His Val Phe
        50                  55                  60

Cys Tyr Gly His Lys Pro Phe Thr Lys Tyr Pro Glu Glu Ile Pro Asp
 65                 70                  75                  80

Tyr Phe Lys Gln Ala Phe Pro Glu Gly Leu Ser Trp Glu Arg Ser Leu
                85                  90                  95

Glu Phe Glu Asp Gly Gly Ser Ala Ser Val Ser Ala His Ile Ser Leu
            100                 105                 110

Arg Gly Asn Thr Phe Tyr His Lys Ser Lys Phe Thr Gly Val Asn Phe
        115                 120                 125

Pro Ala Asp Gly Pro Ile Met Gln Asn Gln Ser Val Asp Trp Glu Pro
    130                 135                 140

Trp Thr Glu Lys Ile Thr Ala Ser Asp Gly Val Leu Lys Gly Asp Val
145                 150                 155                 160

Thr Met Tyr Leu Lys Leu Glu Gly Gly Asn His Lys Cys Gln Phe
                165                 170                 175

Lys Thr Thr Tyr Lys Ala Ala Lys Glu Ile Leu Glu Met Pro Gly Asp
            180                 185                 190

His Tyr Ile Ser His Arg Leu Val Arg Lys Thr Glu Gly Asn Ile Thr
        195                 200                 205

Glu Leu Val Glu Asp Ala Val Ala His Ser
    210                 215
```

<210> SEQ ID NO 10
<211> LENGTH: 657
<212> TYPE: DNA
<213> ORGANISM: Fungia sp.
<220> FEATURE:
<221> NAME/KEY: CDS
<222> LOCATION: (1)..(654)

<400> SEQUENCE: 10

| | | | | | | | | | | | | | | | | |
|---|---|---|---|---|---|---|---|---|---|---|---|---|---|---|---|---|
| atg | gtg | agt | gtg | att | aaa | cca | gag | atg | aag | atg | agg | tac | tac | atg | gac | 48 |
| Met | Val | Ser | Val | Ile | Lys | Pro | Glu | Met | Lys | Met | Arg | Tyr | Tyr | Met | Asp | |
| 1 | | | | 5 | | | | | 10 | | | | | 15 | | |
| ggc | tcc | gtc | aat | ggg | cat | gag | ttc | aca | att | gaa | ggt | gaa | ggc | aca | ggc | 96 |
| Gly | Ser | Val | Asn | Gly | His | Glu | Phe | Thr | Ile | Glu | Gly | Glu | Gly | Thr | Gly | |
| | | | 20 | | | | | 25 | | | | | 30 | | | |
| aga | cct | tac | gag | gga | cat | caa | gag | ctg | aca | cta | cgc | gtc | aca | atg | gcc | 144 |
| Arg | Pro | Tyr | Glu | Gly | His | Gln | Glu | Leu | Thr | Leu | Arg | Val | Thr | Met | Ala | |
| | 35 | | | | | 40 | | | | | 45 | | | | | |
| gag | ggc | ggg | cca | atg | cct | ttc | gcg | ttt | gac | tta | gtg | tca | cac | gtg | ttc | 192 |
| Glu | Gly | Gly | Pro | Met | Pro | Phe | Ala | Phe | Asp | Leu | Val | Ser | His | Val | Phe | |
| 50 | | | | | 55 | | | | | 60 | | | | | | |
| tgt | tac | ggc | cac | aaa | cct | ttt | act | aaa | tat | cca | gaa | gag | ata | cca | gac | 240 |
| Cys | Tyr | Gly | His | Lys | Pro | Phe | Thr | Lys | Tyr | Pro | Glu | Glu | Ile | Pro | Asp | |
| 65 | | | | | 70 | | | | | 75 | | | | | 80 | |
| tat | ttc | aaa | caa | gca | ttt | cct | gaa | ggc | ctg | tca | tgg | gaa | agg | tcg | ttg | 288 |
| Tyr | Phe | Lys | Gln | Ala | Phe | Pro | Glu | Gly | Leu | Ser | Trp | Glu | Arg | Ser | Leu | |
| | | | | 85 | | | | | 90 | | | | | 95 | | |
| gag | ttc | gaa | gat | ggt | ggg | tcc | gct | tca | gtc | agt | gcg | cat | ata | agc | ctt | 336 |
| Glu | Phe | Glu | Asp | Gly | Gly | Ser | Ala | Ser | Val | Ser | Ala | His | Ile | Ser | Leu | |
| | | | 100 | | | | | 105 | | | | | 110 | | | |
| aga | gga | aac | acc | ttc | tac | cac | aaa | tcc | aaa | ttt | act | ggg | gtt | aac | ttt | 384 |
| Arg | Gly | Asn | Thr | Phe | Tyr | His | Lys | Ser | Lys | Phe | Thr | Gly | Val | Asn | Phe | |
| | 115 | | | | | 120 | | | | | 125 | | | | | |
| cct | gcc | gat | ggt | cct | atc | atg | caa | aac | caa | agt | gtt | gat | tgg | gag | cca | 432 |
| Pro | Ala | Asp | Gly | Pro | Ile | Met | Gln | Asn | Gln | Ser | Val | Asp | Trp | Glu | Pro | |
| 130 | | | | | 135 | | | | | 140 | | | | | | |
| tgg | acc | gag | aaa | att | act | gcc | agc | gac | gga | gtt | ctg | aag | ggt | gat | gtt | 480 |
| Trp | Thr | Glu | Lys | Ile | Thr | Ala | Ser | Asp | Gly | Val | Leu | Lys | Gly | Asp | Val | |
| 145 | | | | | 150 | | | | | 155 | | | | | 160 | |
| acg | atg | tac | cta | aaa | ctt | gaa | gga | ggc | ggc | aat | cac | aaa | tgc | caa | ttc | 528 |
| Thr | Met | Tyr | Leu | Lys | Leu | Glu | Gly | Gly | Gly | Asn | His | Lys | Cys | Gln | Phe | |
| | | | | 165 | | | | | 170 | | | | | 175 | | |
| aag | act | act | tac | aag | gcg | gca | aaa | gag | att | ctt | gaa | atg | cca | gga | gac | 576 |
| Lys | Thr | Thr | Tyr | Lys | Ala | Ala | Lys | Glu | Ile | Leu | Glu | Met | Pro | Gly | Asp | |
| | | | 180 | | | | | 185 | | | | | 190 | | | |
| cat | tac | atc | agc | cat | cgc | ctc | gtc | agg | aaa | acc | gaa | ggc | aac | att | act | 624 |
| His | Tyr | Ile | Ser | His | Arg | Leu | Val | Arg | Lys | Thr | Glu | Gly | Asn | Ile | Thr | |
| | 195 | | | | | 200 | | | | | 205 | | | | | |
| gag | ctg | gta | gaa | gat | gca | gta | gct | cat | tcc | taa | | | | | | 657 |
| Glu | Leu | Val | Glu | Asp | Ala | Val | Ala | His | Ser | | | | | | | |
| 210 | | | | | 215 | | | | | | | | | | | |

<210> SEQ ID NO 11
<211> LENGTH: 218
<212> TYPE: PRT
<213> ORGANISM: Fungia sp.

<400> SEQUENCE: 11

Met Val Ser Val Ile Lys Pro Glu Met Lys Met Arg Tyr Tyr Met Asp
 1               5                  10                  15

Gly Ser Val Asn Gly His Glu Phe Thr Ile Glu Gly Glu Gly Thr Gly
             20                  25                  30

```
Arg Pro Tyr Glu Gly His Gln Glu Met Thr Leu Arg Val Thr Met Ala
         35                  40                  45

Glu Gly Gly Pro Met Pro Phe Ala Phe Asp Leu Val Ser His Val Phe
 50                  55                  60

Cys Tyr Gly His Arg Gly Phe Thr Lys Tyr Pro Glu Glu Ile Pro Asp
 65                  70                  75                  80

Tyr Phe Lys Gln Ala Phe Pro Glu Gly Leu Ser Trp Glu Arg Ser Leu
                 85                  90                  95

Glu Phe Glu Asp Gly Gly Ser Ala Ser Val Ser Ala His Ile Ser Leu
             100                 105                 110

Arg Gly Asn Thr Phe Tyr His Lys Ser Lys Phe Thr Gly Val Asn Phe
         115                 120                 125

Pro Ala Asp Gly Pro Ile Met Gln Asn Gln Ser Val Asp Trp Glu Pro
130                 135                 140

Ser Thr Glu Lys Ile Thr Ala Ser Asp Gly Val Leu Lys Gly Asp Val
145                 150                 155                 160

Thr Met Tyr Leu Lys Leu Glu Gly Gly Asn His Lys Cys Gln Phe
                 165                 170                 175

Lys Thr Thr Tyr Lys Ala Ala Lys Glu Ile Leu Glu Met Pro Gly Asp
                 180                 185                 190

His Tyr Ile Gly His Arg Leu Val Arg Lys Thr Glu Gly Asn Ile Thr
         195                 200                 205

Glu Leu Val Glu Asp Ala Val Ala His Ser
         210                 215

<210> SEQ ID NO 12
<211> LENGTH: 657
<212> TYPE: DNA
<213> ORGANISM: Fungia sp.
<220> FEATURE:
<221> NAME/KEY: CDS
<222> LOCATION: (1)..(654)

<400> SEQUENCE: 12 atg gtg agt gtg att aaa cca gag atg aag atg agg tac tac atg gac      48
Met Val Ser Val Ile Lys Pro Glu Met Lys Met Arg Tyr Tyr Met Asp
 1               5                  10                  15 ggc tcc gtc aat ggg cat gag ttc aca att gaa ggt gaa ggc aca ggc      96
Gly Ser Val Asn Gly His Glu Phe Thr Ile Glu Gly Glu Gly Thr Gly
             20                  25                  30 aga cct tac gag gga cat caa gag atg aca cta cgc gtc aca atg gcc     144
Arg Pro Tyr Glu Gly His Gln Glu Met Thr Leu Arg Val Thr Met Ala
         35                  40                  45 gag ggc ggg cca atg cct ttc gcg ttt gac tta gtg tca cac gtg ttc     192
Glu Gly Gly Pro Met Pro Phe Ala Phe Asp Leu Val Ser His Val Phe
 50                  55                  60 tgt tac ggc cac aga ggt ttt act aaa tat cca gaa gag ata cca gac     240
Cys Tyr Gly His Arg Gly Phe Thr Lys Tyr Pro Glu Glu Ile Pro Asp
 65                  70                  75                  80 tat ttc aaa caa gca ttt cct gaa ggc ctg tca tgg gaa agg tcg ttg     288
Tyr Phe Lys Gln Ala Phe Pro Glu Gly Leu Ser Trp Glu Arg Ser Leu
                 85                  90                  95 gag ttc gaa gat ggt ggg tcc gct tca gtc agt gcg cat ata agc ctt     336
Glu Phe Glu Asp Gly Gly Ser Ala Ser Val Ser Ala His Ile Ser Leu
             100                 105                 110 aga gga aac acc ttc tac cac aaa tcc aaa ttt act ggg gtt aac ttt     384
Arg Gly Asn Thr Phe Tyr His Lys Ser Lys Phe Thr Gly Val Asn Phe
         115                 120                 125
```

```
cct gcc gat ggt cct atc atg caa aac caa agt gtt gat tgg gag cca    432
Pro Ala Asp Gly Pro Ile Met Gln Asn Gln Ser Val Asp Trp Glu Pro
    130                 135                 140 tca acc gag aaa att act gcc agc gac gga gtt ctg aag ggt gat gtt    480
Ser Thr Glu Lys Ile Thr Ala Ser Asp Gly Val Leu Lys Gly Asp Val
145                 150                 155                 160 acg atg tac cta aaa ctt gaa gga ggc ggc aat cac aaa tgc caa ttc    528
Thr Met Tyr Leu Lys Leu Glu Gly Gly Gly Asn His Lys Cys Gln Phe
                165                 170                 175 aag act act tac aag gcg gca aaa gag att ctt gaa atg cca gga gac    576
Lys Thr Thr Tyr Lys Ala Ala Lys Glu Ile Leu Glu Met Pro Gly Asp
            180                 185                 190 cat tac atc ggc cat cgc ctc gtc agg aaa acc gaa ggc aac att act    624
His Tyr Ile Gly His Arg Leu Val Arg Lys Thr Glu Gly Asn Ile Thr
        195                 200                 205 gag ctg gta gaa gat gca gta gct cat tcc taa                         657
Glu Leu Val Glu Asp Ala Val Ala His Ser
    210                 215
```

<210> SEQ ID NO 13
<211> LENGTH: 218
<212> TYPE: PRT
<213> ORGANISM: Fungia sp.

<400> SEQUENCE: 13

```
Met Val Ser Val Ile Lys Pro Glu Met Lys Met Arg Tyr Tyr Met Asp
1               5                   10                  15

Gly Ser Val Asn Gly His Glu Phe Thr Ile Glu Gly Glu Gly Thr Gly
            20                  25                  30

Arg Pro Tyr Glu Gly His Gln Glu Met Thr Leu Arg Val Thr Met Ala
        35                  40                  45

Glu Gly Gly Pro Met Pro Phe Ala Phe Asp Leu Val Ser His Val Phe
    50                  55                  60

Cys Tyr Gly His Arg Ala Phe Thr Lys Tyr Pro Glu Glu Ile Pro Asp
65                  70                  75                  80

Tyr Phe Lys Gln Ala Phe Pro Glu Gly Leu Ser Trp Glu Arg Ser Leu
                85                  90                  95

Glu Phe Glu Asp Gly Gly Ser Ala Ser Val Ser Ala His Ile Ser Leu
            100                 105                 110

Arg Gly Asn Thr Phe Tyr His Lys Ser Lys Phe Thr Gly Val Asn Phe
        115                 120                 125

Pro Ala Asp Gly Pro Ile Met Gln Asn Gln Ser Val Asp Trp Glu Pro
    130                 135                 140

Ser Thr Glu Lys Ile Thr Ala Ser Asp Gly Val Leu Lys Gly Asp Val
145                 150                 155                 160

Thr Met Tyr Leu Lys Leu Glu Gly Gly Gly Asn His Lys Cys Gln Phe
                165                 170                 175

Lys Thr Thr Tyr Lys Ala Ala Lys Glu Ile Leu Glu Met Pro Gly Asp
            180                 185                 190

His Tyr Ile Gly His Arg Leu Val Arg Lys Thr Glu Gly Asn Ile Thr
        195                 200                 205

Glu Leu Val Glu Asp Ala Val Ala His Ser
    210                 215
```

<210> SEQ ID NO 14
<211> LENGTH: 657
<212> TYPE: DNA
<213> ORGANISM: Fungia sp.
<220> FEATURE:

```
<221> NAME/KEY: CDS
<222> LOCATION: (1)..(654)

<400> SEQUENCE: 14 atg gtg agt gtg att aaa cca gag atg aag atg agg tac tac atg gac      48
Met Val Ser Val Ile Lys Pro Glu Met Lys Met Arg Tyr Tyr Met Asp
 1               5                  10                  15 ggc tcc gtc aat ggg cat gag ttc aca att gaa ggt gaa ggc aca ggc      96
Gly Ser Val Asn Gly His Glu Phe Thr Ile Glu Gly Glu Gly Thr Gly
             20                  25                  30 aga cct tac gag gga cat caa gag atg aca cta cgc gtc aca atg gcc     144
Arg Pro Tyr Glu Gly His Gln Glu Met Thr Leu Arg Val Thr Met Ala
         35                  40                  45 gag ggc ggg cca atg cct ttc gcg ttt gac tta gtg tca cac gtg ttc     192
Glu Gly Gly Pro Met Pro Phe Ala Phe Asp Leu Val Ser His Val Phe
     50                  55                  60 tgt tac ggc cac aga gct ttt act aaa tat cca gaa gag ata cca gac     240
Cys Tyr Gly His Arg Ala Phe Thr Lys Tyr Pro Glu Glu Ile Pro Asp
 65                  70                  75                  80 tat ttc aaa caa gca ttt cct gaa ggc ctg tca tgg gaa agg tcg ttg     288
Tyr Phe Lys Gln Ala Phe Pro Glu Gly Leu Ser Trp Glu Arg Ser Leu
                 85                  90                  95 gag ttc gaa gat ggt ggg tcc gct tca gtc agt gcg cat ata agc ctt     336
Glu Phe Glu Asp Gly Gly Ser Ala Ser Val Ser Ala His Ile Ser Leu
            100                 105                 110 aga gga aac acc ttc tac cac aaa tcc aaa ttt act ggg gtt aac ttt     384
Arg Gly Asn Thr Phe Tyr His Lys Ser Lys Phe Thr Gly Val Asn Phe
        115                 120                 125 cct gcc gat ggt cct atc atg caa aac caa agt gtt gat tgg gag cca     432
Pro Ala Asp Gly Pro Ile Met Gln Asn Gln Ser Val Asp Trp Glu Pro
    130                 135                 140 tca acc gag aaa att act gcc agc gac gga gtt ctg aag ggt gat gtt     480
Ser Thr Glu Lys Ile Thr Ala Ser Asp Gly Val Leu Lys Gly Asp Val
145                 150                 155                 160 acg atg tac cta aaa ctt gaa gga ggc ggc aat cac aaa tgc caa ttc     528
Thr Met Tyr Leu Lys Leu Glu Gly Gly Gly Asn His Lys Cys Gln Phe
                165                 170                 175 aag act act tac aag gcg gca aaa gag att ctt gaa atg cca gga gac     576
Lys Thr Thr Tyr Lys Ala Ala Lys Glu Ile Leu Glu Met Pro Gly Asp
            180                 185                 190 cat tac atc ggg cat cgc ctc gtc agg aaa acc gaa ggc aac att act     624
His Tyr Ile Gly His Arg Leu Val Arg Lys Thr Glu Gly Asn Ile Thr
        195                 200                 205 gag ctg gta gaa gat gca gta gct cat tcc taa                         657
Glu Leu Val Glu Asp Ala Val Ala His Ser
    210                 215

<210> SEQ ID NO 15
<211> LENGTH: 218
<212> TYPE: PRT
<213> ORGANISM: Fungia sp.

<400> SEQUENCE: 15

Met Val Ser Val Ile Lys Pro Glu Met Lys Met Arg Tyr Tyr Met Asp
 1               5                  10                  15

Gly Ser Val Asn Gly His Glu Phe Thr Ile Glu Gly Glu Gly Thr Gly
             20                  25                  30

Arg Pro Tyr Glu Gly His Gln Glu Met Thr Leu Arg Val Thr Met Ala
         35                  40                  45

Glu Gly Gly Pro Met Pro Phe Ala Phe Asp Leu Val Ser His Val Phe
     50                  55                  60
```

```
Cys Tyr Gly His Arg Ser Phe Thr Lys Tyr Pro Glu Glu Ile Pro Asp
 65                  70                  75                  80

Tyr Phe Lys Gln Ala Phe Pro Glu Gly Leu Ser Trp Glu Arg Ser Leu
                 85                  90                  95

Glu Phe Glu Asp Gly Gly Ser Ala Ser Val Ser Ala His Ile Ser Leu
            100                 105                 110

Arg Gly Asn Thr Phe Tyr His Lys Ser Lys Phe Thr Gly Val Asn Phe
        115                 120                 125

Pro Ala Asp Gly Pro Ile Met Gln Asn Gln Ser Val Asp Trp Glu Pro
130                 135                 140

Ser Thr Glu Lys Ile Thr Ala Ser Asp Gly Val Leu Lys Gly Asp Val
145                 150                 155                 160

Thr Met Tyr Leu Lys Leu Glu Gly Gly Asn His Lys Cys Gln Phe
                165                 170                 175

Lys Thr Thr Tyr Lys Ala Ala Lys Glu Ile Leu Glu Met Pro Gly Asp
            180                 185                 190

His Tyr Ile Gly His Arg Leu Val Arg Lys Thr Glu Gly Asn Ile Thr
        195                 200                 205

Glu Leu Val Glu Asp Ala Val Ala His Ser
    210                 215
```

```
<210> SEQ ID NO 16
<211> LENGTH: 657
<212> TYPE: DNA
<213> ORGANISM: Fungia sp.
<220> FEATURE:
<221> NAME/KEY: CDS
<222> LOCATION: (1)..(654)

<400> SEQUENCE: 16
```

```
atg gtg agt gtg att aaa cca gag atg aag atg agg tac tac atg gac      48
Met Val Ser Val Ile Lys Pro Glu Met Lys Met Arg Tyr Tyr Met Asp
  1               5                  10                  15 ggc tcc gtc aat ggg cat gag ttc aca att gaa ggt gaa ggc aca ggc      96
Gly Ser Val Asn Gly His Glu Phe Thr Ile Glu Gly Glu Gly Thr Gly
             20                  25                  30 aga cct tac gag gga cat caa gag atg aca cta cgc gtc aca atg gcc     144
Arg Pro Tyr Glu Gly His Gln Glu Met Thr Leu Arg Val Thr Met Ala
         35                  40                  45 gag ggc ggg cca atg cct ttc gcg ttt gac tta gtg tca cac gtg ttc     192
Glu Gly Gly Pro Met Pro Phe Ala Phe Asp Leu Val Ser His Val Phe
     50                  55                  60 tgt tac ggc cac aga tct ttt act aaa tat cca gaa gag ata cca gac     240
Cys Tyr Gly His Arg Ser Phe Thr Lys Tyr Pro Glu Glu Ile Pro Asp
 65                  70                  75                  80 tat ttc aaa caa gca ttt cct gaa ggc ctg tca tgg gaa agg tcg ttg     288
Tyr Phe Lys Gln Ala Phe Pro Glu Gly Leu Ser Trp Glu Arg Ser Leu
                 85                  90                  95 gag ttc gaa gat ggt ggg tcc gct tca gtc agt gcg cat ata agc ctt     336
Glu Phe Glu Asp Gly Gly Ser Ala Ser Val Ser Ala His Ile Ser Leu
            100                 105                 110 aga gga aac acc ttc tac cac aaa tcc aaa ttt act ggg gtt aac ttt     384
Arg Gly Asn Thr Phe Tyr His Lys Ser Lys Phe Thr Gly Val Asn Phe
        115                 120                 125 cct gcc gat ggt cct atc atg caa aac caa agt gtt gat tgg gag cca     432
Pro Ala Asp Gly Pro Ile Met Gln Asn Gln Ser Val Asp Trp Glu Pro
130                 135                 140 tca acc gag aaa att act gcc agc gac gga gtt ctg aag ggt gat gtt     480
Ser Thr Glu Lys Ile Thr Ala Ser Asp Gly Val Leu Lys Gly Asp Val
145                 150                 155
```

```
                  145                 150                 155                 160
acg atg tac cta aaa ctt gaa gga ggc ggc aat cac aaa tgc caa ttc              528
Thr Met Tyr Leu Lys Leu Glu Gly Gly Gly Asn His Lys Cys Gln Phe
                165                 170                 175 aag act act tac aag gcg gca aaa gag att ctt gaa atg cca gga gac              576
Lys Thr Thr Tyr Lys Ala Ala Lys Glu Ile Leu Glu Met Pro Gly Asp
            180                 185                 190 cat tac atc ggc cat cgc ctc gtc agg aaa acc gaa ggc aac att act              624
His Tyr Ile Gly His Arg Leu Val Arg Lys Thr Glu Gly Asn Ile Thr
        195                 200                 205 gag ctg gta gaa gat gca gta gct cat tcc taa                                  657
Glu Leu Val Glu Asp Ala Val Ala His Ser
    210                 215

<210> SEQ ID NO 17
<211> LENGTH: 218
<212> TYPE: PRT
<213> ORGANISM: Fungia sp.

<400> SEQUENCE: 17

Met Val Ser Val Ile Lys Pro Glu Met Lys Met Arg Tyr Tyr Met Asp
  1               5                  10                  15

Gly Ser Val Asn Gly His Glu Phe Thr Ile Glu Gly Glu Gly Thr Gly
             20                  25                  30

Arg Pro Tyr Glu Gly His Gln Glu Met Thr Leu Arg Val Thr Met Ala
         35                  40                  45

Glu Gly Gly Pro Met Pro Phe Ala Phe Asp Leu Val Ser His Val Phe
     50                  55                  60

Cys Tyr Gly His Arg Cys Phe Thr Lys Tyr Pro Glu Glu Ile Pro Asp
 65                  70                  75                  80

Tyr Phe Lys Gln Ala Phe Pro Glu Gly Leu Ser Trp Glu Arg Ser Leu
                 85                  90                  95

Glu Phe Glu Asp Gly Gly Ser Ala Ser Val Ser Ala His Ile Ser Leu
            100                 105                 110

Arg Gly Asn Thr Phe Tyr His Lys Ser Lys Phe Thr Gly Val Asn Phe
        115                 120                 125

Pro Ala Asp Gly Pro Ile Met Gln Asn Gln Ser Val Asp Trp Glu Pro
    130                 135                 140

Ser Thr Glu Lys Ile Thr Ala Ser Asp Gly Val Leu Lys Gly Asp Val
145                 150                 155                 160

Thr Met Tyr Leu Lys Leu Glu Gly Gly Gly Asn His Lys Cys Gln Phe
                165                 170                 175

Lys Thr Thr Tyr Lys Ala Ala Lys Glu Ile Leu Glu Met Pro Gly Asp
            180                 185                 190

His Tyr Ile Gly His Arg Leu Val Arg Lys Thr Glu Gly Asn Ile Thr
        195                 200                 205

Glu Leu Val Glu Asp Ala Val Ala His Ser
    210                 215

<210> SEQ ID NO 18
<211> LENGTH: 657
<212> TYPE: DNA
<213> ORGANISM: Fungia sp.
<220> FEATURE:
<221> NAME/KEY: CDS
<222> LOCATION: (1)..(654)

<400> SEQUENCE: 18 atg gtg agt gtg att aaa cca gag atg aag atg agg tac tac atg gac               48
```

```
Met Val Ser Val Ile Lys Pro Glu Met Lys Met Arg Tyr Tyr Met Asp
  1               5                  10                  15 ggc tcc gtc aat ggg cat gag ttc aca att gaa ggt gaa ggc aca ggc      96
Gly Ser Val Asn Gly His Glu Phe Thr Ile Glu Gly Glu Gly Thr Gly
             20                  25                  30 aga cct tac gag gga cat caa gag atg aca cta cgc gtc aca atg gcc     144
Arg Pro Tyr Glu Gly His Gln Glu Met Thr Leu Arg Val Thr Met Ala
         35                  40                  45 gag ggc ggg cca atg cct ttc gcg ttt gac tta gtg tca cac gtg ttc     192
Glu Gly Gly Pro Met Pro Phe Ala Phe Asp Leu Val Ser His Val Phe
     50                  55                  60 tgt tac ggc cac aga tgt ttt act aaa tat cca gaa gag ata cca gac     240
Cys Tyr Gly His Arg Cys Phe Thr Lys Tyr Pro Glu Glu Ile Pro Asp
 65                  70                  75                  80 tat ttc aaa caa gca ttt cct gaa ggc ctg tca tgg gaa agg tcg ttg     288
Tyr Phe Lys Gln Ala Phe Pro Glu Gly Leu Ser Trp Glu Arg Ser Leu
                 85                  90                  95 gag ttc gaa gat ggt ggg tcc gct tca gtc agt gcg cat ata agc ctt     336
Glu Phe Glu Asp Gly Gly Ser Ala Ser Val Ser Ala His Ile Ser Leu
            100                 105                 110 aga gga aac acc ttc tac cac aaa tcc aaa ttt act ggg gtt aac ttt     384
Arg Gly Asn Thr Phe Tyr His Lys Ser Lys Phe Thr Gly Val Asn Phe
        115                 120                 125 cct gcc gat ggt cct atc atg caa aac caa agt gtt gat tgg gag cca     432
Pro Ala Asp Gly Pro Ile Met Gln Asn Gln Ser Val Asp Trp Glu Pro
    130                 135                 140 tca acc gag aaa att act gcc agc gac gga gtt ctg aag ggt gat gtt     480
Ser Thr Glu Lys Ile Thr Ala Ser Asp Gly Val Leu Lys Gly Asp Val
145                 150                 155                 160 acg atg tac cta aaa ctt gaa gga ggc ggc aat cac aaa tgc caa ttc     528
Thr Met Tyr Leu Lys Leu Glu Gly Gly Gly Asn His Lys Cys Gln Phe
                165                 170                 175 aag act act tac aag gcg gca aaa gag att ctt gaa atg cca gga gac     576
Lys Thr Thr Tyr Lys Ala Ala Lys Glu Ile Leu Glu Met Pro Gly Asp
            180                 185                 190 cat tac atc ggc cat cgc ctc gtc agg aaa acc gaa ggc aac att act     624
His Tyr Ile Gly His Arg Leu Val Arg Lys Thr Glu Gly Asn Ile Thr
        195                 200                 205 gag ctg gta gaa gat gca gta gct cat tcc taa                         657
Glu Leu Val Glu Asp Ala Val Ala His Ser
    210                 215

<210> SEQ ID NO 19
<211> LENGTH: 218
<212> TYPE: PRT
<213> ORGANISM: Fungia sp.

<400> SEQUENCE: 19

Met Val Ser Val Ile Lys Pro Glu Met Lys Met Arg Tyr Tyr Met Asp
  1               5                  10                  15

Gly Ser Val Asn Gly His Glu Phe Thr Ile Glu Gly Glu Gly Thr Gly
             20                  25                  30

Arg Pro Tyr Glu Gly His Gln Glu Met Thr Leu Arg Val Thr Met Ala
         35                  40                  45

Glu Gly Gly Pro Met Pro Phe Ala Phe Asp Leu Val Ser His Val Phe
     50                  55                  60

Cys Tyr Gly His Arg Thr Phe Thr Lys Tyr Pro Glu Glu Ile Pro Asp
 65                  70                  75                  80

Tyr Phe Lys Gln Ala Phe Pro Glu Gly Leu Ser Trp Glu Arg Ser Leu
                 85                  90                  95
```

```
Glu Phe Glu Asp Gly Gly Ser Ala Ser Val Ser Ala His Ile Ser Leu
                100                 105                 110

Arg Gly Asn Thr Phe Tyr His Lys Ser Lys Phe Thr Gly Val Asn Phe
            115                 120                 125

Pro Ala Asp Gly Pro Ile Met Gln Asn Gln Ser Val Asp Trp Glu Pro
130                 135                 140

Ser Thr Glu Lys Ile Thr Ala Ser Asp Gly Val Leu Lys Gly Asp Val
145                 150                 155                 160

Thr Met Tyr Leu Lys Leu Glu Gly Gly Asn His Lys Cys Gln Phe
                165                 170                 175

Lys Thr Thr Tyr Lys Ala Ala Lys Glu Ile Leu Glu Met Pro Gly Asp
            180                 185                 190

His Tyr Ile Gly His Arg Leu Val Arg Lys Thr Glu Gly Asn Ile Thr
            195                 200                 205

Glu Leu Val Glu Asp Ala Val Ala His Ser
            210                 215

<210> SEQ ID NO 20
<211> LENGTH: 657
<212> TYPE: DNA
<213> ORGANISM: Fungia sp.
<220> FEATURE:
<221> NAME/KEY: CDS
<222> LOCATION: (1)..(654)

<400> SEQUENCE: 20 atg gtg agt gtg att aaa cca gag atg aag atg agg tac tac atg gac      48
Met Val Ser Val Ile Lys Pro Glu Met Lys Met Arg Tyr Tyr Met Asp
 1               5                  10                  15 ggc tcc gtc aat ggg cat gag ttc aca att gaa ggt gaa ggc aca ggc      96
Gly Ser Val Asn Gly His Glu Phe Thr Ile Glu Gly Glu Gly Thr Gly
                20                  25                  30 aga cct tac gag gga cat caa gag atg aca cta cgc gtc aca atg gcc     144
Arg Pro Tyr Glu Gly His Gln Glu Met Thr Leu Arg Val Thr Met Ala
            35                  40                  45 gag ggc ggg cca atg cct ttc gcg ttt gac tta gtg tca cac gtg ttc     192
Glu Gly Gly Pro Met Pro Phe Ala Phe Asp Leu Val Ser His Val Phe
50                  55                  60 tgt tac ggc cac aga act ttt act aaa tat cca gaa gag ata cca gac     240
Cys Tyr Gly His Arg Thr Phe Thr Lys Tyr Pro Glu Glu Ile Pro Asp
65                  70                  75                  80 tat ttc aaa caa gca ttt cct gaa ggc ctg tca tgg gaa agg tcg ttg     288
Tyr Phe Lys Gln Ala Phe Pro Glu Gly Leu Ser Trp Glu Arg Ser Leu
                85                  90                  95 gag ttc gaa gat ggt ggg tcc gct tca gtc agt gcg cat ata agc ctt     336
Glu Phe Glu Asp Gly Gly Ser Ala Ser Val Ser Ala His Ile Ser Leu
                100                 105                 110 aga gga aac acc ttc tac cac aaa tcc aaa ttt act ggg gtt aac ttt     384
Arg Gly Asn Thr Phe Tyr His Lys Ser Lys Phe Thr Gly Val Asn Phe
            115                 120                 125 cct gcc gat ggt cct atc atg caa aac caa agt gtt gat tgg gag cca     432
Pro Ala Asp Gly Pro Ile Met Gln Asn Gln Ser Val Asp Trp Glu Pro
130                 135                 140 tca acc gag aaa att act gcc agc gac gga gtt ctg aag ggt gat gtt     480
Ser Thr Glu Lys Ile Thr Ala Ser Asp Gly Val Leu Lys Gly Asp Val
145                 150                 155                 160 acg atg tac cta aaa ctt gaa gga ggc ggc aat cac aaa tgc caa ttc     528
Thr Met Tyr Leu Lys Leu Glu Gly Gly Gly Asn His Lys Cys Gln Phe
                165                 170                 175
```

```
aag act act tac aag gcg gca aaa gag att ctt gaa atg cca gga gac      576
Lys Thr Thr Tyr Lys Ala Ala Lys Glu Ile Leu Glu Met Pro Gly Asp
        180                 185                 190 cat tac atc ggc cat cgc ctc gtc agg aaa acc gaa ggc aac att act      624
His Tyr Ile Gly His Arg Leu Val Arg Lys Thr Glu Gly Asn Ile Thr
    195                 200                 205 gag ctg gta gaa gat gca gta gct cat tcc taa                          657
Glu Leu Val Glu Asp Ala Val Ala His Ser
210                 215
```

<210> SEQ ID NO 21
<211> LENGTH: 218
<212> TYPE: PRT
<213> ORGANISM: Fungia sp.

<400> SEQUENCE: 21

```
Met Val Ser Val Ile Lys Pro Glu Met Lys Met Arg Tyr Tyr Met Asp
 1               5                  10                  15

Gly Ser Val Asn Gly His Glu Phe Thr Ile Glu Gly Glu Gly Thr Gly
            20                  25                  30

Arg Pro Tyr Glu Gly His Gln Glu Met Thr Leu Arg Val Thr Met Ala
        35                  40                  45

Glu Gly Gly Pro Met Pro Phe Ala Phe Asp Leu Val Ser His Val Phe
    50                  55                  60

Cys Tyr Gly His Arg Val Phe Thr Lys Tyr Pro Glu Glu Ile Pro Asp
65                  70                  75                  80

Tyr Phe Lys Gln Ala Phe Pro Glu Gly Leu Ser Trp Glu Arg Ser Leu
                85                  90                  95

Glu Phe Glu Asp Gly Gly Ser Ala Ser Val Ser Ala His Ile Ser Leu
            100                 105                 110

Arg Gly Asn Thr Phe Tyr His Lys Ser Lys Phe Thr Gly Val Asn Phe
        115                 120                 125

Pro Ala Asp Gly Pro Ile Met Gln Asn Gln Ser Val Asp Trp Glu Pro
    130                 135                 140

Ser Thr Glu Lys Ile Thr Ala Ser Asp Gly Val Leu Lys Gly Asp Val
145                 150                 155                 160

Thr Met Tyr Leu Lys Leu Glu Gly Gly Gly Asn His Lys Cys Gln Phe
                165                 170                 175

Lys Thr Thr Tyr Lys Ala Ala Lys Glu Ile Leu Glu Met Pro Gly Asp
            180                 185                 190

His Tyr Ile Gly His Arg Leu Val Arg Lys Thr Glu Gly Asn Ile Thr
        195                 200                 205

Glu Leu Val Glu Asp Ala Val Ala His Ser
210                 215
```

<210> SEQ ID NO 22
<211> LENGTH: 657
<212> TYPE: DNA
<213> ORGANISM: Fungia sp.
<220> FEATURE:
<221> NAME/KEY: CDS
<222> LOCATION: (1)..(654)

<400> SEQUENCE: 22

```
atg gtg agt gtg att aaa cca gag atg aag atg agg tac tac atg gac       48
Met Val Ser Val Ile Lys Pro Glu Met Lys Met Arg Tyr Tyr Met Asp
 1               5                  10                  15 ggc tcc gtc aat ggg cat gag ttc aca att gaa ggt gaa ggc aca ggc       96
Gly Ser Val Asn Gly His Glu Phe Thr Ile Glu Gly Glu Gly Thr Gly
            20                  25                  30
```

```
aga cct tac gag gga cat caa gag atg aca cta cgc gtc aca atg gcc    144
Arg Pro Tyr Glu Gly His Gln Glu Met Thr Leu Arg Val Thr Met Ala
         35                  40                  45 gag ggc ggg cca atg cct ttc gcg ttt gac tta gtg tca cac gtg ttc    192
Glu Gly Gly Pro Met Pro Phe Ala Phe Asp Leu Val Ser His Val Phe
 50                  55                  60 tgt tac ggc cac aga gta ttt act aaa tat cca gaa gag ata cca gac    240
Cys Tyr Gly His Arg Val Phe Thr Lys Tyr Pro Glu Glu Ile Pro Asp
 65                  70                  75                  80 tat ttc aaa caa gca ttt cct gaa ggc ctg tca tgg gaa agg tcg ttg    288
Tyr Phe Lys Gln Ala Phe Pro Glu Gly Leu Ser Trp Glu Arg Ser Leu
                 85                  90                  95 gag ttc gaa gat ggt ggg tcc gct tca gtc agt gcg cat ata agc ctt    336
Glu Phe Glu Asp Gly Gly Ser Ala Ser Val Ser Ala His Ile Ser Leu
            100                 105                 110 aga gga aac acc ttc tac cac aaa tcc aaa ttt act ggg gtt aac ttt    384
Arg Gly Asn Thr Phe Tyr His Lys Ser Lys Phe Thr Gly Val Asn Phe
        115                 120                 125 cct gcc gat ggt cct atc atg caa aac caa agt gtt gat tgg gag cca    432
Pro Ala Asp Gly Pro Ile Met Gln Asn Gln Ser Val Asp Trp Glu Pro
130                 135                 140 tca acc gag aaa att act gcc agc gac gga gtt ctg aag ggt gat gtt    480
Ser Thr Glu Lys Ile Thr Ala Ser Asp Gly Val Leu Lys Gly Asp Val
145                 150                 155                 160 acg atg tac cta aaa ctt gaa gga ggc ggc aat cac aaa tgc caa ttc    528
Thr Met Tyr Leu Lys Leu Glu Gly Gly Gly Asn His Lys Cys Gln Phe
                165                 170                 175 aag act act tac aag gcg gca aaa gag att ctt gaa atg cca gga gac    576
Lys Thr Thr Tyr Lys Ala Ala Lys Glu Ile Leu Glu Met Pro Gly Asp
            180                 185                 190 cat tac atc ggc cat cgc ctc gtc agg aaa acc gaa ggc aac att act    624
His Tyr Ile Gly His Arg Leu Val Arg Lys Thr Glu Gly Asn Ile Thr
        195                 200                 205 gag ctg gta gaa gat gca gta gct cat tcc taa                        657
Glu Leu Val Glu Asp Ala Val Ala His Ser
    210                 215

<210> SEQ ID NO 23
<211> LENGTH: 218
<212> TYPE: PRT
<213> ORGANISM: Fungia sp.

<400> SEQUENCE: 23

Met Val Ser Val Ile Lys Pro Glu Met Lys Met Arg Tyr Tyr Met Asp
 1               5                  10                  15

Gly Ser Val Asn Gly His Glu Phe Thr Ile Glu Gly Glu Gly Thr Gly
            20                  25                  30

Arg Pro Tyr Glu Gly His Gln Glu Met Thr Leu Arg Val Thr Met Ala
        35                  40                  45

Glu Gly Gly Pro Met Pro Phe Ala Phe Asp Leu Val Ser His Val Phe
 50                  55                  60

Cys Tyr Gly His Arg Leu Phe Thr Lys Tyr Pro Glu Glu Ile Pro Asp
 65                  70                  75                  80

Tyr Phe Lys Gln Ala Phe Pro Glu Gly Leu Ser Trp Glu Arg Ser Leu
                 85                  90                  95

Glu Phe Glu Asp Gly Gly Ser Ala Ser Val Ser Ala His Ile Ser Leu
            100                 105                 110

Arg Gly Asn Thr Phe Tyr His Lys Ser Lys Phe Thr Gly Val Asn Phe
        115                 120                 125
```

```
Pro Ala Asp Gly Pro Ile Met Gln Asn Gln Ser Val Asp Trp Glu Pro
            130                 135                 140

Ser Thr Glu Lys Ile Thr Ala Ser Asp Gly Val Leu Lys Gly Asp Val
145                 150                 155                 160

Thr Met Tyr Leu Lys Leu Glu Gly Gly Asn His Lys Cys Gln Phe
                165                 170                 175

Lys Thr Thr Tyr Lys Ala Ala Lys Glu Ile Leu Glu Met Pro Gly Asp
                180                 185                 190

His Tyr Ile Gly His Arg Leu Val Arg Lys Thr Glu Gly Asn Ile Thr
            195                 200                 205

Glu Leu Val Glu Asp Ala Val Ala His Ser
210                 215

<210> SEQ ID NO 24
<211> LENGTH: 657
<212> TYPE: DNA
<213> ORGANISM: Fungia sp.
<220> FEATURE:
<221> NAME/KEY: CDS
<222> LOCATION: (1)..(654)

<400> SEQUENCE: 24 atg gtg agt gtg att aaa cca gag atg aag atg agg tac tac atg gac     48
Met Val Ser Val Ile Lys Pro Glu Met Lys Met Arg Tyr Tyr Met Asp
  1               5                  10                  15 ggc tcc gtc aat ggg cat gag ttc aca att gaa ggt gaa ggc aca ggc     96
Gly Ser Val Asn Gly His Glu Phe Thr Ile Glu Gly Glu Gly Thr Gly
             20                  25                  30 aga cct tac gag gga cat caa gag atg aca cta cgc gtc aca atg gcc    144
Arg Pro Tyr Glu Gly His Gln Glu Met Thr Leu Arg Val Thr Met Ala
         35                  40                  45 gag ggc ggg cca atg cct ttc gcg ttt gac tta gtg tca cac gtg ttc    192
Glu Gly Gly Pro Met Pro Phe Ala Phe Asp Leu Val Ser His Val Phe
     50                  55                  60 tgt tac ggc cac aga ctt ttt act aaa tat cca gaa gag ata cca gac    240
Cys Tyr Gly His Arg Leu Phe Thr Lys Tyr Pro Glu Glu Ile Pro Asp
 65                  70                  75                  80 tat ttc aaa caa gca ttt cct gaa ggc ctg tca tgg gaa agg tcg ttg    288
Tyr Phe Lys Gln Ala Phe Pro Glu Gly Leu Ser Trp Glu Arg Ser Leu
                 85                  90                  95 gag ttc gaa gat ggt ggg tcc gct tca gtc agt gcg cat ata agc ctt    336
Glu Phe Glu Asp Gly Gly Ser Ala Ser Val Ser Ala His Ile Ser Leu
            100                 105                 110 aga gga aac acc ttc tac cac aaa tcc aaa ttt act ggg gtt aac ttt    384
Arg Gly Asn Thr Phe Tyr His Lys Ser Lys Phe Thr Gly Val Asn Phe
        115                 120                 125 cct gcc gat ggt cct atc atg caa aac caa agt gtt gat tgg gag cca    432
Pro Ala Asp Gly Pro Ile Met Gln Asn Gln Ser Val Asp Trp Glu Pro
    130                 135                 140 tca acc gag aaa att act gcc agc gac gga gtt ctg aag ggt gat gtt    480
Ser Thr Glu Lys Ile Thr Ala Ser Asp Gly Val Leu Lys Gly Asp Val
145                 150                 155                 160 acg atg tac cta aaa ctt gaa gga ggc ggc aat cac aaa tgc caa ttc    528
Thr Met Tyr Leu Lys Leu Glu Gly Gly Gly Asn His Lys Cys Gln Phe
                165                 170                 175 aag act act tac aag gcg gca aaa gag att ctt gaa atg cca gga gac    576
Lys Thr Thr Tyr Lys Ala Ala Lys Glu Ile Leu Glu Met Pro Gly Asp
            180                 185                 190 cat tac atc ggc cat cgc ctc gtc agg aaa acc gaa ggc aac att act    624
His Tyr Ile Gly His Arg Leu Val Arg Lys Thr Glu Gly Asn Ile Thr
        195                 200                 205
```

```
                    195                 200                  205
gag ctg gta gaa gat gca gta gct cat tcc taa                                  657
Glu Leu Val Glu Asp Ala Val Ala His Ser
        210                 215

<210> SEQ ID NO 25
<211> LENGTH: 218
<212> TYPE: PRT
<213> ORGANISM: Fungia sp.

<400> SEQUENCE: 25

Met Val Ser Val Ile Lys Pro Glu Met Lys Met Arg Tyr Tyr Met Asp
 1               5                  10                  15

Gly Ser Val Asn Gly His Glu Phe Thr Ile Glu Gly Glu Gly Thr Gly
            20                  25                  30

Arg Pro Tyr Glu Gly His Gln Glu Met Thr Leu Arg Val Thr Met Ala
        35                  40                  45

Glu Gly Gly Pro Met Pro Phe Ala Phe Asp Leu Val Ser His Val Phe
    50                  55                  60

Cys Tyr Gly His Arg Tyr Phe Thr Lys Tyr Pro Glu Glu Ile Pro Asp
65                  70                  75                  80

Tyr Phe Lys Gln Ala Phe Pro Glu Gly Leu Ser Trp Glu Arg Ser Leu
                85                  90                  95

Glu Phe Glu Asp Gly Gly Ser Ala Ser Val Ser Ala His Ile Ser Leu
            100                 105                 110

Arg Gly Asn Thr Phe Tyr His Lys Ser Lys Phe Thr Gly Val Asn Phe
        115                 120                 125

Pro Ala Asp Gly Pro Ile Met Gln Asn Gln Ser Val Asp Trp Glu Pro
    130                 135                 140

Ser Thr Glu Lys Ile Thr Ala Ser Asp Gly Val Leu Lys Gly Asp Val
145                 150                 155                 160

Thr Met Tyr Leu Lys Leu Glu Gly Gly Gly Asn His Lys Cys Gln Phe
                165                 170                 175

Lys Thr Thr Tyr Lys Ala Ala Lys Glu Ile Leu Glu Met Pro Gly Asp
            180                 185                 190

His Tyr Ile Gly His Arg Leu Val Arg Lys Thr Glu Gly Asn Ile Thr
        195                 200                 205

Glu Leu Val Glu Asp Ala Val Ala His Ser
    210                 215

<210> SEQ ID NO 26
<211> LENGTH: 657
<212> TYPE: DNA
<213> ORGANISM: Fungia sp.
<220> FEATURE:
<221> NAME/KEY: CDS
<222> LOCATION: (1)..(654)

<400> SEQUENCE: 26 atg gtg agt gtg att aaa cca gag atg aag atg agg tac tac atg gac      48
Met Val Ser Val Ile Lys Pro Glu Met Lys Met Arg Tyr Tyr Met Asp
 1               5                  10                  15 ggc tcc gtc aat ggg cat gag ttc aca att gaa ggt gaa ggc aca ggc      96
Gly Ser Val Asn Gly His Glu Phe Thr Ile Glu Gly Glu Gly Thr Gly
            20                  25                  30 aga cct tac gag gga cat caa gag atg aca cta cgc gtc aca atg gcc     144
Arg Pro Tyr Glu Gly His Gln Glu Met Thr Leu Arg Val Thr Met Ala
        35                  40                  45 gag ggc ggg cca atg cct ttc gcg ttt gac tta gtg tca cac gtg ttc     192
```

```
Glu Gly Gly Pro Met Pro Phe Ala Phe Asp Leu Val Ser His Val Phe
    50                  55                  60 tgt tac ggc cac aga tac ttt act aaa tat cca gaa gag ata cca gac       240
Cys Tyr Gly His Arg Tyr Phe Thr Lys Tyr Pro Glu Glu Ile Pro Asp
65                  70                  75                  80 tat ttc aaa caa gca ttt cct gaa ggc ctg tca tgg gaa agg tcg ttg       288
Tyr Phe Lys Gln Ala Phe Pro Glu Gly Leu Ser Trp Glu Arg Ser Leu
                85                  90                  95 gag ttc gaa gat ggt ggg tcc gct tca gtc agt gcg cat ata agc ctt       336
Glu Phe Glu Asp Gly Gly Ser Ala Ser Val Ser Ala His Ile Ser Leu
            100                 105                 110 aga gga aac acc ttc tac cac aaa tcc aaa ttt act ggg gtt aac ttt       384
Arg Gly Asn Thr Phe Tyr His Lys Ser Lys Phe Thr Gly Val Asn Phe
        115                 120                 125 cct gcc gat ggt cct atc atg caa aac caa agt gtt gat tgg gag cca       432
Pro Ala Asp Gly Pro Ile Met Gln Asn Gln Ser Val Asp Trp Glu Pro
    130                 135                 140 tca acc gag aaa att act gcc agc gac gga gtt ctg aag ggt gat gtt       480
Ser Thr Glu Lys Ile Thr Ala Ser Asp Gly Val Leu Lys Gly Asp Val
145                 150                 155                 160 acg atg tac cta aaa ctt gaa gga ggc ggc aat cac aaa tgc caa ttc       528
Thr Met Tyr Leu Lys Leu Glu Gly Gly Gly Asn His Lys Cys Gln Phe
                165                 170                 175 aag act act tac aag gcg gca aaa gag att ctt gaa atg cca gga gac       576
Lys Thr Thr Tyr Lys Ala Ala Lys Glu Ile Leu Glu Met Pro Gly Asp
            180                 185                 190 cat tac atc ggc cat cgc ctc gtc agg aaa acc gaa ggc aac att act       624
His Tyr Ile Gly His Arg Leu Val Arg Lys Thr Glu Gly Asn Ile Thr
        195                 200                 205 gag ctg gta gaa gat gca gta gct cat tcc taa                           657
Glu Leu Val Glu Asp Ala Val Ala His Ser
    210                 215

<210> SEQ ID NO 27
<211> LENGTH: 218
<212> TYPE: PRT
<213> ORGANISM: Fungia sp.

<400> SEQUENCE: 27

Met Val Ser Val Ile Lys Pro Glu Met Lys Met Arg Tyr Tyr Met Asp
1               5                   10                  15

Gly Ser Val Asn Gly His Glu Phe Thr Ile Glu Gly Glu Gly Thr Gly
                20                  25                  30

Arg Pro Tyr Glu Gly His Gln Glu Met Thr Leu Arg Val Thr Met Ala
            35                  40                  45

Glu Gly Gly Pro Met Pro Phe Ala Phe Asp Leu Val Ser His Val Phe
        50                  55                  60

Cys Tyr Gly His Arg Gln Phe Thr Lys Tyr Pro Glu Glu Ile Pro Asp
65                  70                  75                  80

Tyr Phe Lys Gln Ala Phe Pro Glu Gly Leu Ser Trp Glu Arg Ser Leu
                85                  90                  95

Glu Phe Glu Asp Gly Gly Ser Ala Ser Val Ser Ala His Ile Ser Leu
            100                 105                 110

Arg Gly Asn Thr Phe Tyr His Lys Ser Lys Phe Thr Gly Val Asn Phe
        115                 120                 125

Pro Ala Asp Gly Pro Ile Met Gln Asn Gln Ser Val Asp Trp Glu Pro
    130                 135                 140

Ser Thr Glu Lys Ile Thr Ala Ser Asp Gly Val Leu Lys Gly Asp Val
145                 150                 155                 160
```

```
Thr Met Tyr Leu Lys Leu Glu Gly Gly Gly Asn His Lys Cys Gln Phe
            165                 170                 175

Lys Thr Thr Tyr Lys Ala Ala Lys Glu Ile Leu Glu Met Pro Gly Asp
            180                 185                 190

His Tyr Ile Gly His Arg Leu Val Arg Lys Thr Glu Gly Asn Ile Thr
            195                 200                 205

Glu Leu Val Glu Asp Ala Val Ala His Ser
            210                 215

<210> SEQ ID NO 28
<211> LENGTH: 657
<212> TYPE: DNA
<213> ORGANISM: Fungia sp.
<220> FEATURE:
<221> NAME/KEY: CDS
<222> LOCATION: (1)..(654)

<400> SEQUENCE: 28 atg gtg agt gtg att aaa cca gag atg aag atg agg tac tac atg gac      48
Met Val Ser Val Ile Lys Pro Glu Met Lys Met Arg Tyr Tyr Met Asp
 1               5                  10                  15 ggc tcc gtc aat ggg cat gag ttc aca att gaa ggt gaa ggc aca ggc      96
Gly Ser Val Asn Gly His Glu Phe Thr Ile Glu Gly Glu Gly Thr Gly
            20                  25                  30 aga cct tac gag gga cat caa gag atg aca cta cgc gtc aca atg gcc     144
Arg Pro Tyr Glu Gly His Gln Glu Met Thr Leu Arg Val Thr Met Ala
        35                  40                  45 gag ggc ggg cca atg cct ttc gcg ttt gac tta gtg tca cac gtg ttc     192
Glu Gly Gly Pro Met Pro Phe Ala Phe Asp Leu Val Ser His Val Phe
    50                  55                  60 tgt tac ggc cac aga cag ttt act aaa tat cca gaa gag ata cca gac     240
Cys Tyr Gly His Arg Gln Phe Thr Lys Tyr Pro Glu Glu Ile Pro Asp
65                  70                  75                  80 tat ttc aaa caa gca ttt cct gaa ggc ctg tca tgg gaa agg tcg ttg     288
Tyr Phe Lys Gln Ala Phe Pro Glu Gly Leu Ser Trp Glu Arg Ser Leu
                85                  90                  95 gag ttc gaa gat ggt ggg tcc gct tca gtc agt gcg cat ata agc ctt     336
Glu Phe Glu Asp Gly Gly Ser Ala Ser Val Ser Ala His Ile Ser Leu
            100                 105                 110 aga gga aac acc ttc tac cac aaa tcc aaa ttt act ggg gtt aac ttt     384
Arg Gly Asn Thr Phe Tyr His Lys Ser Lys Phe Thr Gly Val Asn Phe
        115                 120                 125 cct gcc gat ggt cct atc atg caa aac caa agt gtt gat tgg gag cca     432
Pro Ala Asp Gly Pro Ile Met Gln Asn Gln Ser Val Asp Trp Glu Pro
    130                 135                 140 tca acc gag aaa att act gcc agc gac gga gtt ctg aag ggt gat gtt     480
Ser Thr Glu Lys Ile Thr Ala Ser Asp Gly Val Leu Lys Gly Asp Val
145                 150                 155                 160 acg atg tac cta aaa ctt gaa gga ggc ggc aat cac aaa tgc caa ttc     528
Thr Met Tyr Leu Lys Leu Glu Gly Gly Gly Asn His Lys Cys Gln Phe
                165                 170                 175 aag act act tac aag gcg gca aaa gag att ctt gaa atg cca gga gac     576
Lys Thr Thr Tyr Lys Ala Ala Lys Glu Ile Leu Glu Met Pro Gly Asp
            180                 185                 190 cat tac atc ggc cat cgc ctc gtc agg aaa acc gaa ggc aac att act     624
His Tyr Ile Gly His Arg Leu Val Arg Lys Thr Glu Gly Asn Ile Thr
        195                 200                 205 gag ctg gta gaa gat gca gta gct cat tcc taa                         657
Glu Leu Val Glu Asp Ala Val Ala His Ser
    210                 215
```

```
<210> SEQ ID NO 29
<211> LENGTH: 218
<212> TYPE: PRT
<213> ORGANISM: Fungia sp.
<220> FEATURE:
<221> NAME/KEY: MOD_RES
<222> LOCATION: (186)..(186)
<223> OTHER INFORMATION: Any amino acid

<400> SEQUENCE: 29

Met Val Ser Val Ile Lys Pro Glu Met Lys Met Arg Tyr Tyr Met Asp
 1               5                  10                  15

Gly Ser Val Asn Gly His Glu Phe Thr Ile Glu Gly Glu Gly Thr Gly
            20                  25                  30

Arg Pro Tyr Glu Gly His Gln Glu Met Thr Leu Arg Val Thr Met Ala
        35                  40                  45

Glu Gly Gly Pro Met Pro Phe Ala Phe Asp Leu Val Ser His Val Phe
    50                  55                  60

Cys Tyr Gly His Arg Asn Phe Thr Lys Tyr Pro Glu Glu Ile Pro Asp
65                  70                  75                  80

Tyr Phe Lys Gln Ala Phe Pro Glu Gly Leu Ser Trp Glu Arg Ser Leu
                85                  90                  95

Glu Phe Glu Asp Gly Gly Ser Ala Ser Val Ser Ala His Ile Ser Leu
            100                 105                 110

Arg Gly Asn Thr Phe Tyr His Lys Ser Lys Phe Thr Gly Val Asn Phe
        115                 120                 125

Pro Ala Asp Gly Pro Ile Met Gln Asn Gln Ser Val Asp Trp Glu Pro
    130                 135                 140

Ser Thr Glu Lys Ile Thr Ala Ser Asp Gly Val Leu Lys Gly Asp Val
145                 150                 155                 160

Thr Met Tyr Leu Lys Leu Glu Gly Gly Gly Asn His Lys Cys Gln Phe
                165                 170                 175

Lys Thr Thr Tyr Lys Ala Ala Lys Glu Xaa Leu Glu Met Pro Gly Asp
            180                 185                 190

His Tyr Ile Gly His Arg Leu Val Arg Lys Thr Glu Gly Asn Ile Thr
        195                 200                 205

Glu Leu Val Glu Asp Ala Val Ala His Ser
    210                 215

<210> SEQ ID NO 30
<211> LENGTH: 657
<212> TYPE: DNA
<213> ORGANISM: Fungia sp.
<220> FEATURE:
<221> NAME/KEY: CDS
<222> LOCATION: (1)..(654)
<220> FEATURE:
<221> NAME/KEY: modified_base
<222> LOCATION: (556)..(556)
<223> OTHER INFORMATION: a, c, g, t, unknown or other

<400> SEQUENCE: 30 atg gtg agt gtg att aaa cca gag atg aag atg agg tac tac atg gac    48
Met Val Ser Val Ile Lys Pro Glu Met Lys Met Arg Tyr Tyr Met Asp
 1               5                  10                  15 ggc tcc gtc aat ggg cat gag ttc aca att gaa ggt gaa ggc aca ggc    96
Gly Ser Val Asn Gly His Glu Phe Thr Ile Glu Gly Glu Gly Thr Gly
            20                  25                  30 aga cct tac gag gga cat caa gag atg aca cta cgc gtc aca atg gcc   144
Arg Pro Tyr Glu Gly His Gln Glu Met Thr Leu Arg Val Thr Met Ala
        35                  40                  45
```

| | | |
|---|---|---|
| gag ggc ggg cca atg cct ttc gcg ttt gac tta gtg tca cac gtg ttc<br>Glu Gly Gly Pro Met Pro Phe Ala Phe Asp Leu Val Ser His Val Phe<br>50                           55                     60 | | 192 |
| tgt tac ggc cac aga aat ttt act aaa tat cca gaa gag ata cca gac<br>Cys Tyr Gly His Arg Asn Phe Thr Lys Tyr Pro Glu Glu Ile Pro Asp<br>65                      70                      75                  80 | | 240 |
| tat ttc aaa caa gca ttt cct gaa ggc ctg tca tgg gaa agg tcg ttg<br>Tyr Phe Lys Gln Ala Phe Pro Glu Gly Leu Ser Trp Glu Arg Ser Leu<br>                   85                     90                  95 | | 288 |
| gag ttc gaa gat ggt ggg tcc gct tca gtc agt gcg cat ata agc ctt<br>Glu Phe Glu Asp Gly Gly Ser Ala Ser Val Ser Ala His Ile Ser Leu<br>                  100                    105                  110 | | 336 |
| aga gga aac acc ttc tac cac aaa tcc aaa ttt act ggg gtt aac ttt<br>Arg Gly Asn Thr Phe Tyr His Lys Ser Lys Phe Thr Gly Val Asn Phe<br>115                      120                    125 | | 384 |
| cct gcc gat ggt cct atc atg caa aac caa agt gtt gat tgg gag cca<br>Pro Ala Asp Gly Pro Ile Met Gln Asn Gln Ser Val Asp Trp Glu Pro<br>130                      135                    140 | | 432 |
| tca acc gag aaa att act gcc agc gac gga gtt ctg aag ggt gat gtt<br>Ser Thr Glu Lys Ile Thr Ala Ser Asp Gly Val Leu Lys Gly Asp Val<br>145                      150                    155                  160 | | 480 |
| acg atg tac cta aaa ctt gaa gga ggc ggc aat cac aaa tgc caa ttc<br>Thr Met Tyr Leu Lys Leu Glu Gly Gly Gly Asn His Lys Cys Gln Phe<br>                  165                    170                  175 | | 528 |
| aag act act tac aag gcg gca aaa gag ntt ctt gaa atg cca gga gac<br>Lys Thr Thr Tyr Lys Ala Ala Lys Glu Xaa Leu Glu Met Pro Gly Asp<br>                  180                    185                  190 | | 576 |
| cat tac atc ggc cat cgc ctc gtc agg aaa acc gaa ggc aac att act<br>His Tyr Ile Gly His Arg Leu Val Arg Lys Thr Glu Gly Asn Ile Thr<br>195                      200                    205 | | 624 |
| gag ctg gta gaa gat gca gta gct cat tcc taa<br>Glu Leu Val Glu Asp Ala Val Ala His Ser<br>210                      215 | | 657 |

<210> SEQ ID NO 31
<211> LENGTH: 665
<212> TYPE: PRT
<213> ORGANISM: Fungia sp.

<400> SEQUENCE: 31

Met Ala Glu Pro Arg Gln Glu Phe Glu Val Met Glu Asp His Ala Gly
1                  5                      10                    15

Thr Tyr Gly Leu Gly Asp Arg Lys Asp Gln Gly Gly Tyr Thr Met His
                  20                    25                    30

Gln Asp Gln Glu Gly Asp Thr Asp Ala Gly Leu Lys Glu Ser Pro Leu
        35                    40                    45

Gln Thr Pro Thr Glu Asp Gly Ser Glu Glu Pro Gly Ser Glu Thr Ser
50                           55                     60

Asp Ala Lys Ser Thr Pro Thr Ala Glu Asp Val Thr Ala Pro Leu Val
65                      70                      75                  80

Asp Glu Gly Ala Pro Gly Lys Gln Ala Ala Ala Gln Pro His Thr Glu
                  85                    90                    95

Ile Pro Glu Gly Thr Thr Ala Glu Glu Ala Gly Ile Gly Asp Thr Pro
                  100                    105                  110

Ser Leu Glu Asp Glu Ala Ala Gly His Val Thr Gln Ala Arg Met Val
        115                    120                    125

Ser Lys Ser Lys Asp Gly Thr Gly Ser Asp Asp Lys Lys Ala Lys Gly
130                          135                    140

-continued

```
Ala Asp Gly Lys Thr Lys Ile Ala Thr Pro Arg Gly Ala Pro Pro
145                 150                 155                 160

Gly Gln Lys Gly Gln Ala Asn Ala Thr Arg Ile Pro Ala Lys Thr Pro
            165                 170                 175

Pro Ala Pro Lys Thr Pro Pro Ser Ser Gly Glu Pro Pro Lys Ser Gly
        180                 185                 190

Asp Arg Ser Gly Tyr Ser Ser Pro Gly Ser Pro Gly Thr Pro Gly Ser
    195                 200                 205

Arg Ser Arg Thr Pro Ser Leu Pro Thr Pro Pro Thr Arg Glu Pro Lys
210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
                260                 265                 270

Gly Lys Val Gln Ile Ile Asn Lys Lys Leu Asp Leu Ser Asn Val Gln
            275                 280                 285

Ser Lys Cys Gly Ser Lys Asp Asn Ile Lys His Val Pro Gly Gly Gly
        290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu Gly Ser Gly Gly Glu Phe Met
        435                 440                 445

Val Ser Val Ile Lys Pro Glu Met Lys Met Arg Tyr Tyr Met Asp Gly
        450                 455                 460

Ser Val Asn Gly His Glu Phe Thr Ile Glu Gly Glu Gly Thr Gly Arg
465                 470                 475                 480

Pro Tyr Glu Gly His Gln Glu Met Thr Leu Arg Val Thr Met Ala Glu
                485                 490                 495

Gly Gly Pro Met Pro Phe Ala Phe Asp Leu Val Ser His Val Phe Cys
            500                 505                 510

Tyr Gly His Arg Val Phe Thr Lys Tyr Pro Glu Glu Ile Pro Asp Tyr
        515                 520                 525

Phe Lys Gln Ala Phe Pro Glu Gly Leu Ser Trp Glu Arg Ser Leu Glu
530                 535                 540

Phe Glu Asp Gly Gly Ser Ala Ser Val Ser Ala His Ile Ser Leu Arg
545                 550                 555                 560

Gly Asn Thr Phe Tyr His Lys Ser Lys Phe Thr Gly Val Asn Phe Pro
                565                 570                 575
```

```
Ala Asp Gly Pro Ile Met Gln Asn Gln Ser Val Asp Trp Glu Pro Ser
            580                 585                 590

Thr Glu Lys Ile Thr Ala Ser Asp Gly Val Leu Lys Gly Asp Val Thr
        595                 600                 605

Met Tyr Leu Lys Leu Glu Gly Gly Asn His Lys Cys Gln Phe Lys
    610                 615                 620

Thr Thr Tyr Lys Ala Ala Lys Glu Ile Leu Glu Met Pro Gly Asp His
625                 630                 635                 640

Tyr Ile Gly His Arg Leu Val Arg Lys Thr Glu Gly Asn Ile Thr Glu
                645                 650                 655

Leu Val Glu Asp Ala Val Ala His Ser
            660                 665

<210> SEQ ID NO 32
<211> LENGTH: 1998
<212> TYPE: DNA
<213> ORGANISM: Fungia sp.
<220> FEATURE:
<221> NAME/KEY: CDS
<222> LOCATION: (1)..(1995)

<400> SEQUENCE: 32 atg gct gag ccc cgc cag gag ttc gaa gtg atg gaa gat cac gct ggg      48
Met Ala Glu Pro Arg Gln Glu Phe Glu Val Met Glu Asp His Ala Gly
  1               5                  10                  15 acg tac ggg ttg ggg gac agg aaa gat cag ggg ggc tac acc atg cac      96
Thr Tyr Gly Leu Gly Asp Arg Lys Asp Gln Gly Gly Tyr Thr Met His
             20                  25                  30 caa gac caa gag ggt gac acg gac gct ggc ctg aaa gaa tct ccc ctg     144
Gln Asp Gln Glu Gly Asp Thr Asp Ala Gly Leu Lys Glu Ser Pro Leu
         35                  40                  45 cag acc ccc act gag gac gga tct gag gaa ccg ggc tct gaa acc tct     192
Gln Thr Pro Thr Glu Asp Gly Ser Glu Glu Pro Gly Ser Glu Thr Ser
     50                  55                  60 gat gct aag agc act cca aca gcg gaa gat gtg aca gca ccc tta gtg     240
Asp Ala Lys Ser Thr Pro Thr Ala Glu Asp Val Thr Ala Pro Leu Val
 65                  70                  75                  80 gat gag gga gct ccc ggc aag cag gct gcc gcg cag ccc cac acg gag     288
Asp Glu Gly Ala Pro Gly Lys Gln Ala Ala Ala Gln Pro His Thr Glu
                 85                  90                  95 atc cca gaa gga acc aca gct gaa gaa gca ggc att gga gac acc ccc     336
Ile Pro Glu Gly Thr Thr Ala Glu Glu Ala Gly Ile Gly Asp Thr Pro
            100                 105                 110 agc ctg gaa gac gaa gct gct ggt cac gtg acc caa gct cgc atg gtc     384
Ser Leu Glu Asp Glu Ala Ala Gly His Val Thr Gln Ala Arg Met Val
        115                 120                 125 agt aaa agc aaa gac ggg act gga agc gat gac aaa aaa gcc aag ggg     432
Ser Lys Ser Lys Asp Gly Thr Gly Ser Asp Asp Lys Lys Ala Lys Gly
    130                 135                 140 gct gat ggt aaa acg aag atc gcc aca ccg cgg gga gca gcc cct cca     480
Ala Asp Gly Lys Thr Lys Ile Ala Thr Pro Arg Gly Ala Ala Pro Pro
145                 150                 155                 160 ggc cag aag ggc cag gcc aac gcc acc agg att cca gca aaa acc ccg     528
Gly Gln Lys Gly Gln Ala Asn Ala Thr Arg Ile Pro Ala Lys Thr Pro
                165                 170                 175 ccc gct cca aag aca cca ccc agc tct ggt gaa cct cca aaa tca ggg     576
Pro Ala Pro Lys Thr Pro Pro Ser Ser Gly Glu Pro Pro Lys Ser Gly
            180                 185                 190 gat cgc agc ggc tac agc agc ccc ggc tcc cca ggc act ccc ggc agc     624
Asp Arg Ser Gly Tyr Ser Ser Pro Gly Ser Pro Gly Thr Pro Gly Ser
        195                 200                 205
```

-continued

```
              195                 200                 205
cgc tcc cgc acc ccg tcc ctt cca acc cca ccc acc cgg gag ccc aag      672
Arg Ser Arg Thr Pro Ser Leu Pro Thr Pro Pro Thr Arg Glu Pro Lys
    210                 215                 220 aag gtg gca gtg gtc cgt act cca ccc aag tcg ccg tct tcc gcc aag      720
Lys Val Ala Val Val Arg Thr Pro Pro Lys Ser Pro Ser Ser Ala Lys
225                 230                 235                 240 agc cgc ctg cag aca gcc ccc gtg ccc atg cca gac ctg aag aat gtc      768
Ser Arg Leu Gln Thr Ala Pro Val Pro Met Pro Asp Leu Lys Asn Val
        245                 250                 255 aag tcc aag atc ggc tcc act gag aac ctg aag cac cag ccg gga ggc      816
Lys Ser Lys Ile Gly Ser Thr Glu Asn Leu Lys His Gln Pro Gly Gly
    260                 265                 270 ggg aag gtg cag ata att aat aag aag ctg gat ctt agc aac gtc cag      864
Gly Lys Val Gln Ile Ile Asn Lys Lys Leu Asp Leu Ser Asn Val Gln
    275                 280                 285 tcc aag tgt ggc tca aag gat aat atc aaa cac gtc ccg gga ggc ggc      912
Ser Lys Cys Gly Ser Lys Asp Asn Ile Lys His Val Pro Gly Gly Gly
    290                 295                 300 agt gtg caa ata gtc tac aaa cca gtt gac ctg agc aag gtg acc tcc      960
Ser Val Gln Ile Val Tyr Lys Pro Val Asp Leu Ser Lys Val Thr Ser
305                 310                 315                 320 aag tgt ggc tca tta ggc aac atc cat cat aaa cca gga ggt ggc cag     1008
Lys Cys Gly Ser Leu Gly Asn Ile His His Lys Pro Gly Gly Gly Gln
        325                 330                 335 gtg gaa gta aaa tct gag aag ctt gac ttc aag gac aga gtc cag tcg     1056
Val Glu Val Lys Ser Glu Lys Leu Asp Phe Lys Asp Arg Val Gln Ser
        340                 345                 350 aag att ggg tcc ctg gac aat atc acc cac gtc cct ggc gga gga aat     1104
Lys Ile Gly Ser Leu Asp Asn Ile Thr His Val Pro Gly Gly Gly Asn
    355                 360                 365 aaa aag att gaa acc cac aag ctg acc ttc cgc gag aac gcc aaa gcc     1152
Lys Lys Ile Glu Thr His Lys Leu Thr Phe Arg Glu Asn Ala Lys Ala
    370                 375                 380 aag aca gac cac ggg gcg gag atc gtg tac aag tcg cca gtg gtg tct     1200
Lys Thr Asp His Gly Ala Glu Ile Val Tyr Lys Ser Pro Val Val Ser
385                 390                 395                 400 ggg gac acg tct cca cgg cat ctc agc aat gtc tcc tcc acc ggc agc     1248
Gly Asp Thr Ser Pro Arg His Leu Ser Asn Val Ser Ser Thr Gly Ser
        405                 410                 415 atc gac atg gta gac tcg ccc cag ctc gcc acg cta gct gac gag gtg     1296
Ile Asp Met Val Asp Ser Pro Gln Leu Ala Thr Leu Ala Asp Glu Val
        420                 425                 430 tct gcc tcc ctg gcc aag cag ggt ttg gga tcc gga ggt gaa ttc atg     1344
Ser Ala Ser Leu Ala Lys Gln Gly Leu Gly Ser Gly Gly Glu Phe Met
    435                 440                 445 gtg agt gtg att aaa cca gag atg aag atg agg tac tac atg gac ggc     1392
Val Ser Val Ile Lys Pro Glu Met Lys Met Arg Tyr Tyr Met Asp Gly
450                 455                 460 tcc gtc aat ggg cat gag ttc aca att gaa ggt gaa ggc aca ggc aga     1440
Ser Val Asn Gly His Glu Phe Thr Ile Glu Gly Glu Gly Thr Gly Arg
465                 470                 475                 480 cct tac gag gga cat caa gag atg aca cta cgc gtc aca atg gcc gag     1488
Pro Tyr Glu Gly His Gln Glu Met Thr Leu Arg Val Thr Met Ala Glu
        485                 490                 495 ggc ggg cca atg cct ttc gcg ttt gac tta gtg tca cac gtg ttc tgt     1536
Gly Gly Pro Met Pro Phe Ala Phe Asp Leu Val Ser His Val Phe Cys
        500                 505                 510 tac ggc cac aga gta ttt act aaa tat cca gaa gag ata cca gac tat     1584
Tyr Gly His Arg Val Phe Thr Lys Tyr Pro Glu Glu Ile Pro Asp Tyr
```

```
                515                 520                 525
ttc aaa caa gca ttt cct gaa ggc ctg tca tgg gaa agg tcg ttg gag    1632
Phe Lys Gln Ala Phe Pro Glu Gly Leu Ser Trp Glu Arg Ser Leu Glu
    530                 535                 540 ttc gaa gat ggt ggg tcc gct tca gtc agt gcg cat ata agc ctt aga    1680
Phe Glu Asp Gly Gly Ser Ala Ser Val Ser Ala His Ile Ser Leu Arg
545                 550                 555                 560 gga aac acc ttc tac cac aaa tcc aaa ttt act ggg gtt aac ttt cct    1728
Gly Asn Thr Phe Tyr His Lys Ser Lys Phe Thr Gly Val Asn Phe Pro
                565                 570                 575 gcc gat ggt cct atc atg caa aac caa agt gtt gat tgg gag cca tca    1776
Ala Asp Gly Pro Ile Met Gln Asn Gln Ser Val Asp Trp Glu Pro Ser
            580                 585                 590 acc gag aaa att act gcc agc gac gga gtt ctg aag ggt gat gtt acg    1824
Thr Glu Lys Ile Thr Ala Ser Asp Gly Val Leu Lys Gly Asp Val Thr
        595                 600                 605 atg tac cta aaa ctt gaa gga ggc ggc aat cac aaa tgc caa ttc aag    1872
Met Tyr Leu Lys Leu Glu Gly Gly Gly Asn His Lys Cys Gln Phe Lys
    610                 615                 620 act act tac aag gcg gca aaa gag att ctt gaa atg cca gga gac cat    1920
Thr Thr Tyr Lys Ala Ala Lys Glu Ile Leu Glu Met Pro Gly Asp His
625                 630                 635                 640 tac atc ggc cat cgc ctc gtc agg aaa acc gaa ggc aac att act gag    1968
Tyr Ile Gly His Arg Leu Val Arg Lys Thr Glu Gly Asn Ile Thr Glu
                645                 650                 655 ctg gta gaa gat gca gta gct cat tcc taa                            1998
Leu Val Glu Asp Ala Val Ala His Ser
            660                 665

<210> SEQ ID NO 33
<211> LENGTH: 480
<212> TYPE: PRT
<213> ORGANISM: Fungia sp.

<400> SEQUENCE: 33

Met Gly Thr Ile Leu Phe Leu Thr Met Val Ile Ser Tyr Phe Gly Cys
1               5                   10                  15

Met Lys Ala Ala Pro Met Lys Glu Ala Asn Val His Gly Gln Gly Asn
            20                  25                  30

Leu Ala Tyr Pro Ala Val Arg Thr His Gly Thr Leu Glu Ser Val Asn
        35                  40                  45

Gly Pro Arg Ala Gly Ser Arg Gly Leu Thr Thr Thr Ser Leu Ala Asp
    50                  55                  60

Thr Phe Glu His Val Ile Glu Glu Leu Leu Asp Glu Asp Gln Lys Val
65                  70                  75                  80

Arg Pro Asn Glu Glu Asn His Lys Asp Ala Asp Leu Tyr Thr Ser Arg
                85                  90                  95

Val Met Leu Ser Ser Gln Val Pro Leu Glu Pro Pro Leu Leu Phe Leu
            100                 105                 110

Leu Glu Glu Tyr Lys Asn Tyr Leu Asp Ala Ala Asn Met Ser Met Arg
        115                 120                 125

Val Arg Arg His Ser Asp Pro Ala Arg Arg Gly Glu Leu Ser Val Cys
    130                 135                 140

Asp Ser Ile Ser Glu Trp Val Thr Ala Ala Asp Lys Lys Thr Ala Val
145                 150                 155                 160

Asp Met Ser Gly Gly Thr Val Thr Val Leu Glu Lys Val Pro Val Ser
                165                 170                 175

Lys Gly Gln Leu Lys Gln Tyr Phe Tyr Glu Thr Lys Cys Asn Pro Met
```

```
            180             185             190
Gly Tyr Thr Lys Glu Gly Cys Arg Gly Ile Asp Lys Arg His Trp Asn
        195                 200                 205
Ser Gln Cys Arg Thr Thr Gln Ser Tyr Val Arg Ala Leu Thr Met Asp
        210                 215                 220
Ser Lys Lys Arg Ile Gly Trp Arg Phe Ile Arg Ile Asp Thr Ser Cys
225                 230                 235                 240
Val Cys Thr Leu Thr Ile Lys Arg Gly Arg Gly Val Pro Arg Ala Arg
                245                 250                 255
Asp Pro Pro Val Ala Thr Met Val Ser Val Ile Lys Pro Glu Met Lys
                260                 265                 270
Met Arg Tyr Tyr Met Asp Gly Ser Val Asn Gly His Glu Phe Thr Ile
                275                 280                 285
Glu Gly Glu Gly Thr Gly Arg Pro Tyr Glu Gly His Gln Glu Met Thr
                290                 295                 300
Leu Arg Val Thr Met Ala Glu Gly Gly Pro Met Pro Phe Ala Phe Asp
305                 310                 315                 320
Leu Val Ser His Val Phe Cys Tyr Gly His Arg Val Phe Thr Lys Tyr
                325                 330                 335
Pro Glu Glu Ile Pro Asp Tyr Phe Lys Gln Ala Phe Pro Glu Gly Leu
                340                 345                 350
Ser Trp Glu Arg Ser Leu Glu Phe Glu Asp Gly Gly Ser Ala Ser Val
                355                 360                 365
Ser Ala His Ile Ser Leu Arg Gly Asn Thr Phe Tyr His Lys Ser Lys
        370                 375                 380
Phe Thr Gly Val Asn Phe Pro Ala Asp Gly Pro Ile Met Gln Asn Gln
385                 390                 395                 400
Ser Val Asp Trp Glu Pro Ser Thr Glu Lys Ile Thr Ala Ser Asp Gly
                405                 410                 415
Val Leu Lys Gly Asp Val Thr Met Tyr Leu Lys Leu Glu Gly Gly Gly
                420                 425                 430
Asn His Lys Cys Gln Phe Lys Thr Thr Tyr Lys Ala Ala Lys Glu Ile
                435                 440                 445
Leu Glu Met Pro Gly Asp His Tyr Ile Gly His Arg Leu Val Arg Lys
        450                 455                 460
Thr Glu Gly Asn Ile Thr Glu Leu Val Glu Asp Ala Val Ala His Ser
465                 470                 475                 480

<210> SEQ ID NO 34
<211> LENGTH: 1443
<212> TYPE: DNA
<213> ORGANISM: Fungia sp.
<220> FEATURE:
<221> NAME/KEY: CDS
<222> LOCATION: (1)..(1440)

<400> SEQUENCE: 34 atg gga acc atc ctt ttc ctt act atg gtt att tca tac ttc ggt tgc     48
Met Gly Thr Ile Leu Phe Leu Thr Met Val Ile Ser Tyr Phe Gly Cys
1               5                   10                  15 atg aag gct gcg ccc atg aaa gaa gca aac gtc cac gga caa ggc aac     96
Met Lys Ala Ala Pro Met Lys Glu Ala Asn Val His Gly Gln Gly Asn
            20                  25                  30 ttg gcc tac cca gct gtg cgg acc cat ggg act ctg gag agc gtg aat    144
Leu Ala Tyr Pro Ala Val Arg Thr His Gly Thr Leu Glu Ser Val Asn
        35                  40                  45 ggg ccc agg gca ggt tcg aga ggt ctg acg acg acg tcc ctg gct gac    192
```

```
                                                                -continued

Gly Pro Arg Ala Gly Ser Arg Gly Leu Thr Thr Ser Leu Ala Asp
     50                  55                  60 act ttt gag cac gtg atc gaa gag ctg ctg gat gag gac cag aag gtt      240
Thr Phe Glu His Val Ile Glu Glu Leu Leu Asp Glu Asp Gln Lys Val
 65                  70                  75                  80 cgg ccc aac gaa gaa aac cat aag gac gcg gac ttg tac act tcc cgg      288
Arg Pro Asn Glu Glu Asn His Lys Asp Ala Asp Leu Tyr Thr Ser Arg
                 85                  90                  95 gtg atg ctc agc agt caa gtg cct ttg gag cct cct ctg ctc ttt ctg      336
Val Met Leu Ser Ser Gln Val Pro Leu Glu Pro Pro Leu Leu Phe Leu
            100                 105                 110 ctg gag gaa tac aaa aat tac ctg gat gcc gca aac atg tct atg agg      384
Leu Glu Glu Tyr Lys Asn Tyr Leu Asp Ala Ala Asn Met Ser Met Arg
        115                 120                 125 gtt cgg cgc cac tcc gac ccc gcc cgc gtt ggg gag ctg agc gtg tgt      432
Val Arg Arg His Ser Asp Pro Ala Arg Arg Gly Glu Leu Ser Val Cys
    130                 135                 140 gac agt att agc gag tgg gtc aca gcg gca gat aaa aag act gca gtg      480
Asp Ser Ile Ser Glu Trp Val Thr Ala Ala Asp Lys Lys Thr Ala Val
145                 150                 155                 160 gac atg tcc ggt ggg acg gtc aca gtc ctg gag aaa gtc ccg gta tca      528
Asp Met Ser Gly Gly Thr Val Thr Val Leu Glu Lys Val Pro Val Ser
                165                 170                 175 aaa ggc caa ctg aag caa tat ttc tac gag acc aag tgt aat ccc atg      576
Lys Gly Gln Leu Lys Gln Tyr Phe Tyr Glu Thr Lys Cys Asn Pro Met
            180                 185                 190 ggt tac acg aag gaa ggc tgc agg gga ata gac aaa agg cac tgg aac      624
Gly Tyr Thr Lys Glu Gly Cys Arg Gly Ile Asp Lys Arg His Trp Asn
        195                 200                 205 tcg caa tgc cga act acc caa tcg tat gtt cgg gcc ctt act atg gat      672
Ser Gln Cys Arg Thr Thr Gln Ser Tyr Val Arg Ala Leu Thr Met Asp
    210                 215                 220 agc aaa aag aga att ggc tgg cgg ttc ata agg ata gac act tcc tgt      720
Ser Lys Lys Arg Ile Gly Trp Arg Phe Ile Arg Ile Asp Thr Ser Cys
225                 230                 235                 240 gta tgt aca ctg acc att aaa agg gga aga ggg gta ccg cgg gcc cgg      768
Val Cys Thr Leu Thr Ile Lys Arg Gly Arg Gly Val Pro Arg Ala Arg
                245                 250                 255 gac cca ccg gtc gcc acc atg gtg agt gtg att aaa cca gag atg aag      816
Asp Pro Pro Val Ala Thr Met Val Ser Val Ile Lys Pro Glu Met Lys
            260                 265                 270 atg agg tac tac atg gac ggc tcc gtc aat ggg cat gag ttc aca att      864
Met Arg Tyr Tyr Met Asp Gly Ser Val Asn Gly His Glu Phe Thr Ile
        275                 280                 285 gaa ggt gaa ggc aca ggc aga cct tac gag gga cat caa gag atg aca      912
Glu Gly Glu Gly Thr Gly Arg Pro Tyr Glu Gly His Gln Glu Met Thr
    290                 295                 300 cta cgc gtc aca atg gcc gag ggc ggg cca atg cct ttc gcg ttt gac      960
Leu Arg Val Thr Met Ala Glu Gly Gly Pro Met Pro Phe Ala Phe Asp
305                 310                 315                 320 tta gtg tca cac gtg ttc tgt tac ggc cac aga gta ttt act aaa tat     1008
Leu Val Ser His Val Phe Cys Tyr Gly His Arg Val Phe Thr Lys Tyr
                325                 330                 335 cca gaa gag ata cca gac tat ttc aaa caa gca ttt cct gaa ggc ctg     1056
Pro Glu Glu Ile Pro Asp Tyr Phe Lys Gln Ala Phe Pro Glu Gly Leu
            340                 345                 350 tca tgg gaa agg tcg ttg gag ttc gaa gat ggt ggg tcc gct tca gtc     1104
Ser Trp Glu Arg Ser Leu Glu Phe Glu Asp Gly Gly Ser Ala Ser Val
        355                 360                 365 agt gcg cat ata agc ctt aga gga aac acc ttc tac cac aaa tcc aaa     1152
```

```
        Ser Ala His Ile Ser Leu Arg Gly Asn Thr Phe Tyr His Lys Ser Lys
            370                 375                 380 ttt act ggg gtt aac ttt cct gcc gat ggt cct atc atg caa aac caa           1200
Phe Thr Gly Val Asn Phe Pro Ala Asp Gly Pro Ile Met Gln Asn Gln
385                 390                 395                 400 agt gtt gat tgg gag cca tca acc gag aaa att act gcc agc gac gga           1248
Ser Val Asp Trp Glu Pro Ser Thr Glu Lys Ile Thr Ala Ser Asp Gly
            405                 410                 415 gtt ctg aag ggt gat gtt acg atg tac cta aaa ctt gaa gga ggc ggc           1296
Val Leu Lys Gly Asp Val Thr Met Tyr Leu Lys Leu Glu Gly Gly Gly
                420                 425                 430 aat cac aaa tgc caa ttc aag act act tac aag gcg gca aaa gag att           1344
Asn His Lys Cys Gln Phe Lys Thr Thr Tyr Lys Ala Ala Lys Glu Ile
            435                 440                 445 ctt gaa atg cca gga gac cat tac atc ggc cat cgc ctc gtc agg aaa           1392
Leu Glu Met Pro Gly Asp His Tyr Ile Gly His Arg Leu Val Arg Lys
        450                 455                 460 acc gaa ggc aac att act gag ctg gta gaa gat gca gta gct cat tcc           1440
Thr Glu Gly Asn Ile Thr Glu Leu Val Glu Asp Ala Val Ala His Ser
465                 470                 475                 480 taa                                                                       1443

<210> SEQ ID NO 35
<211> LENGTH: 464
<212> TYPE: PRT
<213> ORGANISM: Fungia sp.

<400> SEQUENCE: 35

Met Val Ser Tyr Ser Lys Gln Gly Ile Ala Gln Glu Met Arg Thr Lys
1               5                   10                  15

Tyr Arg Met Glu Gly Ser Val Asn Gly His Glu Phe Thr Ile Glu Gly
            20                  25                  30

Val Gly Thr Gly Asn Pro Tyr Glu Gly Lys Gln Met Ser Glu Leu Val
        35                  40                  45

Ile Ile Lys Ser Lys Gly Lys Pro Leu Pro Phe Ser Phe Asp Ile Leu
    50                  55                  60

Ser Thr Ala Phe Gln Tyr Gly Asn Arg Cys Phe Thr Lys Tyr Pro Ala
65                  70                  75                  80

Asp Met Pro Asp Tyr Phe Lys Gln Ala Phe Pro Asp Gly Met Ser Tyr
                85                  90                  95

Glu Arg Ser Phe Leu Phe Glu Asp Gly Gly Val Ala Thr Ala Ser Trp
            100                 105                 110

Ser Ile Arg Leu Glu Gly Asn Cys Phe Ile His Asn Ser Ile Tyr His
        115                 120                 125

Gly Val Asn Phe Pro Ala Asp Gly Pro Val Met Lys Lys Gln Thr Ile
    130                 135                 140

Gly Trp Asp Lys Ser Phe Glu Lys Met Ser Val Ala Lys Glu Val Leu
145                 150                 155                 160

Arg Gly Asp Val Thr Gln Phe Leu Leu Leu Glu Gly Gly Tyr Gln
                165                 170                 175

Arg Cys Arg Phe His Ser Thr Tyr Lys Thr Glu Lys Pro Val Ala Met
            180                 185                 190

Pro Pro Ser His Val Val Glu His Gln Ile Val Arg Thr Asp Leu Gly
        195                 200                 205

Gln Thr Ala Lys Gly Phe Lys Val Lys Leu Glu Glu His Ala Glu Ala
    210                 215                 220

His Val Asn Pro Leu Lys Val Lys Gly Gly Ser Gly Gly Asp Glu Val
```

```
                    225                 230                 235                 240
Asp Gly Thr Gly Gly Ser Met Val Ser Val Ile Lys Pro Glu Met Lys
                245                 250                 255

Met Arg Tyr Tyr Met Asp Gly Ser Val Asn Gly His Glu Phe Thr Ile
            260                 265                 270

Glu Gly Glu Gly Thr Gly Arg Pro Tyr Glu Gly His Gln Glu Met Thr
        275                 280                 285

Leu Arg Val Thr Met Ala Lys Gly Gly Pro Met Pro Phe Ala Phe Asp
    290                 295                 300

Leu Val Ser His Val Phe Cys Tyr Gly His Arg Pro Phe Thr Lys Tyr
305                 310                 315                 320

Pro Glu Glu Ile Pro Asp Tyr Phe Lys Gln Ala Phe Pro Glu Gly Leu
                325                 330                 335

Ser Trp Glu Arg Ser Leu Glu Phe Glu Asp Gly Gly Ser Ala Ser Val
            340                 345                 350

Ser Ala His Ile Ser Leu Arg Gly Asn Thr Phe Tyr His Lys Ser Lys
        355                 360                 365

Phe Thr Gly Val Asn Phe Pro Ala Asp Gly Pro Ile Met Gln Asn Gln
    370                 375                 380

Ser Val Asp Trp Glu Pro Ser Thr Glu Lys Ile Thr Ala Ser Asp Gly
385                 390                 395                 400

Val Leu Lys Gly Asp Val Thr Met Tyr Leu Lys Leu Glu Gly Gly Gly
                405                 410                 415

Asn His Lys Cys Gln Phe Lys Thr Thr Tyr Lys Ala Ala Lys Lys Ile
            420                 425                 430

Leu Lys Met Pro Gly Ser His Tyr Ile Ser His Arg Leu Val Arg Lys
        435                 440                 445

Thr Glu Gly Asn Ile Thr Glu Leu Val Glu Asp Ala Val Ala His Ser
    450                 455                 460

<210> SEQ ID NO 36
<211> LENGTH: 1395
<212> TYPE: DNA
<213> ORGANISM: Fungia sp.
<220> FEATURE:
<221> NAME/KEY: CDS
<222> LOCATION: (1)..(1392)

<400> SEQUENCE: 36 atg gtg tct tat tca aag caa ggc atc gca caa gaa atg cgg acg aaa        48
Met Val Ser Tyr Ser Lys Gln Gly Ile Ala Gln Glu Met Arg Thr Lys
  1               5                  10                  15 tac cgt atg gaa ggc agt gtc aat ggc cat gaa ttc acg atc gaa ggt       96
Tyr Arg Met Glu Gly Ser Val Asn Gly His Glu Phe Thr Ile Glu Gly
             20                  25                  30 gta gga act gga aac cct tac gaa ggg aaa cag atg tcc gaa tta gtg      144
Val Gly Thr Gly Asn Pro Tyr Glu Gly Lys Gln Met Ser Glu Leu Val
         35                  40                  45 atc atc aag tct aag gga aaa ccc ctt cca ttc tcc ttt gac ata ctg      192
Ile Ile Lys Ser Lys Gly Lys Pro Leu Pro Phe Ser Phe Asp Ile Leu
     50                  55                  60 tca aca gcc ttt caa tat gga aac aga tgc ttc aca aag tac cct gca      240
Ser Thr Ala Phe Gln Tyr Gly Asn Arg Cys Phe Thr Lys Tyr Pro Ala
 65                  70                  75                  80 gac atg cct gac tat ttc aag caa gca ttc cca gat gga atg tca tat      288
Asp Met Pro Asp Tyr Phe Lys Gln Ala Phe Pro Asp Gly Met Ser Tyr
                 85                  90                  95 gaa agg tca ttt cta ttt gag gat gga gga gtt gct aca gcc agc tgg      336
```

|  |  |  |  |  |  |  |  |  |  |  |  |  |  |
|---|---|---|---|---|---|---|---|---|---|---|---|---|---|
| Glu | Arg | Ser | Phe | Leu | Phe | Glu | Asp | Gly | Val | Ala | Thr | Ala | Ser | Trp |
|  |  | 100 |  |  |  | 105 |  |  |  | 110 |  |  |

```
agc att cgt ctc gaa gga aat tgc ttc atc cac aat tcc atc tat cat     384
Ser Ile Arg Leu Glu Gly Asn Cys Phe Ile His Asn Ser Ile Tyr His
        115                 120                 125 ggc gta aac ttt ccc gct gat gga ccc gta atg aag aag cag aca att     432
Gly Val Asn Phe Pro Ala Asp Gly Pro Val Met Lys Lys Gln Thr Ile
130                 135                 140 ggc tgg gat aag tcc ttc gaa aaa atg agt gtg gct aaa gag gtg cta     480
Gly Trp Asp Lys Ser Phe Glu Lys Met Ser Val Ala Lys Glu Val Leu
145                 150                 155                 160 aga ggt gat gtg act cag ttt ctt ctg ctc gaa gga ggt ggt tac cag     528
Arg Gly Asp Val Thr Gln Phe Leu Leu Leu Glu Gly Gly Gly Tyr Gln
            165                 170                 175 aga tgc cgg ttt cac tcc act tac aaa acg gag aag cca gtc gca atg     576
Arg Cys Arg Phe His Ser Thr Tyr Lys Thr Glu Lys Pro Val Ala Met
        180                 185                 190 ccc ccg agt cat gtc gta gaa cat caa att gtg agg acc gac ctt ggc     624
Pro Pro Ser His Val Val Glu His Gln Ile Val Arg Thr Asp Leu Gly
    195                 200                 205 caa act gca aaa ggc ttc aag gtc aag ctg gaa gaa cat gct gag gct     672
Gln Thr Ala Lys Gly Phe Lys Val Lys Leu Glu Glu His Ala Glu Ala
210                 215                 220 cat gtt aac cct ttg aag gtt aaa ggt ggc agc ggt ggc gac gag gtg     720
His Val Asn Pro Leu Lys Val Lys Gly Gly Ser Gly Gly Asp Glu Val
225                 230                 235                 240 gac ggt acc ggt ggc agc atg gtg agt gtg att aaa cca gag atg aag     768
Asp Gly Thr Gly Gly Ser Met Val Ser Val Ile Lys Pro Glu Met Lys
                245                 250                 255 atg agg tac tac atg gac ggc tcc gtc aat ggg cat gag ttc aca att     816
Met Arg Tyr Tyr Met Asp Gly Ser Val Asn Gly His Glu Phe Thr Ile
            260                 265                 270 gaa ggt gaa ggc aca ggc aga cct tac gag gga cat caa gag atg aca     864
Glu Gly Glu Gly Thr Gly Arg Pro Tyr Glu Gly His Gln Glu Met Thr
        275                 280                 285 cta cgc gtc aca atg gcc aag ggc ggg cca atg cct ttc gcg ttt gac     912
Leu Arg Val Thr Met Ala Lys Gly Gly Pro Met Pro Phe Ala Phe Asp
    290                 295                 300 tta gtg tca cac gtg ttc tgt tac ggc cac aga cct ttt act aaa tat     960
Leu Val Ser His Val Phe Cys Tyr Gly His Arg Pro Phe Thr Lys Tyr
305                 310                 315                 320 cca gaa gag ata cca gac tat ttc aaa caa gca ttt cct gaa ggc ctg    1008
Pro Glu Glu Ile Pro Asp Tyr Phe Lys Gln Ala Phe Pro Glu Gly Leu
                325                 330                 335 tca tgg gaa agg tcg ttg gag ttc gaa gat ggt ggg tcc gct tca gtc    1056
Ser Trp Glu Arg Ser Leu Glu Phe Glu Asp Gly Gly Ser Ala Ser Val
            340                 345                 350 agt gcg cat ata agc ctt aga gga aac acc ttc tac cac aaa tcc aaa    1104
Ser Ala His Ile Ser Leu Arg Gly Asn Thr Phe Tyr His Lys Ser Lys
        355                 360                 365 ttt act ggg gtt aac ttt cct gcc gat ggt cct atc atg caa aac caa    1152
Phe Thr Gly Val Asn Phe Pro Ala Asp Gly Pro Ile Met Gln Asn Gln
    370                 375                 380 agt gtt gat tgg gag cca tca acc gag aaa att act gcc agc gac gga    1200
Ser Val Asp Trp Glu Pro Ser Thr Glu Lys Ile Thr Ala Ser Asp Gly
385                 390                 395                 400 gtt ctg aag ggt gat gtt acg atg tac cta aaa ctt gaa gga ggc ggc    1248
Val Leu Lys Gly Asp Val Thr Met Tyr Leu Lys Leu Glu Gly Gly Gly
                405                 410                 415 aat cac aaa tgc caa ttc aag act act tac aag gcg gca aaa aag att    1296
```

```
                Asn His Lys Cys Gln Phe Lys Thr Thr Tyr Lys Ala Ala Lys Lys Ile
                            420                 425                 430 ctt aaa atg cca gga agc cat tac atc agc cat cgc ctc gtc agg aaa              1344
Leu Lys Met Pro Gly Ser His Tyr Ile Ser His Arg Leu Val Arg Lys
        435                 440                 445 acc gaa ggc aac att act gag ctg gta gaa gat gca gta gct cat tcc              1392
Thr Glu Gly Asn Ile Thr Glu Leu Val Glu Asp Ala Val Ala His Ser
    450                 455                 460 taa                                                                           1395

<210> SEQ ID NO 37
<211> LENGTH: 221
<212> TYPE: PRT
<213> ORGANISM: Montipora sp.

<400> SEQUENCE: 37

Met Ser Val Ile Ala Lys Gln Met Thr Tyr Lys Val Tyr Met Ser Gly
  1               5                  10                  15

Thr Val Asn Gly His Tyr Phe Glu Val Glu Gly Asp Gly Lys Gly Lys
             20                  25                  30

Pro Tyr Glu Gly Glu Gln Thr Val Lys Leu Thr Val Thr Lys Gly Gly
         35                  40                  45

Pro Leu Pro Phe Ala Trp Asp Ile Leu Ser Pro Leu Ser Gln Tyr Gly
     50                  55                  60

Ser Ile Pro Phe Thr Lys Tyr Pro Glu Asp Ile Pro Asp Tyr Val Lys
 65                  70                  75                  80

Gln Ser Phe Pro Glu Gly Tyr Thr Trp Glu Arg Ile Met His Phe Glu
                 85                  90                  95

Asp Gly Ala Val Cys Thr Val Ser Asn Asp Ser Ser Ile Gln Gly Asn
            100                 105                 110

Cys Phe Ile Tyr Asn Val Lys Ile Ser Gly Val Asn Phe Pro Pro Asn
        115                 120                 125

Gly Pro Val Met Gln Lys Lys Thr Gln Gly Trp Glu Pro Asn Thr Glu
    130                 135                 140

Arg Leu Phe Ala Arg Asp Gly Met Leu Ile Gly Asn Asn Phe Met Ala
145                 150                 155                 160

Leu Lys Leu Glu Gly Gly Gly His Tyr Leu Cys Glu Phe Lys Ser Thr
                165                 170                 175

Tyr Lys Ala Lys Lys Pro Val Arg Met Pro Gly Tyr His Tyr Val Asp
            180                 185                 190

Arg Lys Leu Asp Val Thr Ser His Asn Lys Asp Tyr Thr Phe Val Glu
        195                 200                 205

Gln Cys Glu Ile Ser Ile Ala Arg His Ser Leu Leu Gly
    210                 215                 220

<210> SEQ ID NO 38
<211> LENGTH: 666
<212> TYPE: DNA
<213> ORGANISM: Montipora sp.
<220> FEATURE:
<221> NAME/KEY: CDS
<222> LOCATION: (1)..(663)

<400> SEQUENCE: 38 atg agt gtg atc gct aaa caa atg acc tac aag gtt tat atg tca ggc               48
Met Ser Val Ile Ala Lys Gln Met Thr Tyr Lys Val Tyr Met Ser Gly
  1               5                  10                  15 acg gtc aat gga cac tac ttt gag gtc gaa ggc gat gga aaa gga aag               96
Thr Val Asn Gly His Tyr Phe Glu Val Glu Gly Asp Gly Lys Gly Lys
```

```
               20                  25                  30
cct tac gag ggg gag cag acg gta aag ctc act gtc acc aag ggt gga      144
Pro Tyr Glu Gly Glu Gln Thr Val Lys Leu Thr Val Thr Lys Gly Gly
         35                  40                  45 cct ctg cca ttt gct tgg gat att tta tca cca ctg tct cag tac gga      192
Pro Leu Pro Phe Ala Trp Asp Ile Leu Ser Pro Leu Ser Gln Tyr Gly
     50                  55                  60 agc ata cca ttc acc aag tac cct gaa gac atc cct gat tat gta aag      240
Ser Ile Pro Phe Thr Lys Tyr Pro Glu Asp Ile Pro Asp Tyr Val Lys
 65                  70                  75                  80 cag tca ttc cct gag gga tat aca tgg gag agg atc atg cac ttt gaa      288
Gln Ser Phe Pro Glu Gly Tyr Thr Trp Glu Arg Ile Met His Phe Glu
                 85                  90                  95 gat ggt gca gtg tgt act gtc agc aat gat tcc agc atc caa ggc aac      336
Asp Gly Ala Val Cys Thr Val Ser Asn Asp Ser Ser Ile Gln Gly Asn
            100                 105                 110 tgt ttc atc tac aat gtc aaa atc tct ggt gtg aac ttt cct ccc aat      384
Cys Phe Ile Tyr Asn Val Lys Ile Ser Gly Val Asn Phe Pro Pro Asn
        115                 120                 125 gga cct gtt atg cag aag aag aca cag ggc tgg gaa ccc aac act gag      432
Gly Pro Val Met Gln Lys Lys Thr Gln Gly Trp Glu Pro Asn Thr Glu
    130                 135                 140 cgt ctc ttt gca cga gat gga atg ctg ata gga aac aac ttt atg gct      480
Arg Leu Phe Ala Arg Asp Gly Met Leu Ile Gly Asn Asn Phe Met Ala
145                 150                 155                 160 ctg aag ttg gaa gga ggt ggt cac tat ttg tgt gaa ttc aaa tct act      528
Leu Lys Leu Glu Gly Gly Gly His Tyr Leu Cys Glu Phe Lys Ser Thr
                165                 170                 175 tac aag gca aag aag cct gtg agg atg cca ggg tat cac tat gtt gac      576
Tyr Lys Ala Lys Lys Pro Val Arg Met Pro Gly Tyr His Tyr Val Asp
            180                 185                 190 cgc aaa ctg gat gta acc agt cac aac aag gat tac aca ttt gtt gag      624
Arg Lys Leu Asp Val Thr Ser His Asn Lys Asp Tyr Thr Phe Val Glu
        195                 200                 205 cag tgt gaa ata tcc att gca cgc cac tct ttg ctc ggt tga              666
Gln Cys Glu Ile Ser Ile Ala Arg His Ser Leu Leu Gly
    210                 215                 220

<210> SEQ ID NO 39
<211> LENGTH: 222
<212> TYPE: PRT
<213> ORGANISM: Montipora sp.

<400> SEQUENCE: 39

Met Val Ser Val Ile Ala Lys Gln Met Thr Tyr Lys Val Tyr Met Ser
 1               5                  10                  15

Gly Thr Val Asn Gly His Tyr Phe Glu Val Glu Gly Asp Gly Lys Gly
            20                  25                  30

Lys Pro Tyr Glu Gly Glu Gln Thr Val Lys Leu Thr Val Thr Lys Gly
        35                  40                  45

Gly Pro Leu Pro Phe Ala Trp Asp Ile Leu Ser Pro Leu Ser Gln Tyr
    50                  55                  60

Gly Ser Ile Pro Phe Thr Lys Tyr Pro Glu Asp Ile Pro Asp Tyr Val
 65                  70                  75                  80

Lys Gln Ser Phe Pro Glu Gly Tyr Thr Trp Glu Arg Ile Met Asn Phe
                 85                  90                  95

Glu Asp Gly Ala Val Cys Thr Val Ser Asn Asp Ser Ser Ile Gln Gly
            100                 105                 110

Asn Cys Phe Ile Tyr Asn Val Lys Ile Ser Gly Val Asn Phe Pro Pro
```

```
                115                 120                 125
      Asn Gly Pro Val Met Gln Lys Lys Thr Gln Gly Trp Glu Pro Ser Thr
          130                 135                 140

Glu Arg Leu Phe Ala Arg Asp Gly Met Leu Ile Gly Asn Asp Phe Met
      145                 150                 155                 160

Ala Leu Lys Leu Glu Gly Gly His Tyr Leu Cys Glu Phe Lys Ser
                      165                 170                 175

Thr Tyr Lys Ala Lys Lys Pro Val Arg Met Pro Gly Tyr His Tyr Val
                  180                 185                 190

Asp Arg Lys Leu Asp Val Thr Ser His Asn Arg Asp Tyr Thr Ser Val
                  195                 200                 205

Glu Gln Cys Glu Ile Ser Ile Ala Arg His Ser Leu Leu Gly
          210                 215                 220

<210> SEQ ID NO 40
<211> LENGTH: 669
<212> TYPE: DNA
<213> ORGANISM: Montipora sp.
<220> FEATURE:
<221> NAME/KEY: CDS
<222> LOCATION: (1)..(666)

<400> SEQUENCE: 40 atg gtg agt gtg atc gct aaa caa atg acc tac aag gtt tat atg tca      48
Met Val Ser Val Ile Ala Lys Gln Met Thr Tyr Lys Val Tyr Met Ser
  1               5                  10                  15 ggc acg gtc aat gga cac tac ttt gag gtc gaa ggc gat gga aaa gga      96
Gly Thr Val Asn Gly His Tyr Phe Glu Val Glu Gly Asp Gly Lys Gly
             20                  25                  30 aag cct tac gag gga gag cag aca gta aag ctc act gtc acc aag ggt     144
Lys Pro Tyr Glu Gly Glu Gln Thr Val Lys Leu Thr Val Thr Lys Gly
         35                  40                  45 gga cct ctg cca ttt gct tgg gat att tta tca cca ctg tct cag tac     192
Gly Pro Leu Pro Phe Ala Trp Asp Ile Leu Ser Pro Leu Ser Gln Tyr
     50                  55                  60 gga agc ata cca ttc acc aag tac cct gaa gac atc cct gat tat gta     240
Gly Ser Ile Pro Phe Thr Lys Tyr Pro Glu Asp Ile Pro Asp Tyr Val
 65                  70                  75                  80 aag cag tca ttc cct gag gga tat aca tgg gag agg atc atg aac ttt     288
Lys Gln Ser Phe Pro Glu Gly Tyr Thr Trp Glu Arg Ile Met Asn Phe
                 85                  90                  95 gaa gat ggt gca gtg tgt act gtc agc aat gat tcc agc atc caa ggc     336
Glu Asp Gly Ala Val Cys Thr Val Ser Asn Asp Ser Ser Ile Gln Gly
            100                 105                 110 aac tgt ttc atc tac aat gtc aaa atc tct ggt gtg aac ttt cct ccc     384
Asn Cys Phe Ile Tyr Asn Val Lys Ile Ser Gly Val Asn Phe Pro Pro
        115                 120                 125 aat gga cct gtt atg cag aag aag aca cag ggc tgg gaa ccc agc act     432
Asn Gly Pro Val Met Gln Lys Lys Thr Gln Gly Trp Glu Pro Ser Thr
    130                 135                 140 gag cgt ctc ttt gca cga gat gga atg ctg ata gga aac gat ttt atg     480
Glu Arg Leu Phe Ala Arg Asp Gly Met Leu Ile Gly Asn Asp Phe Met
145                 150                 155                 160 gct ctg aag ttg gaa gga ggt ggt cac tat ttg tgt gaa ttc aaa tct     528
Ala Leu Lys Leu Glu Gly Gly Gly His Tyr Leu Cys Glu Phe Lys Ser
                165                 170                 175 act tac aag gca aag aag cct gtg agg atg cca ggg tat cac tat gtt     576
Thr Tyr Lys Ala Lys Lys Pro Val Arg Met Pro Gly Tyr His Tyr Val
            180                 185                 190 gac cgc aaa ctg gat gta acc agt cac aac agg gat tac aca tct gtt     624
```

```
Asp Arg Lys Leu Asp Val Thr Ser His Asn Arg Asp Tyr Thr Ser Val
        195                 200                 205 gag cag tgt gaa ata tcc att gca cgc cac tct ttg ctc ggt tga          669
Glu Gln Cys Glu Ile Ser Ile Ala Arg His Ser Leu Leu Gly
        210                 215                 220
```

<210> SEQ ID NO 41
<211> LENGTH: 222
<212> TYPE: PRT
<213> ORGANISM: Montipora sp.

<400> SEQUENCE: 41

```
Met Val Ser Val Ile Ala Lys Gln Met Thr Tyr Lys Val Tyr Met Ser
  1               5                  10                  15

Gly Thr Val Asn Gly His Tyr Phe Glu Val Glu Gly Asp Gly Lys Gly
             20                  25                  30

Lys Pro Tyr Glu Gly Glu Gln Thr Val Lys Leu Thr Val Thr Lys Gly
         35                  40                  45

Gly Pro Leu Pro Phe Ala Trp Asp Ile Leu Ser Pro Leu Phe Gln Tyr
     50                  55                  60

Gly Ser Ile Pro Phe Thr Lys Tyr Pro Glu Asp Ile Pro Asp Tyr Val
 65                  70                  75                  80

Lys Gln Ser Phe Pro Glu Gly Tyr Thr Trp Glu Arg Thr Met Asn Phe
                 85                  90                  95

Glu Asp Gly Ala Val Cys Thr Val Ser Asn Asp Ser Ser Ile Gln Gly
            100                 105                 110

Asn Cys Phe Ile Tyr Asn Val Lys Ile Ser Gly Thr Asn Phe Pro Pro
        115                 120                 125

Asn Gly Pro Val Met Gln Lys Lys Thr Gln Gly Trp Glu Pro Ser Thr
    130                 135                 140

Glu Arg Leu Phe Ala Arg Asp Gly Met Leu Ile Gly Asn Asp Tyr Met
145                 150                 155                 160

Ala Leu Lys Leu Glu Gly Gly Gly His Tyr Leu Cys Glu Phe Lys Ser
                165                 170                 175

Thr Tyr Lys Ala Lys Lys Pro Val Arg Met Pro Gly Tyr His Tyr Ile
            180                 185                 190

Asp Arg Lys Leu Asp Val Thr Ser His Asn Arg Asp Tyr Thr Ser Val
        195                 200                 205

Glu Gln Cys Glu Ile Ala Ile Ala Arg His Ser Leu Leu Gly
    210                 215                 220
```

<210> SEQ ID NO 42
<211> LENGTH: 669
<212> TYPE: DNA
<213> ORGANISM: Montipora sp.
<220> FEATURE:
<221> NAME/KEY: CDS
<222> LOCATION: (1)..(666)

<400> SEQUENCE: 42

```
atg gtg agt gtg atc gct aaa caa atg acc tac aag gtt tat atg tca    48
Met Val Ser Val Ile Ala Lys Gln Met Thr Tyr Lys Val Tyr Met Ser
  1               5                  10                  15 ggc acg gtc aat gga cac tac ttt gag gtc gaa ggc gat gga aaa gga    96
Gly Thr Val Asn Gly His Tyr Phe Glu Val Glu Gly Asp Gly Lys Gly
             20                  25                  30 aag cct tac gag gga gag cag aca gta aag ctc act gtc acc aag ggt   144
Lys Pro Tyr Glu Gly Glu Gln Thr Val Lys Leu Thr Val Thr Lys Gly
         35                  40                  45
```

```
gga cct ctg cca ttt gct tgg gat att tta tca cca ctg ttt cag tac     192
Gly Pro Leu Pro Phe Ala Trp Asp Ile Leu Ser Pro Leu Phe Gln Tyr
 50                  55                  60 gga agc ata cca ttc acc aag tac cct gaa gac atc cct gat tat gta     240
Gly Ser Ile Pro Phe Thr Lys Tyr Pro Glu Asp Ile Pro Asp Tyr Val
 65                  70                  75                  80 aag cag tca ttc cct gag gga tat aca tgg gag agg acc atg aac ttt     288
Lys Gln Ser Phe Pro Glu Gly Tyr Thr Trp Glu Arg Thr Met Asn Phe
                 85                  90                  95 gaa gat ggt gca gtg tgt act gtc agc aat gat tcc agc atc caa ggc     336
Glu Asp Gly Ala Val Cys Thr Val Ser Asn Asp Ser Ser Ile Gln Gly
            100                 105                 110 aac tgt ttc atc tac aat gtc aaa atc tct ggt acg aac ttt cct ccc     384
Asn Cys Phe Ile Tyr Asn Val Lys Ile Ser Gly Thr Asn Phe Pro Pro
        115                 120                 125 aat gga cct gtt atg cag aag aag aca cag ggc tgg gaa ccc agc act     432
Asn Gly Pro Val Met Gln Lys Lys Thr Gln Gly Trp Glu Pro Ser Thr
130                 135                 140 gag cgt ctc ttt gca cga gat gga atg ctg ata gga aac gat tat atg     480
Glu Arg Leu Phe Ala Arg Asp Gly Met Leu Ile Gly Asn Asp Tyr Met
145                 150                 155                 160 gct ctg aag ttg gaa gga ggt ggt cac tat ttg tgt gaa ttt aaa tct     528
Ala Leu Lys Leu Glu Gly Gly His Tyr Leu Cys Glu Phe Lys Ser
                165                 170                 175 act tac aag gca aag aag cct gtg agg atg cca ggg tat cac tat att     576
Thr Tyr Lys Ala Lys Lys Pro Val Arg Met Pro Gly Tyr His Tyr Ile
            180                 185                 190 gac cgc aaa ctg gat gta acc agt cac aac agg gat tac aca tct gtt     624
Asp Arg Lys Leu Asp Val Thr Ser His Asn Arg Asp Tyr Thr Ser Val
        195                 200                 205 gag cag tgt gaa ata gcc att gca cgc cac tct ttg ctc ggt tga          669
Glu Gln Cys Glu Ile Ala Ile Ala Arg His Ser Leu Leu Gly
    210                 215                 220

<210> SEQ ID NO 43
<211> LENGTH: 222
<212> TYPE: PRT
<213> ORGANISM: Montipora sp.

<400> SEQUENCE: 43

Met Val Ser Val Ile Ala Lys Gln Met Thr Tyr Lys Val Tyr Met Ser
 1               5                  10                  15

Gly Thr Val Asn Gly His Tyr Phe Glu Val Glu Gly Asp Gly Lys Gly
                20                  25                  30

Lys Pro Tyr Glu Gly Glu Gln Thr Val Lys Leu Thr Val Thr Lys Gly
            35                  40                  45

Gly Pro Leu Pro Phe Ala Trp Asp Ile Leu Ser Pro Leu Met Cys Tyr
 50                  55                  60

Gly Ser Ile Pro Phe Thr Lys Tyr Pro Glu Asp Ile Pro Asp Tyr Val
 65                  70                  75                  80

Lys Gln Ser Phe Pro Glu Gly Tyr Thr Trp Glu Arg Thr Met Asn Phe
                 85                  90                  95

Glu Asp Gly Ala Val Cys Thr Val Ser Asn Asp Ser Ser Ile Gln Gly
            100                 105                 110

Asn Cys Phe Ile Tyr Asn Val Lys Ile Ser Gly Thr Asn Phe Pro Pro
        115                 120                 125

Asn Gly Pro Val Met Gln Lys Lys Thr Gln Gly Trp Glu Pro Ser Thr
130                 135                 140

Glu Arg Leu Phe Ala Arg Asp Gly Met Leu Ile Gly Asn Asp Tyr Met
```

```
                145                 150                 155                 160
Ala Leu Lys Leu Glu Gly Gly Gly His Tyr Leu Cys Glu Phe Lys Ser
                    165                 170                 175
Thr Tyr Lys Ala Lys Lys Pro Val Arg Met Pro Gly Tyr His Tyr Ile
                    180                 185                 190
Asp Arg Lys Leu Asp Val Thr Ser His Asn Arg Asp Tyr Thr Ser Val
                    195                 200                 205
Glu Gln Cys Glu Ile Ala Ile Ala Arg His Ser Leu Leu Gly
                    210                 215                 220

<210> SEQ ID NO 44
<211> LENGTH: 669
<212> TYPE: DNA
<213> ORGANISM: Montipora sp.
<220> FEATURE:
<221> NAME/KEY: CDS
<222> LOCATION: (1)..(666)

<400> SEQUENCE: 44 atg gtg agt gtg atc gct aaa caa atg acc tac aag gtt tat atg tca        48
Met Val Ser Val Ile Ala Lys Gln Met Thr Tyr Lys Val Tyr Met Ser
  1               5                  10                  15 ggc acg gtc aat gga cac tac ttt gag gtc gaa ggc gat gga aaa gga        96
Gly Thr Val Asn Gly His Tyr Phe Glu Val Glu Gly Asp Gly Lys Gly
                 20                  25                  30 aag cct tac gag gga gag cag aca gta aag ctc act gtc acc aag ggt       144
Lys Pro Tyr Glu Gly Glu Gln Thr Val Lys Leu Thr Val Thr Lys Gly
             35                  40                  45 gga cct ctg cca ttt gct tgg gat att tta tca cca ctg atg tgt tac       192
Gly Pro Leu Pro Phe Ala Trp Asp Ile Leu Ser Pro Leu Met Cys Tyr
         50                  55                  60 gga agc ata cca ttc acc aag tac cct gaa gac atc cct gat tat gta       240
Gly Ser Ile Pro Phe Thr Lys Tyr Pro Glu Asp Ile Pro Asp Tyr Val
 65                  70                  75                  80 aag cag tca ttc cct gag gga tat aca tgg gag agg acc atg aac ttt       288
Lys Gln Ser Phe Pro Glu Gly Tyr Thr Trp Glu Arg Thr Met Asn Phe
                 85                  90                  95 gaa gat ggt gca gtg tgt act gtc agc aat gat tcc agc atc caa ggc       336
Glu Asp Gly Ala Val Cys Thr Val Ser Asn Asp Ser Ser Ile Gln Gly
            100                 105                 110 aac tgt ttc atc tac aat gtc aaa atc tct ggt acg aac ttt cct ccc       384
Asn Cys Phe Ile Tyr Asn Val Lys Ile Ser Gly Thr Asn Phe Pro Pro
        115                 120                 125 aat gga cct gtt atg cag aag aag aca cag ggc tgg gaa ccc agc act       432
Asn Gly Pro Val Met Gln Lys Lys Thr Gln Gly Trp Glu Pro Ser Thr
    130                 135                 140 gag cgt ctc ttt gca cga gat gga atg ctg ata gga aac gat tat atg       480
Glu Arg Leu Phe Ala Arg Asp Gly Met Leu Ile Gly Asn Asp Tyr Met
145                 150                 155                 160 gct ctg aag ttg gaa gga ggt ggt cac tat ttg tgt gaa ttt aaa tct       528
Ala Leu Lys Leu Glu Gly Gly Gly His Tyr Leu Cys Glu Phe Lys Ser
                165                 170                 175 act tac aag gca aag aag cct gtg agg atg cca ggg tat cac tat att       576
Thr Tyr Lys Ala Lys Lys Pro Val Arg Met Pro Gly Tyr His Tyr Ile
            180                 185                 190 gac cgc aaa ctg gat gta acc agt cac aac agg gat tac aca tct gtt       624
Asp Arg Lys Leu Asp Val Thr Ser His Asn Arg Asp Tyr Thr Ser Val
        195                 200                 205 gag cag tgt gaa ata gcc att gca cgc cac tct ttg ctc ggt tga           669
Glu Gln Cys Glu Ile Ala Ile Ala Arg His Ser Leu Leu Gly
    210                 215                 220
```

<210> SEQ ID NO 45
<211> LENGTH: 255
<212> TYPE: PRT
<213> ORGANISM: Montipora sp.

<400> SEQUENCE: 45

Met Arg Gly Ser His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Val Ser Val Ile Ala Lys Gln Met Thr Tyr Lys Val Tyr Met
        35                  40                  45

Ser Gly Thr Val Asn Gly His Tyr Phe Glu Val Glu Gly Asp Gly Lys
    50                  55                  60

Gly Lys Pro Tyr Glu Gly Glu Gln Thr Val Lys Leu Thr Val Thr Lys
65                  70                  75                  80

Gly Gly Pro Leu Pro Phe Ala Trp Asp Ile Leu Ser Pro Gln Phe Gln
                85                  90                  95

Tyr Gly Ser Ile Pro Phe Thr Lys Tyr Pro Glu Asp Ile Pro Asp Tyr
            100                 105                 110

Phe Lys Gln Ser Phe Pro Glu Gly Tyr Thr Trp Glu Arg Ser Met Asn
        115                 120                 125

Phe Glu Asp Gly Ala Val Cys Thr Val Ser Asn Asp Ser Ser Ile Gln
130                 135                 140

Gly Asn Cys Phe Ile Tyr Asn Val Lys Ile Ser Gly Glu Asn Phe Pro
145                 150                 155                 160

Pro Asn Gly Pro Val Met Gln Lys Lys Thr Gln Gly Trp Glu Pro Ser
                165                 170                 175

Thr Glu Arg Leu Phe Ala Arg Asp Gly Met Leu Ile Gly Asn Asp Tyr
            180                 185                 190

Met Ala Leu Lys Leu Glu Gly Gly Gly His Tyr Leu Cys Glu Phe Lys
        195                 200                 205

Ser Thr Tyr Lys Ala Lys Lys Pro Val Arg Met Pro Gly Arg His Glu
    210                 215                 220

Ile Asp Arg Lys Leu Asp Val Thr Ser His Asn Arg Asp Tyr Thr Ser
225                 230                 235                 240

Val Glu Gln Cys Glu Ile Ala Ile Ala Arg His Ser Leu Leu Gly
                245                 250                 255

<210> SEQ ID NO 46
<211> LENGTH: 765
<212> TYPE: DNA
<213> ORGANISM: Montipora sp.
<220> FEATURE:
<221> NAME/KEY: CDS
<222> LOCATION: (1)..(765)

<400> SEQUENCE: 46 atg cgg ggt tct cat cat cat cat cat ggt atg gct agc atg act      48
Met Arg Gly Ser His His His His His Gly Met Ala Ser Met Thr
1               5                   10                  15 ggt gga cag caa atg ggt cgg gat ctg tac gac gat gac gat aag gat  96
Gly Gly Gln Gln Met Gly Arg Asp Leu Tyr Asp Asp Asp Lys Asp
            20                  25                  30 ccc atg gtg agt gtg atc gct aaa caa atg acc tac aag gtt tat atg  144
Pro Met Val Ser Val Ile Ala Lys Gln Met Thr Tyr Lys Val Tyr Met
        35                  40                  45

| | | | | | | | | | | | | | | | |
|---|---|---|---|---|---|---|---|---|---|---|---|---|---|---|---|
| tca | ggc | acg | gtc | aat | gga | cac | tac | ttt | gag | gtc | gaa | ggc | gat | gga | aaa | 192
| Ser | Gly | Thr | Val | Asn | Gly | His | Tyr | Phe | Glu | Val | Glu | Gly | Asp | Gly | Lys |
| | 50 | | | | 55 | | | | | 60 | | | | | |

```
tca ggc acg gtc aat gga cac tac ttt gag gtc gaa ggc gat gga aaa           192
Ser Gly Thr Val Asn Gly His Tyr Phe Glu Val Glu Gly Asp Gly Lys
    50              55                  60 gga aag cct tac gag gga gag cag aca gta aag ctc act gtc acc aag           240
Gly Lys Pro Tyr Glu Gly Glu Gln Thr Val Lys Leu Thr Val Thr Lys
65              70                  75                  80 ggt gga cct ctg cca ttt gct tgg gat att tta tca cca cag ttc cag           288
Gly Gly Pro Leu Pro Phe Ala Trp Asp Ile Leu Ser Pro Gln Phe Gln
                85                  90                  95 tac gga agc ata cca ttc acc aag tac cct gaa gac atc cct gat tat           336
Tyr Gly Ser Ile Pro Phe Thr Lys Tyr Pro Glu Asp Ile Pro Asp Tyr
                100                 105                 110 ttc aag cag tca ttc cct gag gga tat aca tgg gag agg agc atg aac           384
Phe Lys Gln Ser Phe Pro Glu Gly Tyr Thr Trp Glu Arg Ser Met Asn
            115                 120                 125 ttt gaa gat ggt gca gtg tgt act gtc agc aat gat tcc agc atc caa           432
Phe Glu Asp Gly Ala Val Cys Thr Val Ser Asn Asp Ser Ser Ile Gln
        130                 135                 140 ggc aac tgt ttc atc tac aat gtc aaa atc tct ggt gag aac ttt cct           480
Gly Asn Cys Phe Ile Tyr Asn Val Lys Ile Ser Gly Glu Asn Phe Pro
145                 150                 155                 160 ccc aat gga cct gtt atg cag aag aag aca cag ggc tgg gaa ccc agc           528
Pro Asn Gly Pro Val Met Gln Lys Lys Thr Gln Gly Trp Glu Pro Ser
                165                 170                 175 act gag cgt ctc ttt gca cga gat gga atg ctg ata gga aac gat tat           576
Thr Glu Arg Leu Phe Ala Arg Asp Gly Met Leu Ile Gly Asn Asp Tyr
            180                 185                 190 atg gct ctg aag ttg gaa gga ggt ggt cac tat ttg tgt gaa ttt aaa           624
Met Ala Leu Lys Leu Glu Gly Gly Gly His Tyr Leu Cys Glu Phe Lys
        195                 200                 205 tct act tac aag gca aag aag cct gtg agg atg cca ggg cgc cac gag           672
Ser Thr Tyr Lys Ala Lys Lys Pro Val Arg Met Pro Gly Arg His Glu
210                 215                 220 att gac cgc aaa ctg gat gta acc agt cac aac agg gat tac aca tct           720
Ile Asp Arg Lys Leu Asp Val Thr Ser His Asn Arg Asp Tyr Thr Ser
225                 230                 235                 240 gtt gag cag tgt gaa ata gcc att gca cgc cac tct ttg ctc ggt               765
Val Glu Gln Cys Glu Ile Ala Ile Ala Arg His Ser Leu Leu Gly
                245                 250                 255

<210> SEQ ID NO 47
<211> LENGTH: 255
<212> TYPE: PRT
<213> ORGANISM: Montipora sp.

<400> SEQUENCE: 47

Met Arg Gly Ser His His His His His Gly Met Ala Ser Met Thr
1               5                   10                  15

Gly Gly Gln Gln Met Gly Arg Asp Leu Tyr Asp Asp Asp Lys Asp
                20                  25                  30

Pro Met Val Ser Val Ile Ala Lys Gln Met Thr Tyr Lys Val Tyr Met
            35                  40                  45

Ser Gly Thr Val Asn Gly His Tyr Phe Glu Val Glu Gly Asp Gly Lys
50                  55                  60

Gly Lys Pro Tyr Glu Gly Glu Gln Thr Val Lys Leu Thr Val Thr Lys
65                  70                  75                  80

Gly Gly Pro Leu Pro Phe Ala Trp Asp Ile Leu Ser Pro Gln Leu Gln
                85                  90                  95

Tyr Gly Ser Ile Pro Phe Thr Lys Tyr Pro Glu Asp Ile Pro Asp Tyr
                100                 105                 110
```

```
Phe Lys Gln Ser Phe Pro Glu Gly Tyr Thr Trp Glu Arg Ser Met Asn
            115                 120                 125

Phe Glu Asp Gly Ala Val Cys Thr Val Ser Asn Asp Ser Ser Ile Gln
130                 135                 140

Gly Asn Cys Phe Ile Tyr Asn Val Lys Ile Ser Gly Glu Asn Phe Pro
145                 150                 155                 160

Pro Asn Gly Pro Val Met Gln Lys Lys Thr Gln Gly Trp Glu Pro Ser
            165                 170                 175

Thr Glu Arg Leu Phe Ala Arg Asp Gly Met Leu Ile Gly Asn Asp Tyr
            180                 185                 190

Met Ala Leu Lys Leu Glu Gly Gly His Tyr Leu Cys Glu Phe Lys
            195                 200                 205

Ser Thr Tyr Lys Ala Lys Lys Pro Val Arg Met Pro Gly Arg His Glu
            210                 215                 220

Ile Asp Arg Lys Leu Asp Val Thr Ser His Asn Arg Asp Tyr Thr Ser
225                 230                 235                 240

Val Glu Gln Cys Glu Ile Ala Ile Ala Arg His Ser Leu Leu Gly
            245                 250                 255
```

<210> SEQ ID NO 48
<211> LENGTH: 765
<212> TYPE: DNA
<213> ORGANISM: Montipora sp.
<220> FEATURE:
<221> NAME/KEY: CDS
<222> LOCATION: (1)..(765)

<400> SEQUENCE: 48

```
atg cgg ggt tct cat cat cat cat cat cat ggt atg gct agc atg act      48
Met Arg Gly Ser His His His His His His Gly Met Ala Ser Met Thr
 1               5                  10                  15 ggt gga cag caa atg ggt cgg gat ctg tac gac gat gac gat aag gat      96
Gly Gly Gln Gln Met Gly Arg Asp Leu Tyr Asp Asp Asp Asp Lys Asp
            20                  25                  30 ccc atg gtg agt gtg atc gct aaa caa atg acc tac aag gtt tat atg     144
Pro Met Val Ser Val Ile Ala Lys Gln Met Thr Tyr Lys Val Tyr Met
        35                  40                  45 tca ggc acg gtc aat gga cac tac ttt gag gtc gaa ggc gat gga aaa     192
Ser Gly Thr Val Asn Gly His Tyr Phe Glu Val Glu Gly Asp Gly Lys
    50                  55                  60 gga aag cct tac gag gga gag cag aca gta aag ctc act gtc acc aag     240
Gly Lys Pro Tyr Glu Gly Glu Gln Thr Val Lys Leu Thr Val Thr Lys
65                  70                  75                  80 ggt gga cct ctg cca ttt gct tgg gat att tta tca cca cag ctt cag     288
Gly Gly Pro Leu Pro Phe Ala Trp Asp Ile Leu Ser Pro Gln Leu Gln
                85                  90                  95 tac gga agc ata cca ttc acc aag tac cct gaa gac atc cct gat tat     336
Tyr Gly Ser Ile Pro Phe Thr Lys Tyr Pro Glu Asp Ile Pro Asp Tyr
            100                 105                 110 ttc aag cag tca ttc cct gag gga tat aca tgg gag agg agc atg aac     384
Phe Lys Gln Ser Phe Pro Glu Gly Tyr Thr Trp Glu Arg Ser Met Asn
        115                 120                 125 ttt gaa gat ggt gca gtg tgt act gtc agc aat gat tcc agc atc caa     432
Phe Glu Asp Gly Ala Val Cys Thr Val Ser Asn Asp Ser Ser Ile Gln
    130                 135                 140 ggc aac tgt ttc atc tac aat gtc aaa atc tct ggt gag aac ttt cct     480
Gly Asn Cys Phe Ile Tyr Asn Val Lys Ile Ser Gly Glu Asn Phe Pro
145                 150                 155                 160 ccc aat gga cct gtt atg cag aag aag aca cag ggc tgg gaa ccc agc     528
```

```
                                                                              576
act gag cgt ctc ttt gca cga gat gga atg ctg ata gga aac gat tat
Thr Glu Arg Leu Phe Ala Arg Asp Gly Met Leu Ile Gly Asn Asp Tyr
        180                 185                 190

624
atg gct ctg aag ttg gaa gga ggt ggt cac tat ttg tgt gaa ttt aaa
Met Ala Leu Lys Leu Glu Gly Gly Gly His Tyr Leu Cys Glu Phe Lys
        195                 200                 205

672
tct act tac aag gca aag aag cct gtg agg atg cca ggg cgc cac gag
Ser Thr Tyr Lys Ala Lys Lys Pro Val Arg Met Pro Gly Arg His Glu
    210                 215                 220

720
att gac cgc aaa ctg gat gta acc agt cac aac agg gat tac aca tct
Ile Asp Arg Lys Leu Asp Val Thr Ser His Asn Arg Asp Tyr Thr Ser
225                 230                 235                 240

765
gtt gag cag tgt gaa ata gcc att gca cgc cac tct ttg ctc ggt
Val Glu Gln Cys Glu Ile Ala Ile Ala Arg His Ser Leu Leu Gly
                245                 250                 255

<210> SEQ ID NO 49
<211> LENGTH: 747
<212> TYPE: PRT
<213> ORGANISM: Montipora sp.

<400> SEQUENCE: 49

Met Val Ser Lys Gly Glu Glu Leu Phe Thr Gly Val Val Pro Ile Leu
 1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly Leu Arg Ser Arg Ala Gln Ala Ser Asn Ser Ala Val Asp Gly Thr
                245                 250                 255

Ala Gly Pro Leu Tyr Asp Glu Val Asp Lys Asp Pro Met Ala Ser Ser
```

```
                    260                 265                 270
Glu Asp Val Ile Lys Glu Phe Met Arg Phe Lys Val Arg Met Glu Gly
                275                 280                 285

Ser Val Asn Gly His Glu Phe Glu Ile Glu Gly Glu Gly Glu Gly Arg
            290                 295                 300

Pro Tyr Glu Gly Thr Gln Thr Ala Lys Leu Lys Val Thr Lys Gly Gly
305                 310                 315                 320

Pro Leu Pro Phe Ala Trp Asp Ile Leu Ser Pro Gln Phe Gln Tyr Gly
                325                 330                 335

Ser Lys Ala Tyr Val Lys His Pro Ala Asp Ile Pro Asp Tyr Leu Lys
            340                 345                 350

Leu Ser Phe Pro Glu Gly Phe Lys Trp Glu Arg Val Met Asn Phe Glu
                355                 360                 365

Asp Gly Gly Val Val Thr Val Thr Gln Asp Ser Ser Leu Gln Asp Gly
            370                 375                 380

Glu Phe Ile Tyr Lys Val Lys Leu Arg Gly Thr Asn Phe Pro Ser Asp
385                 390                 395                 400

Gly Pro Val Met Gln Lys Lys Thr Met Gly Trp Glu Ala Ser Thr Glu
                405                 410                 415

Arg Met Tyr Pro Glu Asp Gly Ala Leu Lys Gly Glu Ile Lys Met Arg
            420                 425                 430

Leu Lys Leu Lys Asp Gly Gly His Tyr Asp Ala Glu Val Lys Thr Thr
                435                 440                 445

Tyr Met Ala Lys Lys Pro Val Gln Leu Pro Gly Ala Tyr Lys Thr Asp
            450                 455                 460

Ile Lys Leu Asp Ile Thr Ser His Asn Glu Asp Tyr Thr Ile Val Glu
465                 470                 475                 480

Gln Tyr Glu Arg Ala Glu Gly Arg His Ser Thr Gly Ala Ser Gly Leu
                485                 490                 495

Arg Ser Arg Ala Gln Ala Ser Asn Ser Ala Val Asp Gly Thr Ala Gly
            500                 505                 510

Pro Leu Tyr Asp Glu Val Gly Lys Asp Pro Met Ala Ser Ser Glu Asp
                515                 520                 525

Val Ile Lys Glu Phe Met Arg Phe Lys Val Arg Met Glu Gly Ser Val
            530                 535                 540

Asn Gly His Glu Phe Glu Ile Glu Gly Glu Gly Glu Gly Arg Pro Tyr
545                 550                 555                 560

Glu Gly Thr Gln Thr Ala Lys Leu Lys Val Thr Lys Gly Gly Pro Leu
                565                 570                 575

Pro Phe Ala Trp Asp Ile Leu Ser Pro Gln Phe Gln Tyr Gly Ser Lys
            580                 585                 590

Ala Tyr Val Lys His Pro Ala Asp Ile Pro Asp Tyr Leu Lys Leu Ser
            595                 600                 605

Phe Pro Glu Gly Phe Lys Trp Glu Arg Val Met Asn Phe Glu Asp Gly
                610                 615                 620

Gly Val Val Thr Val Thr Gln Asp Ser Ser Leu Gln Asp Gly Glu Phe
625                 630                 635                 640

Ile Tyr Lys Val Lys Leu Arg Gly Thr Asn Phe Pro Ser Asp Gly Pro
                645                 650                 655

Val Met Gln Lys Lys Thr Met Gly Trp Glu Ala Ser Thr Glu Arg Met
                660                 665                 670

Tyr Pro Glu Asp Gly Ala Leu Lys Gly Glu Ile Lys Met Arg Leu Lys
            675                 680                 685
```

-continued

```
Leu Lys Asp Gly Gly His Tyr Asp Ala Glu Val Lys Thr Thr Tyr Met
    690             695                 700
Ala Lys Lys Pro Val Gln Leu Pro Gly Ala Tyr Lys Thr Asp Ile Lys
705             710                 715                 720
Leu Asp Ile Thr Ser His Asn Glu Asp Tyr Thr Ile Val Glu Gln Tyr
                725                 730                 735
Glu Arg Ala Glu Gly Arg His Ser Thr Gly Ala
            740                 745

<210> SEQ ID NO 50
<211> LENGTH: 2241
<212> TYPE: DNA
<213> ORGANISM: Montipora sp.
<220> FEATURE:
<221> NAME/KEY: CDS
<222> LOCATION: (1)..(2241)

<400> SEQUENCE: 50 atg gtg agc aag ggc gag gag ctg ttc acc ggg gtg gtg ccc atc ctg      48
Met Val Ser Lys Gly Glu Glu Leu Phe Thr Gly Val Val Pro Ile Leu
  1               5                  10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
                 20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
             35                  40                  45 tgc acc acc ggc aag ctg ccc gtg ccc tgg ccc acc ctc gtg acc acc     192
Cys Thr Thr Gly Lys Leu Pro Val Pro Trp Pro Thr Leu Val Thr Thr
         50                  55                  60 ctg acc tac ggc gtg cag tgc ttc agc cgc tac ccc gac cac atg aag     240
Leu Thr Tyr Gly Val Gln Cys Phe Ser Arg Tyr Pro Asp His Met Lys
     65                  70                  75                  80 cag cac gac ttc ttc aag tcc gcc atg ccc gaa ggc tac gtc cag gag     288
Gln His Asp Phe Phe Lys Ser Ala Met Pro Glu Gly Tyr Val Gln Glu
                 85                  90                  95 cgc acc atc ttc ttc aag gac gac ggc aac tac aag acc cgc gcc gag     336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc     384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac     432
Ile Asp Phe Lys Glu Asp Gly Asn Ile Leu Gly His Lys Leu Glu Tyr
    130                 135                 140 aac tac aac agc cac aac gtc tat atc atg gcc gac aag cag aag aac     480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc     528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc     576
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg     624
Pro Val Leu Leu Pro Asp Asn His Tyr Leu Ser Thr Gln Ser Ala Leu
        195                 200                 205 agc aaa gac ccc aac gag aag cgc gat cac atg gtc ctg ctg gag ttc     672
Ser Lys Asp Pro Asn Glu Lys Arg Asp His Met Val Leu Leu Glu Phe
    210                 215                 220 gtg acc gcc gcc ggg atc act ctc ggc atg gac gag ctg tac aag tcc     720
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Val | Thr | Ala | Ala | Gly | Ile | Thr | Leu | Gly | Met | Asp | Glu | Leu | Tyr | Lys | Ser |      |
| 225 |     |     |     | 230 |     |     |     |     | 235 |     |     |     |     | 240 |     |      |

```
gga ctc aga tct cga gct caa gct tcg aat tct gca gtc gac ggt acc       768
Gly Leu Arg Ser Arg Ala Gln Ala Ser Asn Ser Ala Val Asp Gly Thr
            245                 250                 255 gcg ggc ccg ctg tac gac gaa gtc gat aag gat ccg atg gcc tcc tcc       816
Ala Gly Pro Leu Tyr Asp Glu Val Asp Lys Asp Pro Met Ala Ser Ser
        260                 265                 270 gag gac gtc atc aag gag ttc atg cgc ttc aag gtg cgc atg gag ggc       864
Glu Asp Val Ile Lys Glu Phe Met Arg Phe Lys Val Arg Met Glu Gly
    275                 280                 285 tcc gtg aac ggc cac gag ttc gag atc gag ggc gag ggc gag ggc cgc       912
Ser Val Asn Gly His Glu Phe Glu Ile Glu Gly Glu Gly Glu Gly Arg
290                 295                 300 ccc tac gag ggc acc cag acc gcc aag ctg aag gtg acc aag ggc ggc       960
Pro Tyr Glu Gly Thr Gln Thr Ala Lys Leu Lys Val Thr Lys Gly Gly
305                 310                 315                 320 ccc ctg ccc ttc gcc tgg gac atc ctg tcc cct cag ttc cag tac ggc      1008
Pro Leu Pro Phe Ala Trp Asp Ile Leu Ser Pro Gln Phe Gln Tyr Gly
            325                 330                 335 tcc aag gcc tac gtg aag cac ccc gcc gac atc ccc gac tac ttg aag      1056
Ser Lys Ala Tyr Val Lys His Pro Ala Asp Ile Pro Asp Tyr Leu Lys
        340                 345                 350 ctg tcc ttc ccc gag ggc ttc aag tgg gag cgc gtg atg aac ttc gag      1104
Leu Ser Phe Pro Glu Gly Phe Lys Trp Glu Arg Val Met Asn Phe Glu
    355                 360                 365 gac ggc ggc gtg gtg acc gtg acc cag gac tcc tcc ctg cag gac ggc      1152
Asp Gly Gly Val Val Thr Val Thr Gln Asp Ser Ser Leu Gln Asp Gly
370                 375                 380 gag ttc atc tac aag gtg aag ctg cgc ggc acc aac ttc ccc tcc gac      1200
Glu Phe Ile Tyr Lys Val Lys Leu Arg Gly Thr Asn Phe Pro Ser Asp
385                 390                 395                 400 ggc ccc gta atg cag aag aag acc atg ggc tgg gag gcc tcc acc gag      1248
Gly Pro Val Met Gln Lys Lys Thr Met Gly Trp Glu Ala Ser Thr Glu
            405                 410                 415 cgg atg tac ccc gag gac ggc gcc ctg aag ggc gag atc aag atg agg      1296
Arg Met Tyr Pro Glu Asp Gly Ala Leu Lys Gly Glu Ile Lys Met Arg
        420                 425                 430 ctg aag ctg aag gac ggc ggc cac tac gac gcc gag gtc aag acc acc      1344
Leu Lys Leu Lys Asp Gly Gly His Tyr Asp Ala Glu Val Lys Thr Thr
    435                 440                 445 tac atg gcc aag aag ccc gtg cag ctg ccc ggc gcc tac aag acc gac      1392
Tyr Met Ala Lys Lys Pro Val Gln Leu Pro Gly Ala Tyr Lys Thr Asp
450                 455                 460 atc aag ctg gac atc acc tcc cac aac gag gac tac acc atc gtg gaa      1440
Ile Lys Leu Asp Ile Thr Ser His Asn Glu Asp Tyr Thr Ile Val Glu
465                 470                 475                 480 cag tac gag cgc gcc gag ggc cgc cac tcc acc ggc gcc tcc gga ctc      1488
Gln Tyr Glu Arg Ala Glu Gly Arg His Ser Thr Gly Ala Ser Gly Leu
            485                 490                 495 aga tct cga gct caa gct tcg aat tct gca gtc gac ggt acc gcg ggc      1536
Arg Ser Arg Ala Gln Ala Ser Asn Ser Ala Val Asp Gly Thr Ala Gly
        500                 505                 510 ccg ctg tac gac gaa gtc ggt aag gat ccg atg gcc tcc tcc gag gac      1584
Pro Leu Tyr Asp Glu Val Gly Lys Asp Pro Met Ala Ser Ser Glu Asp
    515                 520                 525 gtc atc aag gag ttc atg cgc ttc aag gtg cgc atg gag ggc tcc gtg      1632
Val Ile Lys Glu Phe Met Arg Phe Lys Val Arg Met Glu Gly Ser Val
530                 535                 540 aac ggc cac gag ttc gag atc gag ggc gag ggc gag ggc cgc ccc tac      1680
```

```
Asn Gly His Glu Phe Glu Ile Glu Gly Glu Gly Arg Pro Tyr
545                 550                 555                 560 gag ggc acc cag acc gcc aag ctg aag gtg acc aag ggc ggc ccc ctg        1728
Glu Gly Thr Gln Thr Ala Lys Leu Lys Val Thr Lys Gly Gly Pro Leu
        565                 570                 575 ccc ttc gcc tgg gac atc ctg tcc cct cag ttc cag tac ggc tcc aag        1776
Pro Phe Ala Trp Asp Ile Leu Ser Pro Gln Phe Gln Tyr Gly Ser Lys
                580                 585                 590 gcc tac gtg aag cac ccc gcc gac atc ccc gac tac ttg aag ctg tcc        1824
Ala Tyr Val Lys His Pro Ala Asp Ile Pro Asp Tyr Leu Lys Leu Ser
            595                 600                 605 ttc ccc gag ggc ttc aag tgg gag cgc gtg atg aac ttc gag gac ggc        1872
Phe Pro Glu Gly Phe Lys Trp Glu Arg Val Met Asn Phe Glu Asp Gly
        610                 615                 620 ggc gtg gtg acc gtg acc cag gac tcc tcc ctg cag gac ggc gag ttc        1920
Gly Val Val Thr Val Thr Gln Asp Ser Ser Leu Gln Asp Gly Glu Phe
625                 630                 635                 640 atc tac aag gtg aag ctg cgc ggc acc aac ttc ccc tcc gac ggc ccc        1968
Ile Tyr Lys Val Lys Leu Arg Gly Thr Asn Phe Pro Ser Asp Gly Pro
                645                 650                 655 gta atg cag aag aag acc atg ggc tgg gag gcc tcc acc gag cgg atg        2016
Val Met Gln Lys Lys Thr Met Gly Trp Glu Ala Ser Thr Glu Arg Met
            660                 665                 670 tac ccc gag gac ggc gcc ctg aag ggc gag atc aag atg agg ctg aag        2064
Tyr Pro Glu Asp Gly Ala Leu Lys Gly Glu Ile Lys Met Arg Leu Lys
        675                 680                 685 ctg aag gac ggc ggc cac tac gac gcc gag gtc aag acc acc tac atg        2112
Leu Lys Asp Gly Gly His Tyr Asp Ala Glu Val Lys Thr Thr Tyr Met
    690                 695                 700 gcc aag aag ccc gtg cag ctg ccc ggc gcc tac aag acc gac atc aag        2160
Ala Lys Lys Pro Val Gln Leu Pro Gly Ala Tyr Lys Thr Asp Ile Lys
705                 710                 715                 720 ctg gac atc acc tcc cac aac gag gac tac acc atc gtg gaa cag tac        2208
Leu Asp Ile Thr Ser His Asn Glu Asp Tyr Thr Ile Val Glu Gln Tyr
                725                 730                 735 gag cgc gcc gag ggc cgc cac tcc acc ggc gcc                            2241
Glu Arg Ala Glu Gly Arg His Ser Thr Gly Ala
            740                 745

<210> SEQ ID NO 51
<211> LENGTH: 507
<212> TYPE: PRT
<213> ORGANISM: Montipora sp.

<400> SEQUENCE: 51

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Val Ser Lys Gly Glu Glu Leu Phe Thr Gly Val Val Pro Ile
        35                  40                  45

Leu Val Glu Leu Asp Gly Asp Val Asn Gly His Lys Phe Ser Val Ser
    50                  55                  60

Gly Glu Gly Glu Gly Asp Ala Thr Tyr Gly Lys Leu Thr Leu Lys Phe
65                  70                  75                  80

Ile Cys Thr Thr Gly Lys Leu Pro Val Pro Trp Pro Thr Leu Val Thr
                85                  90                  95

Thr Leu Thr Trp Gly Val Gln Cys Phe Ser Arg Tyr Pro Asp His Met
            100                 105                 110
```

```
Lys Gln His Asp Phe Phe Lys Ser Ala Met Pro Gly Tyr Val Gln
        115                 120                 125

Glu Arg Thr Ile Phe Phe Lys Asp Asp Gly Asn Tyr Lys Thr Arg Ala
130                 135                 140

Glu Val Lys Phe Glu Gly Asp Thr Leu Val Asn Arg Ile Glu Leu Lys
145                 150                 155                 160

Gly Ile Asp Phe Lys Glu Asp Gly Asn Ile Leu Gly His Lys Leu Glu
                165                 170                 175

Tyr Asn Tyr Ile Ser His Asn Val Tyr Ile Thr Ala Asp Lys Gln Lys
                180                 185                 190

Asn Gly Ile Lys Ala Asn Phe Lys Ile Arg His Asn Ile Glu Asp Gly
            195                 200                 205

Ser Val Gln Leu Ala Asp His Tyr Gln Gln Asn Thr Pro Ile Gly Asp
210                 215                 220

Gly Pro Val Leu Leu Pro Asp Asn His Tyr Leu Ser Thr Gln Ser Ala
225                 230                 235                 240

Leu Ser Lys Asp Pro Asn Glu Lys Arg Asp His Met Val Leu Leu Glu
                245                 250                 255

Phe Val Thr Ala Ala Gly Ile Thr Leu Gly Met Asp Glu Leu Tyr Lys
                260                 265                 270

Ser Ser Ser Glu Leu Ser Gly Asp Glu Val Asp Gly Thr Met Val Ser
                275                 280                 285

Val Ile Ala Lys Gln Met Thr Tyr Lys Val Tyr Met Ser Gly Thr Val
290                 295                 300

Asn Gly His Tyr Phe Glu Val Glu Gly Asp Gly Lys Gly Lys Pro Tyr
305                 310                 315                 320

Glu Gly Glu Gln Thr Val Lys Leu Thr Val Thr Lys Gly Gly Pro Leu
                325                 330                 335

Pro Phe Ala Trp Asp Ile Leu Ser Pro Leu Phe Gln Tyr Gly Ser Ile
                340                 345                 350

Pro Phe Thr Lys Tyr Pro Glu Asp Ile Pro Asp Tyr Val Lys Gln Ser
                355                 360                 365

Phe Pro Glu Gly Tyr Thr Trp Glu Arg Thr Met Asn Phe Glu Asp Gly
            370                 375                 380

Ala Val Cys Thr Val Ser Asn Asp Ser Ser Ile Gln Gly Asn Cys Phe
385                 390                 395                 400

Ile Tyr Asn Val Lys Ile Ser Gly Thr Asn Phe Pro Pro Asn Gly Pro
                405                 410                 415

Val Met Gln Lys Lys Thr Gln Gly Trp Glu Pro Ser Thr Glu Arg Leu
                420                 425                 430

Phe Ala Arg Asp Gly Met Leu Ile Gly Asn Asp Tyr Met Ala Leu Lys
            435                 440                 445

Leu Glu Gly Gly Gly His Tyr Leu Cys Glu Phe Lys Ser Thr Tyr Lys
    450                 455                 460

Ala Lys Lys Pro Val Arg Met Pro Gly Tyr His Tyr Ile Asp Arg Lys
465                 470                 475                 480

Leu Asp Val Thr Ser His Asn Arg Asp Tyr Thr Ser Val Glu Gln Cys
                485                 490                 495

Glu Ile Ala Ile Ala Arg His Ser Leu Leu Gly
                500                 505

<210> SEQ ID NO 52
<211> LENGTH: 1521
<212> TYPE: DNA
<213> ORGANISM: Montipora sp.
```

<220> FEATURE:
<221> NAME/KEY: CDS
<222> LOCATION: (1)..(1521)

<400> SEQUENCE: 52

```
atg cgg ggt tct cat cat cat cat cat cat ggt atg gct agc atg act      48
Met Arg Gly Ser His His His His His His Gly Met Ala Ser Met Thr
1               5                   10                  15 ggt gga cag caa atg ggt cgg gat ctg tac gac gat gac gat aag gat      96
Gly Gly Gln Gln Met Gly Arg Asp Leu Tyr Asp Asp Asp Asp Lys Asp
            20                  25                  30 ccc atg gtg agc aag ggc gag gag ctg ttc acc ggg gtg gtg ccc atc     144
Pro Met Val Ser Lys Gly Glu Glu Leu Phe Thr Gly Val Val Pro Ile
        35                  40                  45 ctg gtc gag ctg gac ggc gac gta aac ggc cac aag ttc agc gtg tcc     192
Leu Val Glu Leu Asp Gly Asp Val Asn Gly His Lys Phe Ser Val Ser
    50                  55                  60 ggc gag ggc gag ggc gat gcc acc tac ggc aag ctg acc ctg aag ttc     240
Gly Glu Gly Glu Gly Asp Ala Thr Tyr Gly Lys Leu Thr Leu Lys Phe
65                  70                  75                  80 atc tgc acc acc ggc aag ctg ccc gtg ccc tgg ccc acc ctc gtg acc     288
Ile Cys Thr Thr Gly Lys Leu Pro Val Pro Trp Pro Thr Leu Val Thr
                85                  90                  95 acc ctg acc tgg ggc gtg cag tgc ttc agc cgc tac ccc gac cac atg     336
Thr Leu Thr Trp Gly Val Gln Cys Phe Ser Arg Tyr Pro Asp His Met
            100                 105                 110 aag cag cac gac ttc ttc aag tcc gcc atg ccc gaa ggc tac gtc cag     384
Lys Gln His Asp Phe Phe Lys Ser Ala Met Pro Glu Gly Tyr Val Gln
        115                 120                 125 gag cgc acc atc ttc ttc aag gac gac ggc aac tac aag acc cgc gcc     432
Glu Arg Thr Ile Phe Phe Lys Asp Asp Gly Asn Tyr Lys Thr Arg Ala
    130                 135                 140 gag gtg aag ttc gag ggc gac acc ctg gtg aac cgc atc gag ctg aag     480
Glu Val Lys Phe Glu Gly Asp Thr Leu Val Asn Arg Ile Glu Leu Lys
145                 150                 155                 160 ggc atc gac ttc aag gag gac ggc aac atc ctg ggg cac aag ctg gag     528
Gly Ile Asp Phe Lys Glu Asp Gly Asn Ile Leu Gly His Lys Leu Glu
                165                 170                 175 tac aac tac atc agc cac aac gtc tat atc acc gcc gac aag cag aag     576
Tyr Asn Tyr Ile Ser His Asn Val Tyr Ile Thr Ala Asp Lys Gln Lys
            180                 185                 190 aac ggc atc aag gcc aac ttc aag atc cgc cac aac atc gag gac ggc     624
Asn Gly Ile Lys Ala Asn Phe Lys Ile Arg His Asn Ile Glu Asp Gly
        195                 200                 205 agc gtg cag ctc gcc gac cac tac cag cag aac acc ccc atc ggc gac     672
Ser Val Gln Leu Ala Asp His Tyr Gln Gln Asn Thr Pro Ile Gly Asp
    210                 215                 220 ggc ccc gtg ctg ctg ccc gac aac cac tac ctg agc acc cag tcc gcc     720
Gly Pro Val Leu Leu Pro Asp Asn His Tyr Leu Ser Thr Gln Ser Ala
225                 230                 235                 240 ctg agc aaa gac ccc aac gag aag cgc gat cac atg gtc ctg ctg gag     768
Leu Ser Lys Asp Pro Asn Glu Lys Arg Asp His Met Val Leu Leu Glu
                245                 250                 255 ttc gtg acc gcc gcc ggg atc act ctc ggc atg gac gag ctg tac aag     816
Phe Val Thr Ala Ala Gly Ile Thr Leu Gly Met Asp Glu Leu Tyr Lys
            260                 265                 270 tcc tcg tcc gag ctc agc gga gat gag gtc gat ggt acc atg gtg agt     864
Ser Ser Ser Glu Leu Ser Gly Asp Glu Val Asp Gly Thr Met Val Ser
        275                 280                 285 gtg atc gct aaa caa atg acc tac aag gtt tat atg tca ggc acg gtc     912
Val Ile Ala Lys Gln Met Thr Tyr Lys Val Tyr Met Ser Gly Thr Val
```

```
                    290                 295                 300
aat gga cac tac ttt gag gtc gaa ggc gat gga aaa gga aag cct tac      960
Asn Gly His Tyr Phe Glu Val Glu Gly Asp Gly Lys Gly Lys Pro Tyr
305                 310                 315                 320 gag gga gag cag aca gta aag ctc act gtc acc aag ggt gga cct ctg     1008
Glu Gly Glu Gln Thr Val Lys Leu Thr Val Thr Lys Gly Gly Pro Leu
                325                 330                 335 cca ttt gct tgg gat att tta tca cca ctg ttt cag tac gga agc ata     1056
Pro Phe Ala Trp Asp Ile Leu Ser Pro Leu Phe Gln Tyr Gly Ser Ile
            340                 345                 350 cca ttc acc aag tac cct gaa gac atc cct gat tat gta aag cag tca     1104
Pro Phe Thr Lys Tyr Pro Glu Asp Ile Pro Asp Tyr Val Lys Gln Ser
        355                 360                 365 ttc cct gag gga tat aca tgg gag agg acc atg aac ttt gaa gat ggt     1152
Phe Pro Glu Gly Tyr Thr Trp Glu Arg Thr Met Asn Phe Glu Asp Gly
    370                 375                 380 gca gtg tgt act gtc agc aat gat tcc agc atc caa ggc aac tgt ttc     1200
Ala Val Cys Thr Val Ser Asn Asp Ser Ser Ile Gln Gly Asn Cys Phe
385                 390                 395                 400 atc tac aat gtc aaa atc tct ggt acg aac ttt cct ccc aat gga cct     1248
Ile Tyr Asn Val Lys Ile Ser Gly Thr Asn Phe Pro Pro Asn Gly Pro
                405                 410                 415 gtt atg cag aag aag aca cag ggc tgg gaa ccc agc act gag cgt ctc     1296
Val Met Gln Lys Lys Thr Gln Gly Trp Glu Pro Ser Thr Glu Arg Leu
            420                 425                 430 ttt gca cga gat gga atg ctg ata gga aac gat tat atg gct ctg aag     1344
Phe Ala Arg Asp Gly Met Leu Ile Gly Asn Asp Tyr Met Ala Leu Lys
        435                 440                 445 ttg gaa gga ggt ggt cac tat ttg tgt gaa ttt aaa tct act tac aag     1392
Leu Glu Gly Gly Gly His Tyr Leu Cys Glu Phe Lys Ser Thr Tyr Lys
    450                 455                 460 gca aag aag cct gtg agg atg cca ggg tat cac tat att gac cgc aaa     1440
Ala Lys Lys Pro Val Arg Met Pro Gly Tyr His Tyr Ile Asp Arg Lys
465                 470                 475                 480 ctg gat gta acc agt cac aac agg gat tac aca tct gtt gag cag tgt     1488
Leu Asp Val Thr Ser His Asn Arg Asp Tyr Thr Ser Val Glu Gln Cys
                485                 490                 495 gaa ata gcc att gca cgc cac tct ttg ctc ggt                         1521
Glu Ile Ala Ile Ala Arg His Ser Leu Leu Gly
            500                 505
```

<210> SEQ ID NO 53
<211> LENGTH: 507
<212> TYPE: PRT
<213> ORGANISM: Montipora sp.

<400> SEQUENCE: 53

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Val Ser Val Ile Ala Lys Gln Met Thr Tyr Lys Val Tyr Met
        35                  40                  45

Ser Gly Thr Val Asn Gly His Tyr Phe Glu Val Glu Gly Asp Gly Lys
    50                  55                  60

Gly Lys Pro Tyr Glu Gly Glu Gln Thr Val Lys Leu Thr Val Thr Lys
65                  70                  75                  80

Gly Gly Pro Leu Pro Phe Ala Trp Asp Ile Leu Ser Pro Leu Phe Gln
                85                  90                  95
```

-continued

```
Tyr Gly Ser Ile Pro Phe Thr Lys Tyr Pro Glu Asp Ile Pro Asp Tyr
            100                 105                 110

Val Lys Gln Ser Phe Pro Glu Gly Tyr Thr Trp Glu Arg Thr Met Asn
            115                 120                 125

Phe Glu Asp Gly Ala Val Cys Thr Val Ser Asn Asp Ser Ser Ile Gln
130                 135                 140

Gly Asn Cys Phe Ile Tyr Asn Val Lys Ile Ser Gly Thr Asn Phe Pro
145                 150                 155                 160

Pro Asn Gly Pro Val Met Gln Lys Lys Thr Gln Gly Trp Glu Pro Ser
                165                 170                 175

Thr Glu Arg Leu Phe Ala Arg Asp Gly Met Leu Ile Gly Asn Asp Tyr
            180                 185                 190

Met Ala Leu Lys Leu Glu Gly Gly His Tyr Leu Cys Glu Phe Lys
            195                 200                 205

Ser Thr Tyr Lys Ala Lys Lys Pro Val Arg Met Pro Gly Tyr His Tyr
            210                 215                 220

Ile Asp Arg Lys Leu Asp Val Thr Ser His Asn Arg Asp Tyr Thr Ser
225                 230                 235                 240

Val Glu Gln Cys Glu Ile Ala Ile Ala Arg His Ser Leu Leu Gly Ser
                245                 250                 255

Ser Ser Glu Leu Ser Gly Asp Glu Val Asp Gly Thr Met Val Ser Lys
            260                 265                 270

Gly Glu Glu Leu Phe Thr Gly Val Val Pro Ile Leu Val Glu Leu Asp
            275                 280                 285

Gly Asp Val Asn Gly His Lys Phe Ser Val Ser Gly Glu Gly Glu Gly
            290                 295                 300

Asp Ala Thr Tyr Gly Lys Leu Thr Leu Lys Phe Ile Cys Thr Thr Gly
305                 310                 315                 320

Lys Leu Pro Val Pro Trp Pro Thr Leu Val Thr Thr Leu Thr Trp Gly
                325                 330                 335

Val Gln Cys Phe Ser Arg Tyr Pro Asp His Met Lys Gln His Asp Phe
            340                 345                 350

Phe Lys Ser Ala Met Pro Glu Gly Tyr Val Gln Glu Arg Thr Ile Phe
            355                 360                 365

Phe Lys Asp Asp Gly Asn Tyr Lys Thr Arg Ala Glu Val Lys Phe Glu
            370                 375                 380

Gly Asp Thr Leu Val Asn Arg Ile Glu Leu Lys Gly Ile Asp Phe Lys
385                 390                 395                 400

Glu Asp Gly Asn Ile Leu Gly His Lys Leu Glu Tyr Asn Tyr Ile Ser
                405                 410                 415

His Asn Val Tyr Ile Thr Ala Asp Lys Gln Lys Asn Gly Ile Lys Ala
            420                 425                 430

Asn Phe Lys Ile Arg His Asn Ile Glu Asp Gly Ser Val Gln Leu Ala
            435                 440                 445

Asp His Tyr Gln Gln Asn Thr Pro Ile Gly Asp Gly Pro Val Leu Leu
450                 455                 460

Pro Asp Asn His Tyr Leu Ser Thr Gln Ser Ala Leu Ser Lys Asp Pro
465                 470                 475                 480

Asn Glu Lys Arg Asp His Met Val Leu Leu Glu Phe Val Thr Ala Ala
                485                 490                 495

Gly Ile Thr Leu Gly Met Asp Glu Leu Tyr Lys
            500                 505
```

<210> SEQ ID NO 54

```
<211> LENGTH: 1521
<212> TYPE: DNA
<213> ORGANISM: Montipora sp.
<220> FEATURE:
<221> NAME/KEY: CDS
<222> LOCATION: (1)..(1521)

<400> SEQUENCE: 54
```

| | | | | | | | | | | | | | | | | |
|---|---|---|---|---|---|---|---|---|---|---|---|---|---|---|---|---|
| atg | cgg | ggt | tct | cat | cat | cat | cat | cat | cat | ggt | atg | gct | agc | atg | act | 48 |
| Met | Arg | Gly | Ser | His | His | His | His | His | His | Gly | Met | Ala | Ser | Met | Thr | |
| 1 | | | | 5 | | | | | 10 | | | | | 15 | | |
| ggt | gga | cag | caa | atg | ggt | cgg | gat | ctg | tac | gac | gat | gac | gat | aag | gat | 96 |
| Gly | Gly | Gln | Gln | Met | Gly | Arg | Asp | Leu | Tyr | Asp | Asp | Asp | Asp | Lys | Asp | |
| | | | 20 | | | | | 25 | | | | | 30 | | | |
| ccc | atg | gtg | agt | gtg | atc | gct | aaa | caa | atg | acc | tac | aag | gtt | tat | atg | 144 |
| Pro | Met | Val | Ser | Val | Ile | Ala | Lys | Gln | Met | Thr | Tyr | Lys | Val | Tyr | Met | |
| | | | 35 | | | | | 40 | | | | | 45 | | | |
| tca | ggc | acg | gtc | aat | gga | cac | tac | ttt | gag | gtc | gaa | ggc | gat | gga | aaa | 192 |
| Ser | Gly | Thr | Val | Asn | Gly | His | Tyr | Phe | Glu | Val | Glu | Gly | Asp | Gly | Lys | |
| | 50 | | | | | 55 | | | | | 60 | | | | | |
| gga | aag | cct | tac | gag | gga | gag | cag | aca | gta | aag | ctc | act | gtc | acc | aag | 240 |
| Gly | Lys | Pro | Tyr | Glu | Gly | Glu | Gln | Thr | Val | Lys | Leu | Thr | Val | Thr | Lys | |
| 65 | | | | | 70 | | | | | 75 | | | | | 80 | |
| ggt | gga | cct | ctg | cca | ttt | gct | tgg | gat | att | tta | tca | cca | ctg | ttt | cag | 288 |
| Gly | Gly | Pro | Leu | Pro | Phe | Ala | Trp | Asp | Ile | Leu | Ser | Pro | Leu | Phe | Gln | |
| | | | | 85 | | | | | 90 | | | | | 95 | | |
| tac | gga | agc | ata | cca | ttc | acc | aag | tac | cct | gaa | gac | atc | cct | gat | tat | 336 |
| Tyr | Gly | Ser | Ile | Pro | Phe | Thr | Lys | Tyr | Pro | Glu | Asp | Ile | Pro | Asp | Tyr | |
| | | | 100 | | | | | 105 | | | | | 110 | | | |
| gta | aag | cag | tca | ttc | cct | gag | gga | tat | aca | tgg | gag | agg | acc | atg | aac | 384 |
| Val | Lys | Gln | Ser | Phe | Pro | Glu | Gly | Tyr | Thr | Trp | Glu | Arg | Thr | Met | Asn | |
| | | | | 115 | | | | | 120 | | | | | 125 | | |
| ttt | gaa | gat | ggt | gca | gtg | tgt | act | gtc | agc | aat | gat | tcc | agc | atc | caa | 432 |
| Phe | Glu | Asp | Gly | Ala | Val | Cys | Thr | Val | Ser | Asn | Asp | Ser | Ser | Ile | Gln | |
| | 130 | | | | | 135 | | | | | 140 | | | | | |
| ggc | aac | tgt | ttc | atc | tac | aat | gtc | aaa | atc | tct | ggt | acg | aac | ttt | cct | 480 |
| Gly | Asn | Cys | Phe | Ile | Tyr | Asn | Val | Lys | Ile | Ser | Gly | Thr | Asn | Phe | Pro | |
| 145 | | | | | 150 | | | | | 155 | | | | | 160 | |
| ccc | aat | gga | cct | gtt | atg | cag | aag | aag | aca | cag | ggc | tgg | gaa | ccc | agc | 528 |
| Pro | Asn | Gly | Pro | Val | Met | Gln | Lys | Lys | Thr | Gln | Gly | Trp | Glu | Pro | Ser | |
| | | | | 165 | | | | | 170 | | | | | 175 | | |
| act | gag | cgt | ctc | ttt | gca | cga | gat | gga | atg | ctg | ata | gga | aac | gat | tat | 576 |
| Thr | Glu | Arg | Leu | Phe | Ala | Arg | Asp | Gly | Met | Leu | Ile | Gly | Asn | Asp | Tyr | |
| | | | 180 | | | | | 185 | | | | | 190 | | | |
| atg | gct | ctg | aag | ttg | gaa | gga | ggt | ggt | cac | tat | ttg | tgt | gaa | ttt | aaa | 624 |
| Met | Ala | Leu | Lys | Leu | Glu | Gly | Gly | Gly | His | Tyr | Leu | Cys | Glu | Phe | Lys | |
| | | | | 195 | | | | | 200 | | | | | 205 | | |
| tct | act | tac | aag | gca | aag | aag | cct | gtg | agg | atg | cca | ggg | tat | cac | tat | 672 |
| Ser | Thr | Tyr | Lys | Ala | Lys | Lys | Pro | Val | Arg | Met | Pro | Gly | Tyr | His | Tyr | |
| | 210 | | | | | 215 | | | | | 220 | | | | | |
| att | gac | cgc | aaa | ctg | gat | gta | acc | agt | cac | aac | agg | gat | tac | aca | tct | 720 |
| Ile | Asp | Arg | Lys | Leu | Asp | Val | Thr | Ser | His | Asn | Arg | Asp | Tyr | Thr | Ser | |
| 225 | | | | | 230 | | | | | 235 | | | | | 240 | |
| gtt | gag | cag | tgt | gaa | ata | gcc | att | gca | cgc | cac | tct | ttg | ctc | ggt | tcc | 768 |
| Val | Glu | Gln | Cys | Glu | Ile | Ala | Ile | Ala | Arg | His | Ser | Leu | Leu | Gly | Ser | |
| | | | | 245 | | | | | 250 | | | | | 255 | | |
| tcg | tcc | gag | ctc | agc | gga | gat | gag | gtc | gat | ggt | acc | atg | gtg | agc | aag | 816 |
| Ser | Ser | Glu | Leu | Ser | Gly | Asp | Glu | Val | Asp | Gly | Thr | Met | Val | Ser | Lys | |
| | | | 260 | | | | | 265 | | | | | 270 | | | |
| ggc | gag | gag | ctg | ttc | acc | ggg | gtg | gtg | ccc | atc | ctg | gtc | gag | ctg | gac | 864 |
| Gly | Glu | Glu | Leu | Phe | Thr | Gly | Val | Val | Pro | Ile | Leu | Val | Glu | Leu | Asp | |
| | | | | 275 | | | | | 280 | | | | | 285 | | |

```
ggc gac gta aac ggc cac aag ttc agc gtg tcc ggc gag ggc gag ggc         912
Gly Asp Val Asn Gly His Lys Phe Ser Val Ser Gly Glu Gly Glu Gly
        290                 295                 300 gat gcc acc tac ggc aag ctg acc ctg aag ttc atc tgc acc acc ggc         960
Asp Ala Thr Tyr Gly Lys Leu Thr Leu Lys Phe Ile Cys Thr Thr Gly
305                 310                 315                 320 aag ctg ccc gtg ccc tgg ccc acc ctc gtg acc acc ctg acc tgg ggc        1008
Lys Leu Pro Val Pro Trp Pro Thr Leu Val Thr Thr Leu Thr Trp Gly
                325                 330                 335 gtg cag tgc ttc agc cgc tac ccc gac cac atg aag cag cac gac ttc        1056
Val Gln Cys Phe Ser Arg Tyr Pro Asp His Met Lys Gln His Asp Phe
            340                 345                 350 ttc aag tcc gcc atg ccc gaa ggc tac gtc cag gag cgc acc atc ttc        1104
Phe Lys Ser Ala Met Pro Glu Gly Tyr Val Gln Glu Arg Thr Ile Phe
        355                 360                 365 ttc aag gac gac ggc aac tac aag acc cgc gcc gag gtg aag ttc gag        1152
Phe Lys Asp Asp Gly Asn Tyr Lys Thr Arg Ala Glu Val Lys Phe Glu
370                 375                 380 ggc gac acc ctg gtg aac cgc atc gag ctg aag ggc atc gac ttc aag        1200
Gly Asp Thr Leu Val Asn Arg Ile Glu Leu Lys Gly Ile Asp Phe Lys
385                 390                 395                 400 gag gac ggc aac atc ctg ggg cac aag ctg gag tac aac tac atc agc        1248
Glu Asp Gly Asn Ile Leu Gly His Lys Leu Glu Tyr Asn Tyr Ile Ser
                405                 410                 415 cac aac gtc tat atc acc gcc gac aag cag aag aac ggc atc aag gcc        1296
His Asn Val Tyr Ile Thr Ala Asp Lys Gln Lys Asn Gly Ile Lys Ala
            420                 425                 430 aac ttc aag atc cgc cac aac atc gag gac ggc agc gtg cag ctc gcc        1344
Asn Phe Lys Ile Arg His Asn Ile Glu Asp Gly Ser Val Gln Leu Ala
        435                 440                 445 gac cac tac cag cag aac acc ccc atc ggc gac ggc ccc gtg ctg ctg        1392
Asp His Tyr Gln Gln Asn Thr Pro Ile Gly Asp Gly Pro Val Leu Leu
    450                 455                 460 ccc gac aac cac tac ctg agc acc cag tcc gcc ctg agc aaa gac ccc        1440
Pro Asp Asn His Tyr Leu Ser Thr Gln Ser Ala Leu Ser Lys Asp Pro
465                 470                 475                 480 aac gag aag cgc gat cac atg gtc ctg ctg gag ttc gtg acc gcc gcc        1488
Asn Glu Lys Arg Asp His Met Val Leu Leu Glu Phe Val Thr Ala Ala
                485                 490                 495 ggg atc act ctc ggc atg gac gag ctg tac aag                            1521
Gly Ile Thr Leu Gly Met Asp Glu Leu Tyr Lys
            500                 505

<210> SEQ ID NO 55
<211> LENGTH: 411
<212> TYPE: PRT
<213> ORGANISM: Montipora sp.

<400> SEQUENCE: 55

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Val Ser Lys Gly Glu Glu Leu Phe Thr Gly Val Val Pro Ile
                35                  40                  45

Leu Val Glu Leu Asp Gly Asp Val Asn Gly His Arg Phe Ser Val Ser
        50                  55                  60

Gly Glu Gly Glu Gly Asp Ala Thr Tyr Gly Lys Leu Thr Leu Lys Phe
65                  70                  75                  80
```

```
Ile Cys Thr Thr Gly Lys Leu Pro Val Pro Trp Pro Thr Leu Val Thr
                85                  90                  95

Thr Leu Thr Trp Gly Val Gln Cys Phe Ser Arg Tyr Pro Asp His Met
            100                 105                 110

Lys Gln His Asp Phe Phe Lys Ser Ala Met Pro Glu Gly Tyr Val Gln
        115                 120                 125

Glu Arg Thr Ile Phe Phe Lys Asp Asp Gly Asn Tyr Lys Thr Arg Ala
    130                 135                 140

Glu Val Lys Phe Glu Gly Asp Thr Leu Val Asn Arg Ile Glu Leu Lys
145                 150                 155                 160

Gly Ile Asp Phe Lys Glu Asp Gly Asn Ile Leu Gly His Lys Leu Glu
                165                 170                 175

Tyr Asn Tyr Ile Ser His Asn Val Tyr Ile Thr Ala Asp Lys Gln Lys
            180                 185                 190

Asn Gly Ile Lys Ala His Phe Lys Ile Arg His Asn Ile Glu Asp Gly
        195                 200                 205

Ser Val Gln Leu Ala Asp His Tyr Gln Gln Asn Thr Pro Ile Gly Asp
    210                 215                 220

Gly Pro Val Leu Leu Pro Asp Asn His Tyr Leu Ser Thr Gln Ser Ala
225                 230                 235                 240

Leu Ser Lys Asp Pro Asn Glu Lys Arg Asp His Met Val Leu Leu Glu
                245                 250                 255

Phe Val Thr Ala Ala Arg Met His Asp Gln Leu Thr Glu Glu Gln Ile
            260                 265                 270

Ala Glu Phe Lys Glu Ala Phe Ser Leu Phe Asp Lys Asp Gly Asp Gly
        275                 280                 285

Thr Ile Thr Thr Lys Glu Leu Gly Thr Val Met Arg Ser Leu Gly Gln
    290                 295                 300

Asn Pro Thr Glu Ala Glu Leu Gln Asp Met Ile Asn Glu Val Asp Ala
305                 310                 315                 320

Asp Gly Asn Gly Thr Ile Tyr Phe Pro Glu Phe Leu Thr Met Met Ala
                325                 330                 335

Arg Lys Met Lys Asp Thr Asp Ser Glu Glu Ile Arg Glu Ala Phe
            340                 345                 350

Arg Val Phe Asp Lys Asp Gly Asn Gly Tyr Ile Ser Ala Ala Glu Leu
        355                 360                 365

Arg His Val Met Thr Asn Leu Gly Glu Lys Leu Thr Asp Glu Glu Val
    370                 375                 380

Asp Glu Met Ile Arg Glu Ala Asp Ile Asp Gly Asp Gly Gln Val Asn
385                 390                 395                 400

Tyr Glu Glu Phe Val Gln Met Met Thr Ala Lys
                405                 410

<210> SEQ ID NO 56
<211> LENGTH: 1233
<212> TYPE: DNA
<213> ORGANISM: Montipora sp.
<220> FEATURE:
<221> NAME/KEY: CDS
<222> LOCATION: (1)..(1233)

<400> SEQUENCE: 56 atg cgg ggt tct cat cat cat cat cat cat ggt atg gct agc atg act    48
Met Arg Gly Ser His His His His His His Gly Met Ala Ser Met Thr
 1               5                  10                  15 ggt gga cag caa atg ggt cgg gat ctg tac gac gat gac gat aag gat    96
Gly Gly Gln Gln Met Gly Arg Asp Leu Tyr Asp Asp Asp Asp Lys Asp
```

|  |  |  |  |  |  |  |  |  |  |  |  |  |  |  |  |
|---|---|---|---|---|---|---|---|---|---|---|---|---|---|---|---|
|  |  |  | 20 |  |  |  |  | 25 |  |  |  |  | 30 |  |  |

```
ccc atg gtg agc aag ggc gag gag ctg ttc acc ggg gtg gtc ccc atc       144
Pro Met Val Ser Lys Gly Glu Glu Leu Phe Thr Gly Val Val Pro Ile
        35                  40                  45 ctg gtc gag ctg gac ggc gac gta aac ggc cac agg ttc agc gtg tcc       192
Leu Val Glu Leu Asp Gly Asp Val Asn Gly His Arg Phe Ser Val Ser
 50                  55                  60 ggc gag ggc gag ggc gat gcc acc tac ggc aag ctg acc ctg aag ttc       240
Gly Glu Gly Glu Gly Asp Ala Thr Tyr Gly Lys Leu Thr Leu Lys Phe
 65                  70                  75                  80 atc tgc acc acc ggc aag ctg ccc gtg ccc tgg ccc acc ctc gtg acc       288
Ile Cys Thr Thr Gly Lys Leu Pro Val Pro Trp Pro Thr Leu Val Thr
                 85                  90                  95 acc ctg acc tgg ggc gtg cag tgc ttc agc cgc tac ccc gac cac atg       336
Thr Leu Thr Trp Gly Val Gln Cys Phe Ser Arg Tyr Pro Asp His Met
            100                 105                 110 aag cag cac gac ttc ttc aag tcc gcc atg ccc gaa ggc tac gtc cag       384
Lys Gln His Asp Phe Phe Lys Ser Ala Met Pro Glu Gly Tyr Val Gln
        115                 120                 125 gag cgc acc atc ttc ttc aag gac gac ggc aac tac aag acc cgc gcc       432
Glu Arg Thr Ile Phe Phe Lys Asp Asp Gly Asn Tyr Lys Thr Arg Ala
130                 135                 140 gag gtg aag ttc gag ggc gac acc ctg gtg aac cgc atc gag ctg aag       480
Glu Val Lys Phe Glu Gly Asp Thr Leu Val Asn Arg Ile Glu Leu Lys
145                 150                 155                 160 ggc atc gac ttc aag gag gac ggc aac atc ctg ggg cac aag ctg gag       528
Gly Ile Asp Phe Lys Glu Asp Gly Asn Ile Leu Gly His Lys Leu Glu
                165                 170                 175 tac aac tat atc agc cac aac gtc tat atc acc gcc gac aag cag aag       576
Tyr Asn Tyr Ile Ser His Asn Val Tyr Ile Thr Ala Asp Lys Gln Lys
            180                 185                 190 aac ggc atc aag gcc cac ttc aag atc cgc cac aac atc gag gac ggc       624
Asn Gly Ile Lys Ala His Phe Lys Ile Arg His Asn Ile Glu Asp Gly
        195                 200                 205 agc gtg cag ctc gcc gac cac tac cag cag aac acc ccc atc ggc gac       672
Ser Val Gln Leu Ala Asp His Tyr Gln Gln Asn Thr Pro Ile Gly Asp
210                 215                 220 ggc ccc gtg ctg ctg ccc gac aac cac tac ctg agc acc cag tcc gcc       720
Gly Pro Val Leu Leu Pro Asp Asn His Tyr Leu Ser Thr Gln Ser Ala
225                 230                 235                 240 ctg agc aaa gac ccc aac gag aag cgc gat cac atg gtc ctg ctg gag       768
Leu Ser Lys Asp Pro Asn Glu Lys Arg Asp His Met Val Leu Leu Glu
                245                 250                 255 ttc gtg acc gcc gcc cgc atg cat gac caa ctg aca gaa gag cag att       816
Phe Val Thr Ala Ala Arg Met His Asp Gln Leu Thr Glu Glu Gln Ile
            260                 265                 270 gca gag ttc aaa gaa gcc ttc tca tta ttc gac aag gat ggg gac ggc       864
Ala Glu Phe Lys Glu Ala Phe Ser Leu Phe Asp Lys Asp Gly Asp Gly
        275                 280                 285 acc atc acc aca aag gaa ctt ggc acc gtt atg agg tcg ctt gga caa       912
Thr Ile Thr Thr Lys Glu Leu Gly Thr Val Met Arg Ser Leu Gly Gln
290                 295                 300 aac cca acg gaa gca gaa ttg cag gat atg atc aat gaa gtc gat gct       960
Asn Pro Thr Glu Ala Glu Leu Gln Asp Met Ile Asn Glu Val Asp Ala
305                 310                 315                 320 gat ggc aat gga acg att tac ttt cct gaa ttt ctt act atg atg gct      1008
Asp Gly Asn Gly Thr Ile Tyr Phe Pro Glu Phe Leu Thr Met Met Ala
                325                 330                 335 aga aaa atg aag gac aca gac agc gaa gag gaa atc cga gaa gca ttc      1056
Arg Lys Met Lys Asp Thr Asp Ser Glu Glu Glu Ile Arg Glu Ala Phe
```

```
                        340                 345                 350
cgt gtt ttt gac aag gat ggg aac ggc tac atc agc gct gct gaa tta    1104
Arg Val Phe Asp Lys Asp Gly Asn Gly Tyr Ile Ser Ala Ala Glu Leu
        355                 360                 365 cgt cac gtc atg aca aac ctc ggg gag aag tta aca gat gaa gaa gtt    1152
Arg His Val Met Thr Asn Leu Gly Glu Lys Leu Thr Asp Glu Glu Val
370                 375                 380 gat gaa atg ata agg gaa gca gat atc gat ggt gat ggc caa gta aac    1200
Asp Glu Met Ile Arg Glu Ala Asp Ile Asp Gly Asp Gly Gln Val Asn
385                 390                 395                 400 tat gaa gag ttt gta caa atg atg aca gca aag                        1233
Tyr Glu Glu Phe Val Gln Met Met Thr Ala Lys
                405                 410

<210> SEQ ID NO 57
<211> LENGTH: 288
<212> TYPE: PRT
<213> ORGANISM: Montipora sp.

<400> SEQUENCE: 57

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Lys Arg Arg Trp Lys Lys Asn Phe Ile Ala Val Ser Ala Ala Asn
        35                  40                  45

Arg Phe Lys Lys Ile Ser Ser Ser Gly Ala Leu Gly Gly Gly Ser
    50                  55                  60

Glu Leu Met Val Ser Val Ile Ala Lys Gln Met Thr Tyr Lys Val Tyr
65                  70                  75                  80

Met Ser Gly Thr Val Asn Gly His Tyr Phe Glu Val Glu Gly Asp Gly
                85                  90                  95

Lys Gly Lys Pro Tyr Glu Gly Glu Gln Thr Val Lys Leu Thr Val Thr
            100                 105                 110

Lys Gly Gly Pro Leu Pro Phe Ala Trp Asp Ile Leu Ser Pro Leu Phe
        115                 120                 125

Gln Tyr Gly Ser Ile Pro Phe Thr Lys Tyr Pro Glu Asp Ile Pro Asp
    130                 135                 140

Tyr Val Lys Gln Ser Phe Pro Glu Gly Tyr Thr Trp Glu Arg Thr Met
145                 150                 155                 160

Asn Phe Glu Asp Gly Ala Val Cys Thr Val Ser Asn Asp Ser Ser Ile
                165                 170                 175

Gln Gly Asn Cys Phe Ile Tyr Asn Val Lys Ile Ser Gly Thr Asn Phe
            180                 185                 190

Pro Pro Asn Gly Pro Val Met Gln Lys Lys Thr Gln Gly Trp Glu Pro
        195                 200                 205

Ser Thr Glu Arg Leu Phe Ala Arg Asp Gly Met Leu Ile Gly Asn Asp
    210                 215                 220

Tyr Met Ala Leu Lys Leu Glu Gly Gly Gly His Tyr Leu Cys Glu Phe
225                 230                 235                 240

Lys Ser Thr Tyr Lys Ala Lys Lys Pro Val Arg Met Pro Gly Tyr His
                245                 250                 255

Tyr Ile Asp Arg Lys Leu Asp Val Thr Ser His Asn Arg Asp Tyr Thr
            260                 265                 270

Ser Val Glu Gln Cys Glu Ile Ala Ile Ala Arg His Ser Leu Leu Gly
        275                 280                 285
```

-continued

```
<210> SEQ ID NO 58
<211> LENGTH: 864
<212> TYPE: DNA
<213> ORGANISM: Montipora sp.
<220> FEATURE:
<221> NAME/KEY: CDS
<222> LOCATION: (1)..(864)

<400> SEQUENCE: 58
```

| | | | | | | | | | | | | | | | | |
|---|---|---|---|---|---|---|---|---|---|---|---|---|---|---|---|---|
| atg | cgg | ggt | tct | cat | cat | cat | cat | cat | cat | ggt | atg | gct | agc | atg | act | 48 |
| Met | Arg | Gly | Ser | His | His | His | His | His | His | Gly | Met | Ala | Ser | Met | Thr | |
| 1 | | | | 5 | | | | | 10 | | | | | 15 | | |
| ggt | gga | cag | caa | atg | ggt | cgg | gat | ctg | tac | gac | gat | gac | gat | aag | gat | 96 |
| Gly | Gly | Gln | Gln | Met | Gly | Arg | Asp | Leu | Tyr | Asp | Asp | Asp | Asp | Lys | Asp | |
| | | | 20 | | | | | 25 | | | | | 30 | | | |
| ccc | aag | agg | cgc | tgg | aag | aaa | aac | ttc | att | gcc | gtc | agc | gct | gcc | aac | 144 |
| Pro | Lys | Arg | Arg | Trp | Lys | Lys | Asn | Phe | Ile | Ala | Val | Ser | Ala | Ala | Asn | |
| | 35 | | | | | 40 | | | | | 45 | | | | | |
| cgg | ttc | aag | aag | atc | tcc | agc | tcc | ggg | gca | ctg | gga | ggt | gga | ggt | agt | 192 |
| Arg | Phe | Lys | Lys | Ile | Ser | Ser | Ser | Gly | Ala | Leu | Gly | Gly | Gly | Gly | Ser | |
| 50 | | | | | 55 | | | | | 60 | | | | | | |
| gag | ctc | atg | gtg | agt | gtg | atc | gct | aaa | caa | atg | acc | tac | aag | gtt | tat | 240 |
| Glu | Leu | Met | Val | Ser | Val | Ile | Ala | Lys | Gln | Met | Thr | Tyr | Lys | Val | Tyr | |
| 65 | | | | | 70 | | | | | 75 | | | | | 80 | |
| atg | tca | ggc | acg | gtc | aat | gga | cac | tac | ttt | gag | gtc | gaa | ggc | gat | gga | 288 |
| Met | Ser | Gly | Thr | Val | Asn | Gly | His | Tyr | Phe | Glu | Val | Glu | Gly | Asp | Gly | |
| | | | | 85 | | | | | 90 | | | | | 95 | | |
| aaa | gga | aag | cct | tac | gag | gga | gag | cag | aca | gta | aag | ctc | act | gtc | acc | 336 |
| Lys | Gly | Lys | Pro | Tyr | Glu | Gly | Glu | Gln | Thr | Val | Lys | Leu | Thr | Val | Thr | |
| | | | 100 | | | | | 105 | | | | | 110 | | | |
| aag | ggt | gga | cct | ctg | cca | ttt | gct | tgg | gat | att | tta | tca | cca | ctg | ttt | 384 |
| Lys | Gly | Gly | Pro | Leu | Pro | Phe | Ala | Trp | Asp | Ile | Leu | Ser | Pro | Leu | Phe | |
| | | 115 | | | | | 120 | | | | | 125 | | | | |
| cag | tac | gga | agc | ata | cca | ttc | acc | aag | tac | cct | gaa | gac | atc | cct | gat | 432 |
| Gln | Tyr | Gly | Ser | Ile | Pro | Phe | Thr | Lys | Tyr | Pro | Glu | Asp | Ile | Pro | Asp | |
| | 130 | | | | | 135 | | | | | 140 | | | | | |
| tat | gta | aag | cag | tca | ttc | cct | gag | gga | tat | aca | tgg | gag | agg | acc | atg | 480 |
| Tyr | Val | Lys | Gln | Ser | Phe | Pro | Glu | Gly | Tyr | Thr | Trp | Glu | Arg | Thr | Met | |
| 145 | | | | | 150 | | | | | 155 | | | | | 160 | |
| aac | ttt | gaa | gat | ggt | gca | gtg | tgt | act | gtc | agc | aat | gat | tcc | agc | atc | 528 |
| Asn | Phe | Glu | Asp | Gly | Ala | Val | Cys | Thr | Val | Ser | Asn | Asp | Ser | Ser | Ile | |
| | | | | 165 | | | | | 170 | | | | | 175 | | |
| caa | ggc | aac | tgt | ttc | atc | tac | aat | gtc | aaa | atc | tct | ggt | acg | aac | ttt | 576 |
| Gln | Gly | Asn | Cys | Phe | Ile | Tyr | Asn | Val | Lys | Ile | Ser | Gly | Thr | Asn | Phe | |
| | | | 180 | | | | | 185 | | | | | 190 | | | |
| cct | ccc | aat | gga | cct | gtt | atg | cag | aag | aag | aca | cag | ggc | tgg | gaa | ccc | 624 |
| Pro | Pro | Asn | Gly | Pro | Val | Met | Gln | Lys | Lys | Thr | Gln | Gly | Trp | Glu | Pro | |
| | | 195 | | | | | 200 | | | | | 205 | | | | |
| agc | act | gag | cgt | ctc | ttt | gca | cga | gat | gga | atg | ctg | ata | gga | aac | gat | 672 |
| Ser | Thr | Glu | Arg | Leu | Phe | Ala | Arg | Asp | Gly | Met | Leu | Ile | Gly | Asn | Asp | |
| | 210 | | | | | 215 | | | | | 220 | | | | | |
| tat | atg | gct | ctg | aag | ttg | gaa | gga | ggt | cac | tat | ttg | tgt | gaa | ttt | | 720 |
| Tyr | Met | Ala | Leu | Lys | Leu | Glu | Gly | Gly | His | Tyr | Leu | Cys | Glu | Phe | | |
| 225 | | | | | 230 | | | | | 235 | | | | | 240 | |
| aaa | tct | act | tac | aag | gca | aag | aag | cct | gtg | agg | atg | cca | ggg | tat | cac | 768 |
| Lys | Ser | Thr | Tyr | Lys | Ala | Lys | Lys | Pro | Val | Arg | Met | Pro | Gly | Tyr | His | |
| | | | | 245 | | | | | 250 | | | | | 255 | | |
| tat | att | gac | cgc | aaa | ctg | gat | gta | acc | agt | cac | aac | agg | gat | tac | aca | 816 |
| Tyr | Ile | Asp | Arg | Lys | Leu | Asp | Val | Thr | Ser | His | Asn | Arg | Asp | Tyr | Thr | |
| | | | 260 | | | | | 265 | | | | | 270 | | | |
| tct | gtt | gag | cag | tgt | gaa | ata | gcc | att | gca | cgc | cac | tct | ttg | ctc | ggt | 864 |

Ser Val Glu Gln Cys Glu Ile Ala Ile Ala Arg His Ser Leu Leu Gly
        275                 280                 285

<210> SEQ ID NO 59
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ccagagatga agatgaggta ctacatggac ggc                                  33

<210> SEQ ID NO 60
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
catgagttca caattgaagg tgaaggc                                         27

<210> SEQ ID NO 61
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gaaggcacag gcagacctta cgaggga                                         27

<210> SEQ ID NO 62
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ccaatgcctt tcgcgtttga cttagtg                                         27

<210> SEQ ID NO 63
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ttagtgtcac acgtgttctg ttacggc                                         27

<210> SEQ ID NO 64
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gaaaggtcgt tggagttcga agatggt                                         27

<210> SEQ ID NO 65
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gaagatggtg ggtccgcttc agtcagtgcg                                30

<210> SEQ ID NO 66
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
agccttagag gaaacacctt ctaccacaaa tcca                           34

<210> SEQ ID NO 67
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
caaatccaaa tttactgggg ttaactttcc tg                             32

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gccgatggtc ctatcatgca aaaccaaagt                                30

<210> SEQ ID NO 69
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gccgatggtc ctatcatgca aaaccaaagt gttgattggg agcca               45

<210> SEQ ID NO 70
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gagaaaatta ctgccagcga cggagttctg aag                            33

```
<210> SEQ ID NO 71
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gatgttacga tgtacctaaa acttgaagga ggcggcaatc ac                      42

<210> SEQ ID NO 72
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
cttaaaatgc caggaagcca ttacatcagc catcgcctcg tcagg                   45

<210> SEQ ID NO 73
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gatgcagtag ctcattccct cgagcaccac cacc                               34

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gaaggrtgyg tcaayggrca y                                             21

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
acvggdccat ydgvaagaaa rtt                                           23

<210> SEQ ID NO 76
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(25)
<223> OTHER INFORMATION: Inosine
<220> FEATURE:
<221> NAME/KEY: modified_base
<222> LOCATION: (29)..(30)
<223> OTHER INFORMATION: Inosine
```

```
<220> FEATURE:
<221> NAME/KEY: modified_base
<222> LOCATION: (34)..(35)
<223> OTHER INFORMATION: Inosine

<400> SEQUENCE: 76
ggccacgcgt cgactagtac gggnngggnn gggnng                              36

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ctcagggaat gactgcttta cat                                            23

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
ggccacgcgt cgactagtac                                                20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gtcttcaggg tacttggtga                                                20

<210> SEQ ID NO 80
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
atgtaaagca gtcattccct gag                                            23

<210> SEQ ID NO 81
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
cccggatccg accatggcta ccttggttaa aga                                 33

<210> SEQ ID NO 82
<211> LENGTH: 4
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 82

Asp Glu Val Asp
  1

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Met Leu Ser Leu Arg Gln Ser Ile Arg Phe Phe Lys
  1               5                  10

<210> SEQ ID NO 84
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Gly Ser Gly Gly Asp Glu Val Asp Gly Thr Gly Gly Ser
  1               5                  10
```

FLUORESCENT PROTEIN

RELATED APPLICATIONS

The present application is a divisional of U.S. patent application Ser. No. 10/581,551, which is a National Phase application of PCT/JP2004/018437, filed Dec. 3, 2004, which claims priority to Japanese Application Nos. JP2003-404472, filed Dec. 3, 2003 and JP2004-018344, filed Jan. 27, 2004, all of which are hereby incorporated herein in their entirety.

SEQUENCE LISTING

The instant application contains a Sequence Listing which has been submitted in ASCII format via EFS-Web and is hereby incorporated by reference in its entirety. Said ASCII copy, created on Jul. 17, 2012, is named P40478.txt and is 187,936 bytes in size.

BACKGROUND OF THE INVENTION

1. Technical Field

The present invention relates to a novel fluorescent protein which exists in the form of a monomer. More specifically, the present invention relates to a novel fluorescent protein monomerized by introducing a mutation into a florescent protein derived from *Fungia* sp., and a use thereof. Further, the present invention relates to a novel chromoprotein and fluorescent protein. More specifically, the present invention relates to a novel chromoprotein and fluorescent protein derived from *Montipora*. sp, and use thereof.

2. Background Art

Green fluorescent protein (GFP) derived from Aequorea victoria, a jellyfish, has many purposes in biological systems. Recently, various GFP mutants have been produced based on the random mutagenesis and semi-rational mutagenesis, wherein a color is changed, a folding property is improved, luminance is enhanced, or pH sensitivity is modified. Fluorescent proteins such as GFP are fused with other proteins by gene recombinant technique, and monitoring of the expression and transportation of the fusion proteins is carried out.

One of the most commonly used types of GFP mutant is Yellow fluorescent protein (YFP). Among Aequorea-derived GFP mutants, YFP exhibits the fluorescence with the longest wavelength. The values $\epsilon$ and $\phi$ of the majority of YEPs are 60,000 to 100,000 $M^{-1}cm^{-1}$ and 0.6 to 0.8, respectively (Tsien, R Y (1998). Ann. Rev. Biochem. 67, 509-544). These values are comparable to those of the general fluorescent group (fluorescein, rhodamine, etc.). Accordingly, improvement of the absolute luminance of YFP is nearly approaching its limit.

In addition, cyan fluorescent protein (CFP) is another example of the GFP mutant. Of this type of protein, ECFP (enhanced cyan fluorescent protein) has been known. Moreover, red fluorescent protein (RFP) has been isolated from sea anemone (*Discoma* sp.). Of this type of protein, DasRed has been known. Thus, 4 types of fluorescent proteins, that are, green fluorescent protein, yellow fluorescent protein, cyan fluorescent protein, and red fluorescent protein, have successively been developed. The range of the spectrum has significantly been expanded.

Previously, the present inventors had succeeded in amplifying a fluorescent protein gene from among the cDNA library of *Fungia* sp., using preferred primers designed based on the amino acid sequence of a known fluorescent protein, and then cloning it. Thereafter, the present inventors had determined the fluorescence properties of the obtained fluorescent protein derived from *Fungia* sp. As a result, the present inventors had found that the above fluorescent protein has desired fluorescence properties (International Publication W003/54191).

Several GFP homologs derived from Aequorea have a large stokes shift (the difference between an excitation peak value and a fluorescence peak value) (GFPuv and sapphire). These GFP homologs obtain green fluorescence as a result of excitation with UV light at 380 nm. However, the use of such UV light having toxicity is not suitable for observation in organisms. No red fluorescent proteins have a large stokes shift. Under the current circumstances, either excitation or fluorescence must be sacrificed in fluorescence observation.

DISCLOSURE OF THE INVENTION

The molecular weight of the fluorescent protein Kusabira-Orange (KO) isolated from *Fungia* sp. of Scleractinia, described in International Publication WO03/54191, was measured. As a result, the molecular weight was found to be 70 kDa (the molecular weight calculated from the amino acid sequence thereof was 26 kDa). It is considered that this fluorescent protein usually forms a dimer. In recent years, the demand for labeling cells or molecules with a fluorescent protein has rapidly grown. When cells are labeled, even if a fluorescent protein forms a multimer, there are no problems because such a fluorescent protein only floats in the cytoplasm. However, when molecules are labeled, such a fluorescent protein that forms a multimer is problematic. For example, when molecules to be labeled form a multimer, there is a possibility that both the target molecule and a fluorescent protein molecule form multimer and that as a result, they form an enormous polymer. In addition, when the formation of a multimer by either one of them is inhibited, such a molecule that cannot form a multimer loses its original properties. Even in a probe of intramolecular FRET (fluorescence resonance energy transfer) wherein multiple fluorescent proteins are used, when fluorescent proteins that form multimer are allowed to express as a single peptide chain, both proteins form multimer, and as a result, the observation of FRET becomes difficult. It is an object of the present invention to solve the aforementioned problems. Specifically, it is an object of the present invention to provide a novel fluorescent protein, which exists in the form of a monomer without forming a multimer.

When compared with a low molecular weight fluorescent substance, a fluorescent protein has broad excitation and fluorescence spectra. Many fluorescent proteins have overlapped portions between such excitation and fluorescence spectra. Thus, it is extremely difficult to excite at an excitation peak value and then to observe at a fluorescence peak value. It is an object of the present invention to provide a fluorescent protein which is able to solve the aforementioned problem. That is to say, it is an object of the present invention to provide a red or orange fluorescent protein, which is characterized in that the difference (stokes shift) between an excitation peak value (wavelength of maximum absorption) and a fluorescence peak value (wavelength of maximum fluorescence) is greatened, so that the maximum fluorescence can be obtained by the maximum excitation.

As a result of intensive studies directed towards achieving the aforementioned objects, the present inventors have succeeded in estimating a multimer interface from the amino acid sequence of the protein KO described in International Publication WO03/54191, substituting amino acids on such a multimer interface with other amino acids, and further in monomerizing KO, so that it can maintain fluorescence properties.

Moreover, the present inventors have examined the fluorescence properties of the obtained monomer fluorescent protein. As a result, they have found that it has desired fluorescence properties. The present invention has been completed based on these findings.

Furthermore, as a result of intensive studies directed towards achieving the aforementioned objects, the present inventors have attempted to isolate a gene encoding a novel chromoprotein using Montipora sp. as a material, so as to obtain a chromoprotein COCP. Subsequently, the present inventors have substituted histidine at position 94 of the COCP protein with asparagine, asparagine at position 142 with serine, asparagine at position 157 with aspartic acid, lysine at position 201 with arginine, and phenylalanine at position 206 with serine, so as to produce a fluorescent protein COCP-FL having fluorescence properties. COCP-FL has an excitation peak at 560 nm, and because of this excitation, the peak of the fluorescence spectrum was obtained at 600 nm. Further, the present inventors have substituted serine at position 61 of the aforementioned COCP-FL with phenylalanine, isoleucine at position 92 with threonine, valine at position 123 with threonine, phenylalanine at position 158 with tyrosine, valine at position 191 with isoleucine, and serine at position 213 with alanine, so as to produce a protein keima 616, which has fluorescence properties that are different from those of COCP-FL. Such keima 616 has an excitation peak at 440 nm, and because of this excitation, the peak of the fluorescence spectrum was obtained at 616 nm. Its stokes shift was 176 nm, which was an extremely large value. Still further, the present inventors have substituted phenylalanine at position 61 of keima 616 with methionine, and glutamine at position 62 with cysteine, so as to produce a fluorescent protein keima 570. Such keima 570 has an excitation peak at 440 mu as with keima 616, and because of this excitation, it has a fluorescence peak at 570 nm. Its stokes shift was 130 nm, which was a large value. The present invention has been completed based on these findings.

Thus, the present invention provides a fluorescent protein described in the following (a) or (b):
(a) a protein having the amino acid sequence shown in SEQ ID NO: 1; or
(b) a protein, which has an amino acid sequence comprising a deletion, substitution, and/or addition of one or several amino acids with respect to the amino acid sequence shown in SEQ ID NO: 1, which has fluorescence properties equivalent to those of the protein having the amino acid sequence shown in SEQ ID NO: 1, and which exists in the form of a monomer.

Another aspect of the present invention provides a fluorescent protein described in the following (a) or (b):
(a) a protein having the amino acid sequence shown in SEQ ID NO: 3, 5, 7 or 9; or
(b) a protein, which has an amino acid sequence comprising a deletion, substitution, and/or addition of one or several amino acids with respect to the amino acid sequence shown in SEQ ID NO: 3, 5, 7 or 9, and which has fluorescence properties equivalent to those of the protein having the amino acid sequence shown in SEQ ID NO: 3, 5, 7 or 9, respectively.

Further another aspect of the present invention provides a fluorescent protein described in the following (a) or (b):
(a) a protein having the amino acid sequence shown in SEQ ID NO: 11, 13, 15, 17, 19, 21, 23, 25, 27 or 29; or
(b) a protein, which has an amino acid sequence comprising a deletion, substitution, and/or addition of one or several amino acids with respect to the amino acid sequence shown in SEQ ID NO: 11, 13, 15, 17, 19, 21, 23, 25, 27 or 29, and which has fluorescence properties equivalent to those of the protein having the amino acid sequence shown in SEQ ID NO: 11, 13, 15, 17, 19, 21, 23, 25, 27 or 29, respectively.

Further another aspect of the present invention provides DNA encoding a fluorescent protein described in the following (a) or (b):
(a) a protein having the amino acid sequence shown in SEQ ID NO: 1; or
(b) a protein, which has an amino acid sequence comprising a deletion, substitution, and/or addition of one or several amino acids with respect to the amino acid sequence shown in SEQ ID NO: 1, which has fluorescence properties equivalent to those of the protein having the amino acid sequence shown in SEQ ID NO: 1, and which exists in the form of a monomer.

Further another aspect of the present invention provides DNA encoding a fluorescent protein described in the following (a) or (b):
(a) a protein having the amino acid sequence shown in SEQ ID NO: 3, 5, 7 or 9; or
(b) a protein, which has an amino acid sequence comprising a deletion, substitution, and/or addition of one or several amino acids with respect to the amino acid sequence shown in SEQ ID NO: 3, 5, 7 or 9, and which has fluorescence properties equivalent to those of the protein having the amino acid sequence shown in SEQ ID NO: 3, 5, 7 or 9, respectively.

Further another aspect of the present invention provides DNA encoding a fluorescent protein described in the following (a) or (b):
(a) a protein having the amino acid sequence shown in SEQ ID NO: 11, 13, 15, 17, 19, 21, 23, 25, 27 or 29; or
(b) a protein, which has an amino acid sequence comprising a deletion, substitution, and/or addition of one or several amino acids with respect to the amino acid sequence shown in SEQ ID NO: 11, 13, 15, 17, 19, 21, 23, 25, 27 or 29, and which has fluorescence properties equivalent to those of the protein having the amino acid sequence shown in SEQ ID NO: 11, 13, 15, 17, 19, 21, 23, 25, 27 or 29, respectively.

Further another aspect of the present invention provides DNA described in the following (a) or (b):
(a) DNA having the nucleotide sequence shown in SEQ ID NO: 2; or
(b) DNA, which has a nucleotide sequence comprising a deletion, substitution, and/or addition of one or several nucleotides with respect to the nucleotide sequence shown in SEQ ID NO: 2, and which has a nucleotide sequence encoding a protein that has fluorescence properties equivalent to those of the protein encoded by the nucleotide sequence shown in SEQ ID NO: 2 and that exists in the form of a monomer.

Further another aspect of the present invention provides DNA described in the following (a) or (b):
(a) DNA having the nucleotide sequence shown in SEQ ID NO: 4, 6, 8 or 10; or
(b) DNA, which has a nucleotide sequence comprising a deletion, substitution, and/or addition of one or several nucleotides with respect to the nucleotide sequence shown in SEQ ID NO: 4, 6, 8 or 10, and which has a nucleotide sequence encoding a protein that has fluorescence properties equivalent to those of the protein encoded by the nucleotide sequence shown in SEQ ID NO: 4, 6, 8 or 10, respectively.

Further another aspect of the present invention provides DNA described in the following (a) or (b):
(a) DNA having the nucleotide sequence shown in SEQ ID NO: 12, 14, 16, 18, 20, 22, 24, 26, 28 or 30; or
(b) DNA, which has a nucleotide sequence comprising a deletion, substitution, and/or addition of one or several nucleotides with respect to the nucleotide sequence shown in SEQ ID NO: 12, 14, 16, 18, 20, 22, 24, 26, 28 or 30, and which has a nucleotide sequence encoding a protein that has fluorescence properties equivalent to those of the protein encoded by the nucleotide sequence shown in SEQ ID NO: 12, 14, 16, 18, 20, 22, 24, 26, 28 or 30, respectively.

Further, the present invention provides a chromoprotein described in the following (a) or (b):
(a) a protein having the amino acid sequence shown in SEQ ID NO: 37; or
(b) a protein, which has an amino acid sequence comprising a deletion, substitution, and/or addition of one or several amino acids with respect to the amino acid sequence shown in SEQ ID NO: 37, and which has light-absorbing properties.

Another aspect of the present invention provides a fluorescent protein described in the following (a) or (b):
(a) a protein having the amino acid sequence shown in SEQ ID NO: 39; or
(b) a protein, which has an amino acid sequence comprising a deletion, substitution, and/or addition of one or several amino acids with respect to the amino acid sequence shown in SEQ ID NO: 39, and which has fluorescence properties.

Further another aspect of the present invention provides a fluorescent protein described in the following (a) or (b):
(a) a protein having the amino acid sequence shown in SEQ ID NO: 41, 43, 45, or 47; or
(b) a protein, which has an amino acid sequence comprising a deletion, substitution, and/or addition of one or several amino acids with respect to the amino acid sequence shown in SEQ II) NO: 41, 43, 45, or 47, which has fluorescence properties, and which has a stokes shift of 100 nm or greater.

Further another aspect of the present invention provides DNA encoding a chromoprotein described in the following (a) or (b):
(a) a protein having the amino acid sequence shown in SEQ ID NO: 37; or
(b) a protein, which has an amino acid sequence comprising a deletion, substitution, and/or addition of one or several amino acids with respect to the amino acid sequence shown in SEQ ID NO: 37, and which has light-absorbing properties.

Further another aspect of the present invention provides DNA encoding a fluorescent protein described in the following (a) or (b):
(a) a protein having the amino acid sequence shown in SEQ ID NO: 39; or
(b) a protein, which has an amino acid sequence comprising a deletion, substitution, and/or addition of one or several amino acids with respect to the amino acid sequence shown in SEQ ID NO: 39, and which has fluorescence properties.

Further another aspect of the present invention provides DNA encoding a fluorescent protein described in the following (a) or (b):
(a) a protein having the amino acid sequence shown in SEQ ID NO: 41, 43, 45, or 47; or
(b) a protein, which has an amino acid sequence comprising a deletion, substitution, and/or addition of one or several amino acids with respect to the amino acid sequence shown in SEQ ID NO: 41, 43, 45, or 47, which has fluorescence properties, and which has a stokes shift of 100 nm or greater.

Further another aspect of the present invention provides DNA described in the following (a) or (b):
(a) DNA having the nucleotide sequence shown in SEQ ID NO: 38; or
(b) DNA, which has a nucleotide sequence comprising a deletion, substitution, and/or addition of one or several nucleotides with respect to the nucleotide sequence shown in SEQ ID NO: 38, and which has a nucleotide sequence encoding a protein that has light-absorbing properties.

Further another aspect of the present invention provides DNA described in the following (a) or (b):
(a) DNA having the nucleotide sequence shown in SEQ ID NO: 40; or
(b) DNA, which has a nucleotide sequence comprising a deletion, substitution, and/or addition of one or several nucleotides with respect to the nucleotide sequence shown in SEQ ID NO: 40, and which has a nucleotide sequence encoding a protein that has fluorescence properties.

Further another aspect of the present invention provides DNA described in the following (a) or (b):
(a) DNA having the nucleotide sequence shown in SEQ ID NO: 42, 44, 46 or 48; or
(b) DNA, which has a nucleotide sequence comprising a deletion, substitution, and/or addition of one or several nucleotides with respect to the nucleotide sequence shown in SEQ ID NO: 42, 44, 46 or 48, and which has a nucleotide sequence encoding a protein that has fluorescence properties and has a stokes shift of 100 nm or greater.

Further another aspect of the present invention provides a recombinant vector having the DNA according to the present invention as mentioned above.

Further another aspect of the present invention provides a transformant having the DNA or the recombinant vector according to the present invention as mentioned above.

Further another aspect of the present invention provides a fusion protein, which consists of the protein according to the present invention as mentioned above and another protein. Preferably, said another protein is a protein that localizes in a cell. More preferably, said another protein is a protein specific to a cell organella. Preferably, said another protein is a fluorescent protein. In this case, preferably, the fusion protein can generate intramolecular FRET.

Further another aspect of the present invention provides a method for analyzing the localization or dynamics of a protein in a cell, which is characterized in that the fusion protein according to the present invention as mentioned above is allowed to express in the cell.

Further another aspect of the present invention provides a reagent kit, which comprises: the fluorescent protein, the DNA, the recombinant vector, the transformant or the fusion protein according to the present invention as mentioned above.

BEST MODE FOR CARRYING OUT THE INVENTION

Figure 1:
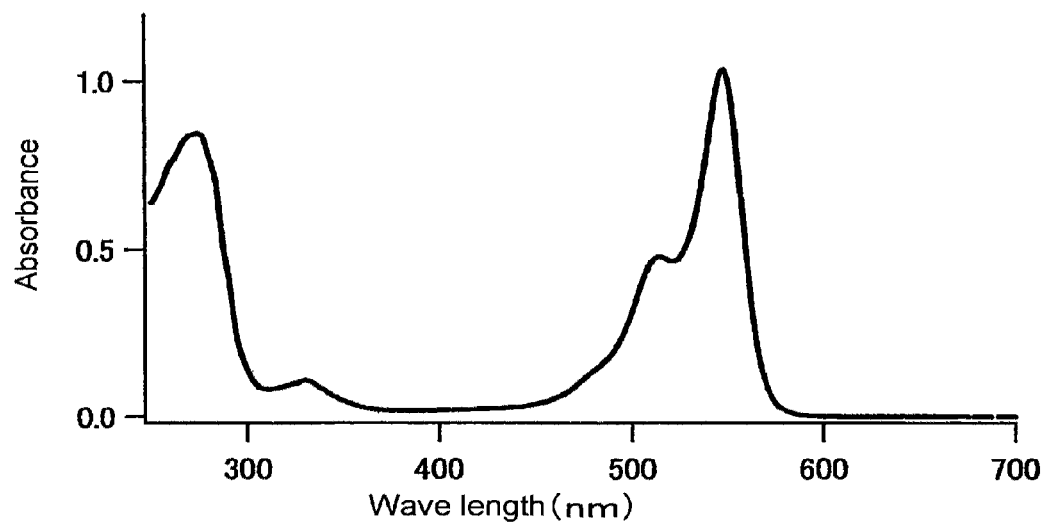
FIG. 1 shows the absorption spectrum of mKO.

The embodiments of the present invention will be described in detail below.
(1) Fluorescent Proteins of the Present Invention
(i) The First Type of Fluorescent Protein of the Present Invention The first type of fluorescent protein of the present invention is a fluorescent protein described in the following (a) or (b):
(a) a protein having the amino acid sequence shown in SEQ ID NO: 1; or
(b) a protein, which has an amino acid sequence comprising a deletion, substitution, and/or addition of one or several amino acids with respect to the amino acid sequence shown in SEQ ID NO: 1, which has fluorescence properties equivalent to those of the protein having the amino acid sequence shown in SEQ ID NO: 1, and which exists in the form of a monomer.

The fluorescent protein of the present invention is characterized in that it has the following properties:
(1) the excitation maximum wavelength is 548 nm, and the fluorescence maximum wavelength is 559 nm;
(2) the molar absorption coefficient at 548 nm is 51,600;
(3) the quantum yield is 0.6; and
(4) the pH sensitivity of fluorescent property is pKa=5.0.

*Fungia* sp. is a certain type of coral. *Fungia* sp. is characterized in that it lives mainly in the western area of the Atlantic Ocean, in that the contour of a colony thereof is polygonal, in that it has long tentacles, and in that the body as a whole presents bright orange color.

In the examples given below of the present specification, *Fungia* sp. was used as a starting material, and the fluorescent protein of the present invention having the aforementioned properties was obtained. However, there are cases where the fluorescent protein of the present invention can also be obtained from coral emitting fluorescence other than *Fungia* sp. The thus obtained fluorescent protein is also included in the scope of the present invention.

The scope of "one or several" in the phrase "an amino acid sequence comprising a deletion, substitution and/or addition of one or several amino acids" used herein is not particularly limited. For example, it means 1 to 20, preferably 1 to 10, more preferably 1 to 7, further preferably 1 to 5, and particularly preferably 1 to 3.

The term "equivalent fluorescence properties" is used in the present specification to mean that a fluorescent protein has equivalent fluorescence intensity, equivalent excitation wavelength, equivalent fluorescence wavelength, equivalent pH sensitivity, and the like.

The method of obtaining the fluorescent protein of the present invention is not particularly limited. The proteins may be either a protein synthesized by chemosynthesis, or recombinant protein produced by a gene recombination technique.

Where a recombinant protein is produced, it is necessary to obtain DNA encoding the protein. Appropriate primers are designed by using information regarding the amino acid sequence and the nucleotide sequence shown in SEQ ID NOS 1 to 30 of the sequence listing of the present specification. Using these primers, PCR is carried out by using cDNA clone of the fluorescent protein described in International Publication WO03/54191 as a template, so that DNA encoding the fluorescent protein of the present invention can be obtained. Where a partial fragment of DNA encoding the fluorescent protein of the present invention is obtained by the above-described PCR, the produced DNA fragments are ligated to one another by a gene recombination technique, so that DNA encoding the desired fluorescent protein can be obtained. The fluorescent protein of the present invention can be produced by introducing this DNA into an appropriate expression system. Expression in an expression system will be described later in the present specification.

In addition, the present invention also provides a mutant protein of the aforementioned protein (mKO) of the present invention. Specifically, there is provided a fluorescent protein described in the following (a) or (b):
(a) a protein having the amino acid sequence shown in SEQ ID NO: 3, 5, 7 or 9; or
(b) a protein, which has an amino acid sequence comprising a deletion, substitution; and/or addition of one or several amino acids with respect to the amino acid sequence shown in SEQ ID NO: 3, 5, 7 or 9, and which has fluorescence properties equivalent to those of the protein having the amino acid sequence shown in SEQ ID NO: 3, 5, 7 or 9, respectively.

As further another example, there is provided a fluorescent protein described in the following (a) or (b):
(a) a protein having the amino acid sequence shown in SEQ ID NO: 11, 13, 15, 17, 19, 21, 23, 25, 27 or 29; or
(b) a protein, which has an amino acid sequence comprising a deletion, substitution, and/or addition of one or several amino acids with respect to the amino acid sequence shown in SEQ ID NO: 11, 13, 15, 17, 19, 21, 23, 25, 27 or 29, and which has fluorescence properties equivalent to those of the protein having the amino acid sequence shown in SEQ ID NO: 11, 13, 15, 17, 19, 21, 23, 25, 27 or 29, respectively.

(ii) The Second Type of Protein of the Present Invention

The second type of proteins of the present invention are: a protein having the amino acid sequence shown in SEQ ID NO: 37, 39, 41, 43, 45, or 47; and a protein, which has an amino acid sequence comprising a deletion, substitution, and/or addition of one or several amino acids with respect to the amino acid sequence shown in SEQ ID NO: 37, 39, 41, 43, 45, or 47, and which has absorption properties or fluorescence properties. The stokes shifts (the difference between the wavelength of maximum absorption and the wavelength of maximum fluorescence) of the proteins having the amino acid sequence shown in SEQ ID NO: 41, 43, 45, or 47, are 176 nm, 130 nm, 180 nm, and 180 nm, respectively. The stokes shifts of the proteins, which have an amino acid sequence comprising a deletion, substitution, and/or addition of one or several amino acids with respect to the amino acid sequence shown in SEQ ID NO: 41, 43, 45, or 47, and which have fluorescence properties, are 100 nm or greater, and more preferably 120 nm or greater.

The proteins of the present invention are characterized in that they have the following properties:
(1) COCP (the amino acid sequence thereof is shown in SEQ ID NO: 37, and the nucleotide sequence thereof is shown in SEQ ID NO: 38)
Wavelength of maximum excitation (wavelength of maximum absorption): 576 mu
Molar absorption coefficient at 576 nm: 64,000
pH sensitivity: absent
(2) COCP-FL (the amino acid sequence thereof is shown in SEQ ID NO: 39, and the nucleotide sequence thereof is shown in SEQ ID NO: 40)
Wavelength of maximum excitation (wavelength of maximum absorption): 560 nm
Wavelength of maximum fluorescence: 600 nm
(3) keima 616 (the amino acid sequence thereof is shown in SEQ ID NO: 41, and the nucleotide sequence thereof is shown in SEQ ID NO: 42)
Wavelength of maximum excitation (wavelength of maximum absorption): 440 nm
Wavelength of maximum fluorescence: 616 nm
pH sensitivity: fluorescence intensity is stable between pH 7.5 and 10
(4) keima 570 (the amino acid sequence thereof is shown in SEQ ID NO: 43, and the nucleotide sequence thereof is shown in SEQ ID NO: 44)
Wavelength of maximum excitation (wavelength of maximum absorption): 440 nm
Wavelength of maximum fluorescence: 570 nm
pH sensitivity: fluorescence intensity is stable between pH 7.5 and 10
(5) cmkeima 620 (the amino acid sequence thereof is shown in SEQ ID NO: 45, and the nucleotide sequence thereof is shown in SEQ ID NO: 46)

Wavelength of maximum excitation (wavelength of maximum absorption): 440 nm
Wavelength of maximum fluorescence: 620 nm
(6) mkeima 620 (the amino acid sequence thereof is shown in SEQ ID NO: 47, and the nucleotide sequence thereof is shown in SEQ ID NO: 48)
Wavelength of maximum excitation (wavelength of maximum absorption): 440 nm
Wavelength of maximum fluorescence: 620 nm In the examples of the present specification, DNA encoding the protein of the present invention was cloned from *Montipora* sp. used as a starting material. *Montipora* sp. is a certain type of coral, which belongs to Acropora, Scleractinia, Hexacorallia, Anthozoa, Cnidaria. It often forms an aggregated or coated colony. It is to be noted that the protein of the present invention can also be obtained from coral emitting fluorescence other than *Montipora* sp. in some cases, and that such a protein is also included in the scope of the present invention.

The scope of "one or several" in the phrase "an amino acid sequence comprising a deletion, substitution and/or addition of one or several amino acids" used herein is not particularly limited. For example, it means 1 to 20, preferably 1 to 10, more preferably 1 to 7, further preferably 1 to 5, and particularly preferably 1 to 3.

The term "protein having light-absorbing properties" is used to mean in the present specification to mean a protein having properties capable of absorbing light with a certain wavelength. The light-absorbing properties of a "protein, which has an amino acid sequence comprising a deletion, substitution, and/or addition of one or several amino acids with respect to the amino acid sequence shown in SEQ ID NO: 37, and which has light-absorbing properties" may be either substantially identical to, or different from those of the protein having the amino acid sequence shown in SEQ ID NO: 37. Such light-absorbing properties can be evaluated based on absorption intensity, excitation wavelength (absorption wavelength), pH sensitivity, etc., for example. Among the proteins of the present invention, chromoproteins, which have light-absorbing properties and do not emit fluorescence, can be used, for example, as (1) an FRET acceptor molecule (energy receptor), or can be used in (2) the development of a system for converting irradiated light energy to energy other than light, or in (3) introduction of a mutation into the amino acid sequence of a protein to modify it, so that it can emit fluorescence.

The term "protein having fluorescence properties" is used in the present specification to mean a protein having properties capable of emitting fluorescence as a result of excitation with light having a certain wavelength. The fluorescence properties of the "proteins, which have an amino acid sequence comprising a deletion, substitution, and/or addition of one or several amino acids with respect to the amino acid sequence shown in SEQ ID NO: 39, 41, 43, 45, or 47, and which have fluorescence properties" may be either identical to or different from the fluorescence properties of the proteins having the amino acid sequence shown in SEQ ID NO: 39, 41, 43, 45, or 47. Such fluorescence properties can be evaluated based on fluorescence intensity, excitation wavelength, fluorescence wavelength, pH sensitivity, etc., for example.

The method of obtaining the fluorescent protein and the chromoproteins of the present invention is not particularly limited. The proteins may be either a protein synthesized by chemosynthesis, or recombinant protein produced by a gene recombination technique.

Where a recombinant protein is produced, it is necessary to obtain DNA encoding the protein. Appropriate primers are designed by using information regarding the amino acid sequence shown in SEQ ID NO: 37, 39, 41, 43, 45 or 47 of the sequence listing of the present specification and the nucleotide sequence shown in SEQ ID NO: 38, 40, 42, 44, 46 or 48 thereof. Using these primers, PCR is carried out by using cDNA library derived from *Montipora* sp. as a template, so that DNA encoding the protein of the present invention can be obtained. Where a partial fragment of DNA encoding the protein of the present invention is obtained by the above-described PCR, the produced DNA fragments are ligated to one another by a gene recombination technique, so that DNA encoding the desired protein can be obtained. The protein of the present invention can be produced by introducing this DNA into an appropriate expression system. Expression in an expression system will be described later in the present specification.

(2) DNA of the Present Invention

The present invention provides genes encoding the first type of fluorescent protein of the present invention.

A specific example of DNA encoding the first type of fluorescent protein of the present invention is DNA encoding a fluorescent protein described in the following (a) or (b):
(a) a protein having the amino acid sequence shown in SEQ ID NO: 1; or
(b) a protein, which has an amino acid sequence comprising a deletion, substitution, and/or addition of one or several amino acids with respect to the amino acid sequence shown in SEQ ID NO: 1, which has fluorescence properties equivalent to those of the protein having the amino acid sequence shown in SEQ ID NO: 1, and which exists in the form of a monomer.

A further example of DNA encoding the fluorescent protein of the present invention is DNA described in the following (a) or (b):
(a) DNA having the nucleotide sequence shown in SEQ ID NO: 2; or
(b) DNA, which has a nucleotide sequence comprising a deletion, substitution, and/or addition of one or several nucleotides with respect to the nucleotide sequence shown in SEQ ID NO: 2, and which has a nucleotide sequence encoding a protein that has fluorescence properties equivalent to those of the protein encoded by the nucleotide sequence shown in SEQ ID NO: 2 and that exists in the form of a monomer.

Further, the DNA encoding the mutant protein of the protein (mKO) of the present invention as described in (1) above, is also included in the scope of the present invention.

Further, the present invention provides genes encoding the second type of protein of the present invention.

A specific example of DNA encoding the protein of the present invention is
(a) a protein having the amino acid sequence shown in SEQ ID NO: 37, 39, 41, 43, 45, or 47; or
(b) a protein, which has an amino acid sequence comprising a deletion, substitution, and/or addition of one or several amino acids with respect to the amino acid sequence shown in SEQ ID NO: 37, 39, 41, 43, 45, or 47, and which has light-absorbing properties or fluorescence properties.

Further specific example of DNA encoding the chromoprotein or fruolescent protein of the present invention is DNA described in the following (a) or (b)
(a) DNA having the nucleotide sequence shown in SEQ ID NO: 38, 40, 42, 44, 46 or 48; or
(b) DNA, which has a nucleotide sequence comprising a deletion, substitution, and/or addition of one or several nucleotides with respect to the nucleotide sequence shown in SEQ ID NO: 38, 40, 42, 44, 46 or 48, and which has a nucleotide sequence encoding a protein that has light-absorbing properties or fluorescence properties.

In the term "a nucleotide sequence comprising a deletion, substitution and/or addition of one or several nucleotides" used in the present specification, the range of "one or several" is not particularly limited, but is, for example, from 1 to 50, preferably 1 to 30, more preferably 1 to 20, still more preferably 1 to 10, and particularly preferably 1 to 5.

The DNA of the present invention can be synthesized by, for example, the phosphoamidite method, or it can also be produced by polymerase chain reaction (PCR) using specific primers. The DNA of the present invention or its fragment is produced by the method described above in the specification.

A method of introducing a desired mutation into a certain nucleic acid sequence is known to a person skilled in the art. For example, known techniques such as a site-directed mutagenesis, PCR using degenerated oligonucleotides, or the exposure of cells containing nucleic acid to mutagens or radioactive rays, are appropriately used, so as to construct DNA having a mutation. Such known techniques are described in, for example, Molecular Cloning: A Laboratory Manual, 2$^{nd}$ Ed., Cold Spring Harbor Laboratory, Cold Spring Harbor, N.Y., 1989; and Current Protocols in Molecular Biology, Supplements 1 to 38, John Wiley & Sons (1987-1997).

(3) Recombinant Vector of the Present Invention

The DNA of the present invention can be inserted into a suitable vector and used. The type of a vector used in the present invention is not particularly limited. For example, it may be either a vector that can autonomously replicate (e.g., a plasmid, etc.), or vector that is incorporated into the genomes of host cells when it is introduced into the host cells and is then replicated together with the chromosome into which it is incorporated.

The vector used in the present invention is preferably an expression vector. In an expression vector, elements necessary for transcription (e.g., a promoter, etc.) are functionally ligated to the DNA of the present invention. The promoter is a DNA sequence which shows a transcriptional activity in host cells, and it is appropriately selected depending on the type of host cells.

Examples of a promoter which can operate in bacterial cells may include a *Bacillus stearothermophilus* maltogenic amylase gene promoter, a *Bacillus licheniformis* alpha-amylase gene promote; a *Bacillus amyloliquefaciens* BAN amylase gene promoter, a *Bacillus subtilis* alkaline protease gene promoter, a *Bacillus pumilus* xylosidase gene promoter, $P_R$ and $P_L$ promoters of phage rhamda, and lac, trp and tac promoters of *Escherichia coli*.

Examples of a promoter which can operate in mammalian cells may include an SV40 promoter, an MT-1 (metallothionein gene) promote; and an adenovirus-2 major late promoter. Examples of a promoter which can operate in insect cells may include a polyhedrin promote; a P10 promoter, an *Autographa californica* polyhedrosis basic protein promote; a baculovirus immediate-early gene 1 promote; and a baculovirus 39K delayed-early gene promoter. Examples of a promoter which can be operate in yeast host cells may include promoters derived from yeast glycolytic genes, an alcohol dehydrogenase gene promoter, a TPI1 promote; and an ADH2-4c promoter.

Examples of a promoter which can operate in filamentous cells may include an ADH3 promoter and a tpiA promoter.

In addition, an appropriate terminator such as a human growth hormone terminator, or a TPI1 terminator or ADH3 terminator for fungal cells, may be functionally bound to the DNA of the present invention, as necessary. The recombinant vector of the present invention may further have elements such as a polyadenylation signal (e.g., one derived from SV40 or the adenovirus 5E1b region), a transcription enhancer sequence (e.g., an SV40 enhancer), or a translation enhancer sequence (e.g., one encoding the adenovirus VA RNA).

The recombinant vector of the present invention may further comprise a DNA sequence which enables the replication of the recombinant vector in host cells. SV40 replication origin is an example of such a sequence (when the host cells are mammalian cells).

The recombinant vector of the present invention may further comprise a selective marker. Examples of such a selective marker may include genes, complements of which are absent from host cells, such as a dihydrofolate reductase (DHFR) gene or a *Shizosaccharomyces pombe* TPI gene, and drug resistant genes such as ampicillin, kanamycin, tetracycline, chloramphenicol, neomycin or hygromycin-resistant genes.

A method for ligating the DNA of the present invention, a promoter and, as desired, a terminator and/or a secretory signal sequence to one another and inserting these items into a suitable vector is known to a person skilled in the art.

(4) Transformant of the Present Invention

A transformant can be produced by introducing the DNA or recombinant vector of the present invention into a suitable host.

Any cell can be used as a host cell into which the DNA or recombinant vector of the present invention is introduced, as long as the DNA construct of the present invention can be expressed therein. Examples of such a cell may include bacteria, yeasts, fungal cells, and higher eukaryotic cells.

Examples of bacteria may include Gram-positive bacteria such as *Bacillus* or *Streptomyces*, and Gram-negative bacteria such as *Escherichia coli*. These bacteria may be transformed by the protoplast method or other known methods, using competent cells.

Examples of mammalian cells may include HEK 293 cells, HeLa cells, COS cells, BHK cells, CHL cells, and CHO cells. A method of transforming mammalian cells and expressing the introduced DNA sequence in the cells is also known. Examples of such a method may include the electroporation, the calcium phosphate method, and the lipofection method.

Examples of yeast cells may include those belonging to *Saccharomyces* or *Shizosaccharomyces*. Examples of such cells may include *Saccharomyces cerevisiae* and *Saccharomyces kluyveri*. Examples of a method of introducing a recombinant vector into yeast host cells may include the electroporation, the spheroplast method, and the lithium acetate method.

Examples of other fungal cells may include those belonging to *Filamentous fungi* such as *Aspergillus, Neurospora, Fusarium* or *Trichoderma*. Where *Filamentous fungi* are used as host cells, transformation can be carried out by incorporating DNA constructs into host chromosomes, so as to obtain recombinant host cells. Incorporation of DNA constructs into the host chromosomes is carried out by known methods, and such known methods may include homologous recombination and heterologous recombination.

Where insect cells are used as host cells, both a vector into which a recombinant gene is introduced and a baculovirus are co-introduced into insect cells, and a recombinant virus is obtained in the culture supernatant of the insect cells. Thereafter, insect cells are infected with the recombinant virus, so as to allow the cells to express proteins (described in, for example, Baculovirus Expression Vectors, A Laboratory Manual; and Current Protocols in Molecular Biology, Bio/Technology, 6, 47 (1988)).

The *Autographa californica* nuclear polyhedrosis virus, which is a virus infecting to insects belonging to *Barathra brassicae*, can be used as baculovirus.

Examples of insect cells used herein may include Sf9 and Sf21, which are *Spodoptera frugiperda* ovarian cells [Baculovirus Expression Vectors, A Laboratory Manual, W. H. Freeman & Company, New York, (1992)], and HiFive (manufactured by Invitrogen), which are *Trichoplusia ni* ovarian cells.

Examples of the method of co-introducing both a vector into which a recombinant gene has been introduced and the above baculovirus into insect cells to prepare a recombinant virus may include the calcium phosphate method and the lipofection method.

The above transformant is cultured in an appropriate nutritive medium under conditions enabling the introduced DNA construct to be expressed. In order to isolate and purify the protein of the present invention from the culture product of the transformant, common methods of isolating and purifying proteins may be used.

For example, where the protein of the present invention is expressed in a state dissolved in cells, after completion of the culture, cells are recovered by centrifugal separation, and the recovered cells are suspended in a water type buffer. Thereafter, the cells are disintegrated using an ultrasonic disintegrator or the like, so as to obtain a cell-free extract. A supernatant is obtained by centrifuging the cell-free extract, and then, a purified sample can be obtained from the supernatant by applying, singly or in combination, the following ordinary protein isolation and purification methods: the solvent extraction, the salting-out method using ammonium sulfate or the like, the desalting method, the precipitation method using an organic solvent, the anion exchange chromatography using resins such as diethylaminoethyl (DEAE) sepharose, the cation exchange chromatography using resins such as S-Sepharose FF (manufactured by Pharmacia), the hydrophobic chromatography using resins such as butyl sepharose or phenyl sepharose, the gel filtration method using a molecular sieve, the affinity chromatography, the chromatofocusing method, and the electrophoresis such as isoelectric focusing.

(5) Use of the Fluorescent Protein of the Present Invention and a Fusion Fluorescent Protein Comprising the Same The fluorescent protein of the present invention can be fused with another protein, so as to construct a fusion fluorescent protein.

A method of obtaining the fusion fluorescent protein of the present invention is not particularly limited. It may be either a protein synthesized by chemosynthesis, or recombinant protein produced by a gene recombination technique.

Where a recombinant protein is produced, it is necessary to obtain DNA encoding the protein. Appropriate primers are designed using the information regarding the amino acid sequence and the nucleotide sequence shown in SEQ ID NOS: 1 to 30 of the sequence listing of the present specification. Using these primers, PCR is carried out using a DNA fragment containing the gene of the fluorescent protein of the present invention as a template, so as to produce DNA fragments necessary for construction of the DNA encoding the fluorescent protein of the present invention. Moreover, DNA fragment encoding a protein to be fused is also obtained in the same above manner.

Subsequently, the thus obtained DNA fragments are ligated to one another by a gene recombination technique, so that DNA encoding the desired fusion fluorescent protein can be obtained. This DNA is then introduced into an appropriate expression system, so that the fusion fluorescent protein of the present invention can be produced.

The fluorescent protein of the present invention has an extremely high utility value as a marker. This is to say, the fluorescent protein of the present invention is purified as a fusion protein with an amino acid sequence to be tested, and the fusion protein is introduced into cells by methods such as the microinjection. By observing the distribution of the fusion protein over time, targeting activity of the amino acid sequence to be tested can be detected in the cells.

The type of another protein (an amino acid sequence to be tested) with which the fluorescent protein of the present invention is fused is not particularly limited. Preferred examples may include proteins localizing in cells, proteins specific for intracellular organelles, and targeting signals (e.g., a nuclear transport signal, a mitochondrial presequence, etc.). In addition, the fluorescent protein of the present invention can be expressed in cells and used, as well as being introduced into cells by the microinjection or the like. In this case, a vector into which the DNA encoding the fluorescent protein of the present invention is inserted in such a way that it can be expressed, is introduced into host cells.

Moreover, the fluorescent protein of the present invention can also be used as a reporter protein to determine promoter activity. This is to say, a vector is constructed such that DNA encoding the fluorescent protein of the present invention is located downstream of a promoter to be tested, and the vector is then introduced into host cells. By detecting the fluorescence of the fluorescent protein of the present invention which is emitted from the cells, the activity of the promoter to be tested can be determined. The type of a promoter to be tested is not particularly limited, as long as it operates in host cells.

A vector used to detect the targeting activity of the above amino acid sequence to be tested or to determine promoter activity is not particularly limited. Examples of a vector preferably used for animal cells may include pNEO (P. Southern, and P. Berg (1982) J. Mol. Appl. Genet. 1: 327), pCAGGS (H. Niwa, K. Yamamura, and J. Miyazaki, Gene 108, 193-200 (1991)), pRc/CMV (manufactured by Invitrogen), and pCDM8 (manufactured by Invitrogen). Examples of a vector preferably used for yeasts may include pRS303, pRS304, pRS305, pRS306, pRS313, pRS314, pRS315, pRS316 (R. S. Sikorski and P. Hieter (1989) Genetics 122: 19-27), pRS423, pRS424, pRS425, pRS426 (T. W. Christianson, R. S. Sikorski, M. Dante, J. H. Shero, and P. Hieter (1992) Gene 110: 119-122).

In addition, the type of cells used herein is also not particularly limited. Various types of animal cells such as L cells, BalbC-3T3 cells, NIH3T3 cells, CHO (Chinese hamster ovary) cells, HeLa cells or NRK (normal rat kidney) cells, yeast cells such as *Saccharomyces cerevisiae, Escherichia coli* cells, or the like can be used. Vector can be introduced into host cells by common methods such as the calcium phosphate method or the electroporation.

The above obtained fusion fluorescent protein of the present invention wherein the fluorescent protein of the present invention is fused with another protein (referred to as a protein X) is allowed to be expressed in cells. By monitoring a fluorescence emitted, it becomes possible to analyze the localization or dynamics of the protein X in cells. That is, cells transformed or transfected with DNA encoding the fusion fluorescent protein of the present invention are observed with a fluorescence microscope, so that the localization and dynamics of the protein X in the cells can be visualized and thus analyzed.

For example, by using a protein specific for an intracellular organella as a protein X, the distribution and movement of a nucleus, a mitochondria, an endoplasmic reticulum, a Golgi body, a secretory vesicle, a peroxisome, etc., can be observed.

Moreover, for example, axis cylinders or dendrites of the nerve cells show an extremely complicated change in strikes in an individual who is under development. Accordingly, fluorescent labeling of these sites enables a dynamic analysis.

The fluorescence of the fluorescent protein of the present invention can be detected with a viable cell. Such detection can be carried out using, for example, a fluorescence microscope (Axiophoto Filter Set 09 manufactured by Carl Zeiss) or an image analyzer (Digital Image Analyzer manufactured by ATTO).

The type of a microscope can be appropriately selected depending on purposes. Where frequent observation such as pursuit of a change over time is carried out, an ordinary incident-light fluorescence microscope is preferable. Where observation is carried out while resolution is emphasized, for example, in the case of searching localization in cells specifically, a confocal laser scanning microscope is preferable. In terms of maintenance of the physiological state of cells and prevention from contamination, an inverted microscope is preferable as a microscope system. When an erecting microscope with a high-powered lens is used, a water immersion lens can be used.

A filter set can be appropriately selected depending on the fluorescence wavelength of a fluorescent protein. Since the fluorescent protein of the present invention has an excitation maximum wavelength of 548 nm, and a fluorescence maximum wavelength of 559 nm, a filter having an excitation light between approximately 530 and 550 nm and a fluorescence between approximately 550 and 600 nm is preferably used.

When viable cells are observed over time using a fluorescence microscope, a high sensitive cooled CCD camera is used, since photography is carried out in a short time. In the case of the cooled CCD camera, CCD is cooled to decrease thermal noise, so that a weak fluorescence image can be clearly photographed by exposure in a short time.

FRET (fluorescence resonance energy transfer) has been known as a means for analyzing the interaction between molecules. In FRET, for example, a first molecule labeled with a cyan fluorescent protein (CFP) acting as a first fluorescent protein is allowed to coexist with a second molecule labeled with a yellow fluorescent protein (YFP) acting as a second fluorescent protein, so as to allow the yellow fluorescent protein (YFP) to act as an acceptor molecule and to allow the cyan fluorescent protein (CFP) to act as a donor molecule. Thus, FRET (fluorescence resonance energy transfer) is allowed to take place between both molecules, so as to visualize the interaction between the first and second molecules. Namely, in FRET, different dyes are introduced into two types of molecules. One dye with a higher energy level (a donor molecule) is selectively excited, and the fluorescence of the dye is measured. Long-wavelength fluorescence from the other dye (an acceptor molecule) is also measured. The interaction between the molecules is visualized by using the difference between the amounts of both fluorescences. Only when both dyes are adjacent to each other due to the interaction of the two types of molecules, a decrease in the fluorescence of the donor molecule and an increase in the fluorescence of the acceptor molecule are observed by single wavelength excitation dual wavelength photometry. However, in a case where a chromoprotein is used as an acceptor molecule, a decrease in the fluorescence of the donor molecule occurs only when both dyes are adjacent to each other by the interaction of the two types of molecules. Such a decrease can be observed by single wavelength excitation single wavelength photometry. Thus, facilitation of measurement apparatuses becomes possible.

The fluorescent protein and chromoprotein and of the present invention is particularly advantageous when it is used as a donor molecule and an acceptor molecule in FRET (fluorescence resonance energy transfer). That is to say, a fused form (a first fused form) of the chromoprotein of the present invention and a test substance is first produced. Then, a fused form (a second fused form) of another test substance interacting with the above test substance and another fluorescent protein is produced. Thereafter, the first fused form is allowed to interact with the second fused form, and the generated fluorescence is analyzed, so that the interaction between the aforementioned two types of test substances can be analyzed. FRET (fluorescence resonance energy transfer) using the chromoprotein of the present invention may be carried out either in a test tube or in a cell.

Further, one or more of either of the fluorescent protein and chromoprotein and of the present invention can be used as a donor protein or an acceptor protein. Thus, a fluorescent indicator having a structure where a donor fruolescent protein and an acceptor fluorescent protein are bound to both ends of a target sequence of an analysed substance respectively, can be prepared. The conformation of the fluorescent indicator is changed based on the presence or absence of binding or action of an analyzed substance to said target sequence, thus the presence or absence of FRET (fluorescence resonance energy transfer) can be generated.

(6) Kit of the Present Invention

The present invention provides a kit for analyzing the localization of intracellular components and/or analyzing physiologically active substances, which is characterized in that it comprises at least one selected from the fluorescent protein, the fusion fluorescent protein, the DNA, the recombinant vector, or the transformant, which are described in the present specification. The kit of the present invention can be produced from commonly used materials that are known per se, by using common methods.

Reagents such as the fluorescent protein or the DNA are dissolved in an appropriate solvent, so that the reagents can be prepared in a form suitable for conservation. Water, ethanol, various types of buffer solution, etc. can be used as such a solvent.

The present invention will be further described in the following examples. However, the present invention is not limited by these examples.

EXAMPLES

Example 1

Production of Multimer Formation-Inhibiting Mutant by Point Mutation Introduction A multimer interface was predicted from the amino acid sequence of KO-1, and the amino acids of the multimer interface were substituted with other amino acids. Moreover, KO-1 was monomerized, so that it could maintain fluorescence properties. Point mutation introduction was carried out, using an *Escherichia coli* expression vector (pRSET$_B$) (an expression vector having DNA encoding KO-1 described in International Publication WO03/54191), into which KO-1 had been inserted, and also using point mutation introduction primers. Specifically, multiple mutation introduction primers were simultaneously annealed on one side chain of a template plasmid, followed by elongation with polymerase. DNA fragments elongated with each primers were ligated to one another using DNA ligase in the same reaction solution, so as to obtain a product, whose portions other than the mutation-introduced portion were complementary to the template. Since the termini of the DNA fragments needed phosphate groups when the fragments were ligated to one another with DNA ligase, the 5'-terminal sides of the used primers had been subjected to phosphorylation.

(1) 5'-Phosphorylation of Primers

| | |
|---|---|
| 100 μM primers | 2 μl |
| 10x T4 polynucleotide kinase buffer | 5 μl |
| 100 μM ATP | 0.5 μl |
| Sterilized water | 41.5 μl |
| T4 polynucleotide kinase (10 U/μl) | 1 μl |

The above mixture was incubated at 37° C. for 30 minutes. As primers used herein, the following primers having the nucleotide sequences shown in SEQ ID NOS: 3 to 17 were used.

```
K11R, F13Y
                                      (SEQ ID NO: 59)
CCAGAGATGAAGATGAGGTACTACATGGACGGC

V25I
                                      (SEQ ID NO: 60)
CATGAGTTCACAATTGAAGGTGAAGGC

K32R
                                      (SEQ ID NO: 61)
GAAGGCACAGGCAGACCTTACGAGGGA

S55A
                                      (SEQ ID NO: 62)
CCAATGCCTTTCGCGTTTGACTTAGTG

T62V
                                      (SEQ ID NO: 63)
TTAGTGTCACACGTGTTCTGTTACGGC

Q96E
                                      (SEQ ID NO: 64)
GAAAGGTCGTTGGAGTTCGAAGATGGT

F102S, A104S
                                      (SEQ ID NO: 65)
GAAGATGGTGGGTCCGCTTCAGTCAGTGCG

C115T, E117Y
                                      (SEQ ID NO: 66)
AGCCTTAGAGGAAACACCTTCTACCACAAATCCA

V123T
                                      (SEQ ID NO: 67)
CAAATCCAAATTTACTGGGGTTAACTTTCCTG

V133I
                                      (SEQ ID NO: 68)
GCCGATGGTCCTATCATGCAAAACCAAAGT

S139V
                                      (SEQ ID NO: 69)
GCCGATGGTCCTATCATGCAAAACCAAAGTGTTGATTGGGAGCCA

T150A, C151S
                                      (SEQ ID NO: 70)
GAGAAAATTACTGCCAGCGACGGAGTTCTGAAG

F162Y, A166E
                                      (SEQ ID NO: 71)
GATGTTACGATGTACCTAAAACTTGAAGGAGGCGGCAATCAC

Q190G, F193Y, G195S
                                      (SEQ ID NO: 72)
CTTAAAATGCCAGGAAGCCATTACATCAGCCATCGCCTCGTCAGG

C217S
                                      (SEQ ID NO: 73)
GATGCAGTAGCTCATTCCCTCGAGCACCACCACC
```

(2) Point Mutation Introduction PCR

| | |
|---|---|
| 5'-phosphorylated primers | 4 μl |
| Template (KO-pRSET$_B$) | 100 ng |
| 10x polymerase buffer | 2.5 μl |
| 10x DNA ligase buffer | 2.5 μl |
| 2.5 mM dNTPs | 1 μl |
| polymerase (pfu) 2.5 U/μl | 1 μl |
| Taq DNA ligase 40 U/μl | 0.5 μl |

The final volume of the mixture was set at 50 μl by addition of sterilized water. Program:
GeneAmp PCR system 9700 was used as a thermal cycler.

| | |
|---|---|
| (1) 65° C. | 5 min |
| (2) 95° C. | 2 min |
| (3) 95° C. | 20 sec |
| (4) 52° C. | 20 sec |
| (5) 65° C. | 8 min |

The operation described in (3) to (5) above was repeated for 25 cycles.

| | |
|---|---|
| (6) 75° C. | 7 min |
| (7) 4° C. | hold |

(3) Dpn1 Treatment

1 μl of Dpn1 was added to the sample obtained after PCR, and the obtained mixture was then incubated at 37° C. for 1 hour, so as to cleave a template plasmid.

(4) Transformation of *Escherichia coli*

*Escherichia coli* JM109 was transformed with the sample treated with Dpn1, so that KO-1 after introduction of the mutation was allowed to express therein.

(5) Amino Acid Sequence of Monomerized Kusabira-Orange (mKO)

The nucleotide sequence of the KO mutant obtained after introduction of the mutation was analyzed, so as to determine the amino acid sequence thereof. As a result, it was found that lysine (K) at position 11 was substituted with arginine (R), phenylalanine (F) at position 13 was substituted with tyrosine (Y), valine (V) at position 25 was substituted with isoleucine (I), lysine (K) at position 32 was substituted with arginine (R), serine (S) at position 55 was substituted with alanine (A), threonine (T) at position 62 was substituted with valine (V), glutamine (Q) at position 96 was substituted with glutamic acid (E), phenylalanine (F) at position 102 was substituted with serine (S), alanine (A) at position 104 was substituted with serine (S), cysteine (C) at position 115 was substituted with threonine (T), glutamic acid (E) at position 117 was substituted with tyrosine (Y), valine (V) at position 123 was substituted with threonine (T), valine (V) at position 133 was substituted with isoleucine (I), serine (S) at position 139 was substituted with valine (V), threonine (T) at position 150 was substituted with alanine (A), cysteine (C) at position 151 was substituted with serine (S), phenylalanine (F) at position 162 was substituted with tyrosine (Y), alanine (A) at position 166 was substituted with glutamic acid (E), glutamine (Q) at position 190 was substituted with glycine (G), phenylalanine (F) at position 193 was substituted with tyrosine (Y), glycine (G) at position 195 was substituted with serine (S), and cysteine (C) at position 217 was substituted with serine (S).

Moreover, in order to add the Kozak sequence, valine (V) was introduced into the position before serine (S) at position 2. This mutant was named as mKO. The amino acid sequence of mKO is shown in SEQ ID NO: 1 of the sequence listing, and the nucleotide sequence thereof is shown in SEQ ID NO: 2 of the sequence listing.

A protein formed by adding His-Tag to mKO was allowed to express in *Escherichia coli* according to common methods, and it was then purified with Ni-Agarose.

Example 2

Analysis of Fluorescence Properties

The fluorescence and absorption spectra of the mKO protein purified in Example 1 were measured as follows. The quantum yield and molar absorption coefficient thereof were calculated.

An absorption spectrum was measured using a 20 μM fluorescent protein and a 50 mM HEPES solution (pH 7.5). A molar absorption coefficient was calculated from the peak value of this spectrum. In the case of mKO, the fluorescent protein was diluted with the aforementioned buffer solution such that the absorption peak was found at 548 nm and such that absorption at 500 nm became 0.0025. Thereafter, the fluorescence spectrum obtained by excitation at 500 nm, and the excitation spectrum obtained by fluorescence at 590 nm, were measured. The fluorescence spectrum of DsRed (CLON1 ECH) was also measured under conditions wherein the absorption at 500 nm became 0.0025. The quantum yield of DsRed was set at 0.29, and the quantum yield of mKO was obtained.

Figure 2:
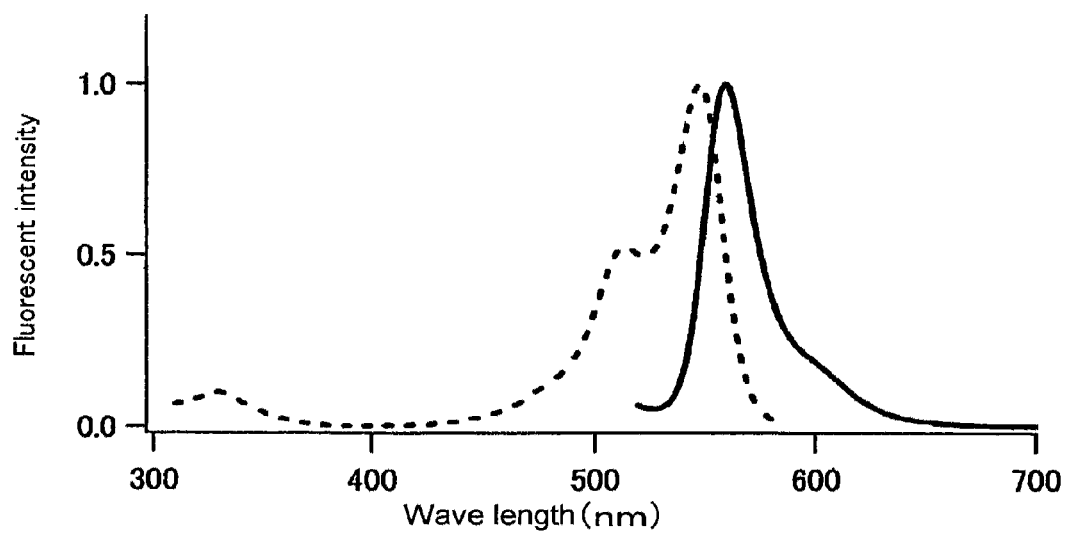
FIG. 2 shows the excitation spectrum (dotted line) and fluorescence spectrum (solid line) of mKO.

The results are shown in Table 1, and FIGS. 1 and 2. Table 1 also shows the data of the KO protein (dimer protein) described in International Publication WO03/54191.

TABLE 1

| | Maximum excitation | Maximum fluorescence | Molar absorption coefficient | Quantum yield | Number of amino acids | multimer formation | pH sensitivity |
|---|---|---|---|---|---|---|---|
| KO | 548 nm | 561 nm | 109750 | 0.45 | 217 | Dimer | pKa < 5.0 |
| mKO | 548 nm | 559 nm | 51600 | 0.6 | 218 | Monomer | PKa = 5.0 |

Example 3

Measurement of Molecular Weight by Ultracentrifugal Analysis

Figure 3:
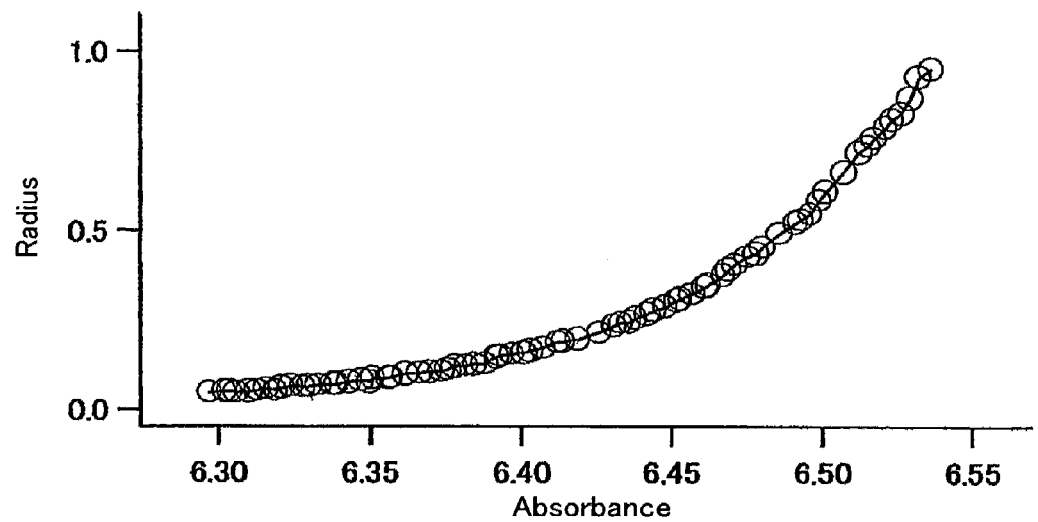
FIG. 3 shows the results of molecular weight measurement by ultracentrifugation. From the measurement results, the molecular weight was found to be 28 kDa.

An mKO protein solution with the composition consisting of 150 mM KCl and 50 mM HEPES-KOH (pH 7.4) was prepared. The molecular weight of mKO was determined by ultracentrifugal analysis. The above solution was centrifuged with an ultracentrifuge XL-1 (Beckman Coulter) at 25,000 rpm for 22 hours, so as to measure absorption at 540 nm around the maximum absorption (548 nm) of mKO. From the measurement results, the molecular weight of mKO was calculated to be 28 kDa (FIG. 3). This value was almost the same as 26 kDa predicted from the amino acid sequence, and thus it was confirmed that mKO exists in the form of a monomer.

Example 4

Figure 4:
FIG. 4 shows the results obtained by labeling the mitochondria of HeLa cells with KO (dimer). The mitochondria were converted to granules, which differ from the form of normal mitochondria.
Figure 5:
FIG. 5 shows the results obtained by labeling the mitochondria of HeLa cells with mKO (monomer). The mitochondria had a normal corded form.

Targeting to Mitochondria 12 amino acids (MLSLRQSIRFFK) (SEQ ID NO: 83) at the N-terminus of cytochrome oxidase subunit 4 derived from yeast were added to each of the N-termini of KO and mKO. Thereafter, targeting to the mitochondria of HeLa cells was conducted, so as to label the mitochondria. As a result, it was confirmed that KO (dimer) was not exactly targeted to the mitochondria, and that the mitochondria was stained in a granulated state (FIG. 4). On the other hand, mKO (monomer) was exactly targeted to the mitochondria, and narrow filamentous mitochondria were observed. Thus, effectiveness obtained by monomerization was confirmed (FIG. 5).

Example 5

Production of mKO Mutant Having Different Fluorescence Properties (1) Mutation Introduction The amino acids of mKO were substituted with other amino acids, so as to produce a fluorescent protein having fluorescence properties that are different from those of mKO. Point mutation introduction was carried out by performing PCR, using an *Escherichia coli* expression vector (pRSET$_5$), into which mKO had been inserted, and also using point mutation introduction primers. The primers used in PCR had been subjected to 5'-phosphorylation.

(a) 5'-phosphorylation of Primers

| | |
|---|---|
| 100 μM primers | 2 μl |
| 10x T4 polynucleotide kinase buffer | 5 μl |
| 100 μM ATP | 0.5 μl |
| Sterilized water | 41.5 μl |
| T4 polynucleotide kinase (10 U/μl) | 1 μl |

The mixture was incubated at 37° C. for 30 minutes.

(b) Point Mutation Introduction PCR

| | |
|---|---|
| 5'-phosphorylated primers | 4 μl |
| Template (mKO-pRSET$_B$) | 100 ng |
| 10x polymerase buffer | 2.5 μl |
| 10x DNA ligase buffer | 2.5 μl |
| 2.5 mM dNTPs | 1 μl |
| polymerase (pfu) 2.5 U/μl | 1 μl |
| Taq DNA ligase 40 U/μl | 0.5 μl |

The final volume of the mixture was set at 50 μl by addition of sterilized water. Program:

GeneAmp PCR system 9700 was used as a thermal cycler.

| | |
|---|---|
| (1) 65° C. | 5 min |
| (2) 95° C. | 2 min |
| (3) 95° C. | 20 sec |
| (4) 52° C. | 20 sec |
| (5) 65° C. | 8 min |
| (6) 75° C. | 7 min |
| (7) 4° C. | hold |

The operation described in (3) to (5) above was repeated for 25 cycles.

(c) Dpn1 Treatment

1 µl of Dpn1 was added to the sample obtained after PCR, and the obtained mixture was then incubated at 37° C. for 1 hour, so as to cleave a template plasmid.

(d) Transformation of *Escherichia coli*

*Escherichia coli* JM109 (DE3) was transformed with the sample treated with Dpn1, so that mKO after introduction of the mutation was allowed to express therein. Thereafter, mKO was analyzed.

(2) Amino Acid-Substituted Site and Fluorescence Properties of mKO Mutant

A fluorospectrophotometer F-2500 (HITACHI) was used for fluorescence measurement. A spectrophotometer U-3310 (HITACHI) was used for absorption measurement.

(i) UV-excited green fluorescent mutant mKUV-1 (the amino acid sequence thereof is shown in SEQ ID NO: 3, and the nucleotide sequence thereof is shown in SEQ ID NO: 4)

Figure 6:
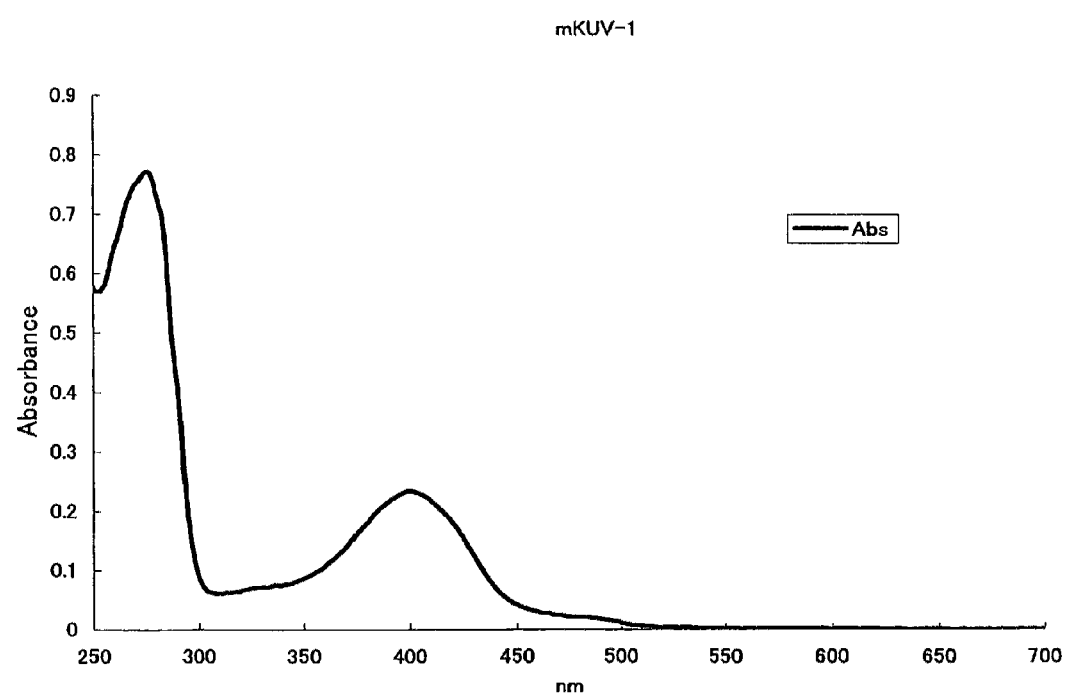
FIG. 6 shows the absorption spectrum of a UV-excited green fluorescent mutant mKVU-1.
Figure 7:
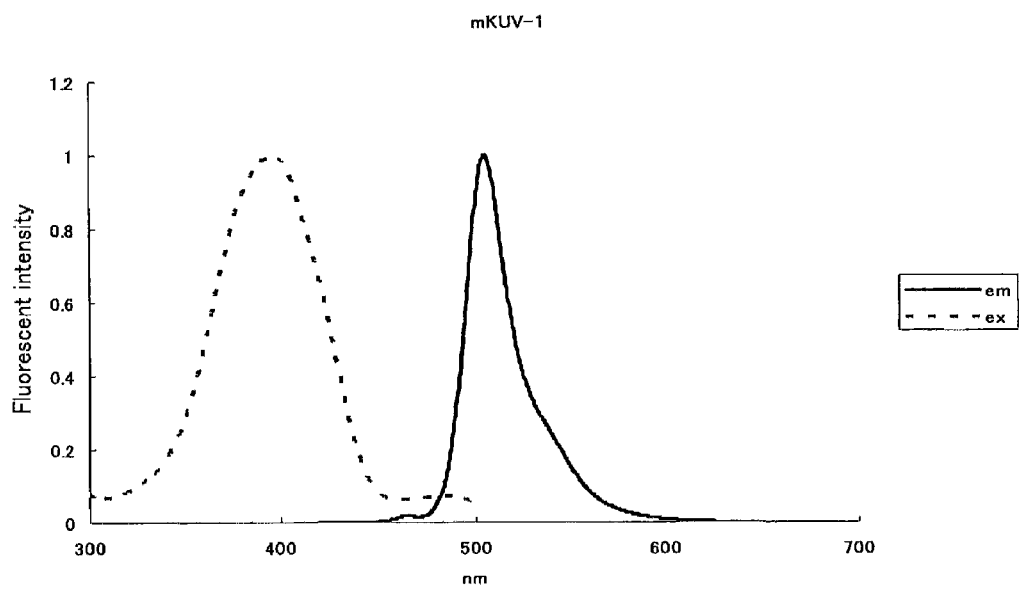
FIG. 7 shows the excitation spectrum and fluorescence spectrum of a UV-excited green fluorescent mutant mKVU-1.

In mKO, proline (P) at position 70 was substituted with cysteine (C), valine (V) at position 160 was substituted with aspartic acid (D), methionine (M) at position 162 was substituted with leucine (L), and phenylalanine (F) at position 176 was substituted with methionine (M), so as to obtain a green fluorescent protein having a fluorescence peak at 505 nm and an excitation peak at 398 nm (FIGS. 6 and 7). The molar absorption coefficient thereof was 10,000, and the quantum yield of fluorescence was 0.27.

(ii) Blue fluorescent mutant mKUV-2 (the amino acid sequence thereof is shown in SEQ ID NO: 5, and the nucleotide sequence thereof is shown in SEQ ID NO: 6)

Figure 8:
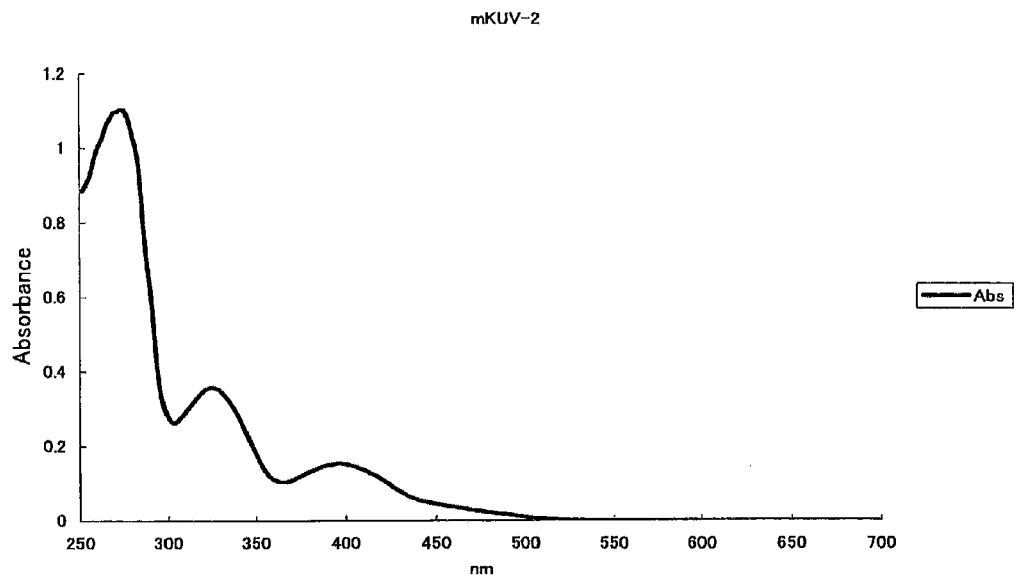
FIG. 8 shows the absorption spectrum of a blue fluorescent mutant mKUV-2.
Figure 9:
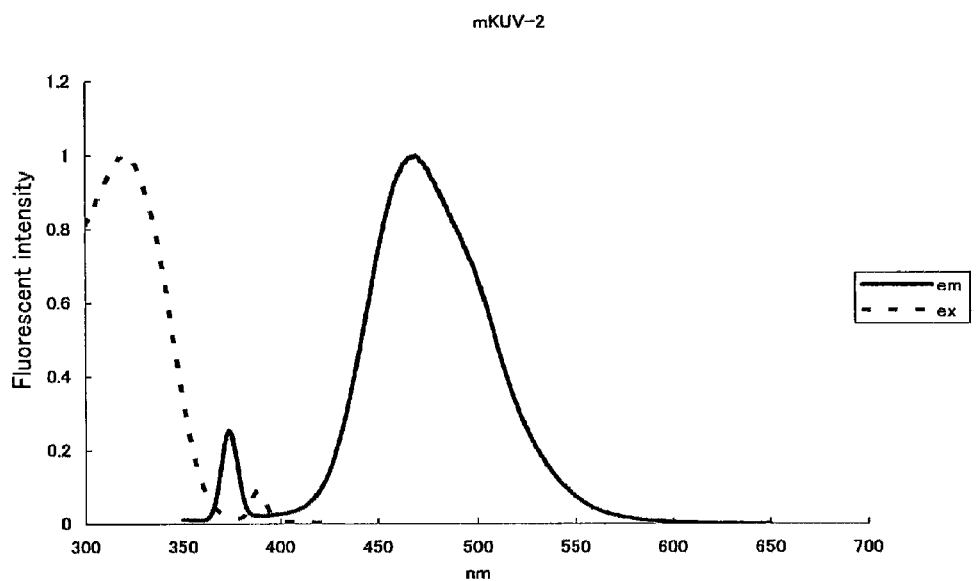
FIG. 9 shows the excitation spectrum and fluorescence spectrum of a blue fluorescent mutant mKUV-2.

In mKO, cysteine (C) at position 65 was substituted with glycine (G), proline (P) at position 70 was substituted with glycine (G), valine (V) at position 160 was substituted with aspartic acid (D), and phenylalanine (F) at position 176 was substituted with methionine (M), so as to obtain a blue fluorescent protein having a fluorescence peak at 469 nm and an excitation peak at 322 nm (FIGS. 8 and 9). The molar absorption coefficient thereof was 12,500, and the quantum yield of fluorescence was 0.2.

(iii) Green fluorescent mutant mKO-FM32 (the amino acid sequence thereof is shown in SEQ ID NO: 7, and the nucleotide sequence thereof is shown in SEQ ID NO: 8)

Figure 10:
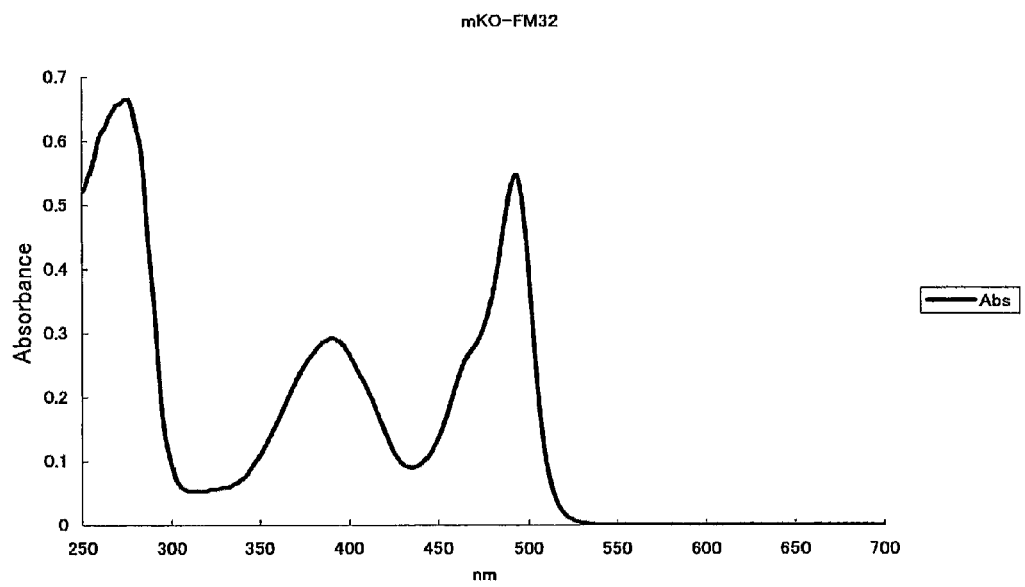
FIG. 10 shows the absorption spectrum of a green fluorescent mutant mKO-FM32.
Figure 11:
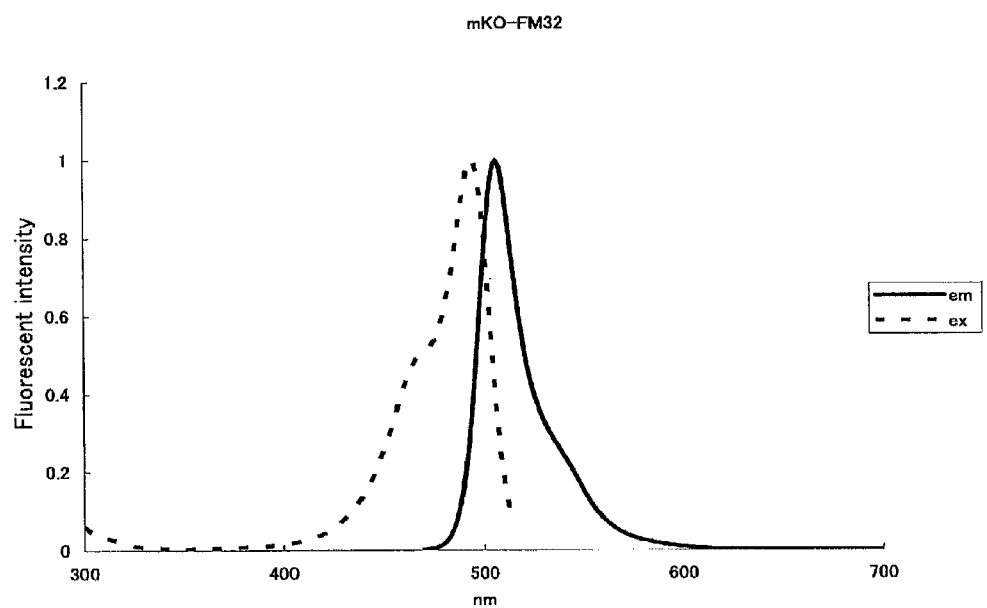
FIG. 11 shows the excitation spectrum and fluorescence spectrum of a green fluorescent mutant mKO-FM32.

In mKO, cysteine (C) at position 65 was substituted with alanine (A), and proline (P) at position 70 was substituted with glycine (G), so as to obtain a green fluorescent protein having a fluorescence peak at 506 nm and an excitation peak at 493 nm (FIGS. 10 and 11). The molar absorption coefficient thereof was 27,500, and the quantum yield of fluorescence was 0.44.

(iv) Red fluorescent mutant mKO-F90 (the amino acid sequence thereof is shown in SEQ ID NO: 9, and the nucleotide sequence thereof is shown in SEQ ID NO: 10)

Figure 12:
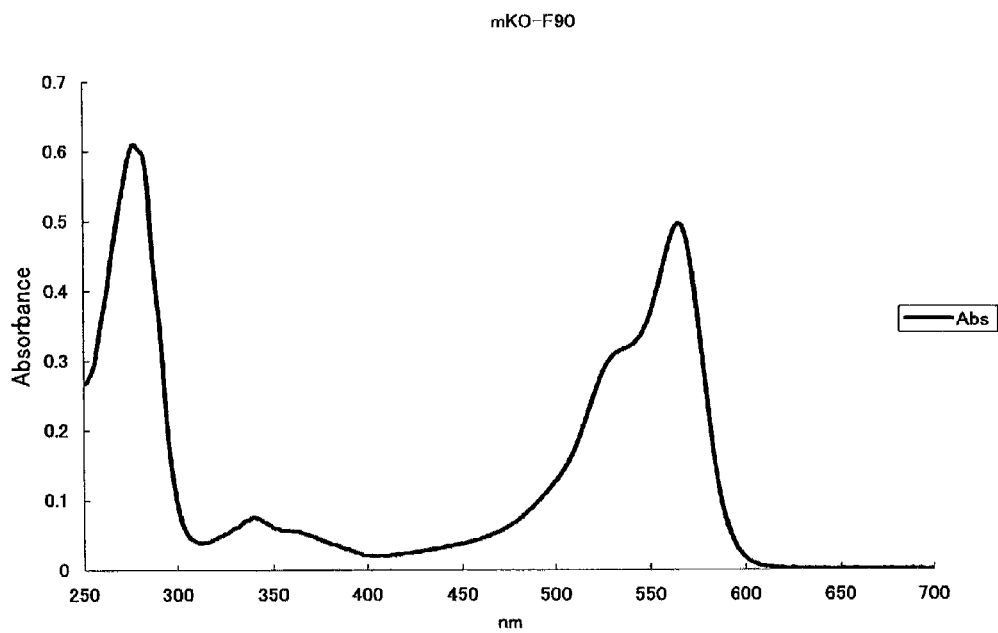
FIG. 12 shows the absorption spectrum of a red fluorescent mutant mKO-F90.
Figure 13:
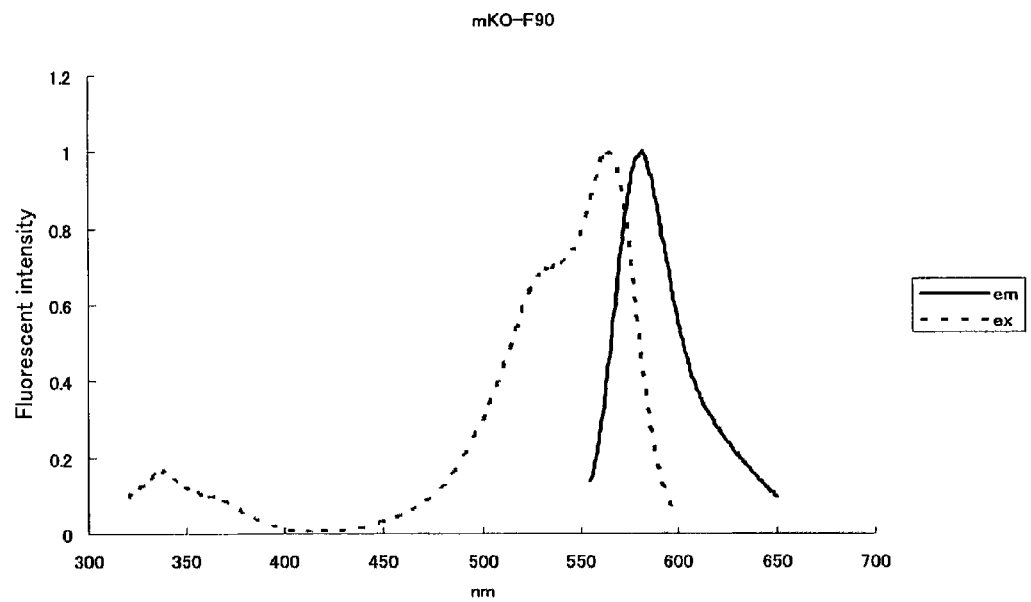
FIG. 13 shows the excitation spectrum and fluorescence spectrum of a red fluorescent mutant mKO-F90.

In mKO, methionine (M) at position 41 was substituted with leucine (L), lysine (K) at position 49 was substituted with glutamic acid (E), arginine (R) at position 69 was substituted with lysine (K), serine (S) at position 145 was substituted with tryptophan (W), lysine (K) at position 185 was substituted with glutamic acid (E), lysine (K) at position 188 was substituted with glutamic acid (E), and serine (S) at position 192 was substituted with aspartic acid (D), so as to obtain a red fluorescent protein having a fluorescence peak at 582 nm and an excitation peak at 564 nm (FIGS. 12 and 13). The molar absorption coefficient thereof was 25,000, and the quantum yield of fluorescence was 0.05.

Example 6

Production of mKO Mutant Emitting both Green and Orange Fluorescence (Time Passage Measurement Probe and Trace Probe)

The amino acids of mKO were substituted with other amino acids, so as to produce a fluorescent protein having fluorescence properties that are different from those of mKO. Immediately after being translated, mKO emitted green fluorescence, and then emitted orange fluorescence. However, since such a shift from green fluorescence to orange fluorescence has been rapidly completed, it is generally invisible. Thus, a fluorescent protein having different ratios between green fluorescence and orange fluorescence depending on various types of time passage was produced. Using this mutant protein, the time passed after expression of the protein can be measured based on the ratio between the green fluorescence and the orange fluorescence. In addition, since such green fluorescence and orange fluorescence exist independently in the mutant, only the orange fluorescence could be quenched. That is, if only the orange fluorescence is quenched and an increase in the orange fluorescence is measured, the measurement of time passage can be reset. Moreover, if any given portion of only the orange color is quenched and the time passage is measured based on the ratio between the green fluorescence and the orange fluorescence, it also becomes possible to measure the behavior of the labeled molecules or cells of such a quenched portion. As a result, it was found that a fluorescent protein having various types of ratios between green fluorescence and orange fluorescence as the time passed, can be produced by substituting proline (P) at position 70 with another amino acid.

(1) Mutation Introduction

The amino acids of mKO were substituted with other amino acids, so as to produce a fluorescent protein having fluorescence properties that are different from those of mKO. Point mutation was introduced by performing PCR using an *Escherichia coli* expression vector (pRSET$_B$), into which mKO had been inserted, and also using point mutation introduction primers. The primers used in PCR had been subjected to 5'-phosphorylation.

(a) 5'-phosphorylation of Primers

| | |
|---|---|
| 100 µM primers | 2 µl |
| 10x T4 polynucleotide kinase buffer | 5 µl |
| 100 µM ATP | 0.5 µl |
| Sterilized water | 41.5 µl |
| T4 polynucleotide kinase (10 U/µl) | 1 µl |

The mixture was incubated at 37° C. for 30 minutes.

(b) Point Mutation Introduction PCR

| | |
|---|---|
| 5'-phosphorylated primers | 4 µl |
| Template (mKO-pRSET$_B$) | 100 ng |
| 10x polymerase buffer | 2.5 µl |
| 10x DNA ligase buffer | 2.5 µl |
| 2.5 mM dNTPs | 1 µl |
| polymerase (pfu) 2.5 U/µl | 1 µl |
| Taq DNA ligase 40 U/µl | 0.5 µl |

The final volume of the mixture was set at 50 μl by addition of sterilized water. Program:

GeneAmp PCR system 9700 was used as a thermal cycler.

| | |
|---|---|
| (1) 65° C. | 5 min |
| (2) 95° C. | 2 min |
| (3) 95° C. | 20 sec |
| (4) 52° C. | 20 sec |
| (5) 65° C. | 8 min |
| (6) 75° C. | 7 min |
| (7) 4° C. | hold |

The operation described in (3) to (5) above was repeated for 25 cycles.

(c) Dpn1 Treatment

1 μl of Dpn1 was added to the sample obtained after PCR, and the obtained mixture was then incubated at 37° C. for 1 hour, so as to cleave a template plasmid.

(d) Transformation of *Escherichia coli*

*Escherichia coli* JM109 (DE3) was transformed with the sample treated with Dpn1, so that mKO after introduction of the mutation was allowed to express therein. Thereafter, mKO was analyzed.

(2) Analysis of mKO Time Passage Mutant

The nucleotide sequence of the produced mKO mutant was analyzed. As a result, it was found that in the mKO mutant, lysine (K) at position 49 was substituted with glutamic acid (E), proline (P) at position 70 was substituted with glycine (G), lysine (K) at position 185 was substituted with glutamic acid (E), lysine (K) at position 188 was substituted with glutamic acid (E), serine (S) at position 192 was substituted with aspartic acid (D), and serine (S) at position 196 was substituted with glycine (G). This mKO mutant was a fluorescent protein whose ratio between the green fluorescence and the orange fluorescence is changed depending on time passage. By substituting proline (P) at position 70 of this mKO mutant with various types of amino acids, the rate of changing the ratio between the green fluorescence and the orange fluorescence depending on time passage was changed.

A mutant where praline (P) at position 70 was substituted with glycine (G) was referred to as mKO-FM9 (the amino acid sequence thereof is shown in SEQ ID NO: 11, and the nucleotide sequence thereof is shown in SEQ ID NO: 12).

A mutant where proline (P) at position 70 was substituted with alanine (A) was referred to as mKO-FM5 (the amino acid sequence thereof is shown in SEQ ID NO: 13, and the nucleotide sequence thereof is shown in SEQ ID NO: 14).

A mutant where proline (P) at position 70 was substituted with serine (S) was referred to as mKO-FM3 (the amino acid sequence thereof is shown in SEQ ID NO: 15, and the nucleotide sequence thereof is shown in SEQ ID NO: 16).

A mutant where proline (P) at position 70 was substituted with cysteine (C) was referred to as mKO-FM20 (the amino acid sequence thereof is shown in SEQ ID NO: 17, and the nucleotide sequence thereof is shown in SEQ ID NO: 18).

A mutant where proline (P) at position 70 was substituted with threonine (T) was referred to as mKO-FM24 (the amino acid sequence thereof is shown in SEQ ID NO: 19, and the nucleotide sequence thereof is shown in SEQ ID NO: 20).

A mutant where proline (P) at position 70 was substituted with valine (V) was referred to as mKO-FM14 (the amino acid sequence thereof is shown in SEQ ID NO: 21, and the nucleotide sequence thereof is shown in SEQ ID NO: 22).

A mutant where proline (P) at position 70 was substituted with leucine (L) was referred to as mKO-FM19 (the amino acid sequence thereof is shown in SEQ ID NO: 23, and the nucleotide sequence thereof is shown in SEQ ID NO: 24).

A mutant where proline (P) at position 70 was substituted with tyrosine (Y) was referred to as mKO-FM23 (the amino acid sequence thereof is shown in SEQ ID NO: 25, and the nucleotide sequence thereof is shown in SEQ ID NO: 26).

A mutant where proline (P) at position 70 was substituted with glutamine (Q) was referred to as mKO-FM21 (the amino acid sequence thereof is shown in SEQ ID NO: 27, and the nucleotide sequence thereof is shown in SEQ ID NO: 28).

A mutant where proline (P) at position 70 was substituted with asparagine (N) was referred to as mKO-FM25 (the amino acid sequence thereof is shown in SEQ ID NO: 29, and the nucleotide sequence thereof is shown in SEQ ID NO: 30).

Figure 14:
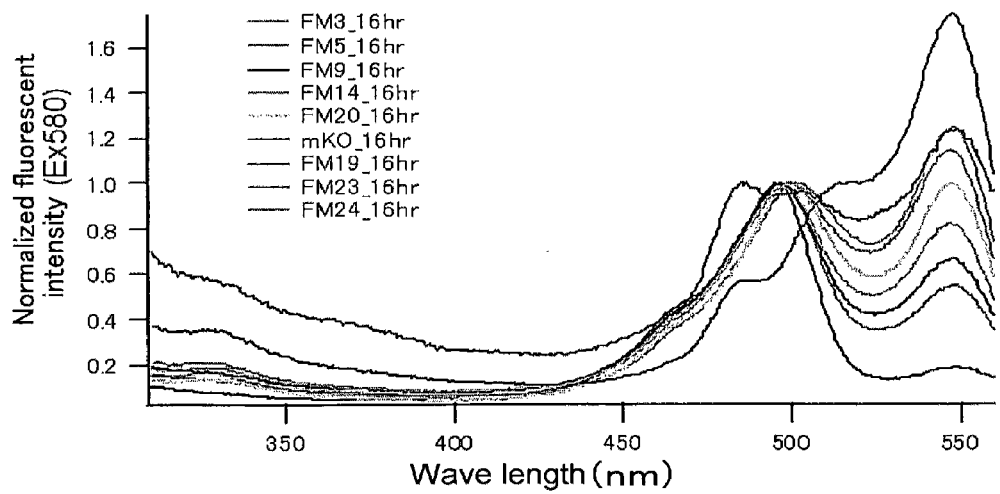
FIG. 14 shows the excitation spectrum at 580 nm of mKO time passage mutant
Figure 15:
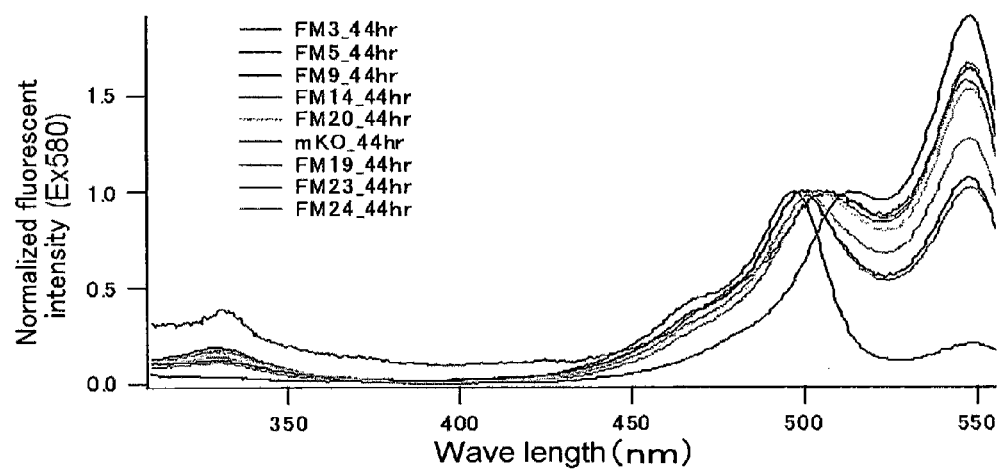
FIG. 15 shows the excitation spectrum at 580 nm of mKO time passage mutant
Figure 16:
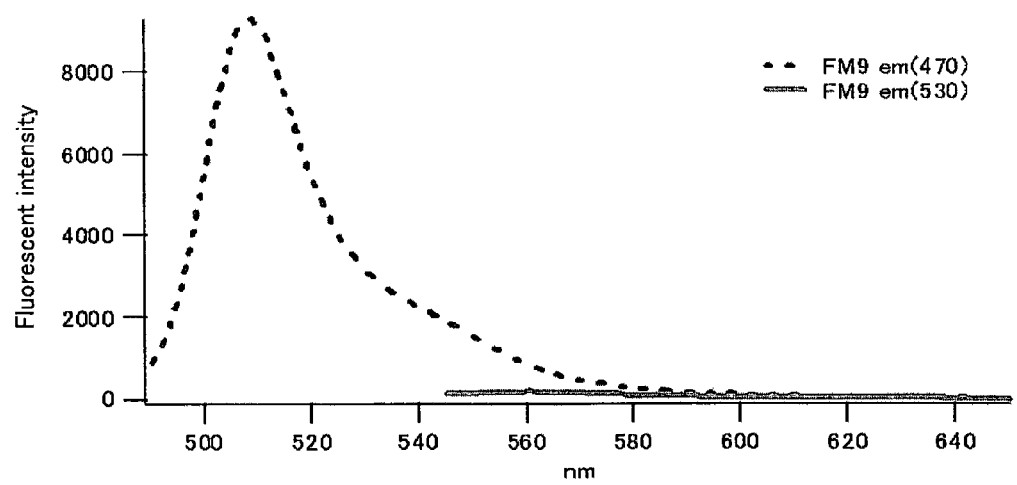
FIG. 16 shows the fluorescence spectrum of mKO time passage mutant
Figure 17:
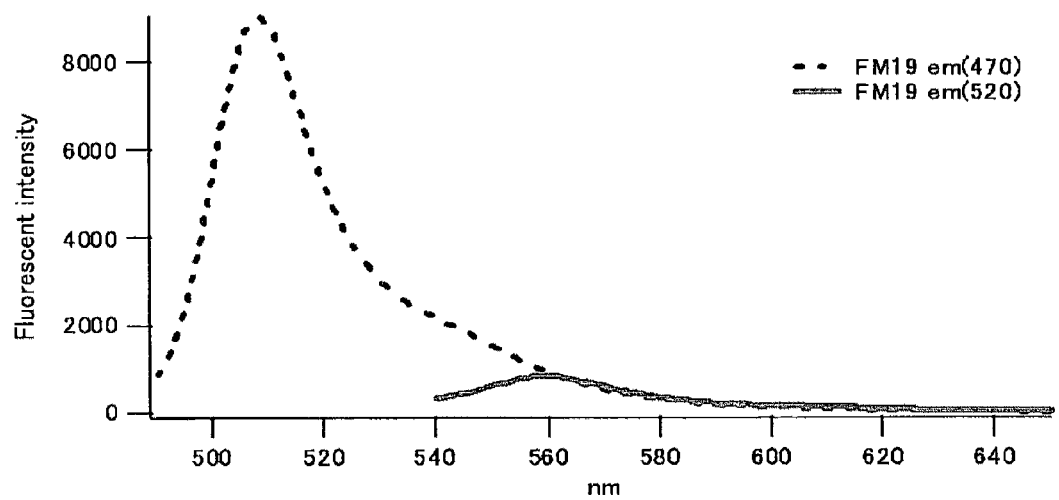
FIG. 17 shows the fluorescence spectrum of mKO time passage mutant
Figure 18:
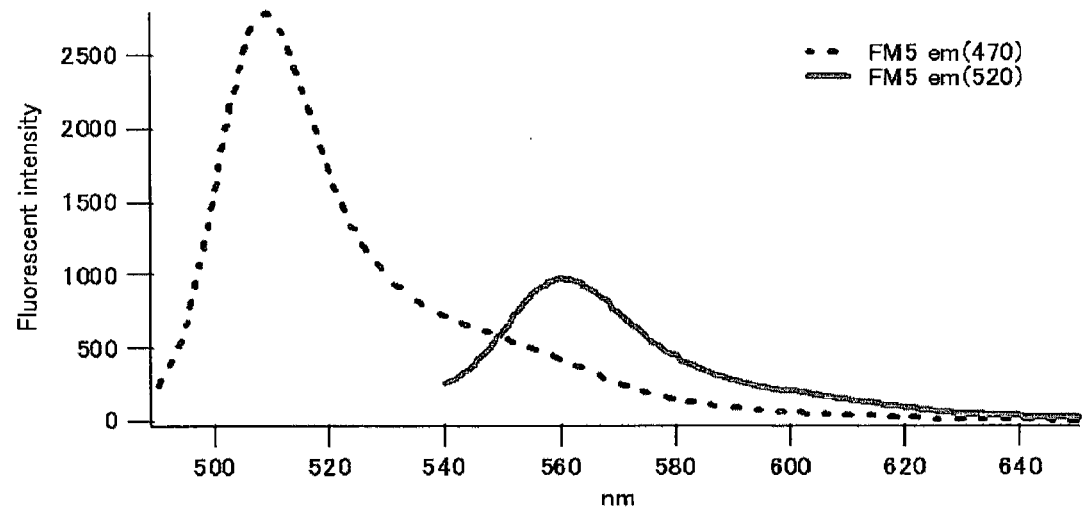
FIG. 18 shows the fluorescence spectrum of mKO time passage mutant
Figure 19:
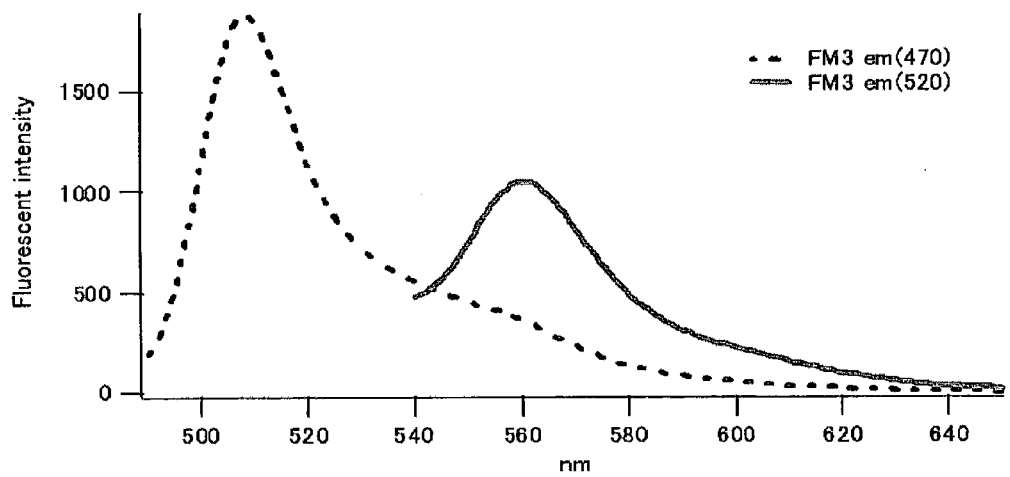
FIG. 19 shows the fluorescence spectrum of mKO time passage mutant
Figure 20:
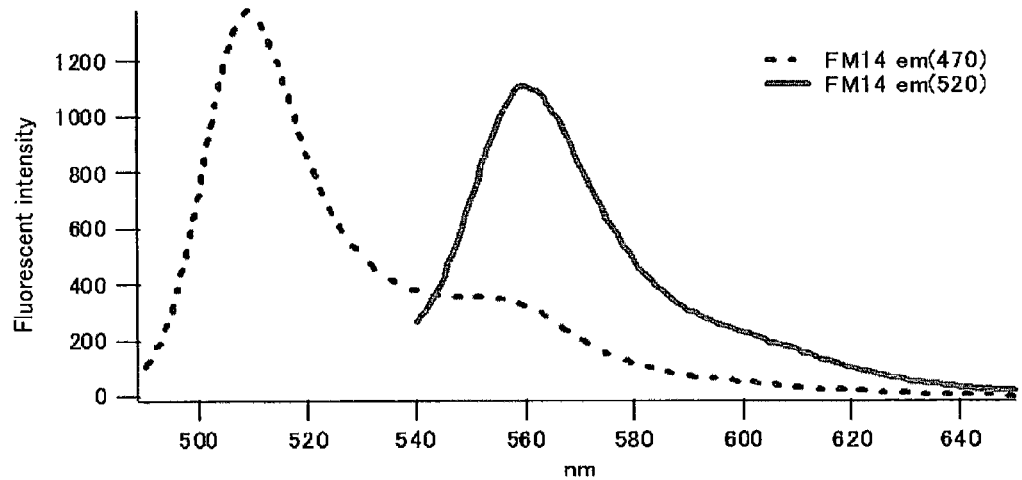
FIG. 20 shows the fluorescence spectrum of mKO time passage mutant
Figure 21:
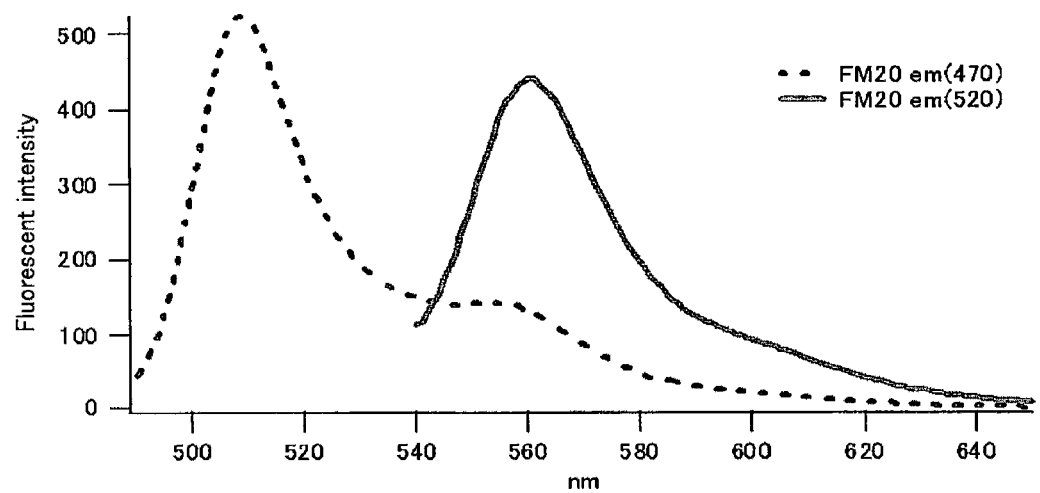
FIG. 21 shows the fluorescence spectrum of mKO time passage mutant
Figure 22:
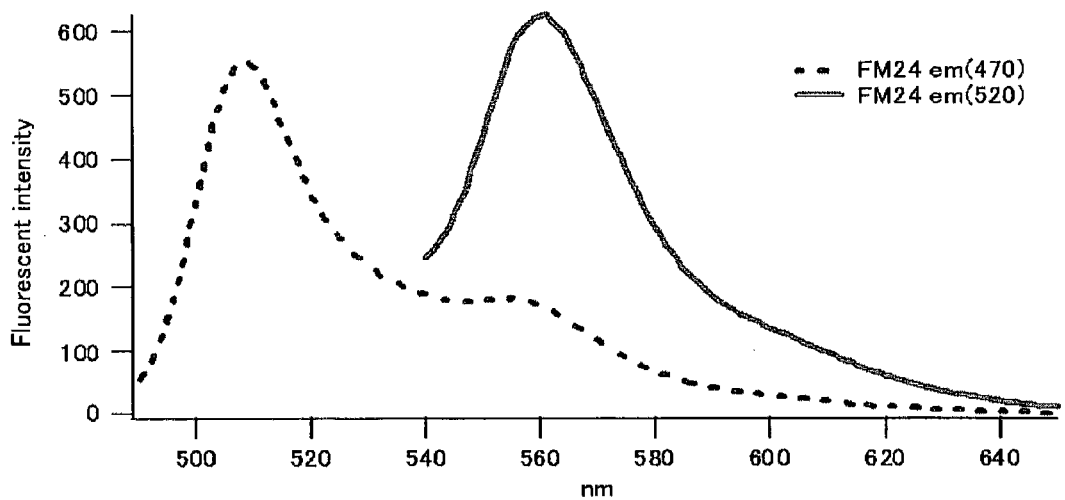
FIG. 22 shows the fluorescence spectrum of mKO time passage mutant
Figure 23:
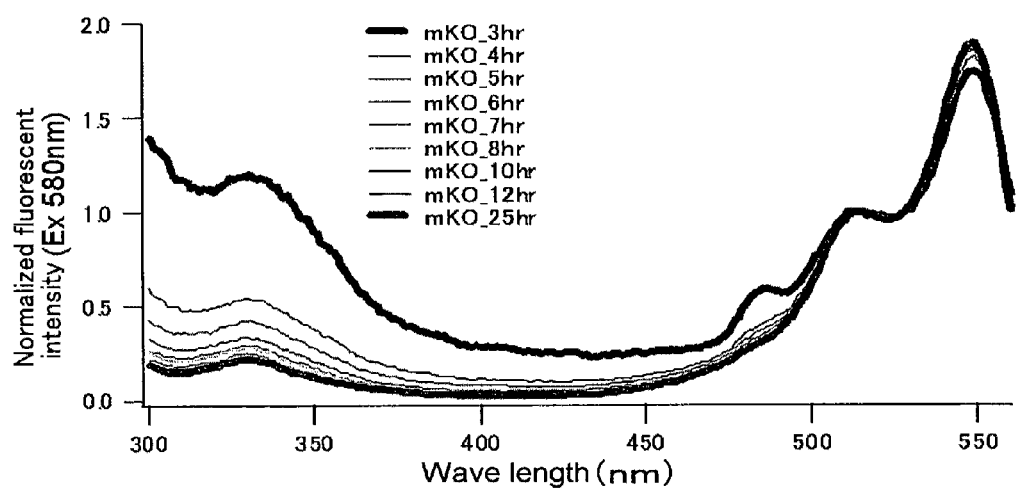
FIG. 23 shows the excitation spectrum at 580 nm obtained until 25 hours after the synthesis of mKO.
Figure 24:
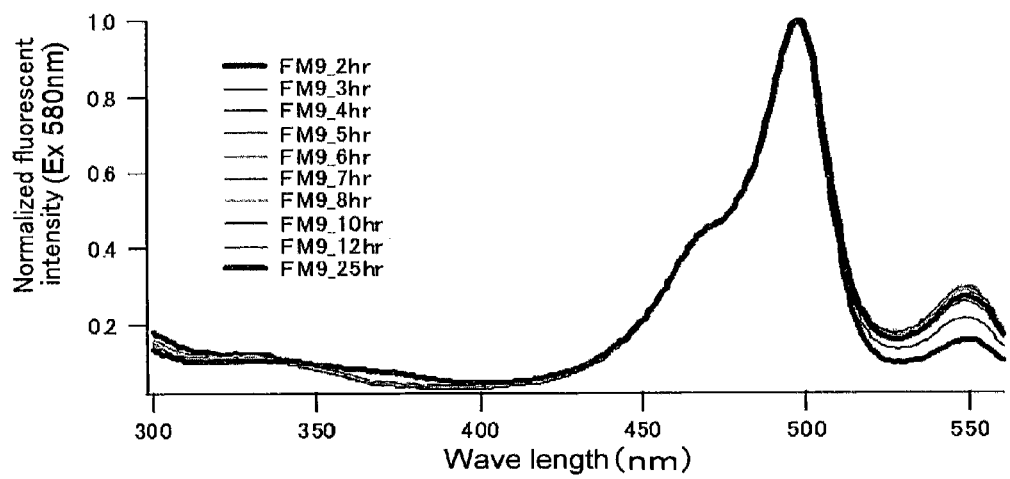
FIG. 24 shows the excitation spectrum at 580 nm obtained until 25 hours after the synthesis of mKO time passage mutant.
Figure 25:
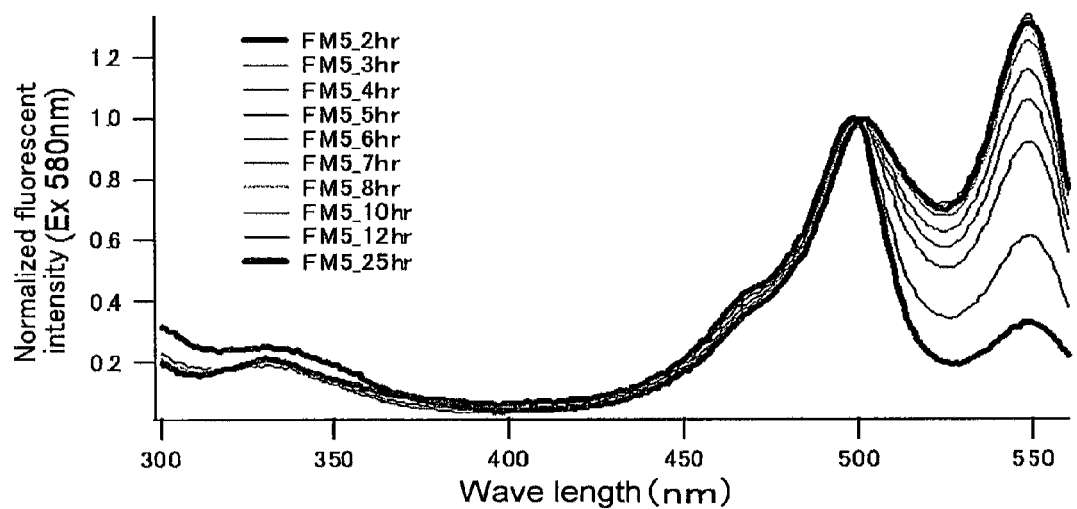
FIG. 25 shows the excitation spectrum at 580 nm obtained until 25 hours after the synthesis of mKO time passage mutant.
Figure 26:
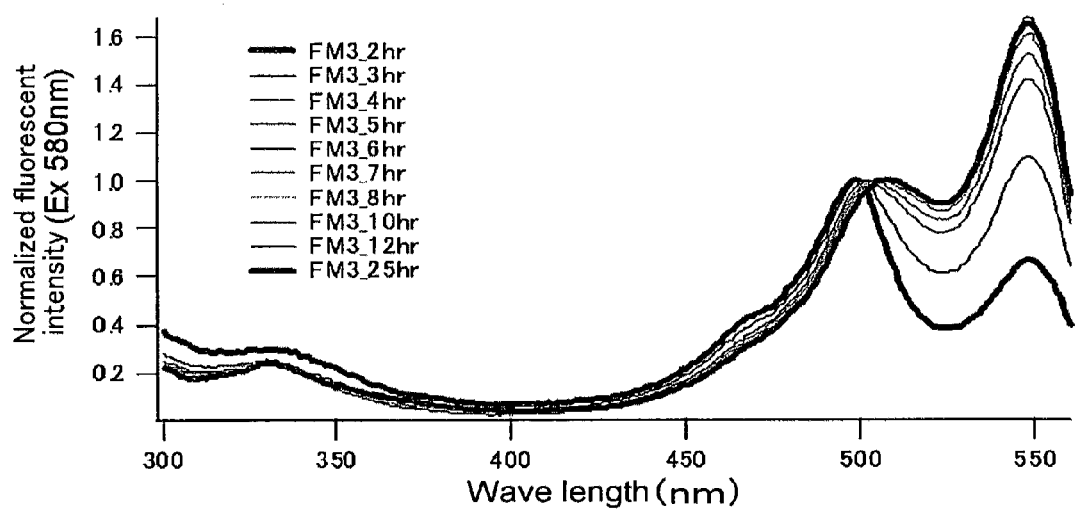
FIG. 26 shows the excitation spectrum at 580 nm obtained until 25 hours after the synthesis of mKO time passage mutant.
Figure 27:
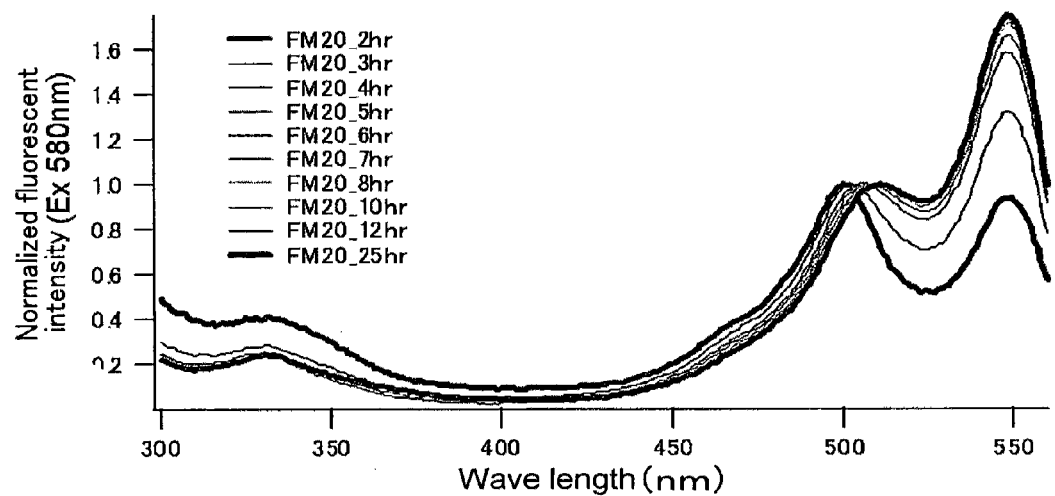
FIG. 27 shows the excitation spectrum at 580 nm obtained until 25 hours after the synthesis of mKO time passage mutant.
Figure 28:
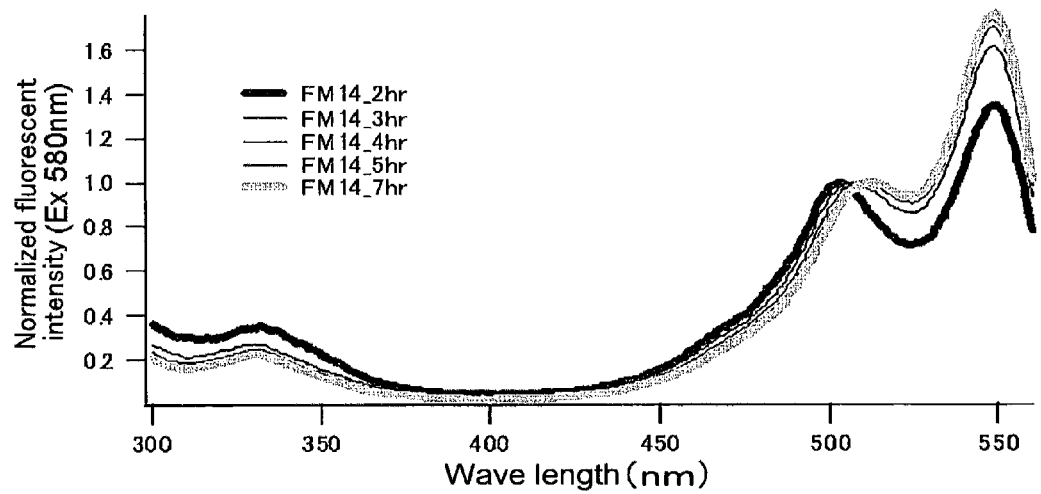
FIG. 28 shows the excitation spectrum at 580 nm obtained until 25 hours after the synthesis of mKO time passage mutant.
Figure 29:
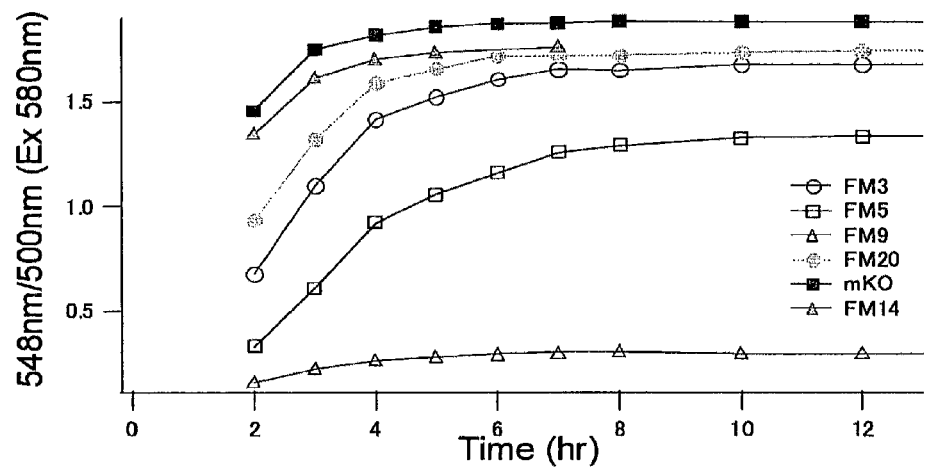
FIG. 29 is a plot showing the ratio between 500 nm as an excitation peak of green fluorescence and 548 nm as an excitation peak of orange fluorescence in an mKO time passage mutant.

The measurement of each mKO time passage mutant was carried out using a recombinant fluorescent protein that was allowed to express in *Escherichia coli* JM109 (DM3), or using the in vitro translation system PURE SYSTEM CLASSIC MINI (Post Genome Institute Co., Ltd.). With regard to measurement in *Escherichia coli*, a culture plate, on which each mutant had been expressed, was incubated at 37° C., and thereafter, sampling was carried out over time, so as to measure an excitation spectrum at 580 nm (FIGS. 14 and 15). As a result, it was found that the peak at 548 nm that is the excitation peak of orange fluorescence increased over time rather than the peak at approximately 500 nm that is the excitation peak of green fluorescence, and that the increase rate differed depending on the type of each mutant. The peak of the green fluorescence was found to be 509 nm, and the peak of the orange fluorescence was found to be 560 nm (FIGS. 16, 17, 18, 19, 20, 21, and 22; each of them was excited with the wavelength described in the parenthesis). A fluorospectrophotometer F-2500 (HITACHI) was used for fluorescence measurement Since novel proteins are intermittently produced in *Escherichia coli*, the time required for a shift from green to orange is apparently prolonged. Thus, the in vitro translation system was used to limit the production time of such proteins, so as to measure a shift from green to orange with more exact time passage. The time required for the synthesis of proteins was set at 1 hour. Immediately after 1 hour had passed, an energy source necessary for the synthesis of proteins, such as ATP, was removed by gel filtration, and the residue was then incubated at 37° C., so as to synthesize proteins. Thereafter, the excitation spectrum at 580 nm was measured until 25 hours after the synthesis (FIGS. 23, 24, 25, 26, 27, and 28). The ratio between the value at 500 nm of the excitation peak portion of the green fluorescence and the value at 548 nm of the excitation peak portion of the orange fluorescence was plotted. As a result, it was found that as the side chains of amino acids relatively greaten (G→A→S→C→T→V→P), the speed of a shift to the orange fluorescence component tends to become rapid (FIG. 29).

Figure 30:
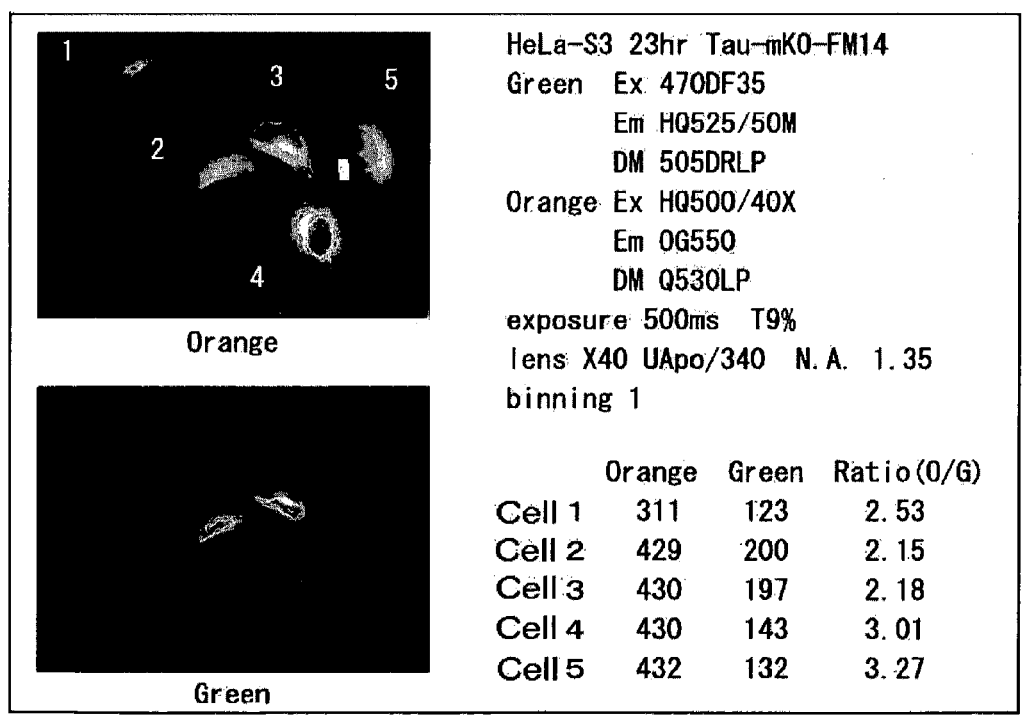
FIG. 30 shows the results obtained by introducing into HeLa-S3 cells, a fusion protein gene obtained by ligating Tau to the N-terminus of mKO-FM14, followed by imaging.

A fusion protein gene (whose amino acid sequence is shown in SEQ ID NO: 31, and nucleotide sequence is shown in SEQ ID NO: 32), which had been obtained by genetically ligating Tau (a protein that binds to a tubulin or the like and promotes microtubule polymerization for stabilization) to the N-terminus of mKO-FM14, was subcloned into the BamHI-XhoI site of the animal cell expression vector pCDNA3. Thereafter, the thus produced vector was introduced into HeLa-S3 cells, using Polyfect (QIAGEN). Twenty-three hours after introduction of the gene, the culture solution was substituted with the MSS (Hanks' Balanced Salt Solution), followed by imaging. As a result, cells with various types of color tones ranging from green to orange were observed, depending on the difference in time wherein the vector was incorporated into the HeLa-S3 cells. From the ratio between the orange color and the green color, it was confirmed that cells 4 and 5 incorporated the vector therein at an early stage, and that cells 1, 2, and 3 then incorporated the vector therein (FIG. 30). IX-70 (OLYMPUS) was used herein as a microscope. In order to detect the green color component, 470DF35 (OMEGA) was used as an excitation filter, HQ525/50M (CHROMA) was used as a fluorescence filter, and 505DRLP (OMEGA) was used as a dichroic mirror. In addition, in order to detect the orange color component, HQ500/40X (CHROMA) was used as an excitation filter, OG550 (OMEGA) was used as a fluorescence filter, and Q530LP (CHROMA) was used as a dichroic mirror.

(3) Trace of Molecules with mKO Time Passage Mutant

Figure 31:
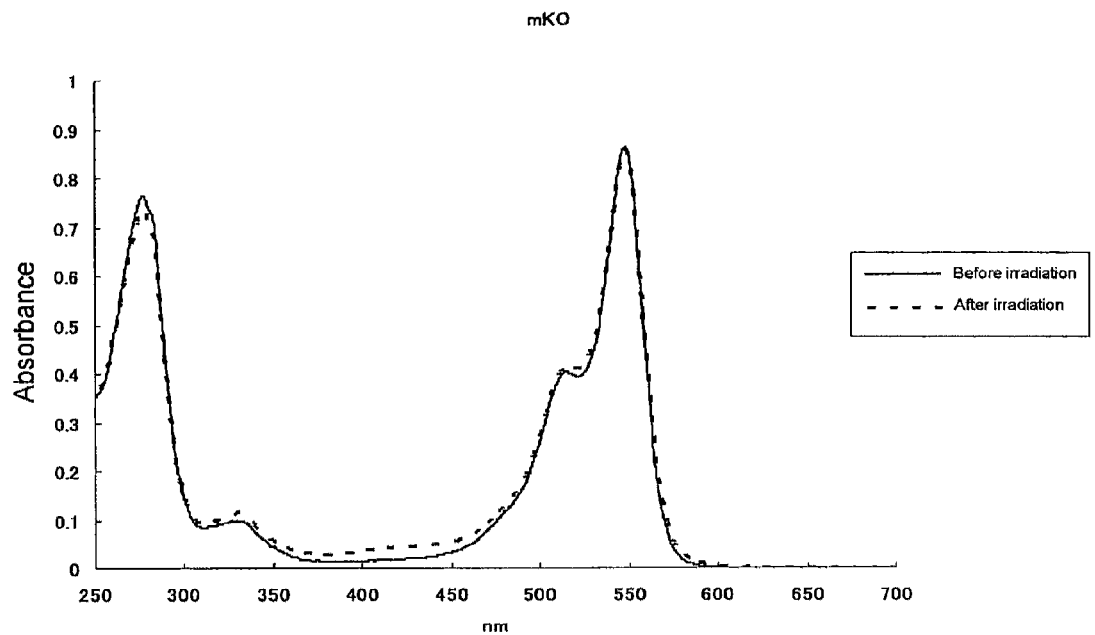
FIG. 31 shows the results obtained by applying strong green light to the mKO protein and measuring the absorption spectrum before and after application of the light.
Figure 32:
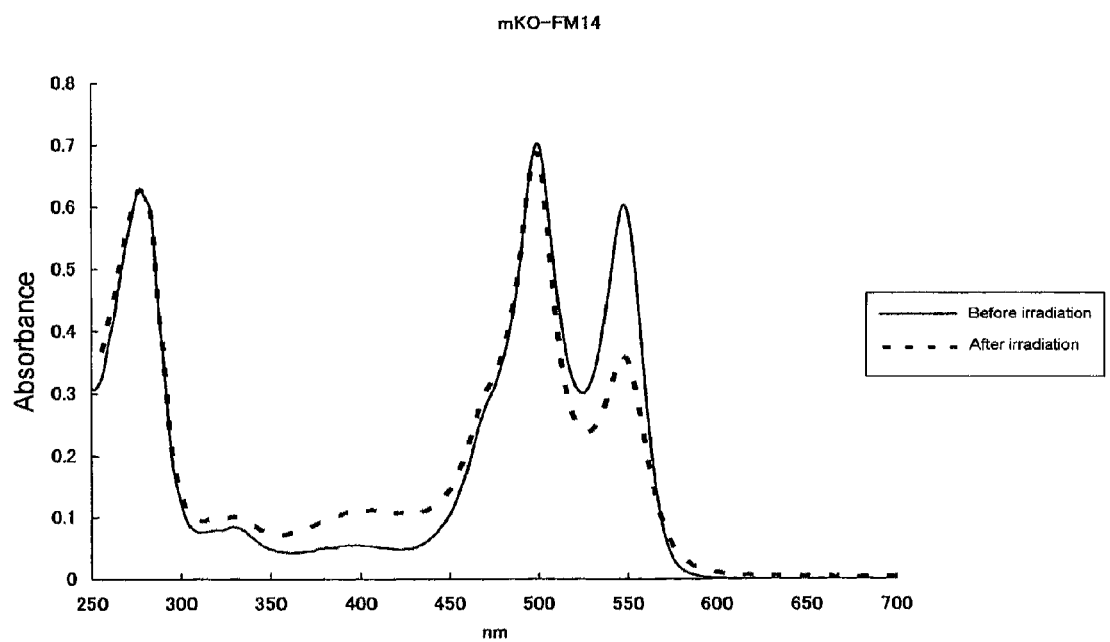
FIG. 32 shows the results obtained by applying strong green light to the mKO-FM14 protein and measuring the absorption spectrum before and after application of the light.

A strong green light was applied to a recombinant mKO-FM14 protein, so as to examine whether it was able to, discolor only the orange-color fluorescence component of the recombinant mKO-FM14 protein. A filter was directly attached to a 100-W xenon lamp, and a strong green light was then applied to the recombinant mKO-FM14 protein. As a filter, 546DF20 (OMEGA) was used. As a control, such a strong green light was also applied to a recombinant mKO protein. Thereafter, the absorption spectrum was measured before and after application of the light, so as to examine whether the absorption value at 548 nm decreased. A spectrophotometer U-3310 (HITACHI) was used to measure absorption. As a result, the absorption value at 548 nm of the recombinant mKO protein used as a control did not change. In contrast, the absorption value at 548 nm of the recombinant mKO-FM14 protein significantly decreased. However, the absorption peak at 500 nm necessary for emission of a green fluorescence component did not change (FIGS. 31 and 32). This indicates that only the orange fluorescence component can be eliminated or decreased by application of a strong green light to the mKO-FM14 protein. In addition, if the ratio between the orange fluorescence signal and the green fluorescence signal is calculated based on the quenching or decrease of the orange fluorescence by application of a strong green light to only a localized portion in a space filled with the mKO-FM14 protein or an mKO-FM14 protein-added product, only the portion can be labeled. Thus, a fusion protein gene (the amino acid sequence thereof is shown in SEQ ID NO: 33, and the nucleotide sequence thereof is shown in SEQ ID NO: 34), which had been obtained by fusion of BDNF (brain-derived neurotrophic factor) to the N-terminus of mKO-FM14, was subcloned into a product obtained by extracting EGFP from pEGFP-N1 (Clontech). The resultant was then allowed to express in rat hippocampus neurons, followed by imaging.

Figure 33:
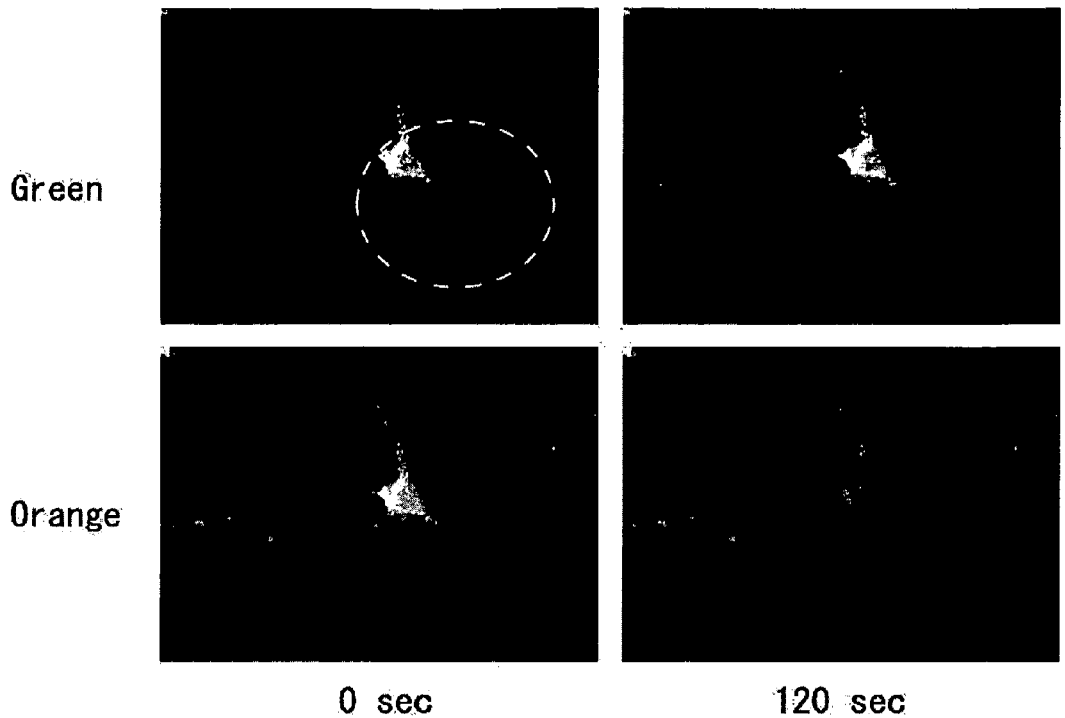
FIG. 33 shows the results obtained by detecting under a fluorescence microscope, a fusion protein expressing in cells approximately 12 hours to 2 days after introduction of a BDNF-mKO-FM14 expression gene vector into the cells, then applying strong green light thereto, and then fading orange fluorescence only in a specific region.
Figure 34:
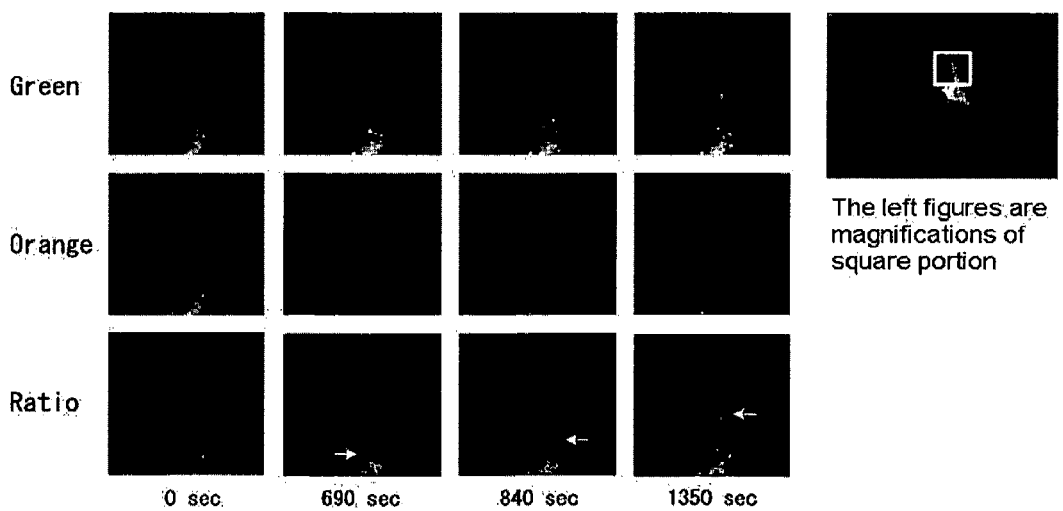
FIG. 34 shows the results obtained by detecting under a fluorescence microscope, a fusion protein expressing in cells approximately 12 hours to 2 days after introduction of a BDNF-mKO-FM14 expression gene vector into the cells, and then tracing the molecule (BDNF-mKO-FM14) based on change in color.

That is, rat hippocampus neurons were prepared. Hippocampal portions (of approximately 10 rats) were excised from fetuses in pregnant rats ($17^{th}$ to $19^{th}$ day after conception), or from newborn rats on the $1^{st}$ to $3^{rd}$ day after the birth, under a microscope. Subsequently, such hippocampal portion were subjected to heat treatment with the digestive enzyme papain over ten minutes, and the resultant was then mechanically dispersed using a pipette, so as to obtain a hippocampal cell suspension that was rich in neurons. This suspension was diluted with a medium as necessary, and it was then inoculated onto a culture plate with a diameter of 35 nm, which had been coated with a cell adhesive substrate such as polylysine. The seeding density was set at approximately 20,000 to 40,000 cells/cm². These cells were adhered to the surface of the culture plate, and a primary culture was then carried out at a high density using an Eagle medium that contained fetal bovine serum and N2-supplement (an additive for neurons). Sixth or seventh days after initiation of the culture, 2 to 4 µg of DNA per 35-mm culture plate was introduced into the cells by the calcium phosphate method using a BDNF-mKO-FM14 expression gene vector at 37° C. for 30 minutes. Approximately 12 hours to 2 days after introduction of this gene, a fluorescent protein expressing in the cells was detected under a fluorescence microscope, and it was then used in an experiment for tracing a change in color. 490DF20 (OMEGA) equipped with a 10% neutral density filter was used for green fluorescence signal excitation. 535DF35 (OMEGA) was used as a green fluorescence signal detection filter. On the other hand, 546DF10 (OMEGA) was used for orange fluorescence signal excitation. 595RDF60 (OMEGA) was used as an orange fluorescence signal detection filter. As a dichroic mirror, 505DRLPXR (OMEGA) was used. The field stop was controlled, and only the orange fluorescence in the soma (cell body) of rat hippocampus neurons was discolored with the strong green light of 550DF30 (OMEGA). The ratio between the orange fluorescence signal and the green fluorescence signal was calculated, and the shift of BDNF-mKO-FM14 from the soma to the neurite was observed (FIGS. 33 and 34). The white arrow in FIG. 34 indicates a state wherein BDNF-mKO-FM14 moves from the soma towards the tip of the neurite.

Example 7

Figure 35:
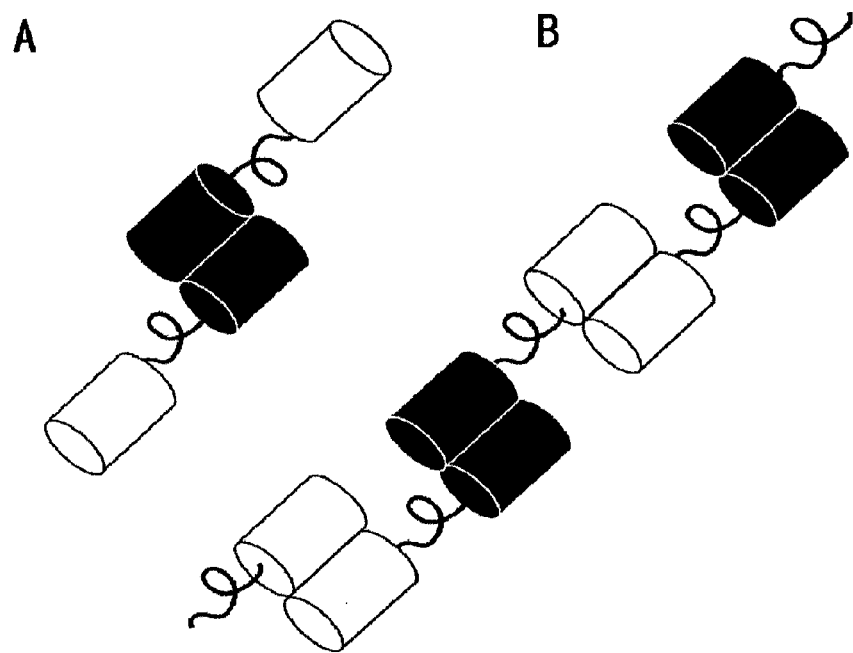
FIG. 35 shows a schematic diagram of a fluorescent protein for carrying out intramolecular FRET.
Figure 36:
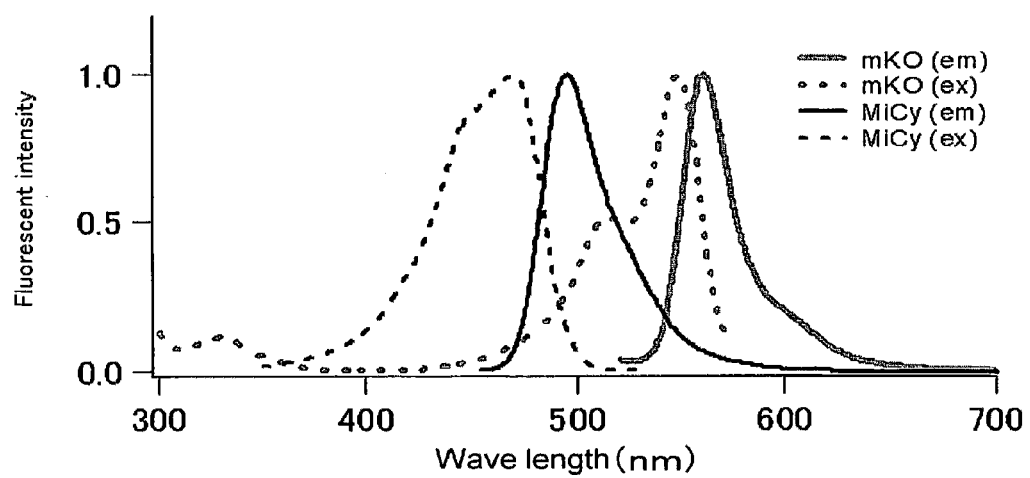
FIG. 36 shows the fluorescence spectrum and absorption spectrum of each of a monomer fluorescent protein mKO and a dimer fluorescent protein MiCy.

Caspase-3 Activity Measurement Probe Using Monomer Fluorescent Protein mKO and Dimer (Multimer) Fluorescent Protein MiCy At least one type of protein used to perform intramolecular FRET should be a monomer. (A) the combination of the monomer (white) with the dimer (black) (FIG. 35A). The combination of the dimer (polymer) fluorescent protein MiCy with the monomer fluorescent protein mKO corresponds to such a pattern. For example, it is considered that the combination of the dimer (white) with the dimer (black) causes a range such as a polymer (FIG. 35B). In the case of the monomer fluorescent protein mKO and the dimer fluorescent protein MiCy, since the fluorescence spectrum of MiCy and the absorption spectrum of mKO partially overlap, it is possible to measure FRET (fluorescence resonance energy transfer method) using both proteins (FIG. 36). Thus, MiCy is ligated to mKO, using a linker that contained DEVD (Asp-Glu-Val-Asp) (SEQ ID NO: 82) as a Caspase-3 recognition sequence (the amino acid sequence thereof is shown in SEQ ID NO: 35, and the nucleotide sequence thereof is shown in SEQ ID NO: 36). Thereafter, the cleavage of the linker sequence due to activation of Caspase-3 was measured by FRET.

(1) In vitro Measurement of Caspase-3 Activity

Figure 37:
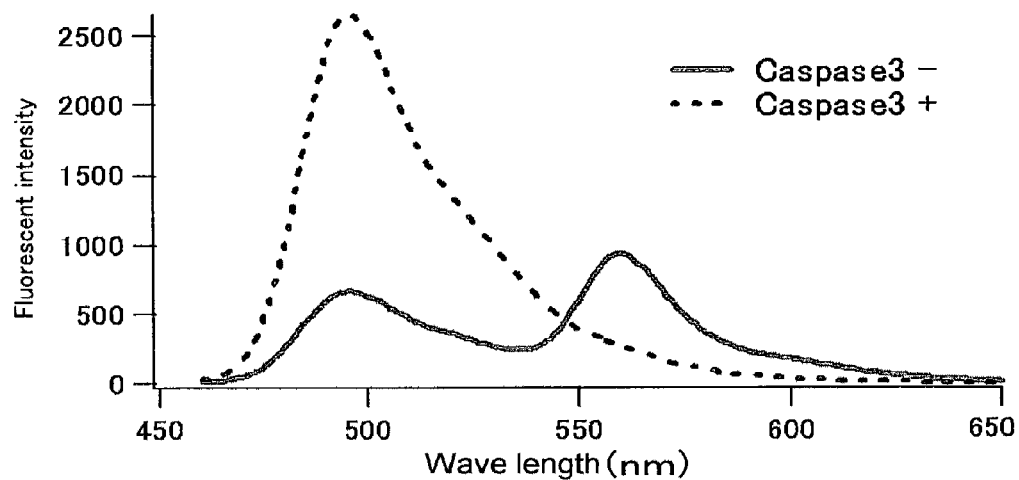
FIG. 37 shows the measurement results obtained by exciting at 440 nm, the fluorescence spectrum of a reaction solution before and after the reaction of MiCy-linker-mKO with Caspase-3.

MiCy, the linker, and mKO were ligated to one another in this order, and the obtained ligate was then subcloned into the BamH1-EcoR1 site of the *Escherichia coli* expression vector pRSET$_B$, so that it was allowed to express in *Escherichia coli* JM109 (DE3). The used linker had the following sequence: GGSGGDEVDGTGGS (Gly-Gly-Ser-Gly-Gly-Asp-Glu-Val-Asp-Gly-Thr-Gly-Gly-Ser) (SEQ ID NO: 84). This construct was referred to as MiCy-DEVD-mKO (SEQ ID NO: 82). The expressed recombinant fusion protein was purified with Ni-NTA agarose. The purified recombinant fusion protein was subjected to gel filtration using a sephadex G-25 column, and the buffer was substituted with a 150 mM KCl and 50 mM HEPES-KOH (pH 7.4) solution. For activity measurement, recombinant Active-Caspase-3 (MBL: BV-1083-9) was used. Each recombinant fusion protein was poured into a solution that contained 20 mM HEPES-KOH (pH7.4), 100 mM NaCl, 0.1% CHAPS, and 10% sucrose, resulting in a concentration of 1 mg/ml. Thereafter, 1 unit of the recombinant Active-Caspase-3 was added thereto, followed by reaction at 30° C. for 3 hours. The fluorescence spectrum of the reaction solution was excited at 440 nm and measured before and after the reaction. For such measurement, a fluorospectrophotometer F-2500 (HITACHI) was used. As a result, it was found that FRET took place and the fluorescence peak (559 nm) of mKO appeared before addition of Caspase-3, but that after the addition thereof, FRET disappeared due to the cleavage of the linker and the fluorescence peak (559 nm) of mKO thereby disappeared, so that only the fluorescence peak (495 nm) of MiCy remained (FIG. 37).

(2) In viva Measurement of Caspase-3 Activity

MiCy-DEVD-mKO (SEQ ID NO: 82) was subcloned into the BamH1-EcoR1 site of the animal cell expression vector pCS2+. The thus prepared vector was introduced into HeLa-S3 cells, using Polyfect (QIAGEN). Twenty-four hours after introduction of the gene, the culture solution was substituted with an HBSS (Hanks' Balanced Salt Solution) that contained 500 ng/ml anti-Fas antibody (CH-11: MBL) and 10 μg/ml cycloheximide, so as to induce apoptosis, followed by the imaging of Caspase-3 activity measurement.

Figure 38:
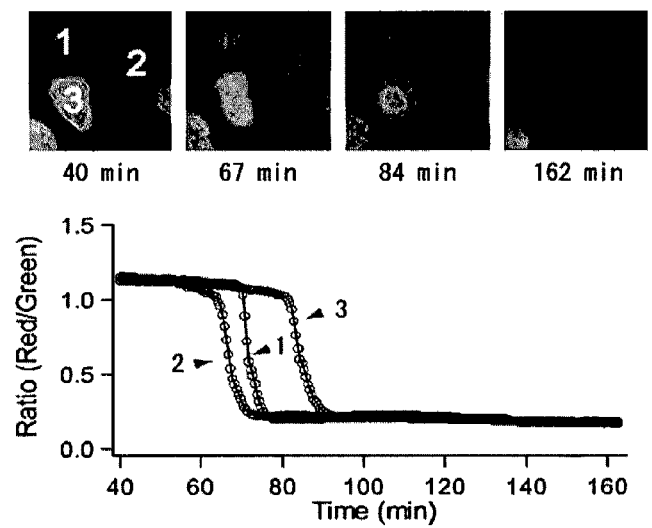
FIG. 38 shows the results obtained by measuring in vivo the activity of Caspase-3 using MiCy-linker-mKO.

IX-70 (OLYMPUS) was used as a microscope. 440AF21 (OMEGA) was used as an excitation filter, and 455DRLP (OMEGA) was used as a dichroic mirror. A fluorescence signal was detected through the 480ALP (OMEGA) filter, using a color 3CCD camera ASHURA (Hamamatsu Photonics K. K.). The fluorescence signal of MiCy was detected in a green channel, and the fluorescence signal of mKO was detected in a red channel. As a result, as apoptosis proceeded in the HeLa cells, Caspase-3 was activated, and a linker of the translated product of the introduced gene was cleaved. Thereby, FRET disappeared, and the phenomenon whereby the signal in the red channel decreased and the signal in the green channel increased was observed. The ratio between red and green decreased, as Caspase-3 was activated. In addition, alteration of the shape due to the apoptosis of the HeLa cells was also observed (FIG. 38).

Example 8

Isolation of Novel Chromoprotein Gene from Stony Coral, Preparation of Novel Fluorescent Protein, and Analysis of Properties Thereof (1) Extraction of Total RNA A chromoprotein gene was isolated from coral. *Montipora* sp. was used as a material. A frozen *Montipora* sp. was crushed in a mortar, and 7.5 ml of "TRIzol" (GIBCO BRL) was then added to 1 g (wet weight) of the crushed *Montipora* sp. Thereafter, the obtained mixture was homogenized and then centrifuged at 1,500×g for 10 minutes. Thereafter, 1.5 ml of chloroform was added to the obtained supernatant, and the mixture was then stirred for 15 seconds. Thereafter, the mixture was left at rest for 3 minutes. The resultant was then centrifuged at 7,500×g for 15 minutes. Thereafter, 3.75 ml of isopropanol was added to the obtained supernatant, and the mixture was then stirred for 15 seconds, followed by leaving the mixture at rest for 10 minutes. Thereafter, the resultant was centrifuged at 17,000×g for 10 minutes. The obtained supernatant was discarded, and 6 ml of 70% ethanol was added to the residue, followed by centrifugation at 17,000×g for 10 minutes. The obtained supernatant was discarded, andthe precipitate was then dissolved in 200 μl of DEPC water.

Total RNA dissolved in the DEPC water was 100 times diluted, and the values of O.D.260 and O.D.280 were then measured, so as to determine RNA concentration. As a result, 53 μg of total RNA was obtained.

(2) Synthesis of First Strand cDNA cDNA (33 μl) was synthesized from 4 μg of the total RNA, using a kit for synthesizing first strand cDNA "Ready To Go" (Amersham Pharmacia).

(3) Degenerated PCR

3 μl of the synthesized first strand cDNA (33 μl) was used as a template to carry out PCR. Primers were produced by making comparison among the amino acid sequences of known fluorescent proteins, extracting similar portions, and converting them to nucleotide sequences.

Primers Used:

```
                                              (SEQ ID NO: 74)
    5'-GAAGGRTGYGTCAAYGGRCAY-3'  (primer 1)

(SEQ ID NO: 75)
    5'-ACVGGDCCATYDGVAAGAAARTT-3'  (primer 2)
```

I represents inosine; R represents A or G; Y represents C or T; V represents A, C, or G; D represents A, G, or T; S represents C or G; H represents A, T, or C Composition of PCR reaction solution:

| Template (first strand cDNA) | 3 μl |
|---|---|
| X10 taq buffer | 5 μl |
| 2.5 mM dNTPs | 4 μl |
| 100 μM primer 1 | 1 μl |
| 100 μM primer 2 | 1 μl |
| Milli-Q | 35 μl |
| taq polymerase (5 U/μl) | 1 μl |

PCR reaction Conditions:
94° C.×1 min (PAD)
94° C.×30 sec (denaturation)
52° C.×30 sec (annealing of primers to template)
72° C.×1 min (primer elongation)
A cycle consisting of the aforementioned 3 steps was repeated 35 times.
72° C.×7 min (final elongation)
4° C. (maintenance)

Using 1 μl of the amplified product obtained in the first PCR reaction as a template, PCR was carried out again under the same above conditions. A 350-bp fragment was cut out via agarose gel electrophoresis, and it was then purified.

(4) Subcloning and Sequencing

The purified DNA fragment was ligated to a pT7-blue vector (Novagen). Escherichia coli (TG1) was transformed therewith, and it was then subjected to blue white selection. Plasmid DNA was purified from white colonies of Escherichia coli, and the nucleotide sequence of the inserted DNA fragment was determined using a DNA sequencer. Thereafter, the obtained nucleotide sequence was compared with the nucleotide sequences of other fluorescent protein genes, so as to determine whether the nucleotide sequence of the DNA fragment was derived from a fluorescent protein. With regard to those that were determined to be a part of the fluorescent protein genes, the full-length genes were cloned by the 5'-RACE method and the 3'-RACE method.

(5) 5'-RACE Method

In order to determine the nucleotide sequence on the 5'-side of the DNA fragment obtained by the degenerated PCR, the 5'-RACE method was applied using 5'-RACE System for Rapid Amplification of cDNA Ends, Version 2.0 (GIBCO BRL). 5 μg of the total RNA prepared in (1) above was used as a template.

The following primers were used in the first amplification of dC-tailed cDNA:

```
                                            (SEQ ID NO: 76)
5'-GGCCACGCGTCGACTAGTACGGGIIGGGIIGGGIIG-3'
(primer 3);
and (SEQ ID NO: 77)
5'-CTCAGGGAATGACTGCTTTACAT-3' (primer 4)
```

Herein, I represents inosine.

The following primers were used in the second amplification:

```
                                            (SEQ ID NO: 78)
       5'-GGCCACGCGTCGACTAGTAC-3' (primer 5)

(SEQ ID NO: 79)
       5'-GTCTTCAGGGTACTTGGTGA-3' (primer 6)
```

PCR reaction conditions were applied in accordance with protocols attached to the kit.

The amplified 350-bp band was cut out of the gel via agarose gel electrophoresis and then purified. The purified DNA fragment was ligated to a pT7-blue vector (Novagen). *Escherichia coli* (TG1) was transformed therewith, and it was then subjected to blue white selection. Plasmid DNA was purified from white colonies of *Escherichia coli*, and the nucleotide sequence of the inserted DNA fragment was determined using a DNA sequencer.

(6) 3'-RACE Method

The nucleotide sequence on the 3'-side of the DNA fragment obtained by the degenerated PCR was obtained by PCR using a primer prepared based on the information obtained by determination of the nucleotide sequence in (4) above and an oligo dT primer. 3 μl of the first strand cDNA prepared in (2) above was used as a template. The prepared primer was 5'-ATGTAAAGCAGTCATTCCCTGAG-3' (primer7) (SEQ ID NO: 80).

Composition of PCR Reaction Solution:

| Template (first strand cDNA) | 3 μl |
| X10 taq buffer | 5 μl |
| 2.5 mM dNTPs | 4 μl |
| 20 μM primer 7 | 1 μl |
| 10 μM oligo dT primer | 1 μl |
| Milli-Q | 35 μl |
| Taq polymerase (5 U/μl) | 1 μl |

PCR Reaction Conditions:
94° C.×1 minute (PAD)
94° C.×30 seconds (denaturation)
52° C.×30 seconds (annealing of primers to template)
72° C.×1 minute (primer elongation)

A cycle consisting of the aforementioned 3 steps was repeated 30 times.
72° C.×7 minutes (final elongation)
4° C. (maintenance)

The amplified band with a length of approximately 650 bp was cut out of the gel via agarose gel electrophoresis and then purified. The purified DNA fragment was ligated to a pT7-blue vector (Novagen). Escherichia coli (TG1) was transformed therewith, and it was then subjected to blue white selection. Plasmid DNA was purified from white colonies of *Escherichia coli*, and the nucleotide sequence of the inserted DNA fragment was determined using a DNA sequencer.

(7) Expression of Protein in *Escherichia coli*

Based on the obtained full-length nucleotide sequence, a primer was produced with a portion corresponding to the N-terminus of the protein. An oligo dT primer was used as a primer corresponding to the C-terminal side thereof. Thereafter, using such primers, PCR was carried out employing the first strand cDNA prepared in (2) above as a template. The obtained full-length amino acid sequence and nucleotide sequence are shown in SEQ ID NOS: 37 and 38 of the sequence listing. This protein having the amino acid sequence shown in SEQ ID NO: 37 was named COCP.

Primer Used:

```
                                            (SEQ ID NO: 81)
5'-CCCGGATCCGACCATGGCTACCTTGGTTAAAGA-3' (primer 8)
```

Composition of PCR Reaction Solution:

| Template (first strand cDNA) | 3 μl |
| X10 pyrobest buffer | 5 μl |
| 2.5 mM dNTPs | 4 μl |
| 100 μM primer 8 | 1 μl |
| 100 μM oligo dT primer | 1 μl |
| Milli-Q | 35 μl |
| Pyrobest polymerase (5 U/μl) | 1 μl |

PCR Reaction Conditions:
94° C.×1 minute (PAD)
94° C.×30 seconds (denaturation)
52° C.×30 seconds (annealing of primers to template)
72° C.×1 minute (primer elongation)

A cycle consisting of the aforementioned 3 steps was repeated 30 times.
72° C.×7 minutes (final elongation)
4° C. (maintenance)

The amplified band with a length of approximately 800 bp was cut out of the gel via agarose gel electrophoresis and then purified. The purified DNA fragment was subcloned into the BamHI-EcoRI site of a pRSET vector (Invitrogen), and it was then allowed to express in *Escherichia coli* (3M109-DE3). The expressed protein was constructed such that His-tag was attached to the N-terminus thereof, and thus it was purified with Ni-Agarose gel (QIAGEN). Purification was carried out in accordance with the attached protocols. Subsequently, the properties of the purified protein were analyzed.

(8) Analysis of Light-Absorbing Properties

Figure 39:
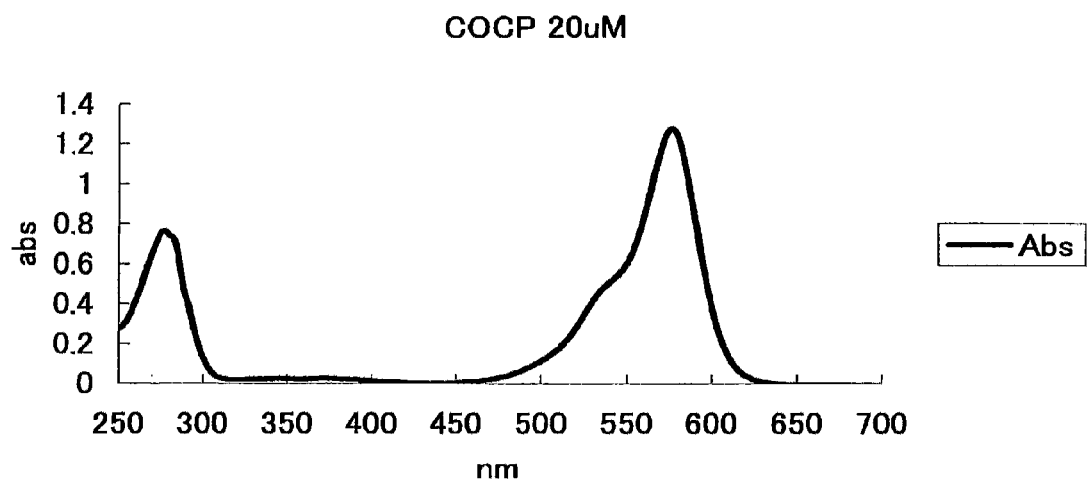
FIG. 39 shows the absorption spectrum of COCP.
Figure 40:
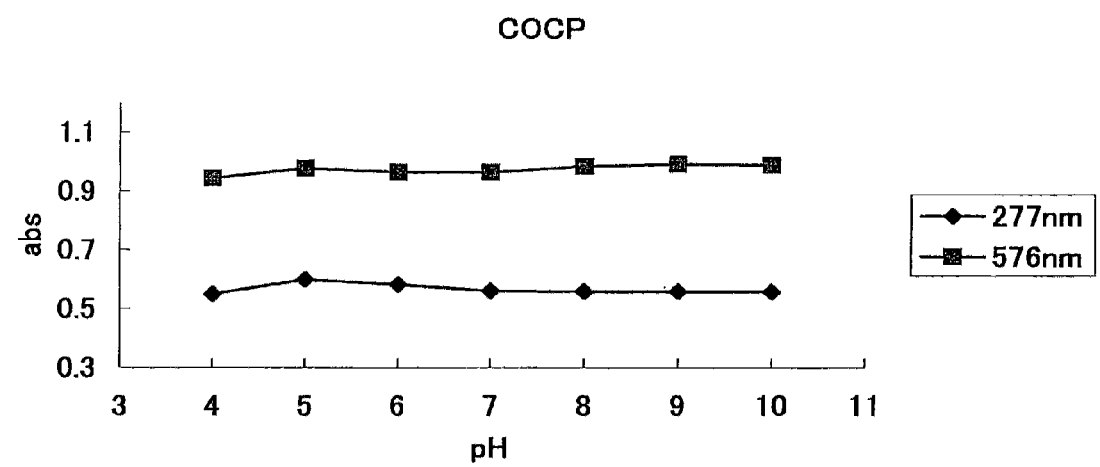
FIG. 40 shows the results obtained by measuring the pH sensitivity of COCP.

Using a solution comprising 20 μM chromoprotein and 50 mM HEPES (pH 7.9), the absorption spectrum was measured. Thereafter, the molar absorption coefficient of the protein was calculated from the value of the peak of the spectrum. In the chromoprotein (COCP) derived from *Montipora* sp., the absorption peak was observed at 576 nm (Table 2, FIG. 39. Also, it was stable at pH4 to 10.

Properties of chromoprotein (COCP) isolated from *Montipora* sp.

TABLE 1

| | Maximum absorption | Maximum fluorescence | Molar absorption coefficient | Quantum yield | pH sensitivity | Number of amino acids |
|---|---|---|---|---|---|---|
| COCP | 576 nm | — | 64000 (576 nm) | — | Absent | 221 a.a. |
| keima 616 | 440 nm | 616 nm | 28000 (440 nm) | 0.24 | Present | 222 a.a. |

(9) Modification from Chromoprotein to Fluorescent Protein

COCP is not a fluorescent protein. However, valine was inserted into the portion between methionine at position 1 of COCP and serine at position 2 thereof, histidine at position 94 was substituted with asparagine, asparagine at position 142 was substituted with serine, asparagine at position 157 was substituted with aspartic acid, lysine at position 202 was substituted with arginine, and phenylalanine at position 206 was substituted with serine, so as to acquire fluorescence properties. This modified fluorescent protein was named as COCP-FL (the amino acid sequence thereof is shown in SEQ ID NO: 39, and the nucleotide sequence thereof is shown in SEQ ID NO: 40). COCP-FL has an excitation peak at 560 nm. By this excitation, the fluorescence spectrum has a peak at 600 nm.

(10) Production of Red Fluorescent Protein with Large Stokes Shift

Figure 41:
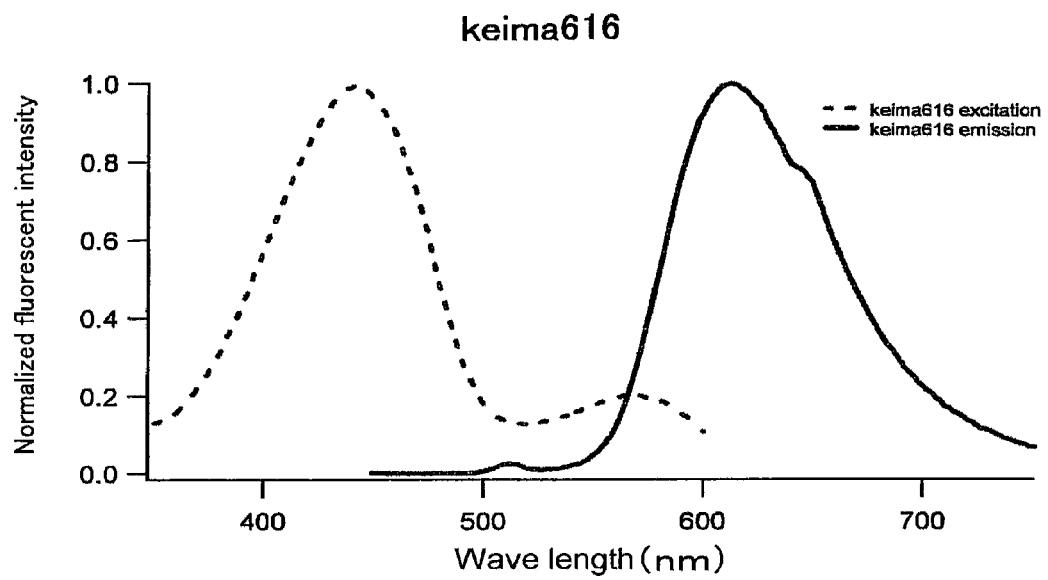
FIG. 41 shows the excitation spectrum and fluorescence spectrum of keima 616.

In COCP-FL, serine at position 62 was substituted with phenylalanine, isoleucine at position 93 was substituted with threonine, valine at position 124 was substituted with threonine, phenylalanine at position 159 was substituted with tyrosine, valine at position 192 was substituted with isoleucine, and serine at position 214 was substituted with alanine, so as to acquire a protein having different fluorescence from that of COCP-FL. This modified fluorescent protein was named as keima 616 (the amino acid sequence thereof is shown in SEQ ID NO: 41, and the nucleotide sequence thereof is shown in SEQ ID NO: 42). keima 616 has an excitation peak at 440 nm. By this excitation, the fluorescence spectrum has a peak at 616 nm (FIG. 41, Table 2). Its stokes shift is 176 nm, which is an extremely large value. When compared with the conventional fluorescent protein, this protein is able to have a large excitation wavelength region and a large fluorescence wavelength region, and thus fluorescence can be efficiently measured. In addition, it is also possible to simultaneously measure multiple colors of fluorescence. Using fluorochromes having identical excitation wavelengths, photometry can be conducted with two wavelengths by excitation with a single wavelength such as a laser. In the case of the conventional fluorescent proteins, since proteins having the same excitation spectrum have not existed, such photometry has not been conducted. Using these proteins, a problem regarding deviation in measurement due to difference in excitation can be solved.

(11) Production of Orange Fluorescent Protein Having Large Stokes Shift

In keima 616, phenylalanine at position 62 was substituted with methionine, and glutamine at position 63 was substituted with cysteine, so as to obtain a fluorescent protein. This modified fluorescent protein was named as keima 570 (the amino acid sequence thereof is shown in SEQ ID NO: 43, and the nucleotide sequence thereof is shown in SEQ ID NO: 44).

Figure 42:
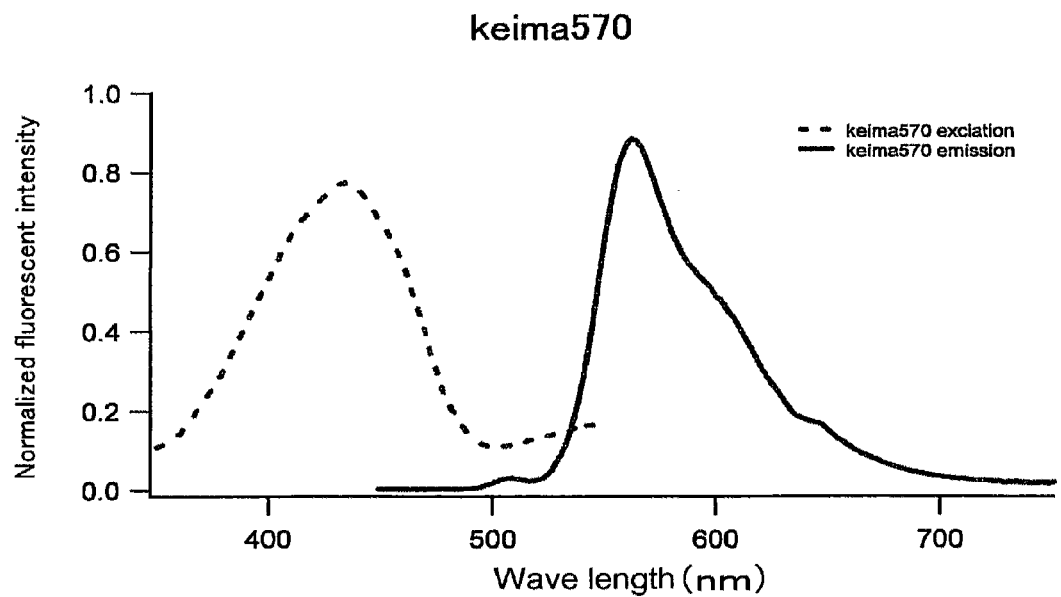
FIG. 42 shows the excitation spectrum and fluorescence spectrum of keima 570.

As with keima 616, keima 570 also has an excitation peak at 440 nm. By this excitation, the fluorescence spectrum has a peak at 570 nm (FIG. 42). Its stokes shift is 130 nm, which is a large value. When compared with the conventional fluorescent protein, this protein is able to have a large excitation wavelength region and a large fluorescence wavelength region, and thus fluorescence can be efficiently measured. In addition, it is also possible to simultaneously measure multiple colors of fluorescence. Using fluorochromes having identical excitation wavelengths, photometry can be conducted with two wavelengths by excitation with a single wavelength such as a laser. In the case of the conventional fluorescent proteins, since proteins having the same excitation spectrum have not existed, such photometry has not been conducted. Using these proteins, a problem regarding deviation in measurement due to difference in excitation can be solved.

(12) Measurement of pH Sensitivity

Figure 43:
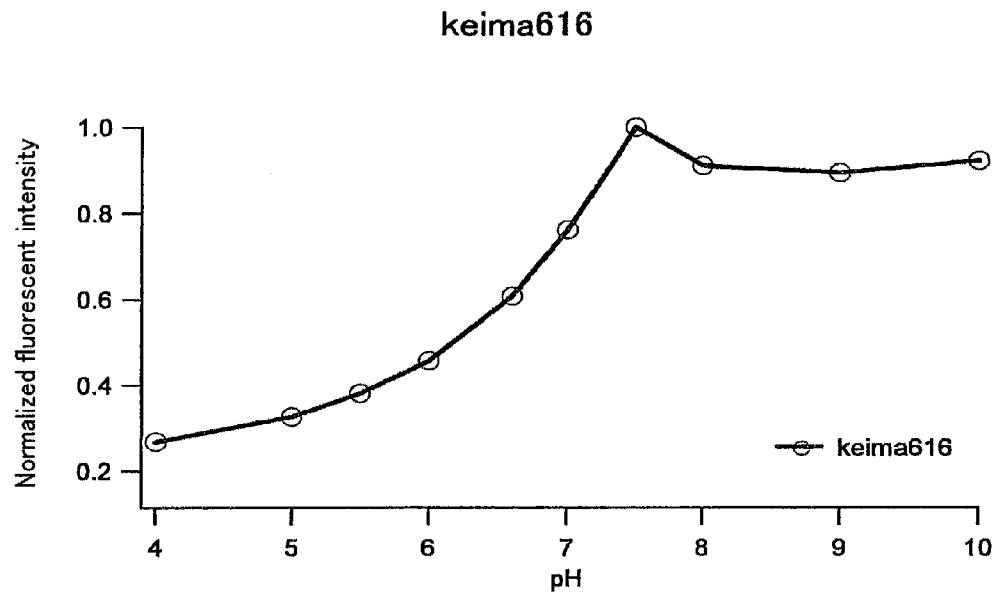
FIG. 43 shows the results obtained by measuring the pH sensitivity of keima 616.
Figure 44:
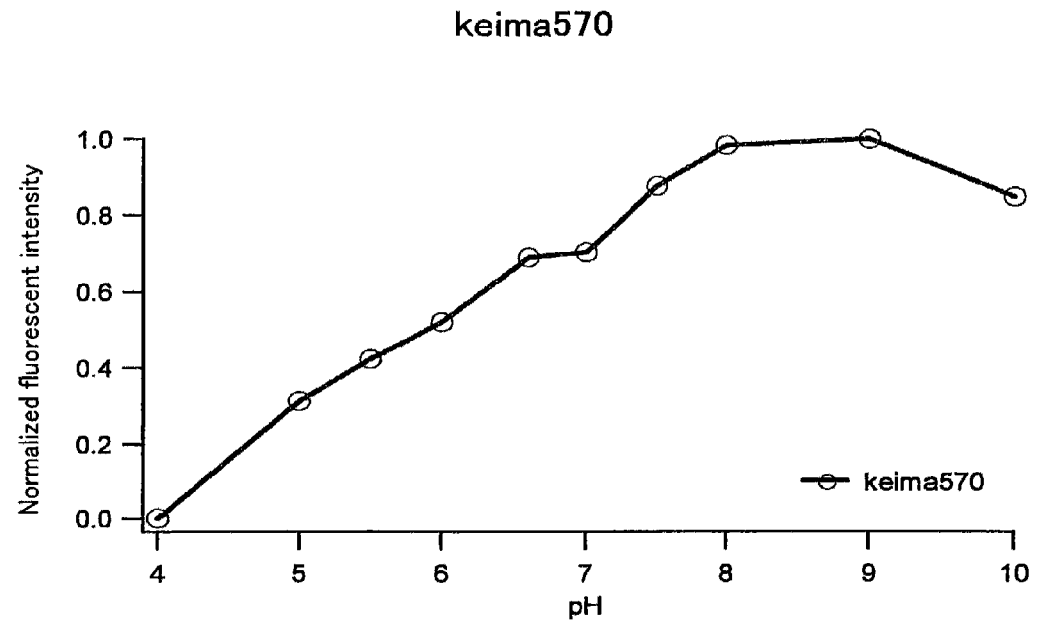
FIG. 44 shows the results obtained by measuring the pH sensitivity of keima 570.

The absorption spectra of the proteins (keima 616 and keima 570) were measured in the following 50 mM buffer solutions (FIGS. 43 and 44):

The pH of each buffer solution is as follows:
pH 4, 5, and 5.5: acetate buffer
pH 6: phosphate buffer
pH 6.6: MOPS buffer
pH 7, 7.5, and 8: HEPES buffer
pH 9 and 10: glycine buffer The peak value was stable between pH 7.5 and 10 (FIGS. 43 and 44).

Example 9

(1) Production of Monomer Red Fluorescent Protein Having Large Stokes Shift

Figure 45:
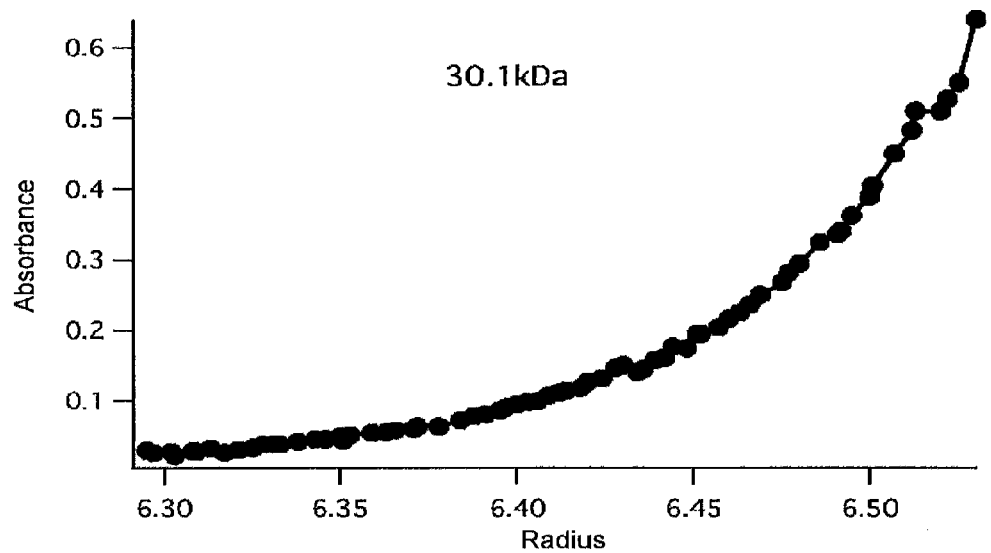
FIG. 45 shows the results obtained by measuring the molecular weight of cmkeima 620 by ultracentrifugation.
Figure 46:
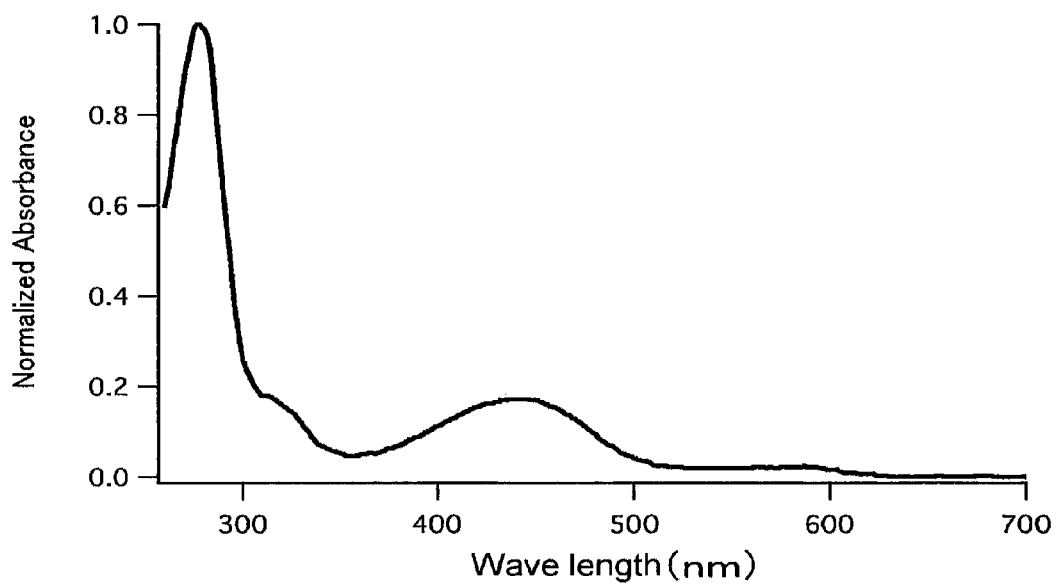
FIG. 46 shows the absorption spectrum of cmkeima 620.

In keima 616, leucine at position 61 was substituted with glutamine, threonine at position 93 was substituted with serine, threonine at position 124 was substituted with glutamic acid, tyrosine at position 189 was substituted with arginine, and tyrosine at position 191 was substituted with glutamic acid, so as to obtain a keima 616 protein as a monomer. This protein was considered to be a monomer keima 616 protein because its molecular weight, 30.1 kDa, obtained as a result of the ultracentrifugal molecular weight measurement, is almost the same as 29 kDa predicted from the amino acid sequence. This modified fluorescent protein was named as cmkeima 620 (FIG. 45) (the amino acid sequence thereof is shown in SEQ ID NO: 45, and the nucleotide sequence thereof is shown in SEQ ID NO: 46). This protein has an excitation peak at 440 nm. By this excitation, the fluorescence spectrum has a peak at 620 nm (FIG. 46). Its stokes shift is 180 nm, which is an extremely large value. When compared with the conventional fluorescent protein, this protein is able to have a large excitation wavelength region and a large fluorescence wavelength region, and thus fluorescence can be efficiently measured. In addition, it is also possible to simultaneously measure multiple types of fluorescence. Using fluorochromes having identical excitation wavelengths, photometry can be conducted with two wavelengths by excitation with a single wavelength such as a laser. In the case of the conventional fluorescent proteins, since proteins having the same excitation spectrum have not existed, such photometry has not been conducted. Using these proteins, a problem regarding deviation in measurement due to difference in excitation can be solved. Moreover, the entire molecular weight is suppressed, and there is no interaction due to multimer formation between fluorescent proteins. Accordingly, a change in the properties of labeled molecules can be reduced to the minimum.

(2) Modification of Monomer Red Fluorescent Protein Having Large Stokes Shift

Figure 47:
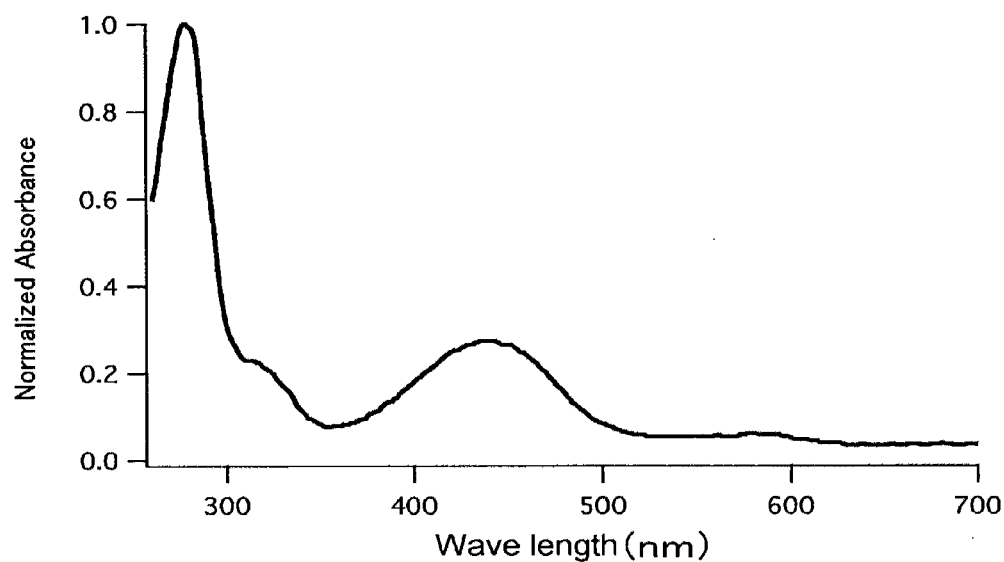
FIG. 47 shows the absorption spectrum of mkeima 620.

Phenylalanine at position 62 of cmkeima 616 was substituted with leucine, so as to obtain a modified cmkeima 620 protein having an increased folding efficiency. This modified fluorescent protein was named as mkeima 620 (the amino acid sequence thereof is shown in SEQ ID NO: 47, and the nucleotide sequence thereof is shown in SEQ ID NO: 48). This protein has an excitation peak at 440 nm. By this excitation, the fluorescence spectrum has a peak at 620 nm. Its stokes shift is 180 nm, which is an extremely large value. Since this protein has fluorescence intensity that is relatively higher than that of cmkeima 620 (FIGS. 46 and 47), although this is a monomer, it is sufficiently usable, as with keima 616.

Example 10

Development of Measurement System for one Wavelength Excitation Two Wavelengths Photometry Fluorescence Cross-Correlation Spectroscopy, Using Protein with Large Stokes Shift Fluorescence cross correlation spectroscopy (FCCS) using fluorescent molecules is a method for measuring an intermolecular interaction. In this method, two fluorescent molecules are used as probes, so as to monitor an intermolecular interaction.

Figure 48:
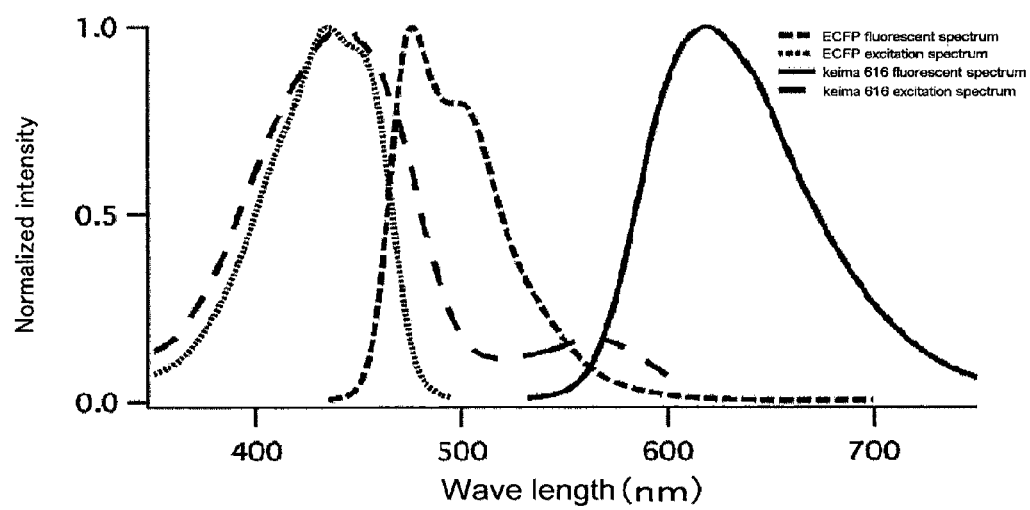
FIG. 48 shows the excitation spectrum and fluorescence spectrum of each of keima 616 and ECFP.

A great factor for deteriorating the sensitivity of cross-correlation in the currently used two wavelengths excitation FCCS measurement using two different fluorescent molecules is a deviation in the overlapped portions of two wavelengths measurement regions due to chromatic aberration. One wavelength excitation FCCS involving the combined use of fluorescent proteins capable of exciting with one wavelength and also separating fluorescence, such as keima 616 and ECFP, is able to avoid such a problem. Accordingly, an increase in the sensitivity of FCCS measurement is anticipated (FIG. 48). Moreover, since such one wavelength excitation FCCS is able to avoid fluorescence resonance energy transfer (FRET), the measurement by FCCS is facilitated, and thus this method is suitable for detection of an interaction between proteins by FCCS. Accordingly, it is considered that, using keima 616 which is a fluorescent protein having a large stokes shift, detection of interaction between proteins can be easily and strongly carried out by FCCS.

(1) Detection of Caspase-3 Activity
(a) Devices used for Fluorescence Cross-Correlation Measurement TCS SP2 SOBS (Leica) and the FCCS system were used for fluorescence cross-correlation measurement. For EGFP-(spacer) DEVD-mRFP1 (SEQ ID NO: 82), 458-nm Argon ion Laser and 594-nm HeNe Laser were used, and two wavelengths excitation was carried out. In addition, as the combination of ECFP with the keima 616 protein, 458-nm Argon Laser was used. Further, as light receiving band-pass filters, the following filters were used: EGFP: 500-550; mRFP1: 607-683; ECFP: 470-500; and keima 616: 535-585.

(b) Analysis of Fluorescence Cross-Correlation Measurement

Figure 49:
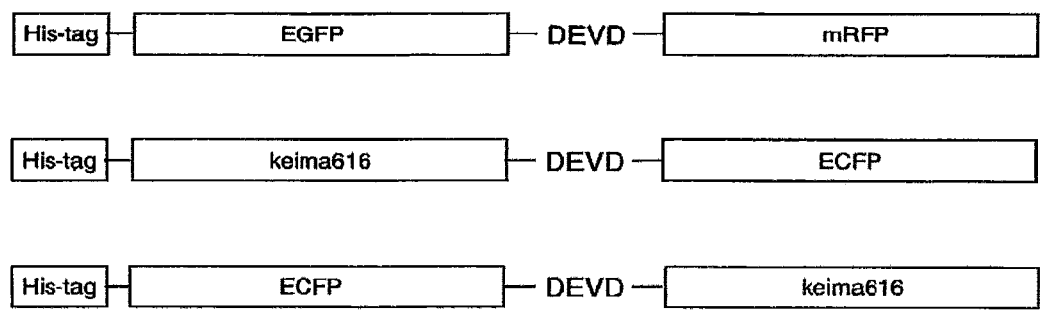
FIG. 49 shows a protein motif used in the measurement of the activity of Caspase-3 (peptide disclosed as SEQ ID NO: 82).

The amino acid sequence DEVD (SEQ ID NO: 82) which is cleaved with Caspase-3 was introduced into the portion between EGFP and mRFP and also into the portion between keima 616 and ECFP (FIG. 49). The recombinant EGFP-DEVD-mRFP1 (SEQ ID NO: 82) (×2) (the amino acid sequence is shown in SEQ ID NO: 49, and the nucleotide sequence thereof is shown in SEQ ID NO: 50), ECFP-(spacer) DEVD-keima (SEQ ID NO: 82) 616 (the amino acid sequence is shown in SEQ ID NO: 51, and the nucleotide sequence thereof is shown in SEQ ID NO: 52), and keima 616-(spacer) DEVD-ECFP (SEQ ID NO: 82) (the amino acid sequence is shown in SEQ ID NO: 53, and the nucleotide sequence thereof is shown in SEQ ID NO: 54), were produced. Since the expressed proteins were constructed such that His-tag was attached to the N-terminus thereof, they were purified with Ni-agarose gel (QIAGEN). Purification was carried out in accordance with the protocols included therewith. Subsequently, these proteins were used to analyze cross-correlation.

Figure 50:
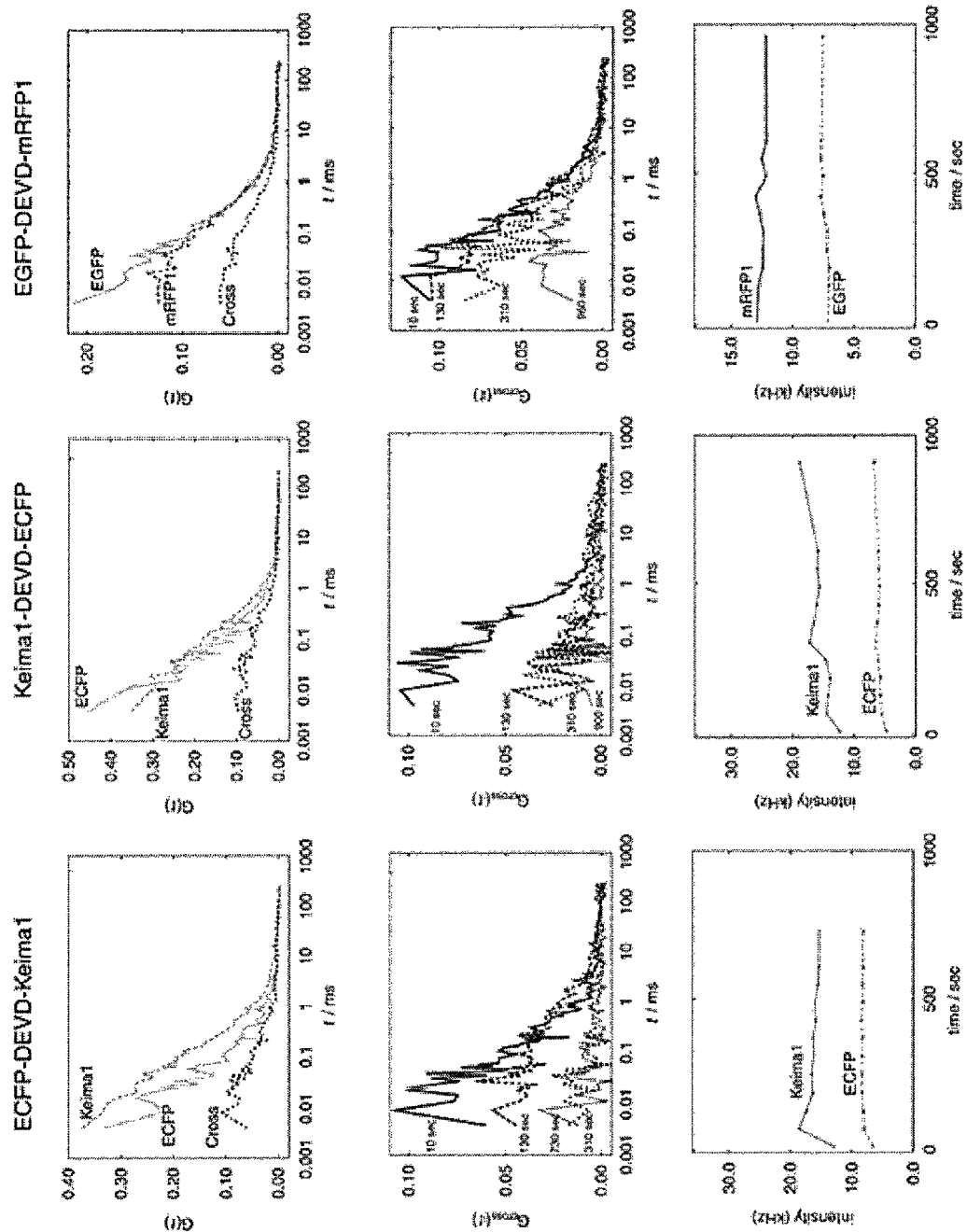
FIG. 50 shows a cross correlation with in vitro protease activity. Three types of tandem fluorescent protein samples obtained by insertion of the DEVD (SEQ ID NO: 82) sequence into a linker portion were prepared: ECFP-keima 616, keima 616-ECFP, and EGFP-mRFP1 (×2). The upper case indicates autocorrelation and cross correlation functions obtained before addition of Caspase-3. The middle case indicates a cross correlation function obtained after addition of Caspase-3. The lower case indicates fluorescence intensity obtained after addition of Caspase-3.
Figure 51:
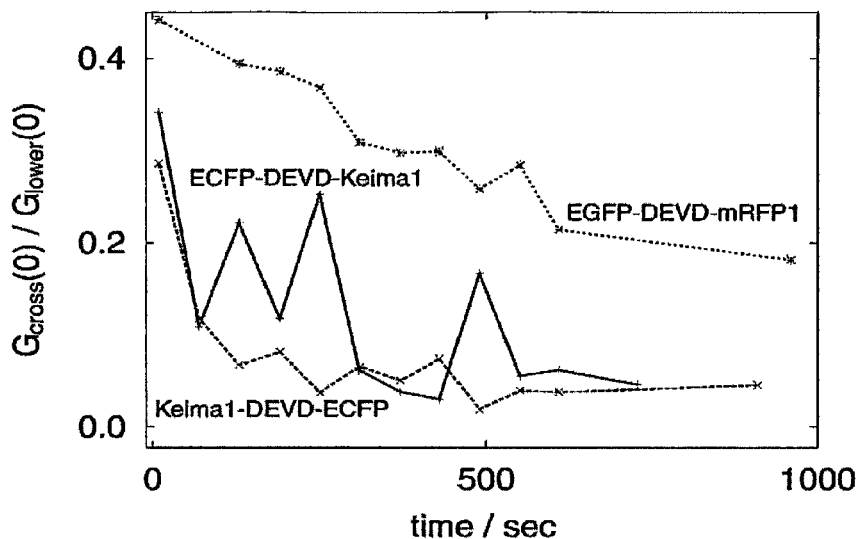
FIG. 51 shows a relative amplitude in each fusion protein motif (peptide disclosed as SEQ ID NO: 82).

For quantitative evaluation of cross-correlation, a value obtained by dividing the amplitude ($G_{cross}(0)$) of a cross-correlation function known as a relative amplitude by the amplitude ($G_{lower}(0)$) of an autocorrelation function. In the case of EGFP-DEVD-mRFP1 (SEQ ID NO: 82) (×2), the value of $G_{cross}(0)/G_{lower}(0)$ was approximately 0.4 (FIG. 51). A decrease in $G_{cross}(0)$ was observed as a result of addition of Caspase-3 (FIG. 50).

In the case of the combination of ECFP with keima 616, the value of $G_{cross}(0)/G_{lower}(0)$ was 0.4 (FIG. 51). A rapid decrease in $G_{cross}(0)$ was observed as a result of addition of Caspase-3. A decrease in $G_{cross}(0)$ indicates that fluorescence correlation disappeared as a result of addition of Caspase-3. In the case of the combined use of ECFP with keima 616, such correlation disappeared in a shorter time than in the case of EGFP-DEVD-mRFP (SEQ ID NO: 82). From these results, it became clear that the combined use of ECFP with keima 616 exhibits the interaction between proteins more easily and rapidly by the fluorescence cross-correlation method.

(c) Analysis of Interaction Between Proteins by SDS-PAGE

Figure 52:
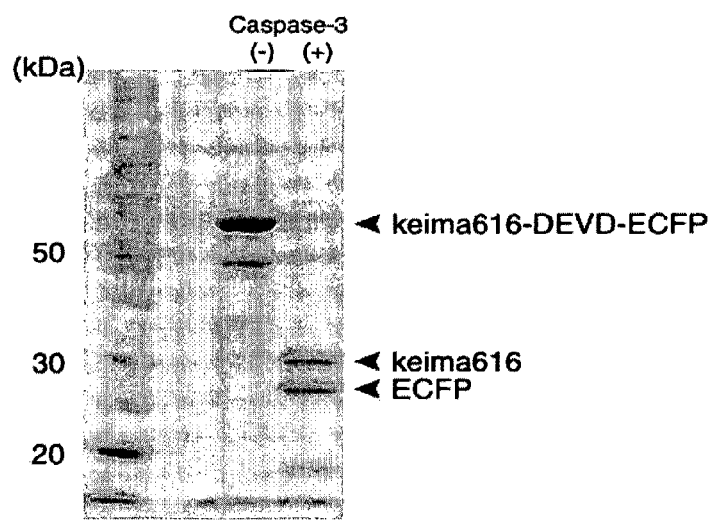
FIG. 52 shows detection of the cleavage of a peptide chain with Caspase-3 (SDS-PAGE) (peptide disclosed as SEQ ID NO: 82).

When keima 616-DEVD-ECFP (SEQ ID NO: 82) was reacted with Caspase-3, the bands with the sizes of keima 616 and ECFP could be confirmed. The presence of such proteins means that DEVD (SEQ ID NO: 82) was cleaved with Caspase-3 (FIG. 52). In the case of Native-PAGE as well, two bands were confirmed after the reaction. The two bands were identified to be keima 616 and ECFP, and thus it was found that the activity of Caspase-3 could be detected also by fluorescence detection (FIG. 52).

(2) Interaction with Calmodulin
(a) Synthesis and Expression of Protein

Figure 53:
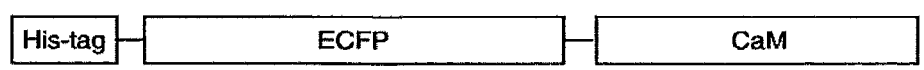
FIG. 53 shows a fusion protein motif used in detection of an interaction between proteins.
Figure 53:

ECFP was ligated to calmodulin, and keima 616 was ligated to M13 (FIG. 53). The amino acid sequence of ECFP-calmodulin is shown in SEQ ID NO: 55, and the nucleotide sequence thereof is shown in SEQ ID NO: 56. In addition, the amino acid sequence of M13-keima 616 is shown in SEQ ID NO: 57, and the nucleotide sequence thereof is shown in SEQ ID NO: 58. Such fusion proteins were allowed to express in the *Escherichia coli* strain (JM109-DE3). The expressied proteins were constructed such that His-tag was attached to the N-terminus. Thus, they were purified with Ni-agarose gel (QIAGEN). Purification was carried out in accordance with the protocols included therewith. Subsequently, these proteins were used to analyze cross-correlation.

(b) Devices for Fluorescence Cross-Correlation Measurement

ConfoCor2 (Carl Zeiss) and LSM 510, version 3.2, were used for fluorescence cross-correlation measurement. 458-nm Argon ion Laser was used. The following fight receiving band-pass filters were used: EGFP: 475-525; and keima 616: LP610.

(c) Analysis of Fluorescence Cross-Correlation Measurement

Figure 54:
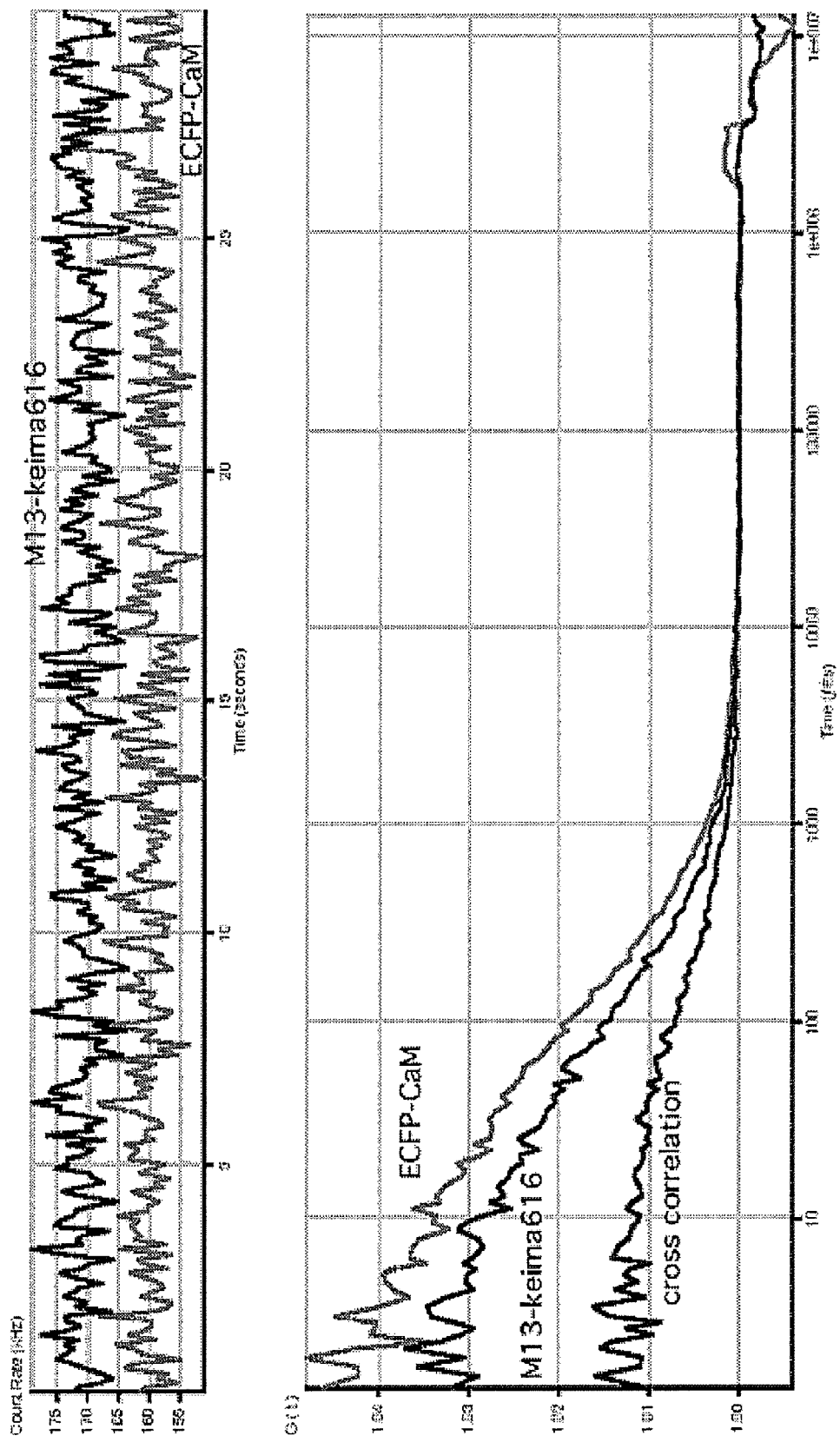
FIG. 54 shows the fluorescence cross correlation function of ECFP-CaM and M13-keima 616 when $CaCl_2$ is (+).
Figure 55:
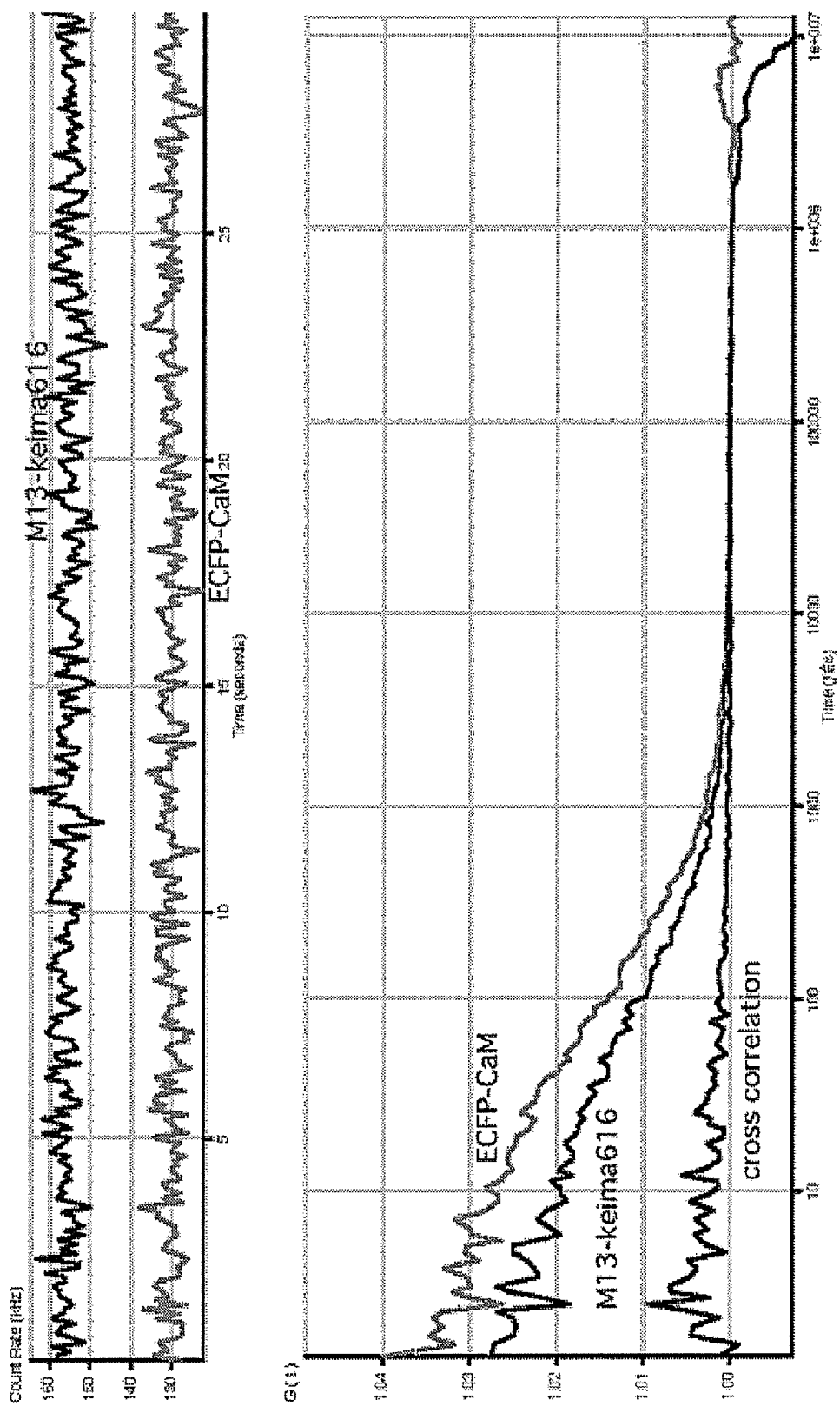
FIG. 55 shows the fluorescence cross correlation function of ECFP-CaM and M13-keima 616 when $CaCl_2$ is (−).

For quantitative evaluation of cross-correlation, a value obtained by dividing the amplitude ($G_{cross}(0)$) of a cross-correlation function known as a relative amplitude by the amplitude ($G_{lower}(0)$) of an autocorrelation function. In the case of a sample obtained by chelating calcium ions with EGTA, the value of $G_{cross}(0)/G_{lower}(0)$ was approximately 0.005 (FIG. 54). However, an increase in $G_{cross}(0)$ was observed as a result of addition of calcium ions (FIG. 55). These results show that calcium-dependent interaction between proteins was detected. From the results, it became clear that the interaction between proteins can be measured by the fluorescence cross-correlation method more rapidly and easily.

INDUSTRIAL APPLICABILITY

The present invention provides a novel fluorescent protein (mKO), which is able to exist in the form of a monomer. When the mitochondria of HeLa cells are labeled with a dimer fluorescent protein KO, the mitochondria are labeled in a granulated state, and thus the original image of such mitochondria cannot be obtained. However, when the mitochondria are labeled with a monomer fluorescent protein mKO, the image of normal narrow filamentous mitochondria is obtained, and the dynamic movement thereof is also observed. Such effectiveness obtained by monomerization was confirmed by the labeling of mitochondrial molecules.

In addition, the fluorescent proteins (keima 616 and keima 570) of the present invention emit red and orange fluorescence, and the excitation peak thereof is 440 nm (blue). The conventional red fluorescent proteins (DsRed and HcRed) have a stokes shift (the difference between an excitation peak value and a fluorescence peak value) between 20 and 30 nm. In contrast, the red fluorescent protein of the present invention has a stokes shift of 176 nm, and the orange fluorescent protein of the present invention has a stokes shift of 130 nm. Thus, the fluorescent proteins of the present invention have extremely large values. Accordingly, the fluorescent protein of the present invention is characterized in that the maximum fluorescence can be obtained by the maximum excitation. Moreover, since the excitation peak is at 440 nm, in the simultaneous excitation staining with a cyan fluorescent protein (CFP) or a green fluorescent protein (GFP), it becomes possible to extremely effectively obtain the fluorescence of both proteins. Furthermore, the excitation peak of the conventional red fluorescent proteins is between 560 nm and 590 nm. In contrast, the fluorescent protein of the present invention has an excitation peak at 440 nm. Thus, by changing excitation light, it makes possible to stain the present fluorescent protein, simultaneously with the conventional red fluorescent protein.

---

What is claimed is:

1. An isolated DNA encoding a fluorescent protein described in the following (a) or (b):
   (a) a protein having the amino acid sequence shown in amino acids 34-255 of SEQ ID NO: 47, amino acids 34-255 of SEQ ID NO: 45, full-length SEQ ID NO: 41, or full-length SEQ ID NO: 43; or
   (b) a protein having the amino acid sequence shown in amino acids 34-255 of SEQ ID NO: 47, amino acids 34-255 of SEQ ID NO: 45, full-length SEQ ID NO: 41, or full-length SEQ ID NO: 43 except that one to 10 amino acids have been mutated by deletion, substitution, and/or addition, and which has fluorescence properties and a stokes shift of 100 nm or greater.

2. A recombinant vector having the isolated DNA according to claim 1.

3. A transformant having the isolated DNA according to claim 1.

4. A transformant having the recombinant vector according to claim 2.

5. A reagent kit, which comprises the isolated DNA of claim 1.

6. A reagent kit, which comprises the recombinant vector of claim 2.

7. A reagent kit, which comprises the transformant of claim 3.

8. An isolated DNA encoding a fluorescent protein described in the following (a) or (b):
   (a) a protein having the amino acid sequence shown in SEQ ID NO: 47, 45, 41, or 43; or
   (b) a protein having the amino acid sequence shown SEQ ID NO: 47, 45, 41, or 43 except that one to 10 amino acids have been mutated by deletion, substitution, and/or addition, and which has fluorescence properties and a stokes shift of 100 nm or greater.

* * * * *